(12) United States Patent
Johnson et al.

(10) Patent No.: US 12,269,155 B2
(45) Date of Patent: *Apr. 8, 2025

(54) MULTIVALENT VACCINES FOR RABIES VIRUS AND CORONAVIRUSES

(71) Applicants: THE UNITED STATES OF AMERICA, AS REPRESENTED BY THE SECRETARY, DEPARTMENT OF HEALTH AND HUMAN SERVICES, Bethesda, MD (US); Thomas Jefferson University, Philadelphia, PA (US); University of Maryland, Baltimore, Baltimore, MD (US)

(72) Inventors: Reed F. Johnson, Frederick, MD (US); Matthias Schnell, Harleysville, PA (US); Lisa E. Hensley, Frederick, MD (US); Christoph Wirblich, Philadelphia, PA (US); Christopher M. Coleman, Owings Mills, MD (US); Matthew S. Frieman, Baltimore, MD (US)

(73) Assignees: THE UNITED STATES OF AMERICA, AS REPRESENTED BY THE SECRETARY, DEPARTMENT OF HEALTH AND HUMAN SERVICES, Bethesda, MD (US); Thomas Jefferson University, Philadelphia, PA (US); University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/307,066

(22) Filed: May 4, 2021

(65) Prior Publication Data
US 2022/0072697 A1 Mar. 10, 2022

Related U.S. Application Data

(63) Continuation of application No. 16/091,005, filed as application No. PCT/US2017/025623 on Mar. 31, 2017, now Pat. No. 11,041,170.
(Continued)

(51) Int. Cl.
| | | |
|---|---|---|
| *A61K 39/205* | (2006.01) | |
| *A61K 39/12* | (2006.01) | |
| *A61K 39/215* | (2006.01) | |
| *B25H 3/00* | (2006.01) | |
| *C12N 15/86* | (2006.01) | |
| *A61K 39/00* | (2006.01) | |

(52) U.S. Cl.
CPC ............ *B25H 3/003* (2013.01); *A61K 39/12* (2013.01); *A61K 39/205* (2013.01); *A61K 39/215* (2013.01); *C12N 15/86* (2013.01); *A61K 2039/5254* (2013.01); *A61K 2039/5256* (2013.01); *C12N 2760/20034* (2013.01); *C12N 2760/20043* (2013.01); *C12N 2760/20134* (2013.01); *C12N 2760/20143* (2013.01); *C12N 2770/20022* (2013.01); *C12N 2770/20034* (2013.01)

(58) Field of Classification Search
CPC ............ A61K 2039/5254; A61K 39/12; A61K 39/215; A61K 2039/5256; A61K 39/205; C12N 2760/20043; C12N 2760/20143; C12N 2760/20111; C12N 2760/00; C12N 2760/20011; C12N 15/86; C12N 2760/20034; C12N 2760/20134; C12N 2770/20034; C12N 2770/20022; C12N 2770/20011; C12N 2760/20041; C12N 2760/20141; C12N 2760/20161; C12N 2760/20171; C12N 2770/20031; C12N 2770/20071

See application file for complete search history.

(56) References Cited

U.S. PATENT DOCUMENTS

| | | | |
|---|---|---|---|
| 11,041,170 B2 * | 6/2021 | Johnson | ............... A61K 39/205 |
| 11,478,543 B1 * | 10/2022 | Schnell | ................... C12N 7/00 |
| 2011/0064764 A1 | 3/2011 | Faber | |

FOREIGN PATENT DOCUMENTS

| | | |
|---|---|---|
| WO | 02089728 A2 | 11/2002 |
| WO | 2002089728 | 11/2002 |

(Continued)

OTHER PUBLICATIONS

Schwegmann-Wessels C, Ren X, Herrler G. 2006. Intracellular transport of the S proteins of coronaviruses. Adv Exp Med Biol 581:271-275.

(Continued)

*Primary Examiner* — Bao Q Li
(74) *Attorney, Agent, or Firm* — Riverside Law LLP

(57) ABSTRACT

The present disclosure provides methods and compositions for inducing an immune response that confers dual protection against infections by either or both of a rabies virus and a coronavirus, and/or which can be used therapeutically for an existing infection with rabies virus and/or a coronavirus to treat at least one symptom thereof and/or to neutralize or clear the infecting agents. In particular, the present disclosure provides a recombinant rabies virus vector comprising a nucleotide sequence encoding at least one coronavirus immunogenic glycoprotein fragment, as well as pharmaceutical compositions comprising the vaccine vectors.

24 Claims, 11 Drawing Sheets

Specification includes a Sequence Listing.

Related U.S. Application Data

(60) Provisional application No. 62/318,087, filed on Apr. 4, 2016.

(56) References Cited

FOREIGN PATENT DOCUMENTS

| WO | 2012106490 A1 | 8/2012 |
|---|---|---|
| WO | 2014055289 A1 | 4/2014 |

OTHER PUBLICATIONS

Siler C A, McGettigan J P, Dietzschold B, Herrine S K, Dubuisson J, Pomerantz R J, Schnell M J. 2002. Live and killed rhabdovirus-based vectors as potential hepatitis C vaccines. Virology 292:24-34.
Smith M E, Koser M, Xiao S, Siler C, McGettigan J P, Calkins C, Pomerantz R J, Dietzschold B, Schnell M J. 2006. Rabies virus glycoprotein as a carrier for anthrax protective antigen. Virology 353:344-356.
Volz A, Kupke A, Song F, Jany S, Fux R, Shams-Eldin H, Schmidt J, Becker C, Eickmann M, Becker S, Sutter G. 2015. Protective Efficacy of Recombinant Modified Vaccinia Virus Ankara Delivering Middle East Respiratory Syndrome Coronavirus Spike Glycoprotein. J Virol 89:8651-8656.
Wang L, Shi W, Joyce M G, Modjarrad K, Zhang Y, Leung K, Lees C R, Zhou T, Yassine H M, Kanekiyo M, Yang Z Y, Chen X, Becker M M, Freeman M, Vogel L, Johnson J C, Olinger G, Todd J P, Bagci U, Solomon J, Mollura D J, Hensley L, Jahrling P, Denison M R, Rao S S, Subbarao K, Kwong P D, Mascola J R, Kong W P, Graham BS. 2015. Evaluation of candidate vaccine approaches for MERS-COV. Nat Commun 6:7712. 11 pages.
WHO. 2015. Rabies, Fact Sheet #99. 5 pages.
Willet M, Kurup D, Papaneri A, Wirblich C, Hooper J W, Kwilas S A, Keshwara R, Hudacek A, Beilfuss S, Rudolph G, Pommerening E, Vos A, Neubert A, Jahrling P, Blaney J E, Johnson R F, Schnell M J. 2015. Preclinical Development of Inactivated Rabies Virus-Based Polyvalent Vaccine Against Rabies and Filoviruses. J Infect Dis doi:10.1093/infdis/jiv251. 11 pages.
Winter C, Schwegmann-Wessels C, Neumann U, Herrler G. 2008. The spike protein of infectious bronchitis virus is retained intracellularly by a tyrosine motif. J Virol 82:2765-2771.
Wirblich Christoph et al, "One-Health: a Safe, Efficient, Dual-Use Vaccine for Humans and Animals against Middle East Respiratory Syndrome Coronavirus and Rabies Virus", BIOSIS, Biosciences Information Service, Philadelphia, PA, US, (Jan. 2017), Database accession No. PREV201700240013, XP009194667.
Yang Y, Deng Y, Wen B, Wang H, Meng X, Lan J, Gao G F, Tan W. 2014. The amino acids 736-761 of the MERS-CoV spike protein induce neutralizing antibodies: implications for the development of vaccines and antiviral agents. Viral Immunol 27:543-550.
Zaki A M, van Boheemen S, Bestebroer T M, Osterhaus A D, Fouchier R A. 2012. Isolation of a novel coronavirus from a man with pneumonia in Saudi Arabia. N Engl J Med 367:1814-1820.
Zhang N, Channappanavar R, Ma C, Wang L, Tang J, Garron T, Tao X, Tasneem S, Lu L, Tseng C T, Zhou Y, Perlman S, Jiang S, Du L. 2015. Identification of an ideal adjuvant for receptor-binding domain-based subunit vaccines against Middle East respiratory syndrome coronavirus. Cell Mol Immunol doi:10.1038/cmi.2015.03. 11 pages.
Zhao J, Li K, Wohlford-Lenane C, Agnihothram S S, Fett C, Gale M J, Jr., Baric R S, Enjuanes L, Gallagher T, McCray P B, Jr., Perlman S. 2014. Rapid generation of a mouse model for Middle East respiratory syndrome. Proceedings of the National Academy of Sciences of the United States of America 111:4970-4975.
Zhu X, Liu Q, Du L, Lu L, Jiang S. 2013. Receptor-binding domain as a target for developing SARS vaccines. J Thorac Dis 5 Suppl 2:S142-148.
Anna H. Malczyk et al, "A Highly Immunogenic and Protective Middle East Respiratory Syndrome Coronavirus Vaccine Based on a Recombinant Measles Virus Vaccine Platform Abstract", Journal of Virology., US, (Sep. 9, 2015), vol. 89, No. 22, doi:10.1128/JVI.01815-15, ISSN 0022-538X, pp. 11654-11667, XP055257597.
Anonymous. 2013. WHO Statement on the third meeting of the IHR Emergency committee concerning Middle East respiratory syndrome coronavirus (MERS-CoV). Wkly Epidemiol Rec 88:435-436.
Azhar E I, El-Kafrawy S A, Farraj S A, Hassan A M, Al-Saeed M S, Hashem A M, Madani T A. 2014. Evidence for camel-to-human transmission of MERS coronavirus. N Engl J Med 370:2499-2505.
Blaney J E, Marzi A, Willet M, Papaneri A B, Wirblich C, Feldmann F, Holbrook M, Jahrling P, Feldmann H, Schnell M J. 2013. Antibody quality and protection from lethal Ebola virus challenge in nonhuman primates immunized with rabies virus based bivalent vaccine. PLoS Pathog 9:e1003389.13 pages.
Blaney J E, Wirblich C, Papaneri A B, Johnson R F, Myers C J, Juelich T L, Holbrook M R, Freiberg A N, Bernbaum J G, Jahrling P B, Paragas J, Schnell M J. 2011. Inactivated or live-attenuated bivalent vaccines that confer protection against rabies and Ebola viruses. J Virol 85:10605-10616.
Cauchemez S, Van Kerkhove M D, Riley S, Donnelly C A, Fraser C, Ferguson N M. 2013. Transmission scenarios for Middle East Respiratory Syndrome Coronavirus (MERS-CoV) and how to tell them apart. Euro Surveill 18. 13 pages.
Chan PK, Ma S, Ngai S M. 2011. Identification of T-cell epitopes of SARS-coronavirus for development of peptide-based vaccines and cellular immunity assessment methods. Hong Kong Med J 17 Suppl 6:26-30.
Cliquet F, Aubert M. 2004. Elimination of terrestrial rabies in Western European countries. Dev Biol (Basel) 119:185-204. abstract.
Coleman C M, Frieman M B. 2015. Growth and Quantification of MERS-CoV Infection. Current protocols in microbiology 37:15E 12 11-19.
Coleman C M, Liu Y V, Mu H, Taylor J K, Massare M, Flyer D C, Glenn G M, Smith G E, Frieman M B. 2014. Purified coronavirus spike protein nanoparticles induce coronavirus neutralizing antibodies in mice. Vaccine 32:3169-3174.
Coleman C M, Matthews K L, Goicochea L, Frieman M B. 2013. Wild type and innate immune deficient mice are not susceptible to the Middle East Respiratory Syndrome Coronavirus. J Gen Virol doi: 10.1099/vir.0.060640-0. 5 pages.
Conzelmann K K, Cox J H, Schneider L G, Thiel H J. 1990. Molecular cloning and complete nucleotide sequence of the attenuated rabies virus SAD B19. Virology 175:485-499.
Drosten C, Kellam P, Memish Z A. 2014. Evidence for camel-to-human transmission of MERS coronavirus. N Engl J Med 371:1359-1360.
Du L, Jiang S. 2015. Middle East respiratory syndrome: current status and future prospects for vaccine development. Expert Opin Biol Ther 15:1647-1651.
Du L, Zhao G, Kou Z, Ma C, Sun S, Poon VK, Lu L, Wang L, Debnath A K, Zheng B J, Zhou Y, Jiang S. 2013. Identification of a receptor-binding domain in the S protein of the novel human coronavirus Middle East respiratory syndrome coronavirus as an essential target for vaccine development. J Virol 87:9939-9942.
Foley et al. PNAS, 2000, vol. 97 (26), pp. 14680-14685.
Fukushi S, Mizutani T, Saijo M, Matsuyama S, Miyajima N, Taguchi F, Itamura S, Kurane I, Morikawa S. 2005. Vesicular stomatitis virus pseudotyped with severe acute respiratory syndrome coronavirus spike protein. J Gen Virol 86:2269-2274.
Guo X, Deng Y, Chen H, Lan J, Wang W, Zou X, Hung T, Lu Z, Tan W. 2015. Systemic and mucosal immunity in mice elicited by a single immunization with human adenovirus type 5 or 41 vector-based vaccines carrying the spike protein of Middle East respiratory syndrome coronavirus. Immunology 145:476-484.
Hudacek A W, Al-Saleem F H, Willet M, Eisemann T, Mattis J A, Simpson L L, Schnell M J. 2014. Recombinant rabies virus particles presenting botulinum neurotoxin antigens elicit a protective humoral response in vivo. Molecular Therapy-Methods & Clinical Development 1. 9 pages.
Huttner A, Dayer J A, Yerly S, Combescure C, Auderset F, Desmeules J, Eickmann M, Finckh A, Goncalves A R, Hooper J W, Kaya G, Krahling V, Kwilas S, Lemaitre B, Matthey A, Silvera P, Becker S, Fast P E, Moorthy V, Kieny M P, Kaiser L, Siegrist C A, Consortium

(56) References Cited

OTHER PUBLICATIONS

VS-E. 2015. The effect of dose on the safety and immunogenicity of the VSV Ebola candidate vaccine: a randomised double-blind, placebo-controlled phase 1/2 trial. Lancet Infect Dis 15:1156-1166.
International Preliminary Report on Patentability for App. No. PCT/US2017/025623, dated Oct. 9, 2018, 13 pages.
International Search Report and Written Opinion for PCT Application No. PCT/2017/025623, dated Aug. 8, 2018.
J. P. McGettigan et al., "Second-Generation Rabies Virus-Based Vaccine Vectors Expressing Human Immunodeficiency Virus Type 1 Gag Have Greatly Reduced Pathogenicity but Are Highly Immunogenic", Journal of Virology, (Jan. 1, 2003), vol. 77, No. 1, doi:10.1128/JVI.77.1.237-244.2003, ISSN 0022-538X, pp. 237-244, XP055028019.
Kawase et al. Journal of Virology, 2019, vol. 93, Issue 19, pp. 00785-19.
Khan A, Farooqui A, Guan Y, Kelvin D J. 2015. Lessons to learn from MERS-CoV outbreak in South Korea. J Infect Dev Ctries 9:543-546.
Kim E, Okada K, Kenniston T, Raj V S, AlHajri M M, Farag E A, AlHajri F, Osterhaus A D, Haagmans B L, Gambotto A. 2014 Immunogenicity of an adenoviral-based Middle East Respiratory Syndrome coronavirus vaccine in BALB/c mice. Vaccine 32:5975-5982.
Kurup D, Wirblich C, Feldmann H, Marzi A, Schnell M J. 2014. Rhabdoviral-Based Vaccine Platforms against Henipaviruses. J Virol doi:10.1128/JVI.0.2308-14. 11 pages.
Lontok E, Corse E, Machamer C E. 2004. Intracellular targeting signals contribute to localization of coronavirus spike proteins near the virus assembly site. J Virol 78:5913-5922.
M. Faber: "A single immunization with a rhabdovirus-based vector expressing severe acute respiratory syndrome ronavirus (SARS-CoV)S protein results in the production of high levels of SARS-CoV-neutralizing antibodies", Journal of General Virology., vol. 86, No. 5, May 1, 2005 (May 1, 2005), pp. 1435-1440, XP055380471, GB SSNI: 0022-1317, DOL 10.1099/vir.0.80844-0.
Ma C, Li Y, Wang L, Zhao G, Tao X, Tseng C T, Zhou Y, Du L, Jiang S. 2014. Intranasal vaccination with recombinant receptor-binding domain of MERS-CoV spike protein induces much stronger local mucosal immune responses than subcutaneous immunization: Implication for designing novel mucosal MERS vaccines. Vaccine 32:2100-2108.
Ma C, Wang L, Tao X, Zhang N, Yang Y, Tseng C T, Li F, Zhou Y, Jiang S, Du L. 2014. Searching for an ideal vaccine candidate among different MERS coronavirus receptor-binding fragments—the importance of immunofocusing in subunit vaccine design. Vaccine 32:6170-6176.
Madani T A, Azhar E I, Hashem A M. 2014. Evidence for camel-to-human transmission of MERS coronavirus. N Engl J Med 371:1360.
McGettigan J P, Naper K, Orenstein J, Koser M, McKenna P M, Schnell M J. 2003. Functional human immunodeficiency virus type 1 (HIV-1) Gag-Pol or HIV-1 Gag-Pol and env expressed from a single rhabdovirus-based vaccine vector genome. J Virol 77:10889-10899.
McKenna P M, Pomerantz R J, Dietzschold B, McGettigan J P, Schnell M J. 2003. Covalently linked human immunodeficiency virus type 1 gp120/gp41 is stably anchored in rhabdovirus particles and exposes critical neutralizing epitopes. J Virol 77:12782-12794.
Memish Z A, Zumla A I, Assiri A. 2013. Middle East respiratory syndrome coronavirus infections in health care workers. N Engl J Med 369:884-886.

Milne-Price S, Miazgowicz K L, Munster V J. 2014. The emergence of the Middle East respiratory syndrome coronavirus. Pathog Dis 71:121-136.
Mou H, Raj V S, van Kuppeveld F J, Rottier P J, Haagmans B L, Bosch B J. 2013. The receptor binding domain of the new Middle East respiratory syndrome coronavirus maps to a 231-residue region in the spike protein that efficiently elicits neutralizing antibodies. J Virol 87:9379-9383.
Munster, Pneumonia from Human Coronavirus in a Macaque Model. N Engl J Med, 2012, 368.1560-1562. http://www.nejm.org/doi/abs/10.1056/NEJMc1215691.
Muthumani K, Falzarano D, Reuschel E L, Tingey C, Flingai S, Villarreal D O, Wise M, Patel A, Izmirly A, Aljuaid A, Seliga A M, Soule G, Morrow M, Kraynyak K A, Khan A S, Scott D P, Feldmann F, LaCasse R, Meade-White K, Okumura A, Ugen K E, Sardesai N Y, Kim J J, Kobinger G, Feldmann H, Weiner D B. 2015. A synthetic consensus anti-spike protein DNA vaccine induces protective immunity against Middle East respiratory syndrome coronavirus in non-human primates. Sci Transl Med 7:301ra132. 29 pages.
Papaneri A B, Wirblich C, Cann J A, Cooper K, Jahrling P B, Schnell M J, Blaney J E. 2012. A replication-deficient rabies virus vaccine expressing Ebola virus glycoprotein is highly attenuated for neurovirulence. Virology 434:18-26.
Papaneri A B, Wirblich C, Cooper K, Jahrling P B, Schnell M J, Blaney J E. 2012. Further characterization of the immune response in mice to inactivated and live rabies vaccines expressing Ebola virus glycoprotein. Vaccine 30:6136-6141.
Papaneri A B, Wirblich C, Marissen W E, Schnell M J. 2013. Alanine scanning of the rabies virus glycoprotein antigenic site III using recombinant rabies virus: implication for post-exposure treatment. Vaccine 31:5897-5902.
Park H Y, Lee E J, Ryu Y W, Kim Y, Kim H, Lee H, Yi S J. 2015. Epidemiological investigation of MERS-CoV spread in a single hospital in South Korea, May to Jun. 2015. Euro Surveill 20:1-6.
Pascal K E, Coleman C M, Mujica A O, Kamat V, Badithe A, Fairhurst J, Hunt C, Strein J, Berrebi A, Sisk J M, Matthews KL, Babb R, Chen G, Lai KM, Huang T T, Olson W, Yancopoulos G D, Stahl N, Frieman M B, Kyratsous C A. 2015. Pre-and postexposure efficacy of fully human antibodies against Spike protein in a novel humanized mouse model of MERS-CoV infection. Proceedings of the National Academy of Sciences of the United States of America 112:8738-8743.
Petersen E, Pollack M M, Madoff L C. 2014. Health-care associate transmission of Middle East Respiratory Syndrome Corona virus, MERS-CoV, in the Kingdom of Saudi Arabia. Int J Infect Dis 29:299-300.
Pfaller C K, Cattaneo R, Schnell M J. 2015. Reverse genetics of Mononegavirales: How they work, new vaccines, and new cancer therapeutics. Virology (60 year edition), accepted. 34 pages.
Roper R L, Rehm K E. 2009. SARS vaccines: where are we? Expert Rev Vaccines 8:887-898.
Schnell M J, Foley H D, Siler C A, McGettigan J P, Dietzschold B, Pomerantz R J. 2000. Recombinant rabies virus as potential live-viral vaccines for HIV-1. Proc Natl Acad Sci U S A 97:3544-3549.
Schwegmann-Wessels C, Al-Falah M, Escors D, Wang Z, Zimmer G, Deng H, Enjuanes L, Naim H Y, Herrler G. 2004. A novel sorting signal for intracellular localization is present in the S protein of a porcine coronavirus but absent from severe acute respiratory syndrome-associated coronavirus. J Biol Chem 279:43661-43666.
Schwegmann-Wessels C, Glende J, Ren X, Qu X, Deng H, Enjuanes L, Herrler G. 2009. Comparison of vesicular stomatitis virus pseudotyped with the S proteins from a porcine and a human coronavirus. J Gen Virol 90:1724-1729.

\* cited by examiner

FIG. 1

BNSP333: [BsiWI [MERS-S-constructs] NheI] E333 — N | P | M | G | L

BNSP333-S: SP | S1 [RBD] | FP | S2 [HR1 | HR2 | TMCD]
22 ... 1353

BNSP333-SΔ29:
22 ... 1334

BNSP333-SΔ19:
22 ... 1324

BNSP333-S1: SP | S1 [RBD] | RABV-G [E3 TMCD]
22 ... 750

FIG. 2A.

BNSP333-S

α-RABV G    α-MERS CoV S1

FIG. 2B.

BNSP333-GP

α-RABV G     α-MERS CoV S1

FIG. 2C.

BNSP333-SΔ19

α-RABV G     α-MERS CoV S1

FIG. 2D.

BNSP333-SΔ29

α-RABV G     α-MERS CoV S1

FIG. 2E.

BNSP333-S1

α-RABV G     α-MERS CoV S1

MULTIVALENT VACCINES FOR RABIES VIRUS AND CORONAVIRUSES

CROSS-REFERENCE TO RELATED APPLICATIONS

This application is a continuation application of U.S. patent application Ser. No. 16/091,005, filed on Oct. 3, 2018, which is the national phase application filed under 35 U.S.C. § 371 claiming benefit to International Patent Application No. PCT/US2017/025623, filed on Mar. 31, 2017, which is entitled to priority to U.S. Provisional Patent Application No. 62/318,087, filed on Apr. 4, 2016, each of which is incorporated by reference in its entirety.

GOVERNMENT FUNDING

Research supporting this application was carried out by the United States of America as represented by the Secretary, Department of Health and Human Services.

INCORPORATION BY REFERENCE

The present application hereby incorporates by reference the entire contents of the text file named "205961-0033-01US_Sequence_Listing.txt" in ASCII format. The text file containing the Sequence Listing of the present application was created on Nov. 12, 2021 and is 257,192 bytes in size.

BACKGROUND OF THE INVENTION

1. Field of the Invention

The present disclosure relates generally to the field of vaccines and to methods and compositions for treating and/or immunizing against viral infections. In particular, the present disclosure relates to multivalent vaccines as a single therapeutic or immunization agent against infections with one or both of a rabies virus and/or a Coronavirus, such as Middle East Respiratory Syndrome Coronavirus (MERS-CoV).

2. Background

Coronaviridae is a family of viruses (e.g., MERS-CoV and Severe Acute Respiratory Syndrome (SARS-CoV)) that primarily infect the upper respiratory and gastrointestinal tracts of mammals and birds, and that are responsible for acute and chronic diseases of the respiratory, hepatic, gastrointestinal and neurological systems. Coronaviruses are enveloped positive-sense, single-stranded RNA viruses with a nucleocapsid of helical symmetry and virions with a crown-like appearance. The genomes of coronaviruses range from about 26 to about 32 kilobases.

The virions of each coronavirus are approximately 100 nm with a crown-like appearance because of the club-shaped spike (S) proteins projecting from the surface of the envelope. The spike protein is the viral membrane protein that is responsible for cell entry and includes an S1 domain, which is responsible for binding the cell surface receptor, and an S2 domain, which is a membrane-anchored subunit.

Upon entering an infected cell, coronaviruses transcribe their RNA and the viruses replicate in the cytoplasm of the infected cell. Replication is mediated by the synthesis of an antisense RNA strand, which is provided as a template for additional viral genomes and transcription. The viruses then assemble and released from the infected cell.

The MERS-CoV is a recently emerged highly pathogenic human coronavirus. Since its identification in 2012, MERS-CoV has caused over 1700 infections with a case fatality rate of approximately 35%. According to epidemiological and sequencing evidence, MERS-CoV is a zoonotic virus that transmits to humans via the Egyptian Tomb Bat and one-humped camels. A short piece of the MERS-CoV genome was found in an Egyptian Tomb bat sample while several studies have found infectious MERS-CoV, MERS-CoV RNA, and anti-MERS-CoV antibodies in camels in the Middle East and Africa. The spread of MERS-CoV from animal reservoir-to-human has been epidemiologically linked, and human-to-human spread has been observed in hospital settings in the Middle East and South Korea. The exact mechanism of zoonotic or human-to-human transmission has yet to be established, however it is presumed to be transmitted by respiratory secretions or small respiratory droplets.

The approximately 30 kilobase single-strand, positive sense RNA genome of MERS-CoV encodes 10 proteins: two replicase proteins, three structural proteins (E, N, and M), a surface (spike) glycoprotein (S), and five nonstructural proteins.

The human disease that follows MERS-CoV infection is also poorly understood. The most severe MERS patients present with fever, lower respiratory tract symptoms, malaise, and often pneumonia. Chest X-rays and CT scans provide evidence of severe lung inflammation that leads to reduced lung function and death in approximately 35% of cases.

Research has focused on developing MERS-CoV countermeasures, and several groups have identified drugs, vaccines, antibodies, and other therapeutics that are effective in vitro and in small animal models. In related work, researchers have also developed various vaccine platforms that are effective in small animal models for another human pathogenic coronavirus: SARS-CoV. Recently, researchers have developed several promising approaches for a MERS-CoV vaccine; however, no vaccines have entered clinical trials or are approved for use in humans or other animals.

Most vaccine design has focused on the major immunodominant antigen, the Spike (S) protein located on the surface of the virion, which serves as the ligand for the MERS-CoV receptor dipeptidyl peptidase 4 (DPP4, also known as CD26). MERS-CoV S is a transmembrane glycoprotein that is cleaved into S1 and S2 domains. Virus neutralizing antibodies (VNA), which are produced in response to infection or vaccination with MERS-CoV S, neutralize virus infection in vitro and protect lungs from infection in mouse models of disease. Vaccine approaches have utilized MERS-CoV S protein either as full-length S protein or as recombinant S protein from *E. coli* or insect cells formulated as nanoparticles. Other platforms have used plasmid-based expression or expressed spike variants in viral vectors, like the modified vaccine virus Ankara (MVA) or adenoviruses-expressing MERS-CoV S. Each of these different MERS-CoV vaccine approaches comes with individual strengths and weaknesses, such as ease of production, immunogenicity, potential adverse effects, and residual pathogenicity. These factors must be balanced in order to create a vaccine that is ultimately feasible for use in animals or humans.

For example, several different vaccines against MERS-CoV are currently in development, but none of them are available for use. As for all vaccines, major considerations for their use include cost, safety, and immunogenicity. Viral vectors have been shown to be highly effective, but safety concerns do exist. For instance, although different adenoviruses expressing MERS-CoV S or S1 have been found immunogenic in mice, concerns include pre-existing immunity and the longevity of the induced immune responses, at least for such vectors like Ad5. Pre-existing immunity is not a major concern for MVA-based vectors, which are replication-deficient in humans, but they may not be effective without multiple inoculations. DNA vaccines or recombinant MERS-CoV S protein-based vaccines are the safest for immunocompromised individuals. DNA vaccines, however, require relatively large amounts of DNA (e.g. 0.5-2 mg) and multiple inoculations in order to induce potent immune responses in mice and rhesus macaques. Other approaches with recombinant S protein or subunit thereof have also been successfully studied as MERS-CoV vaccines. Lastly, DNA vaccination followed by boosting with recombinant protein is protective in rhesus macaques. Whereas all of these approaches have shown encouraging results, it remains to be seen whether they translate to a human MERS-CoV vaccine.

As such, there is a need for the development of additional vaccine candidates for treating or immunizing against coronaviruses, e.g. MERS-CoV. A Rhabdovirus-based vaccine possesses a balance of factors that could prove effective for a MERS-CoV vaccine. Rhabdovirus-vectored vaccines based on rabies virus (RABV) and vesicular stomatitis virus (VSV) have been studied for several human pathogens. More recently both RABV and VSV have been successfully utilized as Ebola virus vaccines (EBOV) and both approaches are either close to clinical trials (RABV) or have already entered phase 2 clinical trials (VSV). Whereas the VSV-based vaccines are mostly based on live, replication-competent VSV expressing the foreign protein of interest, the RABV vaccine platform is based on live and highly attenuated RABV vaccine strains or inactivated RABV virions carrying foreign proteins incorporated into the viral envelope. Live-attenuated and inactivated RABV-EBOV have been utilized successfully against EBOV. In particular, vaccines based on inactivated RABV are widely used and safe for humans whereas vaccines based on either infectious or inactivated RABV are shown to be safe for animals. As dual vaccines, RABV-based vectors induce neutralizing antibodies against both the rabies virus and the target pathogen. The live RABV vaccine is widely used in wildlife animals and has successfully eliminated rabies in Western Europe. Meanwhile, about 15 million doses of inactivated RABV vaccines are used successfully in humans every year.

SUMMARY

The present disclosure relates to novel recombinant vaccine constructs that are based on genetically modifying a rabies virus vaccine vector to express one or more coronavirus immunogenic polypeptides, e.g., an MERS-CoV or SARS-CoV glycoprotein (e.g., spike (S) glycoprotein), such that humoral and/or cellular immune responses are induced against infection by a rabies virus and/or a coronavirus upon administering a recombinant vaccine construct of the disclosure or a recombinant virion based thereon. Preferably, the rabies virus vaccine vector is attenuated to remove or mitigate its capacity for neurological damage to a safe level. The disclosure also provides compositions and methods for immunizing against or treating infections by either or both a rabies virus and a coronavirus, e.g., MERS-CoV or SARS-CoV. The recombinant vaccine constructs of the disclosure may be referred to as "bivalent" or "multivalent" because they are as a single construct capable of simultaneous induction of an immune response against two or more viral pathogens, e.g., rabies virus and MERS-CoV. The vaccine constructs of the disclosure may be used prophylactically, i.e., to induce a humoral and/or cellular immune response as protection against a subsequent infection or challenge by either or both a rabies virus and/or a coronavirus, or used therapeutically, i.e., to induce a humoral and/or cellular immune response to aid in neutralizing or clearing a preexisting infection by either or both a rabies virus and a coronavirus.

Thus, the present disclosure relates to methods and compositions for use in inducing an immune response that confers dual protection against infections by either or both of a rabies virus and a coronavirus, and/or which can be used therapeutically for an existing infection with rabies virus and/or a coronavirus to treat at least one symptom thereof and/or to neutralize or clear the infecting agents.

Thus, in one aspect, the present disclosure provides a recombinant rabies virus vector comprising a nucleotide sequence encoding at least one immunogenic glycoprotein or fragment thereof of at least one coronavirus. Each immunogenic glycoprotein or fragment thereof can contain a truncation of a coronavirus glycoprotein, e.g. a c-terminal truncation of a spike protein, or a chimeric protein comprising an S1 domain of a spike protein and a membrane anchor. In an embodiment, the c-terminal truncation of a spike protein includes an S1 domain of the spike protein. In an additional embodiment, a range of about 15 to about 35 amino acids are removed in the c-terminal truncation (e.g., about 16 amino acids to about 23 amino acids, about 17 to about 21 amino acids, about 25 to about 33 amino acids, about 27 to about 31 amino acids, about 19 amino acids, or about 29 amino acids). The membrane anchor can be from a virus other than a coronavirus, e.g., RABV. In a particular embodiment, the membrane anchor is derived from the RABV glycoprotein (G), e.g. the membrane anchor can include a portion of at least one of an ectodomain, a transmembrane domain, and a cytoplasmic domain of the RABV glycoprotein.

In a particular aspect, the present disclosure provides a recombinant rabies virus vector comprising a nucleotide sequence encoding at least one immunogenic glycoprotein or fragment thereof of at least one coronavirus and/or a chimeric protein comprising at least one immunogenic glycoprotein or fragment thereof of at least one coronavirus.

In yet another aspect, the present disclosure provides a multivalent vaccine that is effective to protect against infection with one or both a rabies virus and a coronavirus, comprising a recombinant rabies virus vector that expresses at least one immunogenic glycoprotein or fragment thereof of at least one coronavirus.

In still another aspect, the present disclosure provides a vaccine composition that comprises at least one multivalent vaccine that is effective to protect against infection with one or both a rabies virus and a coronavirus, comprising a recombinant rabies virus vector that expresses at least one immunogenic glycoprotein or fragment thereof of at least one coronavirus. In an embodiment, the vaccine composition further comprises a pharmaceutically acceptable carrier.

In another aspect still, the present disclosure provides a method of inducing an immune response protective against an infection by one or both of a coronavirus and a rabies virus in a subject, comprising administering to the subject a therapeutically effective amount of a multivalent vaccine comprising a recombinant rabies virus vaccine vector that expresses at least one immunogenic glycoprotein or fragment thereof of at least one coronavirus.

In a further aspect, the disclosure provides a method of inducing neutralizing antibodies against a coronavirus and/or a rabies virus in a subject infected with or having been exposed to either or both of said viruses, comprising administering to the subject a therapeutically effective amount of a multivalent vaccine comprising a recombinant rabies virus vaccine vector that expresses at least one immunogenic protein or fragment thereof derived from at least one coronavirus glycoprotein.

In yet a further aspect, the disclosure involves a method of treating a subject infected with a coronavirus and/or a rabies virus, comprising administering to the subject a therapeutically effective amount of a multivalent vaccine comprising a recombinant rabies virus vaccine vector that expresses at least one coronavirus glycoprotein immunogenic protein or fragment thereof, wherein said vaccine induces an effective immune response against one or both of said viruses.

In certain embodiments, the coronavirus immunogenic glycoprotein or fragment thereof encoded by the recombinant rabies vaccine vector used in the different aspects of the present disclosure is a MERS-CoV glycoprotein. The MERS-CoV immunogenic glycoprotein or fragment thereof, in various embodiments and aspects herein, can be a polypeptide comprising the amino acid sequence of SEQ ID NO: 8, 12 or 14.

In certain other embodiments, the coronavirus immunogenic glycoprotein or fragment thereof encoded by the recombinant rabies vaccine vector used in the different aspects of the disclosure is a SARS-CoV glycoprotein.

In certain other embodiments, the recombinant rabies virus vector used in the various aspects of the disclosure further expresses one or more additional coronavirus proteins or immunogenic fragments thereof. In various embodiments, the additional coronavirus proteins can be a protein, or an immunogenic fragment thereof, selected from the group consisting of a coronavirus a replicase polyprotein, E protein, N protein, M protein, or a nonstructural protein, for example, from MERS-CoV or SARS-CoV. In various embodiments, the additional coronavirus proteins are selected from the group consisting of any one of the coronavirus proteins, or an immunogenic fragment thereof. In various other embodiments, the additional coronavirus proteins are selected from the group consisting of any one of the MERS-CoV proteins, or immunogenic fragments thereof.

The disclosure further contemplates that the coronavirus glycoprotein expressed by the recombinant rabies virus vaccine vectors used in the various aspects of the disclosure is expressed as immunogenic fragments. An immunogenic fragment of a coronavirus protein is, for the purposes of this disclosure, any segment of a coronavirus protein this is capable of inducing substantially the same immune response as the full-length counterpart protein. Substantially the same immune response can refer to, for example, where the concentration of antibodies induced against the fragment is about the same, or at least about 75%, or 80%, or 90%, or 95%, or 99% or more of the concentration of antibodies induced against the full length coronavirus protein tested under the same conditions. In a particular embodiment, the coronavirus immunogenic glycoprotein fragment includes the S1 domain of the spike protein.

The disclosure further contemplates that any additional coronavirus protein expressed by the recombinant rabies virus vaccine vectors used in the various aspects of the disclosure can be expressed as immunogenic fragments. An immunogenic fragment of a coronavirus protein is, for the purposes of this disclosure, any segment of a coronavirus protein this is capable of inducing substantially the same immune response as the full-length counterpart protein. Substantially the same immune response can refer to, for example, where the concentration of antibodies induced against the fragment is about the same, or at least about 75%, or 80%, or 90%, or 95%, or 99% or more of the concentration of antibodies induced against the full length coronavirus protein tested under the same conditions.

In other embodiments, the recombinant rabies virus vaccine is attenuated, such that its neurovirulence properties have been eliminated or substantially mitigated such that neurological damage typical of the rabies virus is substantially avoided.

In certain embodiments, the recombinant rabies virus vaccine is the live attenuated "SAD B19 RABV" vaccine, which was attenuated by tissue culture passage and has been used as a live oral vaccine for wildlife in Europe for many years.

In certain other embodiments, the recombinant rabies virus vaccine is derived from SAD B19 RABV by introducing additional genetic changes that result in further attenuation of the virus. For the purpose of the disclosure, the term "derived" refers to a modified nucleic acid molecule (e.g., vaccine vector) relative to a wildtype or other source molecule into which the changes are introduced, where the changes include genetic changes and/or chemical changes, including single nucleotide substitutions (point mutations), deletions, insertions, inversions, multiple point mutations, and chemical changes such as DNA methylation or acetylation. In a particular embodiment, the SAD B19 RABV was derived to form "BNSP" by introducing a novel RABV stop-start transcription signal sequence flanked by unique BsiWI and NheI restriction sites between the nucleoprotein (N) and the phosphoprotein (P) genes for introduction of foreign genes (see FIG. 1). In a still further embodiment, the BNSP vector was further derived (and attenuated) by introducing an Arg→Glu change at amino acid 333 of the RABV G protein (see FIG. 1). The 333 mutation has been shown to greatly attenuate neurovirulence of RABV in adult mice.

In certain other embodiments, the disclosure provides host cells that can be transfected with the recombinant rabies virus vaccines of the disclosure for purposes of, including, expressing proteins encoded by the virus vaccines and/or for generating recombinant rabies virions, which can be isolated therefrom and utilized in vaccine compositions in accordance with other aspects and embodiments of the disclosure. Suitable host cells can include any cell susceptible to being transfected or infected in vitro with a rabies virus vaccine, including any human cell lines or animal cell lines.

It is preferred that the rabies vaccine viruses and the production of any virus virions and their use as vaccines be done in accordance with any necessary national and/or international requirements for health and safety with regard to rabies virus and coronavirus, e.g., in accordance with the requirements of the U.S. Center for Disease Control ("CDC") or the World Health Organization ("WHO").

The vaccine compositions of the disclosure, in certain embodiments, can include a pharmaceutically acceptable carrier or excipient, as further described below.

In yet another embodiment of the disclosure, the disclosure provides recombinant rabies virus vaccine vectors of the Examples, which include: (a) BNSP333-GP (a replication-competent, recombinant rabies virus vector vaccine expressing ZEBOV GP of strain Mayinga); (b) BNSP333-S (a replication-competent, recombinant rabies virus vector vaccine expressing the S protein of MERS-CoV); (c)

BNSP333-SΔ29 (a replication-competent, recombinant rabies virus vector vaccine expressing the S protein of MERS-CoV with the 29 c-terminal amino acid truncation); (d) BNSP333-SΔ19 (a replication-competent, recombinant rabies virus vector vaccine expressing the S protein of MERS-CoV with the 29 c-terminal amino acid truncation); (e) BNSP333-S1 (a replication-competent, recombinant rabies virus vector vaccine expressing a chimeric protein comprising the S1 domain of the S glycoprotein of MERS-CoV and the ectodomain domain, transmembrane domain, and cytoplasmic domain of RABV G). Other specific constructs are well within the spirit and scope of the disclosure and these Examples of specific constructs are not meant to limit the disclosure in any manner. It will be appreciated further that, where a replication-defective rabies vaccine vector is used, cell lines which provide the missing/defective functions in trans may be necessary to propagate the viruses and/or to allow preparation of virions. Such in trans functionalities and cell lines are well known in the art and pertain to the use of the rabies vaccine vectors.

The full nucleotide sequences of these four vaccine constructs of the disclosure are as follows: BNSP333-GP; BNSP333-S(SEQ ID NO: 22); BNSP333-SΔ29 (SEQ ID NO: 23); BNSP333-SΔ19 (SEQ ID NO: 24); and BNSP333-S1 (SEQ ID NO: 21), said sequence of which are provided herein.

These and other embodiments are disclosed or are contemplated variations from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 provides a schematic illustration of some MERS-CoV vaccine constructs described and used herein. Spike protein cDNA was inserted between the N and P genes of the SAD-B19-derived rabies virus (RABV) vaccine vector BNSP333, which contains a mutation in the glycoprotein gene that eliminates neurotropism of the parent SAD-B19 strain (SEQ ID NO: 20). BNSP333-S(SEQ ID NO: 22) contains the wild-type coding sequence of the Spike protein of MERS-CoV (SEQ ID NO: 9), thereby producing a wild-type spike protein (SEQ ID NO: 10). The constructs BNSP333-SΔ29 (SEQ ID NO: 23) and BNSP-SΔ19 (SEQ ID NO: 24) include truncated spike protein nucleic acids (SEQ ID NO: 11 and SEQ ID NO: 13, respectively) that are expressed to produce truncated spike proteins, which lacks the C-terminal 29 or 19 amino acids (SEQ ID NO: 12 and SEQ ID NO: 14), respectively. The BNSP333-S1 construct (SEQ ID NO: 21) expresses a chimeric protein that contains the entire S1 domain fused to the C-terminal part of the RABV G glycoprotein (amino acids 428-524) (SEQ ID NO: 8), which encompasses the entire cytoplasmic domain (CD), the transmembrane domain (TM), plus 31 amino acids of the ectodomain (E31) of RABV G. Different structural elements of the spike protein are indicated in the full length construct: signal peptide (SP), receptor-binding domain (RBD), fusion peptide (FP), heptad repeat regions 1 and 2 (HR1 and HR2), transmembrane domain (TM), and cytoplasmic domain (CD). Numbers indicate amino acid positions in the Spike protein.

FIGS. 2A, 2B, 2C, 2D, and 2E provide expression data of the RABV-G and the S1-G fusion proteins in VERO E6 cells. Cells were infected for 60 hours and, following fixation and permeabilization, stained with monoclonal antibody against RABV G (left panel) and polyclonal antiserum against the S1 subunit of the MERS CoV S protein (right panel).

FIGS. 3A, 3B, and 3C provide data for RABV virions where full-length spike protein has been incorporated. BSR and VERO cells were infected with BNSP333-S and either the parent vector BNSP333 or a RABV vector expressing the wild-type SAD-B19 glycoprotein (SPBN) without the attenuating mutation at position 333 of the glycoprotein. Virus particles were purified from the supernatant and resolved by SDS-PAGE followed by staining with SYPRO-Ruby (A) or western blotting with polyclonal antiserum against the S1 subunit (B) or polyclonal antiserum against the RABV glycoprotein (C). Arrows indicate the RABV nucleoprotein (N), glycoprotein (G), and polymerase protein (L). Incorporation of the RABV glycoprotein is dramatically reduced in the presence of the full-length MERS CoV spike protein.

FIGS. 4A, 4B, and 4C demonstrate the effect of C-terminal truncations of the Spike protein on glycoprotein incorporation into RABV particles. VERO cells were infected with BNSP333 expressing full-length S or truncated S lacking the C-terminal 19 or 29 amino acids. The parent vector BNSP333 expressing no additional glycoprotein was used as control. Purified virus particles were analyzed by SDS-PAGE (A) and western blotting with polyclonal antiserum specific for RABV G (C) and the S1 subunit of MERS CoV S (B). Truncations of S lead to increased incorporation of RABV G into particles compared to virus expressing full-length MERS-CoV S. RABV glycoprotein incorporation is still reduced compared to the parent vector expressing no additional glycoprotein. Arrows indicate the RABV nucleoprotein (N), glycoprotein (G) and polymerase protein (L). Numbers to the left indicate the sizes of the molecular weight standard.

FIGS. 6A, 6B, 6C, and 6D demonstrate that the viruses of the present disclosure produce strong immune responses. Analysis of the immune response to BNSP333-S1/G in mice was examined using Balb/c mice that were immunized three times (day 0, 7, and 21) with 10 µg chemically inactivated particles of BNSP333-S1/G (FIGS. 6A and 6B), or BNSP333 expressing ZEBOV GP (FIlorab1) (FIG. 6A) or mock-immunized with PBS (FIG. 6D). All mice immunized with BNSP333-S1/G developed a strong humoral immune response to the S1 subunit. No response above background was detected in the control mice.

DETAILED DESCRIPTION

Figure 3A:
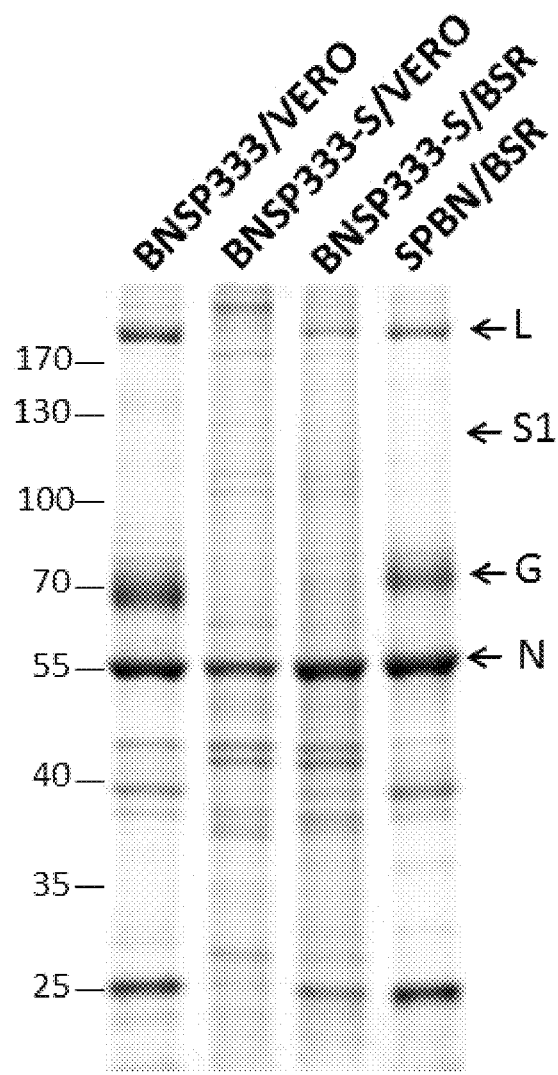

The present disclosure may be understood more readily by reference to the following detailed description of preferred embodiments of the disclosure and the Examples included therein. Before the present methods and techniques are disclosed and described, it is to be understood that the present disclosure is not limited to specific methods and compositions, as such may, of course, vary. It is also to be understood that the terminology used herein is for the purpose of describing particular embodiments only and is not intended to be limiting. Unless defined otherwise, all technical and scientific terms used herein have the meaning commonly understood by one of ordinary skill in the art to which this disclosure belongs.

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The term "patient" or "subject" is used throughout the specification to describe an animal, including human, non-human primates (e.g., ape or monkey) or a wild or domesticated animal, to whom treatment, including prophylactic treatment, with the compositions according to the present disclosure is provided. For treatment of those infections, conditions or disease states which are specific for a specific animal such as a human patient, the term patient refers to that specific animal, including a wild or domesticated animal, such as a camelid (e.g. camels, alpacas, or llamas), a dog, a cat, a mouse, a hamster, or a farm animal such as a horse, cow, sheep, donkey, pig, chicken, etc. In general, in the present disclosure, the term patient refers to a human patient unless otherwise stated or implied from the context of the use of the term.

Furthermore, one of skill in the art will recognize that individual substitutions, deletions or additions in the amino acid sequence, or in the nucleotide sequence encoding for the amino acids, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art. The following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). Other terms are defined or otherwise described herein.

As used herein, the terms "biological sample" or "patient sample" or "test sample" or "sample" as used herein, refer to a sample obtained from an organism or from components (e.g., cells) of a subject or patient for the purpose of diagnosis, prognosis, or evaluation of a subject of interest. The sample can be, for example, blood, which potentially is at risk of containing infection with RABV, or lung tissue, which potentially is at risk of containing infection with MERS-CoV. In certain embodiments, such a sample may be obtained for assessing the presence of antibodies specific for coronavirus or a rabies virus following a suspected infection or following the vaccination using a vaccine construct of the disclosure. The disclosure contemplates the practice of any necessary safety and/or Governmental-imposed procedures for the handling and processing of any sample suspected of containing an infection with a rabies virus or a coronavirus, e.g., MERS-CoV or SARS-CoV.

As used herein, the term "specifically binds to" or is "specific for" in the context of antibody/antigen interactions is intended to mean the specific binding of an antibody to a cognate antigen via specific one or more epitopes recognized by the antibody, without substantially binding to molecules that lack such epitopes.

As used herein, the term "treatment" or "treating" includes any process, action, application, therapy, or the like, wherein a subject (or patient), including a human being, is provided with or administered an agent or composition, e.g., a therapeutic vaccine composition, with the aim of improving the subject's condition, directly or indirectly, or slowing the progression of a condition or disorder in the subject (e.g., fever or shortness of breath due to coronavirus infection), or ameliorating at least one symptom of the disease or disorder under treatment (e.g., cough or diarrhea caused by a coronavirus infection). As used in the context of disease caused by rabies, MERS-CoV or another coronavirus, the terms "treat," "treatment," and the like, refer to relief from or alleviation of a pathological process mediated by said viruses.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy. One therapy can be based on the dual-protective vaccines of the disclosure. A second therapy can be based on a known therapy for the disorder being treated. For example, alternative anti-virus drugs may be co-administered with the vaccine vectors of the disclosure or therapeutic agents to ameliorate symptoms or conditions cause by the infection. The order of administration of two or more sequentially co-administered therapeutic agents is not limited. The administration of the two or more therapeutic agents may also be administered by different routes, e.g., by a local route (e.g., mucosal delivery of a dual vaccine of the disclosure) and a systemic route (e.g., parenteral delivery of an anti-rabies or anti-coronavirus small molecule inhibitor).

The term "effective" is used to describe an amount of a compound, composition or component which, when used within the context of its intended use, effects an intended result. The term effective subsumes all other effective amount or effective concentration terms, which are otherwise described or used in the present application.

As used herein, the phrases "therapeutically effective amount" and "prophylactically effective amount" refer to an amount that provides a therapeutic benefit in the treatment, prevention, or management of pathological processes mediated by an infection with rabies virus, MERS-CoV or another coronavirus, or an overt symptom of pathological processes mediated by rabies or MERS-CoV or another coronavirus. The specific amount that is therapeutically effective can be readily determined by ordinary medical practitioner, and may vary depending on factors known in the art, such as, e.g. the type of pathological processes mediated by virus infection, the patient's history and age, the stage of pathological processes mediated by the virus infection, and the administration of other anti-pathological processes mediated by infection.

As used herein, a "pharmaceutical composition" comprises a pharmacologically effective amount of a vaccine construct and a pharmaceutically acceptable carrier. As used herein, "pharmacologically effective amount," "therapeutically effective amount" or simply "effective amount" refers to that amount of a vaccine effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter. Further, the pharmaceutical composition can be designed to enhance targeting cells involved in the underlying virus infection such as dendritic cells, macrophages, hepatocytes, and other parenchymal cells. As used herein, the term "pharmaceutically acceptable" means that the subject item is appropriate for use in a pharmaceutical product.

As used herein, a "vaccine construct" shall refer to a nucleic acid molecule constituting the recombinant rabies virus vector expressing one or more coronavirus antigens (e.g., MERS-CoV or SARS-CoV glycoprotein or a truncation or fragment thereof) of the disclosure. The disclosure also contemplates the use of recombinant vaccine "virions" which are produced by the vaccine constructs of the disclosure when they are introduced into a host cell susceptible to infection therefrom, and which are then allowed to propagate and form whole virus virions in the cell, which are then obtained and/or purified. A "virion" refers to a complete virus particle resulting from an infection cycle of the recombinant rabies genome in a cell capable of hosting the rabies genome. The "vaccine" or "recombinant vaccines" of the disclosure encompass both "genetic vaccines," i.e., the vaccine constructs of the disclosure, and the traditional vaccines, which are the virions themselves. Depending on the recombinant genome of the vaccine construct, the virions can be replication-competent or replication-deficient. Where they are replication-deficient, their propagation in host cells in vitro or in vivo may require a "helper" virus or cell, in which certain replication functions would be provided in trans by either the helper virus or the cell in which the infection is taking place. Vaccine compositions may also include both vaccine constructs, as well as the virions themselves. The virions also may be of the "killed virus" type, whereby the virion is chemically treated or otherwise deactivated by some means of deactivation such that the virion has no or minimal ability to replication. Killed virus vaccines generally rely on their surface-presented polypeptides (e.g., the coronavirus spike protein or a portion thereof) to induce a humoral-based immune response. Typically, a cellular-based immune response does not occur with the killed-virus type vaccines because these virions do not generally access the interior of cells.

As used herein, the term "isolated" or "purified" polypeptide or protein or virion or biologically-active portion or vaccine construct thereof is substantially free of cellular material or other contaminating proteins from the cell or tissue source from which the polypeptide (e.g., coronavirus glycoprotein protein or truncation/fragment thereof) or virion (e.g., RABV virus expressing a coronavirus glycoprotein protein or a truncation/fragment thereof) is obtained.

As used herein, "pharmaceutically acceptable carrier" includes any material which, when combined with an active ingredient of a composition, allows the ingredient to retain biological activity and without causing disruptive reactions with the subject's immune system. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration are phosphate buffered saline or normal (0.9%) saline. Compositions comprising such carriers are formulated by well-known conventional methods (see, for example, Remington's Pharmaceutical Sciences, Chapter 43, 14th Ed., Mack Publishing Col, Easton Pa. 18042, USA). Pharmaceutically acceptable excipients have been amply described in a variety of publications, including, for example, A. Gennaro (2000) "Remington: The Science and Practice of Pharmacy," 20th edition, Lippincott, Williams, & Wilkins; Remington's Pharmaceutical Sciences, 14th Ed. or latest edition, Mack Publishing Col, Easton Pa. 18042, USA; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc. Further discussion is provided herein.

The present disclosure relates to novel recombinant vaccine constructs that are based on genetically modifying a rabies virus vaccine vector to express one or more coronavirus immunogenic polypeptides, e.g., a MERS-CoV or SARS-CoV glycoprotein (e.g., spike (S) glycoprotein) or a truncation or fragment thereof, such that humoral and/or cellular immune responses are induced against infection by a rabies virus and/or a coronavirus upon administering a recombinant vaccine construct of the disclosure or a recombinant virion based thereon. In an embodiment, the rabies virus vaccine vector is attenuated to remove or mitigate to a safe level its capacity for neurological damage. The disclosure also provides compositions and methods for immunizing against or treating infections by either or both a rabies virus and a coronavirus, e.g., MERS-CoV or SARS-CoV.

Recombinant vaccine constructs of the disclosure are a single construct capable of simultaneously inducing an immune response against two or more viral pathogens, e.g., rabies virus and MERS-CoV, and may therefore be referred to as "bivalent" or "multivalent". The vaccine constructs of the disclosure can be used to induce a humoral and/or cellular immune response to protect against a subsequent infection or challenge by a rabies virus and/or a coronavirus (preventative), or used to induce a humoral and/or cellular immune response to aid in neutralizing or clearing a preexisting infection by a rabies virus and/or a coronavirus (therapeutic).

The methods and compositions of the disclosure may induce an immune response that confers dual protection against infections by a rabies virus and/or at least one coronavirus, and/or which can be used therapeutically for an existing infection with rabies virus and/or a coronavirus to treat at least one symptom thereof and/or to neutralize or clear the infecting agents.

The present disclosure provides for a recombinant rabies virus vector comprising a nucleotide sequence encoding at least one immunogenic glycoprotein or fragment thereof of at least one coronavirus. For example, each of the at least one immunogenic glycoprotein or fragment thereof is independently selected from any clinically relevant coronavirus.

The at least one immunogenic glycoprotein or fragment thereof comprises a truncation of a coronavirus glycoprotein, e.g. a c-terminal truncation of a spike glycoprotein. For example, the c-terminal truncation of a spike glycoprotein can result in a portion of the cytoplasmic domain being removed. In a particular embodiment, the c-terminal truncation of a spike protein results in the removal of at least a portion of an S2 domain of the spike protein, e.g. the entire S2 domain. In another embodiment, the c-terminal truncation of a spike glycoprotein comprises an immunogenic portion of an S1 domain of a spike protein, e.g. the entire S1 domain of the spike glycoprotein. In another embodiment, the at least one immunogenic glycoprotein or fragment thereof includes an about 13 to about 25 amino acids or about 23 to about 35 amino acids c-terminal truncation of the spike glycoprotein. For example, the c-terminal truncation of the spike glycoprotein of a coronavirus (e.g., MERS-CoV or SARS-CoV) is a truncation of about 13 to about 35 amino acids, about 13 to about 34 amino acids, about 13 to about 33 amino acids, about 13 to about 32 amino acids, about 13 to about 31 amino acids, about 13 to about 30 amino acids, about 13 to about 29 amino acids, about 13 to about 28 amino acids, about 13 to about 27 amino acids, about 13 to about 26 amino acids, about 13 to about 25 amino acids, about 13 to about 24 amino acids, about 13 to about 23 amino acids, about 13 to about 22 amino acids, about 13 to about 21 amino acids, about 13 to about 20 amino acids, about 13 to about 19 amino acids, about 13 to about 18 amino acids, about 13 to about 17 amino acids, about 13 to about 16 amino acids, about 13 to about 15 amino acids, about 13 to about 14 amino acids, about 14 to about 35 amino acids, about 14 to about 34 amino acids, about 14 to about 33 amino acids, about 14 to about 32 amino acids, about 14 to about 31 amino acids, about 14 to about 30 amino acids, about 14 to about 29 amino acids, about 14 to about 28 amino acids, about 14 to about 27 amino acids, about 14 to about 26 amino acids, about 14 to about 25 amino acids, about 14 to about 24 amino acids, about 14 to about 23 amino acids, about 14 to about 22 amino acids, about 14 to about 21 amino acids, about 14 to about 20 amino acids, about 14 to about 19 amino acids, about 14 to about 18 amino acids, about 14 to about 17 amino acids, about 14 to about 16 amino acids, about 14 to about 15 amino acids, about 15 to about 35 amino acids, about 15 to about 34 amino acids, about 15 to about 33 amino acids, about 15 to about 32 amino acids, about 15 to about 31 amino acids, about 15 to about 30 amino acids, about 15 to about 29 amino acids, about 15 to about 28 amino acids, about 15 to about 27 amino acids, about 15 to about 26 amino acids, about 15 to about 25 amino acids, about 15 to about 24 amino acids, about 15 to about 23 amino acids, about 15 to about 22 amino acids, about 15 to about 21 amino acids, about 15 to about 20 amino acids, about 15 to about 19 amino acids, about 15 to about 18 amino acids, about 15 to about 17 amino acids, about 15 to about 16 amino acids, about 16 to about 35 amino acids, about 16 to about 34 amino acids, about 16 to about 33 amino acids, about 16 to about 32 amino acids, about 16 to about 31 amino acids, about 16 to about 30 amino acids, about 16 to about 29 amino acids, about 16 to about 28 amino acids, about 16 to about 27 amino acids, about 16 to about 26 amino acids, about 16 to about 25 amino acids, about 16 to about 24 amino acids, about 16 to about 23 amino acids, about 16 to about 22 amino acids, about 16 to about 21 amino acids, about 16 to about 20 amino acids, about 16 to about 19 amino acids, about 16 to about 18 amino acids, about 16 to about 17 amino acids, about 17 to about 35 amino acids, about 17 to about 34 amino acids, about 17 to about 33 amino acids, about 17 to about 32 amino acids, about 17 to about 31 amino acids, about 17 to about 30 amino acids, about 17 to about 29 amino acids, about 17 to about 28 amino acids, about 17 to about 27 amino acids, about 17 to about 26 amino acids, about 17 to about 25 amino acids, about 17 to about 24 amino acids, about 17 to about 23 amino acids, about 17 to about 22 amino acids, about 17 to about 21 amino acids, about 17 to about 20 amino acids, about 17 to about 19 amino acids, about 17 to about 18 amino acids, about 18 to about 35 amino acids, about 18 to about 34 amino acids, about 18 to about 33 amino acids, about 18 to about 32 amino acids, about 18 to about 31 amino acids, about 18 to about 30 amino acids, about 18 to about 29 amino acids, about 18 to about 28 amino acids, about 18 to about 27 amino acids, about 18 to about 26 amino acids, about 18 to about 25 amino acids, about 18 to about 24 amino acids, about 18 to about 23 amino acids, about 18 to about 22 amino acids, about 18 to about 21 amino acids, about 18 to about 20 amino acids, about 18 to about 19 amino acids, about 19 to about 35 amino acids, about 19 to about 34 amino acids, about 19 to about 33 amino acids, about 19 to about 32 amino acids, about 19 to about 31 amino acids, about 19 to about 30 amino acids, about 19 to about 29 amino acids, about 19 to about 28 amino acids, about 19 to about 27 amino acids, about 19 to about 26 amino acids, about 19 to about 25 amino acids, about 19 to about 24 amino acids, about 19 to about 23 amino acids, about 19 to about 22 amino acids, about 19 to about 21 amino acids, about 19 to about 20 amino acids, about 20 to about 35 amino acids, about 20 to about 34 amino acids, about 20 to about 33 amino acids, about 20 to about 32 amino acids, about 20 to about 31 amino acids, about 20 to about 30 amino acids, about 20 to about 29 amino acids, about 20 to about 28 amino acids, about 20 to about 27 amino acids, about 20 to about 26 amino acids, about 20 to about 25 amino acids, about 20 to about 24 amino acids, about 20 to about 23 amino acids, about 20 to about 22 amino acids, about 20 to about 21 amino acids, about 21 to about 35 amino acids, about 21 to about 34 amino acids, about 21 to about 33 amino acids, about 21 to about 32 amino acids, about 21 to about 31 amino acids, about 21 to about 30 amino acids, about 21 to about 29 amino acids, about 21 to about 28 amino acids, about 21 to about 27 amino acids, about 21 to about 26 amino acids, about 21 to about 25 amino acids, about 21 to about 24 amino acids, about 21 to about 23 amino acids, about 21 to about 22 amino acids, about 22 to about 35 amino acids, about 22 to about 34 amino acids, about 22 to about 33 amino acids, about 22 to about 32 amino acids, about 22 to about 31 amino acids, about 22 to about 30 amino acids, about 22 to about 29 amino acids, about 22 to about 28 amino acids, about 22 to about 27 amino acids, about 22 to about 26 amino acids, about 22 to about 25 amino acids, about 22 to about 24 amino acids, about 22 to about 23 amino acids, about 23 to about 35 amino acids, about 23 to about 34 amino acids, about 23 to about 33 amino acids, about 23 to about 32 amino acids, about 23 to about 31 amino acids, about 23 to about 30 amino acids, about 23 to about 29 amino acids, about 23 to about 28 amino acids, about 23 to about 27 amino acids, about 23 to about 26 amino acids, about 23 to about 25 amino acids, about 23 to about 24 amino acids, about 24 to about 35 amino acids, about 24 to about 34 amino acids, about 24 to about 33 amino acids, about 24 to about 32 amino acids, about 24 to about 31 amino acids, about 24 to about 30 amino acids, about 24 to about 29 amino acids, about 24 to about 28 amino acids, about 24 to about 27 amino acids, about 24 to about 26 amino acids, about 24 to about 25 amino acids, about 25 to about 35 amino acids, about 25 to about 34 amino acids, about 25 to about 33 amino acids, about 25 to about 32 amino acids, about 25 to about 31 amino acids, about 25 to about 30 amino acids, about 25 to about 29 amino acids, about 25 to about 28 amino acids, about 25 to about 27 amino acids, about 25 to about 26 amino acids, about 26 to about 35 amino acids, about 26 to about 34 amino acids, about 26 to about 33 amino acids, about 26 to about 32 amino acids, about 26 to about 31 amino acids, about 26 to about 30 amino acids, about 26 to about 29 amino acids, about 26 to about 28 amino acids, about 26 to about 27 amino acids, about 27 to about 35 amino acids, about 27 to about 34 amino acids, about 27 to about 33 amino acids, about 27 to about 32 amino acids, about 27 to about 31 amino acids, about 27 to about 30 amino acids, about 27 to about 29 amino acids, about 27 to about 28 amino acids, about 28 to about 35 amino acids, about 28 to about 34 amino acids, about 28 to about 33 amino acids, about 28 to about 32 amino acids, about 28 to about 31 amino acids, about 28 to about 30 amino acids, about 28 to about 29 amino acids, about 29 to about 35 amino acids, about 29 to about 34 amino acids, about 29 to about 33 amino acids, about 29 to about 32 amino acids, about 29 to about 31 amino acids, about 29 to about 30 amino acids, about 30 to about 35 amino acids, about 30 to about 34 amino acids, about 30 to about 33 amino acids, about 30 to about 32 amino acids, about 30 to about 31 amino acids, about 31 to about 35 amino acids, about 31 to about 34 amino acids, about 31 to about 33 amino acids, about 31 to about 32 amino acids, about 32 to about 35 amino acids, about 32 to about 34 amino acids, about 32 to about 33 amino acids, about 33 to about 35 amino acids, or about 33 to about 34 amino acids.

For example, the c-terminal truncation of the spike glycoprotein of a coronavirus (e.g., MERS-CoV or SARS-CoV) is a truncation of about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, about 20 amino acids, about 21 amino acids, about 22 amino acids, about 23 amino acids, about 24 amino acids, about 25 amino acids, about 26 amino acids about 27 amino acids, about 28 amino acids, about 29 amino acids, about 30 amino acids, about 31 amino acids, about 32 amino acids, about 33 amino acids, about 34 amino acids, or about 35 amino acids.

In an additional embodiment, the at least one immunogenic glycoprotein or fragment thereof is a chimeric/fusion protein comprising at least a portion of a coronavirus glycoprotein, which is immunogenic, and a membrane anchor. In certain embodiments, the at least a portion of the coronavirus glycoprotein includes at least a portion of a spike glycoprotein. In yet another embodiment, the at least a portion of the coronavirus glycoprotein includes at least a portion of an S1 domain of a spike glycoprotein, e.g., the entire S1 domain of a spike glycoprotein. For example, the at least a portion of the coronavirus glycoprotein can include amino acids 1 to 750 or amino acids 22 to 750 of the MERS-CoV spike glycoprotein.

In certain embodiments, the membrane anchor includes at least one transmembrane domain. In some embodiments, the membrane anchor is selected from a virus other than a coronavirus, e.g., a virus from the Rhabdoviridae family such as RABV. In a particular embodiment, the membrane anchor is derived from a glycoprotein from the Rhabdoviridae family (e.g., RABV), e.g. the membrane anchor can include a portion of at least one of: an ectodomain, a transmembrane domain, and a cytoplasmic domain of a Rhabdoviridae glycoprotein. For example, the membrane anchor can comprise a portion of a Rhabdoviridae G glycoprotein comprising the cytoplasmic domain, the transmembrane domain, and a portion of the ectodomain. For example, in an embodiment, the chimeric/fusion protein includes about 15 to about 55 amino acids of the ectodomain of a Rhabdoviridae G glycoprotein (e.g., about 15 amino acids, about 16 amino acids, about 17 amino acids, about 18 amino acids, about 20 amino acids, about 21 amino acids, about 22 amino acids, about 23 amino acids, about 24 amino acids, about 25 amino acids, about 26 amino acids, about 27 amino acids, about 28 amino acids, about 29 amino acids, about 30 amino acids, about 31 amino acids, about 32 amino acids, about 33 amino acids, about 34 amino acids, about 35 amino acids, about 36 amino acids, about 37 amino acids, about 38 amino acids, about 39 amino acids, about 40 amino acids, about 41 amino acids, about 42 amino acids, about 43 amino acids, about 44 amino acids, about 45 amino acids, about 46 amino acids, about 47 amino acids, about 48 amino acids, about 49 amino acids, about 50 amino acids, about 51 amino acids, about 52 amino acids, about 53 amino acids, about 54 amino acids, or about 55 amino acids of the ectodomain, which can include at least a portion of the amino acid sequence of SEQ ID NO: 16).

In another embodiment, the membrane anchor protein includes about 96 amino acids from the c-terminus of a Rhabdoviridae G glycoprotein, for example, amino acids 428-524 of RABV G glycoprotein (SEQ ID NO: 16). In certain embodiments, the membrane anchor protein is about 90 to about 150 amino acids from the c-terminus of a Rhabdoviridae G glycoprotein, such as RABV. For example, the membrane anchor protein can be about 90 amino acids, about 91 amino acids, about 92 amino acids, about 93 amino acids, about 94 amino acids, about 95 amino acids, about 96 amino acids, about 97 amino acids, about 98 amino acids, about 99 amino acids, about 100 amino acids, about 101 amino acids, about 102 amino acids, about 103 amino acids, about 104 amino acids, about 105 amino acids, about 106 amino acids, about 107 amino acids, about 108 amino acids, about 108 amino acids, about 110 amino acids, about 111 amino acids, about 112 amino acids, about 113 amino acids, about 114 amino acids, about 115 amino acids, about 116 amino acids, about 117 amino acids, about 118 amino acids, about 119 amino acids, about 120 amino acids, about 121 amino acids, about 122 amino acids, about 123 amino acids, about 124 amino acids, about 125 amino acids, about 126 amino acids, about 127 amino acids, about 128 amino acids, about 129 amino acids, about 130 amino acids, about 131 amino acids, about 132 amino acids, about 133 amino acids, about 134 amino acids, about 135 amino acids, about 136 amino acids, about 137 amino acids, about 138 amino acids, about 139 amino acids, about 140 amino acids, about 141 amino acids, about 142 amino acids, about 143 amino acids, about 144 amino acids, about 145 amino acids, about 146 amino acids, about 147 amino acids, about 148 amino acids, about 149 amino acids, or about 150 amino acids from the c-terminus of a Rhabdoviridae G glycoprotein, such as RABV).

In a particular aspect, the present disclosure provides a recombinant rabies virus vector comprising a nucleotide sequence encoding at least one immunogenic glycoprotein or fragment thereof of at least one coronavirus and/or a chimeric protein comprising at least one immunogenic glycoprotein or fragment thereof of at least one coronavirus.

In yet another aspect, the present disclosure provides a multivalent vaccine that is effective to protect against infection with one or both a rabies virus and a coronavirus, comprising a recombinant rabies virus vector that expresses at least one immunogenic glycoprotein or fragment thereof of at least one coronavirus.

In still another aspect, the present disclosure provides a vaccine composition that comprises at least one multivalent vaccine that is effective to protect against infection with one or both a rabies virus and a coronavirus, comprising a recombinant rabies virus vector that expresses at least one immunogenic glycoprotein or fragment thereof of at least one coronavirus. In an embodiment, the vaccine composition further comprises a pharmaceutically acceptable carrier.

In another aspect still, the present disclosure provides a method of inducing an immune response protective against an infection by one or both of a coronavirus and a rabies virus in a subject, comprising administering to the subject a therapeutically effective amount of a multivalent vaccine comprising a recombinant rabies virus vaccine vector that expresses at least one immunogenic glycoprotein or fragment thereof of at least one coronavirus.

In a further aspect, the disclosure provides a method of inducing neutralizing antibodies against a coronavirus and/or a rabies virus in a subject infected with or having been exposed to either or both of said viruses, comprising administering to the subject a therapeutically effective amount of a multivalent vaccine comprising a recombinant rabies virus vaccine vector that expresses at least one immunogenic glycoprotein or fragment derived from at least one coronavirus glycoprotein.

In yet a further aspect, the disclosure involves a method of treating a subject infected with a coronavirus and/or a rabies virus, comprising administering to the subject a therapeutically effective amount of a multivalent vaccine comprising a recombinant rabies virus vaccine vector that expresses at least one coronavirus immunogenic glycoprotein or fragment thereof, wherein said vaccine induces an effective immune response against one or both of said viruses.

In certain embodiments, the coronavirus immunogenic glycoprotein or fragment thereof encoded by the recombinant rabies vaccine vector used in the different aspects of the present disclosure is a MERS-CoV glycoprotein. The MERS-CoV immunogenic glycoprotein or fragment thereof, in various embodiments and aspects herein, can be a polypeptide comprising the amino acid sequence of SEQ ID NO: 8, 12, or 14.

In certain other embodiments, the coronavirus immunogenic glycoprotein or fragment thereof encoded by the recombinant rabies vaccine vector used in the different aspects of the disclosure is a SARS-CoV glycoprotein.

In certain other embodiments, the recombinant rabies virus vector used in the various aspects of the disclosure further expresses one or more additional coronavirus proteins or immunogenic fragments thereof. In various embodiments, the additional coronavirus proteins can be a protein (or an immunogenic fragment thereof) selected from the group consisting of a coronavirus a replicase polyprotein, E protein, N protein, M protein, or a nonstructural protein, for example, from MERS-CoV or SARS-CoV. In various embodiments, the additional coronavirus proteins are selected from the group consisting of any one of the coronavirus proteins, or an immunogenic fragment thereof. In various other embodiments, the additional coronavirus proteins are selected from the group consisting of any one of the MERS-CoV proteins, or immunogenic fragments thereof.

The disclosure further contemplates that the coronavirus glycoprotein expressed by the recombinant rabies virus vaccine vectors used in the various aspects of the disclosure is expressed as immunogenic fragments. An immunogenic fragment of a coronavirus protein is, for the purposes of this disclosure, any segment of a coronavirus protein this is capable of inducing substantially the same immune response as the full-length counterpart protein. Substantially the same immune response can refer to, for example, where the concentration of antibodies induced against the fragment is about the same, or at least about 75%, or 80%, or 90%, or 95%, or 99% or more of the concentration of antibodies induced against the full length coronavirus protein tested under the same conditions. In a particular embodiment, the coronavirus immunogenic glycoprotein fragment includes the S1 domain of the spike protein.

The disclosure further contemplates that any additional coronavirus protein expressed by the recombinant rabies virus vaccine vectors used in the various aspects of the disclosure can be expressed as immunogenic fragments. An immunogenic fragment of a coronavirus protein is, for the purposes of this disclosure, any segment of a coronavirus protein this is capable of inducing substantially the same immune response as the full-length counterpart protein. Substantially the same immune response can refer to, for example, where the concentration of antibodies induced against the fragment is about the same, or at least about 75%, or 80%, or 90%, or 95%, or 99% or more the concentration of antibodies induced against the full length coronavirus protein tested under the same conditions.

In other embodiments, the recombinant rabies virus vaccine is attenuated, such that its neurovirulence properties have been eliminated or substantially mitigated such that neurological damage typical of the rabies virus is substantially avoided.

In certain embodiments, the recombinant rabies virus vaccine is the live attenuated "SAD B19 RABV" vaccine, which was attenuated by tissue culture passage and has been used as a live oral vaccine for wildlife in Europe for many years.

In certain other embodiments, the recombinant rabies virus vaccine is derived from SAD B19 RABV by introducing additional genetic changes that result in further attenuation of the virus. For the purpose of the disclosure, the term "derived" refers to a modified nucleic acid molecule (e.g., vaccine vector) relative to a wildtype or other source molecule into which the changes are introduced, where the changes include genetic changes and/or chemical changes, including single nucleotide substitutions (point mutations), deletions, insertions, inversions, multiple point mutations, and chemical changes such as DNA methylation or acetylation. In a particular embodiment, the SAD B19 RABV was derived to form "BNSP" by introducing a novel RABV stop-start transcription signal sequence flanked by unique BsiWI and NheI restriction sites between the nucleoprotein (N) and the phosphoprotein (P) genes for introduction of foreign genes (see FIG. 1). In a still further embodiment, the BNSP vector was further derived (and attenuated) by introducing an Arg→Glu change at amino acid 333 of the RABV G protein (see FIG. 1). The 333 mutation has been shown to greatly attenuate neurovirulence of RABV in adult mice.

In certain other embodiments, the disclosure provides host cells that can be transfected with the recombinant rabies virus vaccines of the disclosure for purposes of, including, expressing proteins encoded by the virus vaccines and/or for generating recombinant rabies virions, which can be isolated therefrom and utilized in vaccine compositions in accordance with other aspects and embodiments of the disclosure.

Suitable host cells can include any cell susceptible to being transfected or infected in vitro with a rabies virus vaccine, including any human cell lines or animal cell lines. Such cell lines and their use in expressing proteins and forming rabies virions is well known in the art and described in more detail in, for example, Barrett P N et al., Expert Rev Vaccines. 2009 May; 8(5):607-18; Tordo N et al., Dev Biol (Basel). 2008; 131:467-76; Toovey S. et al., Travel Med Infect Dis. 2007 November; 5(6):327-48; Chelbi-Alix M K, J Interferon Cytokine Res. 2006 May; 26(5):271-80; Morenweiser R. et al., Gene Ther. 2005 October; 12 Suppl 1:S103-10; Morimoto K et al., Virus Res. 2005 July; 111(1):61-7. Epub 2005 Apr. 11; Finke S et al., Virus Res. 2005 August; 111(2):120-31; and Halder M., Altern Lab Anim. 2002 January-February; 30(1):93-108; and Montagnon B J et al., Dev Biol Stand. 1998; 93:119-23, each of which are incorporated herein by reference.

It is preferred that the rabies vaccine viruses and the production of any virus virions and their use as vaccines be done in accordance with any necessary national and/or international requirements for health and safety with regard to rabies virus and coronavirus, e.g., in accordance with the requirements of the U.S. Center for Disease Control ("CDC") or the World Health Organization ("WHO").

The vaccine compositions of the disclosure, in certain embodiments, can include a pharmaceutically acceptable carrier or excipient, as further described below.

In yet another embodiment of the disclosure, the inventors have specifically constructed the five recombinant rabies virus vaccine vectors of the Examples, which include: (a) BNSP333-GP (a replication-competent, recombinant rabies virus vector vaccine expressing ZEBOV GP of strain Mayinga); (b) BNSP333-S (a replication-competent, recombinant rabies virus vector vaccine expressing the S protein of MERS-CoV); (c) BNSP333-SΔ29 (a replication-competent, recombinant rabies virus vector vaccine expressing the S protein of MERS-CoV with the 29 c-terminal amino acid truncation); (d) BNSP333-SΔ19 (a replication-competent, recombinant rabies virus vector vaccine expressing the S protein of MERS-CoV with the 29 c-terminal amino acid truncation); (e) BNSP333-S1 (a replication-competent, recombinant rabies virus vector vaccine expressing a chimeric protein comprising the S1 domain of the S glycoprotein of MERS-CoV and the ectodomain domain, transmembrane domain, and cytoplasmic domain of RABV G). Other specific constructs are well within the spirt and scope of the disclosure and these Examples of specific constructs are not meant to limit the disclosure in any manner. It will be appreciated further that, where a replication-defective rabies vaccine vector is used, cell lines which provide the missing/ defective functions in trans may be necessary to propagate the viruses and/or to allow preparation of virions. Such in trans functionalities and cell lines are well known in the art and pertain to the use of the rabies vaccine vectors.

The present disclosure contemplates that any suitable rabies virus genome or vector can be used to construct the recombinant vaccines of the disclosure. Thus, the rabies virus genome can be obtained from any suitable strain or isolate of rabies virus, so long as it is or is made to be attenuated. For the purposes of this disclosure, the term "attenuated," as it pertains to a property of a rabies virus genome of the disclosure, shall mean that the rabies virus genome or vector is capable of viral attachment, entry, and in some cases, replication in a host cell. However, attenuated rabies virus genomes—as compared to non-attenuated rabies viruses or rabies virus genomes—have substantially or completely lost the property of neurovirulence. In other words, the neurotropic character of the attenuated RVs of the disclosure preferably have been abolished or substantially abolished such that the RV vectors of the disclosure are safe for administering to a subject or animal without a substantial concern for neurovirulence effects.

The basic biology of the rabies virus is well-known. Rabies virus is a non-segmented negative-strand RNA virus of the Rhabdoviridae family, and which is the causative agent of rabies. Rabies is a disease that can occur in all warm-blooded species. Infection with rabies virus followed by the outbreak of the clinical features in nearly all instances results in death of the infected species. In Europe, the USA and Canada wild life rabies still exists and is an important factor in the cause of most human rabies cases that occur. On the other hand, urban rabies constitutes the major cause of human rabies in developing countries and entire continents, such as Africa.

Rabies virus (RV) virions are composed of two major structural components: a nucleocapsid or ribonucleoprotein (RNP), and an envelope in the form of a bilayer membrane surrounding the RNP core. The infectious component of all Rhabdoviruses is the RNP core which consists of the RNA genome encapsidated by the nucleocapsid (N) protein in combination with two minor proteins, i.e. RNA-dependent RNA-polymerase (L) and phosphoprotein (P). The membrane surrounding the RNP core consists of two proteins: a trans-membrane glycoprotein (G) and a matrix (M) protein located at the inner site of the membrane.

The G protein, also referred to as spike protein, is responsible for cell attachment and membrane fusion in RV and additionally is the main target for the host immune system. The amino acid region at position 330 to 340 (referred to as antigenic site III) of the G protein has been identified to be responsible for the virulence of the virus, in particular the Arg residue at position 333. All RV strains have this virulence determining antigenic site III in common.

Although wild type rabies virus almost always causes a fatal central nervous system (CNS) disease in mammalian species, attenuated form(s) of rabies virus typically do not cause such problems.

Suitable attenuated rabies virus genome or vectors can be found described elsewhere, for example, in U.S. Pat. Nos. 7,544,791; 7,419,816; 6,887,479; 6,719,981; and 6,706,523, each of which are incorporated herein by reference.

In a preferred embodiment, the attenuated rabies virus genome of the disclosure is based on the replication-competent rabies virus strain SAD B19, which is a RV strain that has been used for oral immunization of wild-life animals in Europe for more than 20 years and which has a good safety record. The nucleotide sequence for SAD B19 is publicly available as Genbank accession No. M31046.1 (SEQ ID NO: 20).

The disclosure also relates to the coronavirus polypeptide of interest—and to their associated nucleotide and amino acid sequences—the genes of which are to be incorporated into the attenuated recombinant rabies vectors of the disclosure. The invention contemplates using any coronavirus protein, including any virion surface glycoprotein, nucleoprotein, structural protein or element of replication machinery, or an immunogenic fragment thereof, which is to be incorporated using standard and well-known techniques in molecular biology into the attenuated rabies virus genomes of the disclosure. In preferred embodiments, the coronavirus proteins are those identified from coronavirus, including any of a replicase polyprotein, an envelope protein, a nucleocapsid protein, a membrane protein, a spike protein, and a nonstructural protein.

The corresponding nucleotide and amino acid sequences for these coronaviruses proteins, as well as, corresponding structural and non-structural proteins of coronaviruses, are readily available in the art and can be easily utilized by the present disclosure. Accordingly, the following Table 1 provides pertinent information regarding a non-exhaustive listing of publicly available sequences contemplated by the present disclosure, in particular with respect to coronavirus spike glycoprotein:

TABLE 1

Sequence information of publicly available Coronavirus Spike Protein amino acid sequences

| Coronavirus Protein | Coronavirus Genus | Genbank No. Nucleotide Sequence(s) | AA SEQ ID NO: |
|---|---|---|---|
| Spike (S) | MERS-CoV | NC_019843.3 | SEQ ID NO: 3 |
| Spike (S) | MERS-CoV | AHV00721.1 | SEQ ID NO: 4 |
| Spike (S) | SARS-CoV | AAR86775.1 | SEQ ID NO: 5 |
| Spike (S) | SARS-CoV | AAR86775.1 | SEQ ID NO: 7 |

The disclosure further contemplates that the rabies vaccine of the disclosure can be engineered—using well-known techniques—to express not only a coronavirus glycoprotein or an immunogenic fragment thereof, but also to express one or more additional coronavirus proteins or immunogenic fragments thereof (e.g., additional MERS-CoV or SARS-CoV proteins). In this manner, use of a bivalent or multivalent attenuated rabies virus vector is possible in accordance with the disclosure.

It is understood in the art that certain changes to the nucleotide sequence employed in a genetic construct have little or no bearing on the proteins encoded by the construct. Such changes result either from silent point mutations or point mutations that encode different amino acids that do not appreciably alter the behavior of the encoded protein. It is also understood that portions of the coding region can be eliminated without affecting the ability of the construct to achieve the desired effect, namely induction of a protective immune response against a coronavirus challenge. It is further understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the coronavirus glycoprotein genes are equivalents within the scope of the present disclosure.

Any suitable means, including any appropriate geneticbased or molecular biology-based techniques and the like can be used to construct the recombinant rabies vaccine vectors of the present disclosure.

In one embodiment, the skilled artisan may first obtain a rabies virus vector suitable for purposes of the disclosure. Preferably, the rabies virus vectors that are suitable are those that are attenuated, such there are no harmful effects by the rabies virus vector on the central nervous system when administered to a subject. Suitable rabies virus vectors can be readily obtained. Such vectors can be modified to enhance the degree of attenuation by known methods. In a preferred embodiment, the present inventors utilized BNSP RABV vaccine vector (FIG. 1), which was derived from SAD B19 vaccine strain, which was attenuated by tissue culture passage and has been previously used as a live oral vaccine for wildlife in Europe.

This particular construct, as discussed in Example 1 herein, was engineered to contain a novel RABV stop-start transcription signal sequence flanked by unique BsiWI and NheI restriction sites between the nucleoprotein (N) and phosphoprotein (P) genes of the rabies virus genome for the introduction of foreign genes. Moreover, to completely remove neurovirulence observed for this construct, a further attenuated derivate ("BNSP333") was generated which contains an Arg→Glu change at amino acid 333 of RABV G, which has been shown to greatly attenuate neurovirulence of RABV vaccine vectors in adult mice.

As discussed in more detail in the Examples, the inventors constructed five different recombinant rabies virus vaccines based on the BNSP333 attenuated rabies virus vaccine, which included: (a) BNSP333-GP (a replication-competent, recombinant rabies virus vector vaccine expressing ZEBOV GP of strain Mayinga); (b) BNSP333-S (a replication-competent, recombinant rabies virus vector vaccine expressing the S protein of MERS-CoV); (c) BNSP333-SΔ29 (a replication-competent, recombinant rabies virus vector vaccine expressing the S protein of MERS-CoV with the 29 c-terminal amino acid truncation); (d) BNSP333-SΔ19 (a replication-competent, recombinant rabies virus vector vaccine expressing the S protein of MERS-CoV with the 29 c-terminal amino acid truncation); (e) BNSP333-S1 (a replication-competent, recombinant rabies virus vector vaccine expressing a chimeric protein comprising the S1 domain of the S glycoprotein of MERS-CoV and the ectodomain domain, transmembrane domain, and cytoplasmic domain of RABV G)

In constructing the rabies virus vector constructs of the disclosure, a desired coronavirus immunogenic polypeptide (e.g., MERS-CoV or SARS Co-V spike glycoprotein) can be selected and obtained based on publicly available sequences and with the use of well-known molecular biology techniques. For example, one interested in using the rabies virus vaccine to introduce MERS-CoV spike protein, or a portion thereof, into a subject may obtain the nucleotide sequence of the spike glycoprotein gene from coronavirus by using readily available public information (e.g., the data site operated by the National Center for Biotechnology Information). A PCR-based strategy could be used to amplify the spike gene from a suitable source of template DNA, also readily obtainable by those of ordinary skill in the art, using oligonucleotide primers designed from the gene sequence itself. Once amplified, standard methods for cloning, sequence verification, expression, and transfer of the nucleotide sequence to the BSNP333 rabies vector (or any other suitable rabies vector of the disclosure) could be performed to obtain the desired recombinant rabies virus vector expressing a MERS-CoV spike glycoprotein. It will be readily apparent, however, that any work performed using sequences or materials from MERS-CoV or any other coronavirus may need to be performed in the appropriate Biosafety Level given the obvious dangers in working and handling coronaviruses.

The disclosure further contemplates introducing more than a single coronavirus polypeptide immunogen into the same recombinant rabies virus vector. For example, one could, using similar procedures offered above, as well as any other suitable procedures, prepare two or more nucleotide sequences that encode different coronavirus polypeptide immunogens of interest, e.g., where one polypeptide of interest is the MERS-CoV glycoprotein and a fragment thereof and a second polypeptide of interest or a fragment thereof is a coronavirus (e.g., MERS-CoV) replicase polyprotein, envelope protein, nucleocapsid protein, membrane protein, spike protein, and nonstructural protein. Thus, the present disclosure contemplates administering a rabies virus vector that contains and expresses both a single coronavirus (e.g., MERS-CoV or SARS-CoV) glycoprotein and another coronavirus (e.g., MERS-CoV or SARS-CoV) polypeptide fragment immunogen.

Moreover, two or more different rabies virus vaccine constructs can be combined into single administration or via co-administration, wherein each of the rabies virus vaccines is engineered to express a different coronavirus immunogen polypeptide fragment.

It is further contemplated that, where cross-reactivity occurs, i.e., where antibodies or a cytotoxic T-cell response induced in response to one MERS-CoV or coronavirus polypeptide can be cross-reactive with the corresponding polypeptide from a different type of MERS-CoV or even a different genus of coronavirus, the disclosure envisions a single vaccine that expresses a single coronavirus polypeptide or fragment thereof (e.g., a MERS-CoV spike glycoprotein fragment) that induces an immune response that is cross-reactive against other types of MERS-CoV or even other coronaviruses (e.g., SARS-CoV). The disclosure also contemplates vaccine compositions that comprise individual recombinant rabies vaccine vectors which express specific immunogenic spike proteins or fragments thereof of different coronaviruses so that a single vaccine composition effective against a variety of coronaviruses (e.g., MERS-CoV and SARS-CoV) can be administered.

These and other methods for obtaining and/or preparing the rabies virus vaccine constructs can be found in, for example, Current Protocols in Molecular Biology, Ausubel et al. (eds.), John Wiley and Sons, Inc.

The disclosure further contemplates that host cells transfected by the recombinant rabies virus vectors of the disclosure can be used to express virus-encoded protein and/or to form recombinant rabies virions. Methods and techniques for maintaining continuous cell cultures for infection by rabies viruses are well known in the art. A cell line can be infected (or transfected) with a recombinant rabies vaccine vector of the disclosure. The cell lines may be used to express the viral proteins, or they can be used to produce whole rabies virions containing the expressed MERS-CoV or otherwise desired coronavirus polypeptide or fragments thereof expressed from the recombinant rabies vaccine vector used to infect the cells. Suitable host cells can include any cell susceptible to being transfected or infected in vitro with a rabies virus vaccine, including any human cell lines or animal cell lines. Such cell lines and their use in expressing proteins and forming rabies virions are well known in the art and described in more detail in, for example, Barrett P N et al., Expert Rev Vaccines. 2009 May; 8(5):607-18; Tordo N et al., Dev Biol (Basel). 2008; 131:467-76; Toovey S. et al., Travel Med Infect Dis. 2007 November; 5(6):327-48; Chelbi-Alix M K, J Interferon Cytokine Res. 2006 May; 26(5):271-80; Morenweiser R. et al., Gene Ther. 2005 October; 12 Suppl 1:S103-10; Morimoto K et al., Virus Res. 2005 July; 111(1):61-7. Epub 2005 Apr. 11; Finke S et al., Virus Res. 2005 August; 111(2):120-31; and Halder M., Altern Lab Anim. 2002 January-February; 30(1):93-108; Montagnon B J et al., Dev Biol Stand. 1998; 93:119-23, each of which is incorporated herein by reference.

It is preferred that the rabies vaccine viruses and the production of any virus virions and their use as vaccines be done in accordance with any necessary national and/or international requirements for health and safety with regard to rabies virus and coronaviruses, e.g., in accordance with the requirements of the U.S. Center for Disease Control ("CDC") or the World Health Organization ("WHO").

In another aspect of the disclosure, the recombinant rabies virus vector vaccines of the disclosure, or recombinant rabies virion vaccines (which express the desired coronavirus polypeptide(s) fragment therein or thereon) may be formulated as compositions in accordance with known methods for preparing medicinal formulations and pharmaceutical compositions. The type and components of the pharmaceutical compositions of the disclosure can depend on the mode of administration, e.g., oral, parenteral or skin.

Pharmaceutical compositions and formulations for oral administration can include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable.

Pharmaceutical compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present disclosure can also include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. In general, the formulations are prepared by uniformly and intimately bringing into association the active ingredients with liquid carriers or finely divided solid carriers or both, and then, if necessary, shaping the product.

In certain embodiments, the pharmaceutical compositions of the present disclosure can incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid, such as a rabies vaccine vector of the disclosure, and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

The pharmaceutical compositions of the disclosure may also include a "pharmaceutical carrier" or "excipient", which for purposes of the disclosure, is a pharmaceutically acceptable solvent, suspending agent or any other pharmacologically inert vehicle for delivering one or more nucleic acids (e.g., a recombinant rabies virus vector of the disclosure) or polypeptide or virus virion (e.g., a recombinant rabies virion expressing the one or more coronavirus glycoproteins (including fragments thereof) of the disclosure) to an animal. The excipient may be liquid or solid and is selected, with the planned manner of administration in mind, so as to provide for the desired bulk, consistency, etc., when combined with an active agent of the disclosure (e.g., rabies vaccine vector, virion, or expressed polypeptides) the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with the active agents of the disclosure (e.g., rabies vaccine vector, virion, or expressed polypeptides) can also be used to formulate the compositions of the present disclosure. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

The pharmaceutical compositions of the present disclosure may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the disclosure provide pharmaceutical compositions containing one or more other additional therapeutic agents, for example, anti-viral small molecule drug that inhibits some aspect of MERS-CoV entry and/or replication and/or assembly, or which helps to mitigate one or more symptoms of a MERS-CoV infection, or an infection by another coronavirus, such as SARS-CoV. Examples of such therapeutic agents include, but are not limited to, aspirin, codeine, benzonatate, chlorpheniramine, pseudoephedrine, hydrocodone, colistimethate, guafenesin, homatropine, levodropropizine, noscapine, oxymetazoline, triprolidine, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the disclosure, such therapeutic agents may be used individually, sequentially, or in combination with one or more other such therapeutic agents. Anti-inflammatory drugs, including but not limited to nonsteroidal anti-inflammatory drugs (e.g., naproxen dodium, celecoxib, sulindac, oxaprozin, salsalate, diflunisal, piroxicam, indomethacin, etodolac, meloxicam, naproxen, nabumetone, ketorolac tromethamine, naproxen/esomeprazole, diclofenac, ibuprofine, and/or aspirin) and corticosteroids (e.g., bethamethasone, prednisone, prednisolone, triamcinolone, methylprednisolone, dexamethasone, hydrocortisone, cortisone, ethamethasoneb, and/or fludrocortisone), and antiviral drugs (including but not limited to amantadine, rimantadine, oseltamivir, zanamivi, acyclovir, brivudine, docosanol, famiciclovir, idoxuridine, penciclovir, valacyclovir, ribavirin, gangciclovir, trifluoridine, zidovudine, didanosine, zalcitabine, lamivudine, abacavir, atazanavir, atripla, zidovudine, combivir, darunavir, didanosine, delavirdine, dolutegravir, efavirenz, elvitegravir, enfuvirtide, etravirine, eviplera, fosamprenavir, emtricitabine, indinavir, kivexa, lopinavir, ritonavir, maraviroc, nelfinavir, nevirapine, raltegravir, rilpivirine, ritonavir, saquinavir, stribild, tenofovir, tenofovir, tipranavir, triomine, trizivir, truvada, and α-interfereon) may also be combined in compositions of the disclosure. See, generally, The Merck Manual of Diagnosis and Therapy, 15th Ed., Berkow et al., eds., 1987, Rahway, N.J., pages 2499-2506 and 46-49, respectively). Other therapeutic agents are also within the scope of this disclosure. Two or more combined compounds may be used together or sequentially. Such compounds may be administered using a separate administration schedule relative to the administration schedule of the active agents of the disclosure. The administration schedules may also be the same or have overlap.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the disclosure lies generally within a range of circulating concentrations that include the ED50 with little or no toxicity. The dosage may vary within this range depending upon the dosage form employed and the route of administration utilized. For any compound used in the method of the disclosure, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms), as determined in cell culture. Such information can be used to more accurately determine useful doses for a patient, as defined above (includes, e.g., humans, camelids, camel, llamas, and alpacas). Levels in plasma may be measured, for example, by high performance liquid chromatography.

In addition to their administration individually or as a plurality, as discussed above, the vaccines of the disclosure can be administered in combination with other known agents effective in treatment of pathological processes mediated by MERS-CoV expression or by another coronavirus—such as those listed above and others as well. In any event, the administering physician can adjust the amount and timing of vaccine administration on the basis of results observed using standard measures of efficacy known in the art or described herein.

The present disclosure contemplates any suitable means or method for administering the vaccine compositions of the disclosure. The skilled artisan will appreciate that the particular means of administration may depend upon whether the vaccine composition comprises recombinant rabies virus virions (e.g., with expressed MERS-CoV glycoprotein fragment presented at surface of the virion) or whether the vaccine to be administered is a nucleic acid-based vaccine, i.e., where the vaccine comprises a recombinant rabies virus vector of the disclosure which has been modified to express a coronavirus immunogenic protein fragment.

In certain embodiments, administration of any of the vaccines of the disclosure may be carried out by, for example, parenteral injection (such as intraperitoneal, subcutaneous, or intramuscular injection), in ovo injection of birds, orally, or by topical application of the virus (typically carried in a pharmaceutical formulation) to an airway surface. Topical application of a vaccine of the disclosure to an airway surface can be carried out by intranasal administration (e.g., by use of dropper, swab, or inhaler which deposits a pharmaceutical formulation intranasally). Topical application of a vaccine of the disclosure to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known, and any conventional technique can be employed. Oral administration may be in the form of an ingestible liquid or solid formulation. As noted above, one particular embodiment is subcutaneous injection, and another is intramuscular injection.

When the vaccine of the disclosure is RNA or DNA (e.g., a recombinant rabies virus vaccine vector expressing a coronavirus glycoprotein fragment, e.g., MERS-CoV glycoprotein fragment), the vaccine vector RNA or DNA can be administered directly using techniques such as delivery on gold beads (gene gun), delivery by liposomes, or by direct injection, among other methods known to those of ordinary skill in the art. Any one or more nucleotide constructs described above can be use in any combination effective to elicit an immunogenic response in a subject. Generally, the nucleic acid vaccine administered may be in an amount of about 1-5 μg of nucleic acid per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

Lipid based microsphere delivery systems can also be used to deliver the vaccines of the disclosure, in particular, the vaccine vector molecules of the disclosure. Optionally, such systems can be modified such that they specifically target specific cells and/or tissues and/or organs of the body, e.g., infection sites. Methods for preparing such systems will be well known to those having ordinary skill in the art. For example, such vector-delivering microspheres can be modified to comprise one or more ligands or targeting moieties which allow the microsphere to bind and/or interact specifically with a receptor or other target on a target cell or tissue.

Accordingly, in one aspect, the present disclosure provides recombinant rabies vector formulations comprised of a lipid-based carrier system, such as a stabilized nucleic acid-lipid particle, cationic lipid or liposome nucleic acid complexes (i.e., lipoplexes), a liposome, a micelle, a virosome, or a mixture thereof, which optionally may be modified to contain a moiety that enables it to be targeted to one or more cells or tissues of the gastrointestinal tract. In other embodiments, the carrier system is a polymer-based carrier system such as a cationic polymer-nucleic acid complex (i.e., polyplex), which optionally may be modified to contain a moiety that enables it to be targeted to one or more desired cells or tissues. In additional embodiments, the carrier system is a cyclodextrin-based carrier system, such as a cyclodextrin polymer-nucleic acid complex, which optionally may be modified to contain a moiety that enables it to be targeted to one or more desired cells or tissues. In further embodiments, the carrier system is a protein-based carrier system such as a cationic peptide-nucleic acid complex. Nucleic acid-lipid and/or protein-lipid particles and their method of preparation are disclosed in, e.g., U.S. Pat. Nos. 5,753,613; 5,785,992; 5,705,385; 5,976,567; 5,981,501; 6,110,745; and 6,320,017; and PCT Publication No. WO 96/40964, which are all herein incorporated by reference.

The lipoplexes of the disclosure can include non-cationic lipids used in the formulations of the present disclosure, which include any of a variety of neutral uncharged, zwitterionic, or anionic lipids capable of producing a stable complex. Such non-cationic lipids can be neutral or negatively charged. Examples of non-cationic lipids include, without limitation, phospholipid-related materials such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipahnitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), and stearoyloleoyl-phosphatidylethanolamine (SOPE).

Non-cationic lipids or sterols such as cholesterol may also be present in such microspheres. Additional nonphosphorous containing lipids include, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, diacylphosphatidylcholine, diacylphosphatidylethanolamine, and the like. Other lipids such as lysophosphatidylcholine and lysophosphatidylethanolamine may be present. Non-cationic lipids also include polyethylene glycol (PEG)-based polymers such as PEG 2000, PEG 5000, and polyethylene glycol conjugated to phospholipids or to ceramides (referred to as PEG-Cer), as described in U.S. patent application Ser. No. 08/316,429.

Non-limiting examples of additional lipid-based carrier systems suitable for use in the present disclosure include lipoplexes (see, e.g., U.S. Patent Publication No. 20030203865; and Zhang et al., J Control Release, 100:165-180 (2004)), pH-sensitive lipoplexes (see, e.g., U.S. Patent Publication No. 2002/0192275), reversibly masked lipoplexes (see, e.g., U.S. Patent Publication Nos. 2003/0180950), cationic lipid-based compositions (see, e.g., U.S. Pat. No. 6,756,054; and U.S. Patent Publication No. 2005/0234232), cationic liposomes (see, e.g., U.S. Patent Publication Nos. 2003/0229040, 2002/0160038, and 2002/0012998; U.S. Pat. No. 5,908,635; and PCT Publication No. WO 01/72283), anionic liposomes (see, e.g., U.S. Patent Publication No. 2003/0026831), pH-sensitive liposomes (see, e.g., U.S. Patent Publication No. 2002/0192274; and AU 2003/210303), antibody-coated liposomes (see, e.g., U.S. Patent Publication No. 2003/0108597; and PCT Publication No. WO 00/50008), cell-type specific liposomes (see, e.g., U.S. Patent Publication No. 2003/0198664), liposomes containing nucleic acid and peptides (see, e.g., U.S. Pat. No. 6,207,456), liposomes containing lipids derivatized with releasable hydrophilic polymers (see, e.g., U.S. Patent Publication No. 2003/0031704), lipid-entrapped nucleic acid (see, e.g., PCT Publication Nos. WO 03/057190 and WO 03/059322), lipid-encapsulated nucleic acid (see, e.g., U.S. Patent Publication No. 2003/0129221; and U.S. Pat. No. 5,756,122), other liposomal compositions (see, e.g., U.S. Patent Publication Nos. 2003/0035829 and 2003/0072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 2005/0037086).

In another embodiment, administration may be by accelerated-particle gene delivery.

The technique of accelerated-particle gene delivery is based on the coating of genetic constructions to be delivered into cells onto extremely small carrier particles, which are designed to be small in relation to the cells sought to be transformed by the process. The coated carrier particles are then physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in procaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. Therefore, the accelerated particle method is also preferred in that it allows a genetic vaccine construction capable of eliciting an immune response to be directed both to a particular tissue, and to a particular cell layer in a tissue, by varying the delivery site and the force with which the particles are accelerated, respectively. This technique is thus particularly suited for delivery of genes for antigenic proteins into the epidermis.

Thus, with regard to delivery of the recombinant rabies vaccine vectors of the disclosure, the disclosure also contemplates that aqueous droplets containing naked vector can be delivered by suitable acceleration techniques into the tissues of the individual sought to be vaccinated. At some frequency, such "naked" vector material will be taken up in the treated tissues.

The general approach of accelerated particle gene transfection technology is described in U.S. Pat. No. 4,945,050. An instrument based on an improved variant of that approach is available commercially from BioRad Laboratories. An alternative approach to an accelerated particle transfection apparatus is disclosed in U.S. Pat. No. 5,015,580 which, while directed to the transfection of soybean plants, describes an apparatus which is equally adaptable for use with mammalian cells and intact whole mammals. U.S. Pat. No. 5,149,655 describes a convenient hand-held version of an accelerated particle gene delivery device. Other such devices can be based on other propulsive sources using, for example, compressed gas as a motive force. A preferred apparatus and method for delivering genetic material in the present disclosure is described in published PCT patent application PCT/US95/00780 and in U.S. Pat. No. 5,584,807 which will issue on Dec. 17, 1996. Both are incorporated herein by reference.

A "genetic vaccine," i.e., a recombinant rabies vaccine vector (as opposed to a composition of rabies virions, which are also contemplated herein) can be delivered in a non-invasive manner to a variety of susceptible tissue types in order to achieve the desired antigenic response in the individual. Most advantageously, the genetic vaccine can be introduced into the epidermis. Such delivery, it has been found, will produce a systemic humoral immune response, a memory response, and a cytotoxic immune response. When delivering a genetic vaccine to skin cells, it was once thought desirable to remove or perforate the stratum corneum.

To obtain additional effectiveness from this technique, it may also be desirable that the genes be delivered to a mucosal tissue surface, in order to ensure that mucosal, humoral and cellular immune responses are produced in the vaccinated individual. It is envisioned that there are a variety of suitable delivery sites available including any number of sites on the epidermis, peripheral blood cells, i.e. lymphocytes, which could be treated in vitro and placed back into the individual, and a variety of oral, upper respiratory, and genital mucosal surfaces.

The term "transfected" is used herein to refer to cells which have incorporated the delivered foreign genetic vaccine construction (e.g., the recombinant rabies vaccine vectors), whichever delivery technique is used. The term transfection is used in preference to the term "transformation," to avoid the ambiguity inherent in the latter term, which is also used to refer to cellular changes in the process of oncogenesis. The term "infection" pertains to the normal molecular cellular uptake process by which a virus is introduced into a cell. Such cells are sometimes said to be "susceptible" to infection.

In some embodiments, when inducing cellular, humoral, and protective immune responses after genetic vaccination, preferred target cells are epidermal cells, rather than cells of deeper skin layers such as the dermis. Epidermal cells are preferred recipients of genetic vaccines because they are the most accessible cells of the body and may, therefore, be immunized non-invasively. Secondly, in addition to eliciting a humoral immune response, genetically immunized epidermal cells also elicit a cytotoxic immune response that is stronger than that generated in sub-epidermal cells. Delivery to epidermis also has the advantages of being less invasive and delivering to cells which are ultimately sloughed by the body.

The administration of the vaccines of the present disclosure (e.g., the recombinant rabies virions and/or the recombinant rabies vaccine vectors of the disclosure) by any of the above-described means can be in accordance with any suitable vaccination schedule, e.g., day 0, one month, four months, and twelve months from day 0. However, generally speaking, the vaccines described herein may also be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Other examples of suitable immunization schedules include: (i) 0, 1 month and 6 months, (ii) 0, 7 days and 1 month, (iii) 0 and 1 month, (iv) 0 and 6 months, (v) 0, 1 month and 2 months, or other schedules sufficient to elicit the desired immune responses expected to confer protective immunity, or reduce disease symptoms, or reduce severity of disease.

The present disclosure, in other aspects, provides methods for evaluating a sample for the presence of antibodies raised against rabies and/or a coronavirus, e.g., MERS-CoV. The disclosure contemplates that such methods may be useful, for example, in evaluating whether a tissue sample contains antibodies against MERS-CoV, another coronavirus or rabies, which may be useful in detecting whether a person or animal was exposed to such pathogens. Such detection methods may also be useful in monitoring a subject's blood or other tissues for evidence that an immune response has been induced against a vaccine of the disclosure.

In a further embodiment, the present disclosure relates to a method of detecting the presence of antibodies against MERS-CoV in a sample. Using standard methodology well known in the art, a diagnostic assay can be constructed by coating on a surface (i.e. a solid support for example, a microtitration plate, a membrane (e.g. nitrocellulose membrane) or a dipstick), all or a unique portion of any of the MERS-CoV proteins described above or any combination thereof, and contacting it with the serum of a person or animal suspected of having MERS-CoV. The presence of a resulting complex formed between the MERS-CoV protein(s) and serum antibodies specific therefor can be detected by any of the known methods common in the art, such as fluorescent antibody spectroscopy or colorimetry. This method of detection can be used, for example, for the diagnosis of MERS-CoV infection and for determining the degree to which an individual has developed virus-specific antibodies after administration of a vaccine.

In yet another embodiment, the present disclosure relates to methods for detecting the presence of virion proteins from rabies, a coronavirus or MERS-CoV in a sample. Antibodies against glycoproteins and nucleoproteins could be used for diagnostic assays. Using standard methodology well known in the art, a diagnostics assay can be constructed by coating on a surface (i.e. a solid support, for example, a microtitration plate or a membrane (e.g. nitrocellulose membrane)), antibodies specific for any of the MERS-CoV proteins described above, and contacting it with serum or a tissue sample of a person suspected of having MERS-CoV infection. The presence of a resulting complex formed between the protein or proteins in the serum and antibodies specific therefor can be detected by any of the known methods common in the art, such as fluorescent antibody spectroscopy or colorimetry. This method of detection can be used, for example, for the diagnosis of MERS-CoV infection.

In yet another embodiment, the present disclosure relates to DNA or nucleotide sequences for use in detecting the presence of rabies virus or coronavirus, e.g., MERS-CoV, using the reverse transcription-polymerase chain reaction (RT-PCR) or by some other suitable means for detection of specific nucleotide sequences. The nucleotide sequence of the present disclosure can be used to design primers which specifically bind to the viral RNA for the purpose of detecting the presence of MERS-CoV or for measuring the amount of MERS-CoV in a sample. The primers can be any length ranging from 7 to 400 nucleotides, preferably at least 10 to 15 nucleotides, or more preferably 18 to 40 nucleotides. Reagents and controls necessary for PCR reactions are well known in the art. The amplified products can then be analyzed for the presence of viral sequences, for example by gel fractionation, with or without hybridization, by radiochemistry, and immunochemistry techniques, or other suitable techniques.

In yet another embodiment, the present disclosure relates to a diagnostic kit that includes a vaccine composition of the disclosure, and optionally a means for detecting whether an immune response is induced following the administration of the vaccine, and further, optionally a means for administering the vaccine of the disclosure, and still further, optionally a set of instructions indicated a procedure for administering the vaccine and evaluating its effectivity on the immune response.

Depending on how the kit is to be operated, the kit may also include one or more additional vaccine compositions of the disclosure, wherein each vaccine composition comprises a recombinant rabies virus vector expressing a different coronavirus protein fragment, e.g., an MERS-CoV glycoprotein immunogenic fragment.

It will be appreciated that certain components of the kits will vary depending on what subject is being vaccinated and/or from which samples are to be drawn. Certain subjects can include, for example, human, non-human primate, animal, e.g., horse, donkey, pig, mouse, hamster, monkey, or other mammals, birds. For example, where a rabies vaccine vector is to be administered to a human, the kit may include a skin path, whereas where the administration is to a non-human primate, the kit may include instead a syringe.

In certain embodiments, the kits may also include an immunodetection reagent or label for the detection of the antibodies induced by the vaccination or to detect samples for the presence of rabies or coronavirus peptides or fragments thereof. Suitable detection reagents are well known in the art as exemplified by radioactive, enzymatic or otherwise chromogenic ligands, which are typically employed in association with the antigen and/or antibody, or in association with a second antibody having specificity for first antibody. Thus, the reaction is detected or quantified by means of detecting or quantifying the label. Immunodetection reagents and processes suitable for application in connection with the novel methods of the present disclosure are generally well known in the art.

The reagents may also include ancillary agents such as buffering agents and protein stabilizing agents, e.g., polysaccharides and the like. The kit may further include, where necessary, agents for reducing background interference in a test, agents for increasing signal, apparatus for conducting a test, calibration curves and charts, standardization curves and charts, and the like.

In a further embodiment, such a kit can comprise instructions for suitable operational parameters in the form of a label or separate insert.

The following examples are included to demonstrate preferred embodiments of the disclosure. It should be appreciated by those of skill in the art that the techniques disclosed in the examples which follow represent techniques discovered by the inventors and thought to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

EXAMPLES

The materials, compositions, and methods described herein are intended to be representative examples of the invention, and it will be understood that the scope of the invention is not limited by the scope of the examples. Those skilled in the art will recognize that the invention may be practiced with variations on the disclosed materials, compositions and methods, and such variations are regarded as within the ambit of the disclosure.

The collective objective of these Examples was to identify novel vaccine candidates for MERS-CoV with a maximum potential of licensure and utilization. To this end, the rabies virus (RABV) vaccine platform was chosen. This platform would allow rapid development of replication-competent, replication-deficient, and chemically inactivated vaccine candidates to increase the likelihood that an appropriate balance between vaccine immunogenicity and reactogenicity could be achieved.

RABV is a non-segmented, negative strand RNA virus of the Rhabdoviridae family. Although wild type RABV almost always causes a fatal CNS disease in mammalian species (Schnell et al., 2010), in its attenuated form, the RABV vaccine does not cause fatal CNS disease (Cenna et al., 2008; Faber et al., 2005; Faul et al., 2009; Faul et al., 2008; McGettigan et al., 2006; McGettigan et al., 2003a; McGettigan et al., 2003b; Siler et al., 2002; Snook et al., 2008; Tan et al., 2005). The RABV vaccine vectors can be generated from a reverse genetics system derived from the live attenuated SAD B19 RABV vaccine that is used for wildlife vaccination in Europe (Vos et al., 1999; Vos et al., 2002). Further attenuated RABV vectored vaccines have been generated by the introduction of mutations in the RABV glycoprotein (G), as well as the deletion of the RABV G that are propagated on trans-complementing cell lines that express RABV G (Gomme et al., 2010; McGettigan et al., 2003b; McKenna et al., 2004). These recombinant viruses have been demonstrated to be growth-deficient or -restricted in vitro and in vivo and are strongly immunogenic (Gomme et al., 2010; McGettigan et al., 2003b; McKenna et al., 2004). Furthermore, beta-propiolactone-mediated inactivation of RABV vectored vaccines has been used to generate killed vaccine candidates that should have optimal safety profiles (Siler et al., 2002; Smith et al., 2006).

The Examples that follow describe the generation of live-attenuated and inactivated RABV vaccines expressing MERS-CoV S protein or portions thereof and demonstrate their molecular properties, virulence, immunogenicity, and protective efficacy against RABV and MERS-CoV in mice. In addition to the advantages of the RABV vaccine platform described above, it is anticipated that the current advanced state of RABV vaccine safety, production, and distribution may ease the clinical development of these MERS-CoV S vaccines. In addition, RABV causes an estimated 24,000 deaths per year in Africa so a bivalent RABV/MERS-CoV vaccine would be an effective public health tool in Central Africa.

To determine if a RABV-based vaccine would be safe and effective against MERS-CoV, the inventors produced a RABV vector that contains the MERS-CoV S1 domain of the MERS-CoV S gene fused to the RABV G protein C terminal end. The inventors then chemically inactivated the virus and tested the vaccine in a mouse model of MERS-CoV infection. The mice produced high titers of neutralizing antibody with vaccination and were then challenged with MERS-CoV. The RABV/MERS-S vaccinated mice were fully protected from MERS-CoV, whereas the control mice displayed high levels of MERS-CoV in the lungs. These data demonstrate the utility of an inactivated RABV/MERS-S-based vaccine for blocking MERS-CoV replication in vivo, suggesting that RABV vaccines have potential for use in both camels and humans in areas with endemic MERS-CoV infections Example 1. Methods and Materials Used Throughout Examples cDNA Construction of Vaccine Vectors. The vaccine vector BNSP333 has been described previously (36). Full-length MERS-CoV S protein cDNA and fragments of S with C-terminal truncations were amplified from a wild-type MERS-CoV cDNA clone provided by the Armed Forces Health Surveillance Center, Division of Global Emerging Infections Surveillance and Response System). Primers were designed to include a BsiWI site at the 5'-end and a SpeI site at the 3'-end to allow insertion into BNSP333. The S1-RABV G chimera was assembled using overlap extension PCR from codon-optimized cDNA encoding amino acids 1-750 of MERS-CoV S (Sinobiological) and codon-optimized cDNA encoding amino acids 428-524 of the SAD-B19 RABV glycoprotein (Genscript). Recombinant clones were verified by DNA sequencing and used to recover infectious virus as previously described. Codons 18-750 of the spike protein gene were amplified using codon-optimized cDNA as a template to generate the expression plasmid for production of soluble S1. The PCR product was digested with BglII and NotI and cloned into the pDISPLAY vector (Invitrogen Inc.).

Virus Purification. Recombinant RABV were recovered as described previously (37). For large-scale purification of virus particles, 2-stack cell culture chambers were seeded with VERO cells in Dulbecco's Modified Eagle Medium, (DMEM) supplemented with 5% fetal calf serum (FCS). Prior to adding virus, the cells were washed with phosphate-buffered saline (PBS) and then infected at low multiplicity of infection (0.01-0.05) in serum-free medium at 34° C. Supernatant was collected at 3- to 4-day intervals and replaced with fresh serum-free medium. Cell culture media were centrifuged at low speed for 10 min to remove debris and filtered through 0.45 µm PES membrane filters. The filtered supernatant was then concentrated by tangential flow filtration in mPES hollow fiber cartridges (SpectrumLabs) followed by ultracentrifugation on 20% sucrose cushions in a SW32Ti rotor for 2 hours at 25000 rpm (46000 g). Pelleted virus was resuspended in PBS and protein content measured using a BCA Protein Assay Kit (PIERCE). Following the addition of PBS to adjust the protein concentration to 1 mg/ml, beta-Propriolactone was added at a concentration of 0.05% (v/v) to inactivate virus. After overnight incubation at 4° C., inactivated particles were incubated at 37° C. for 30 minutes and subsequently frozen in aliquots at −80° C. To verify complete inactivation/absence of infectious virus, 10 µg of inactivated virus was inoculated in a flask seeded with BSR cells. Four days after inoculation, 1/10th of supernatant was passaged on fresh BSR cells. Four days post inoculation, the cells were fixed and stained with FITC-labeled monoclonal antibody against RABV nucleoprotein.

Protein Gel Analysis and Western Blotting. Purified virus particles were denatured in urea buffer (125 mM Tris-HCl pH 6.8, 8 M urea, 4% sodium dodecyl sulfate, 5% beta-mercaptoethanol, 0.02% bromophenol blue) at 95° C. for 5 minutes. Then 3 µg of protein were resolved on a 10% SDS-polyacrylamide gel and thereafter stained overnight with Sypro Ruby for total protein analysis or transferred onto a nitrocellulose membrane in Towbin buffer (192 mM glycine, 25 mm Tris, 20% methanol) for western blot (WB) analysis. The nitrocellulose membrane was then blocked in TBST (100 mM Tris-HCl pH 7.9, 150 mM NaCl, 0.01% Tween20) containing 5% (w/v) non-fat dried milk at room temperature for 1 h. After blocking, the membrane was incubated overnight with rabbit antisera specific for the RABV glycoprotein (kindly provided by Dr. Dietzschold, Thomas Jefferson University) or rabbit serum against the S1 or S2 subunit of MERS-CoV S (Sinobiological) at a dilution of 1:1000 in PBS containing 5% BSA. After washing, the blot was incubated for 1 hour with anti-rabbit-IgG HRP diluted 1:50,000 in blocking buffer. Bands were developed with SuperSignal West Dura Chemiluminescent substrate (PIERCE). Images were captured using a FluorChem M CCD imaging system (ProteinSimple). PageRuler prestained protein ladder (ThermoScientific) was used for molecular weight determination.

Immunofluorescence. VERO E6 cells were seeded on coverslips in DMEM and infected the following day with MERS-S expressing RABV or control RABV in Optimem at 34° C. for 1 hour. After removal of the inoculum and addition of fresh DMEM medium containing 5% FCS, the cells were incubated at 34° C. for 60 hours. At the end of the incubation, the cells were washed with PBS, fixed in 2% PFA for 30 minutes, permeabilized in PBS containing 0.2% Tween-20 for 15 min, washed with PBS, and blocked with PBS containing 5% BSA. The cells were then stained for 1-2 hours at room temperature with rabbit polyclonal antiserum against MERS-CoV S (Sinobiological, 4 µg/ml), monoclonal antibody 1C5 against RABV glycoprotein (Abcam, 4 µg/ml), or FITC-conjugated monoclonal antibody against RABV nucleoprotein (Fujirebio) diluted 1:200 in PBS containing 2% BSA. Following washing with PBS and incubation with Cy2- or Cy3-conjugated anti-rabbit IgG secondary antibody (Jackson Immunoresearch, 1:250 in PBS containing 5% BSA), the cells were mounted in ProLong Gold antifade solution. Images were acquired using a microscope (Axioskop 40, Carl Zeiss) equipped with 20× and 40×

PlanNeofluar lenses and a cooled CCD camera (ProgresCFcool, Jenoptik). Composite images were prepared using Image J.

Animal Ethics Statement. This study was carried out in strict adherence to recommendations described in the Guide for the Care and Use of Laboratory Animals, the Office of Animal Welfare and the United States Department of Agriculture. All animal work was approved by the Institutional Animal Care and Use Committee (IACUC) at Thomas Jefferson University and at the University of Maryland. All procedures were carried out under isoflurane anesthesia by trained personnel and under the supervision of veterinary staff. Mice were housed in cages in groups of five, under controlled humidity, temperature, and light (12 hour light/12 hour dark cycles) conditions. Food and water were available ad libidum.

Immunizations. Six-to-eight week old female BALB/c mice were purchased from the Jackson Laboratory. Ten mice were inoculated intramuscularly with 10 µg of chemically inactivated BNSP333-S1-G particles in 100 µl PBS and boosted twice with the same amount of virus on day 7 and day 21, respectively. Groups of five mice were immunized with BNSP333-GP, BNSP333, or PBS as controls following the same immunization schedule. Blood samples were collected by retro-orbital bleed immediately prior to the first immunization and in weekly intervals thereafter until day 35 post immunization.

ELISA. Humoral responses to RABV G and EBOV GP protein were measured by an indirect ELISA as described previously (28). To determine antibody responses to the S protein of MERS-CoV, an indirect ELISA was developed utilizing purified S1 protein. The soluble S1 protein was produced by transfecting 293T cells with a plasmid that expresses a secreted S1 ectodomain (amino acids 18-750) fused to an N-terminal HA tag. Purification of the HA-tagged protein from the supernatant of transfected cells was carried out as described previously (38). Maxisorp 4 HBX 96-well plates (Nunc) were coated overnight at 4° C. with 100 µl of purified S1 (0.5 µg/ml) in 50 mM carbonate buffer (pH 9.6). Following washing with PBS containing 0.05% (w/v) Tween 20 (PBST) and blocking with PBST buffer containing 5% dried milk, the plates were incubated overnight with threefold serial dilutions of mouse sera in PBS containing 0.5% (w/v) BSA. This was followed by three wash cycles, incubation with HRP-conjugated goat anti-mouse-IgG secondary antibody (Jackson Immunoresearch, 1:10.000 in PBST) for 2 hours at room temperature, three more wash cycles, and the addition of OPD substrate (Sigma-Aldrich). Color development was stopped by the addition of 50 µl of 3M $H_2SO_4$ per well, and optical density was measured at 490 nm using an ELX800 plate reader (Biotek). Data were analyzed with GraphPad Prism (Version 6.0 g) using 4-parameter nonlinear regression.

Infection and Analysis of MERS-CoV Replication in Vaccinated Mice. Vaccinated mice were transduced with an adenovirus vector by intranasal inoculation and left for 4 days to ensure expression of DPP4, as has been described previously (39). Transduced mice were then infected with MERS-CoV (Jordan) as described previously (40), except that mice were inoculated with $2.5 \times 10^3$ pfu of MERS-CoV (Jordan) in 50 µl total volume. At 4 days post-infection, MERS-CoV (Jordan) titers were determined by plaque assay as described previously (40). MERS-CoV RNA was determined by PCR, as described previously (40), except that the endogenous control was mouse transferrin receptor protein 1 (TFRC) using the following forward primer: ATGACGTT-GAATTGAACCTGGACTA (SEQ ID NO: 17); reverse primer: GTCTCCACGAGCGGAATACAG (SEQ ID NO: 18); and probe: ABY-ATCAGGGATATGGGTCTAAGTC-TACAGTGG-QSY (SEQ ID NO: 19) in triplex with the previously described MERS-CoV primer/probe sets to UpE and membrane (M) protein mRNA (41).

MERS-CoV neutralization assays. Serum from vaccinated mice was assessed for MERS-CoV neutralization activity as described previously (20).

Example 2. Construction of an Attenuated RABV Expressing MERS-CoV Spike Protein

The BNSP333 vaccine vector utilized here is derived from the attenuated RABV strain SAD-B19 (42). Several modifications were introduced into the parent strain to increase safety and maximize expression of foreign genes. The inventors have previously shown that foreign genes can be stably introduced into this vector (28, 36, 38, 43, 44). Moreover, the inventors showed that expression of foreign antigens from a position between the RABV N and P gene, as well as codon optimization for human cells of the target gene, results in the highest expression level of the foreign antigen. Additionally, replacing the arginine with glutamic acid at position 333 (333R→333E) within the RABV glycoprotein (G) further reduces the pathogenicity of the already highly attenuated vector (36). The inventors have successfully used this improved vector to generate candidate vaccines against several emerging zoonotic viral diseases like Ebola virus (EBOV) and Henipaviruse (HeV) (28, 38).

Based on our previous work in constructing a vaccine for EBOV, the inventors chose to introduce the MERS-CoV S protein into the cBNSP333. MERS-CoV S is a glycoprotein anchored in the membrane of the MERS-CoV virions, and therefore a major target for protective antibodies. First, the inventors produced a BNSP333 clone containing the full length wild-type MERS-CoV S gene (FIG. 1). The inventors recovered the recombinant BNSP333-S virus and prepared viral stocks of BNSP333-S on BSR cells (a Baby Hamster Kidney (BHK) cell clone) and Vero cells. The inventors used both cell lines because while the parental RABV vector BNSP333 grows to the highest titers on BSR cells, Vero cells are more appropriate for the production of human vaccines.

Next, the inventors analyzed the expression of MERS-CoV S from BNSP333-S. For this approach, Vero cells were infected at a multiplicity of infection (MOI) of 0.01 with BNSP333-S or BNSP333-GP as a control. When coronavirus S proteins were expressed on the surface of hDDP4-expressing cells in heterologous expression systems, they led to fusion and syncytia formation with neighboring cells expressing the cognate receptor. Analysis by immune fluorescence and staining with RABV G-specific antibodies indicated that the cells were infected (FIGS. 2A and 2B, left panels). Moreover, BNSP333-S infected cells showed large multinucleated cells (FIG. 2A, left panel), which indicated fusion-competent MERS-CoV S protein expression from BNSP333-S.

Example 3. Expression of Full Length MERS-CoV S Inhibits Expression of RABV G Protein and Reduces Viral Titers Dramatically After recovery of the new vaccine vector, the inventors noticed that the cells infected with BNSP333-S produced less virus when compared to cells infected with BNSP333 or to other vaccine vectors based on BNSP333, such as FILORAB1. Additionally, the inventors wanted to analyze MERS-CoV S protein incorporation into RABV virions because incorporation is a prerequisite to using this vaccine in an inactivated form. To analyze the growth and incorporation of MERS-CoV S into RABV particles, Vero and BSR cells in T-150 flasks were infected at an MOI of 0.01 with BNSP333, SPBN, or BNSP333-S, and tissue culture supernatants were harvested over a period of 10-14 days. The inventors used ultracentrifugation to concentrate virus particles in clarified supernatant and analyzed SDS-PAGE for RABV G and MERS-CoV S antigens. After staining with SyproRuby, several protein bands were detected for BNSP333 and SPBN, and these bands corresponded in size to the RABV N, P, M, G, and L proteins in both BSR and VERO cells (FIG. 3A). However, the virions collected from the supernatants of cells infected with BNSP333-S seemed to contain no RABV G protein, or at least a greatly reduced amount. However, the inventors detected additional bands of the expected size for MERS-CoV S protein (180 kDa) and the S1 subunit (110-120 kDa) in both Vero and BSR cells.

Figure 3B:
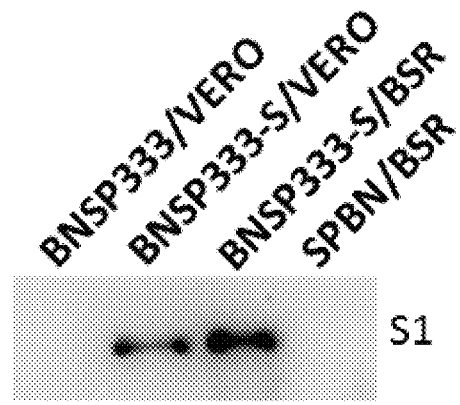
Figures 3C, 4B, 4C:
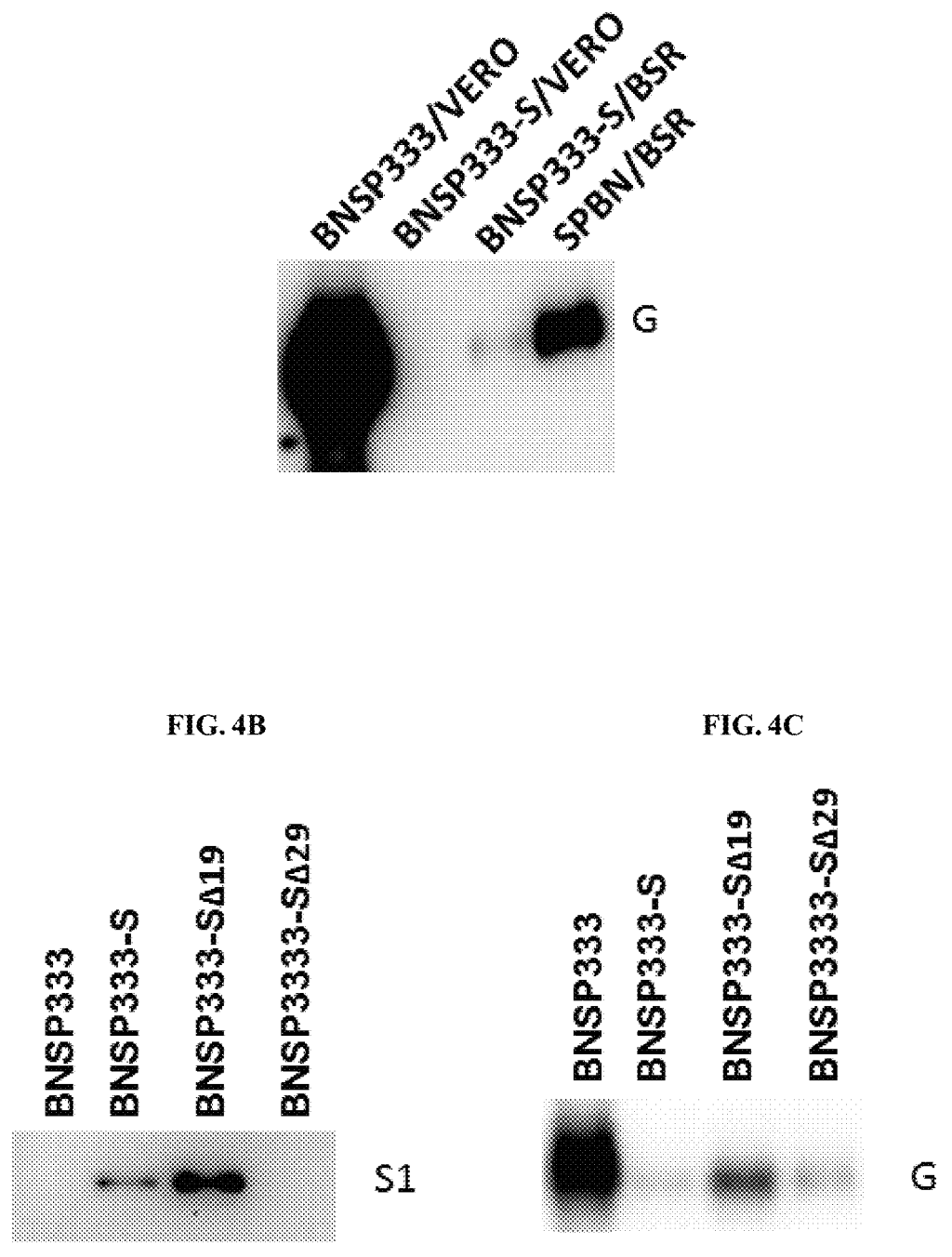

To verify the reduced level of RABV G in the virions of BNSP333-S, as well as to confirm the presence of MERS-CoV S, the inventors performed a WB analysis. Using a rabbit serum specific for MERS-CoV S, the inventors detected a protein of the expected size for S1 BNSP333-S in BNSP333-S virions derived from Vero or BSR cells (FIG. 3B). The inventors transferred a similar SDS-PAGE as described above to a nitrocellulose membrane and then incubated the WB with a mixture of four different monoclonal antibodies directed against RABV G. As shown in FIG. 3C, the RABV G was greatly reduced in BNSP333-S virions.

Figure 4A:
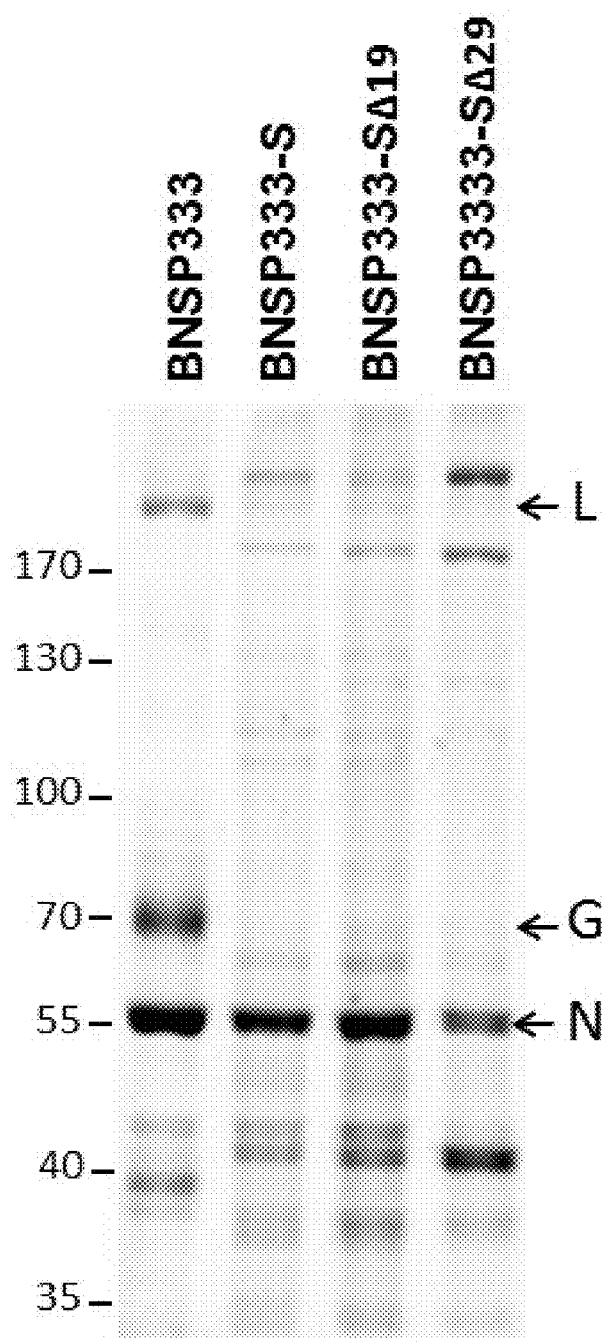

Example 4. Deletion of the ER Retention Signal of MERS-CoV S Improves its Expression and Incorporation The S protein of coronaviruses accumulates in intracellular compartments where budding and maturation of virus particles occurs. The inventors therefore hypothesized that the retention of MERS-CoV S in the ER might interfere with proper processing and transport of the RABV G protein. This hypothesis was supported by prior observations that truncation of the C-terminal domains of the SARS and TGEV S proteins increases incorporation of the S protein into VSV particles. Therefore, the inventors constructed two MERS-CoV S deletion mutants by deleting 19 or 29 amino acids of the MERS-CoV S protein cytoplasmic domain (CD) (FIG. 1 BNSP333-SΔ19 and BNSP333-SΔ29). Virions were purified from the supernatants of BSR and VERO cells infected with BSNP333, BNSP333 S, BNSP333 SΔ19, and BNSP333Δ29. Analysis by SDS-PAGE and WB showed that removing 19 amino acids significantly improved the incorporation of MERS-CoV S protein in BNSP333 Δ19 (FIG. 4). Removing 29 amino acids of the CD within BNSP333-SΔ29 substantially decreased MERS-CoV S incorporation into virions. However, expression of RABV G was still severely affected by the expression of MERS-CoV S, SΔ19, or SΔ29, and RABV G was only detected by WB. Of note, the lack of RABV G incorporation also reduced the titers of BNSP333-SΔ19 and BNSP333-SΔ29, and therefore, these constructs were not considered suitable for further development of the MERS-CoV vaccine.

Example 5. Expression of S1 Fused to the C-Terminal Part of RABV G Results in Strong Incorporation of RABV G-MERS-CoV-S1 Fusion Protein Previous studies have shown that the fusion domain of MERS-CoV S is located within the S2 subunit of the MERS-CoV S, whereas the S1 subunit of MERS-CoV S contains the receptor-binding domain (RBD). The inventors hypothesized that the putative retention signals in the CD and the fusion activity of the S2 domain interfered with transport of RABV G through the Golgi complex and incorporation of G into virus particles at the plasma membrane. Moreover, research by others indicates that antibodies directed against the RBD can protect against disease, and therefore expression of S1 might be sufficient to induce protective immune responses against MERS-CoV. Hence, the inventors constructed a new vaccine vector (BNSP333-S1) expressing the N-terminal 750 amino acids of MERS S1 fused to a truncated RABV glycoprotein, which comprises 31 amino acids of the ectodomain (ED) of RABV G and the complete CD and the transmembrane domain of RABV G to allow chimeric glycoprotein incorporation into RABV virions. The chimeric MERS-CoV S1/RABV G protein utilizes the original MERS-CoV ER translocation sequence (SS) and was generated by PCR of codon optimized cDNA fragments (FIG. 1).

Infectious virus was recovered as described above. In contrast to the recombinant RABV expressing MERS-CoV S or deletion mutants thereof, BNSP333-S1 grew to titers similar to other recombinant RABV vectors, roughly $10^8$ FFU/mL.

Figure 5A:
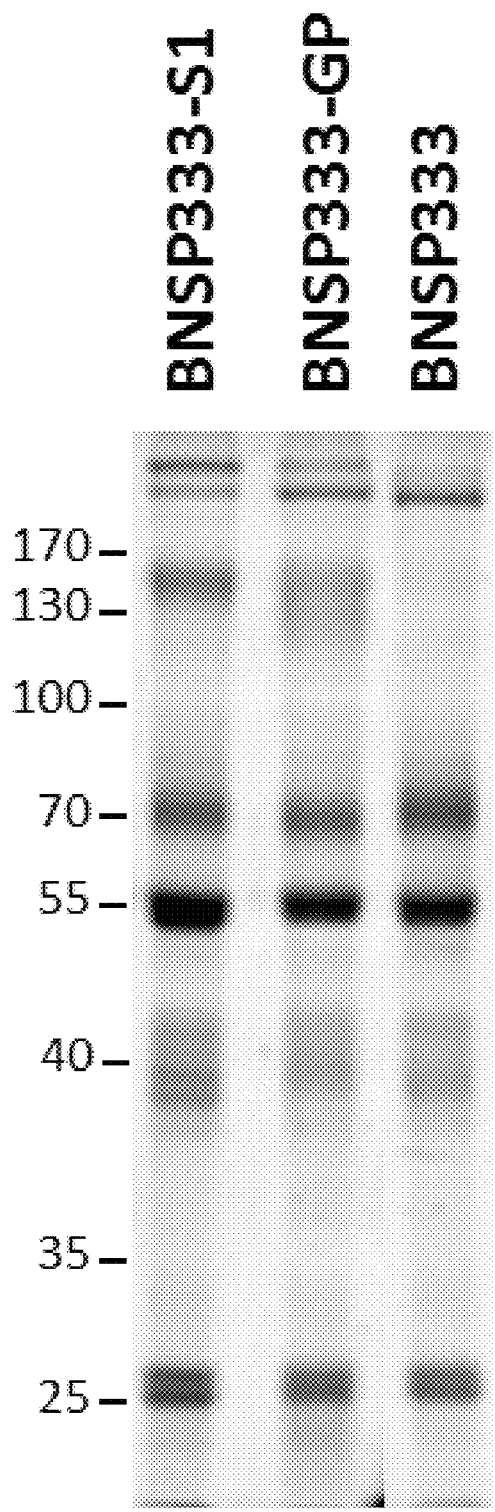
FIGS. 5A, 5B, and 5C demonstrate that the removal of the S2 subunit dramatically improves glycoprotein incorporation into RABV particles. A chimeric glycoprotein containing S1, but lacking the entire S2 subunit was constructed by fusing the first 750 amino acids of S to the C-terminal 96 amino acids of the RABV glycoprotein. VERO cells were infected with BNSP333 expressing the S1-G fusion protein, glycoprotein of Zaire Ebola virus, or parent vector BNSP333 expressing no additional glycoprotein. Purified virus particles were analyzed by SDS-PAGE (A) and western blotting with polyclonal antiserum specific for RABV G (C) and the S1 subunit of MERS CoV S (B). Particles contained nearly equal amount of the S1-G fusion protein and the RABV glycoprotein and showed no reduced G content compared to control virus expressing ZEBOV GP. Arrows indicate the RABV nucleoprotein (N), glycoprotein (G), and polymerase protein (L). Numbers to the left indicate the sizes of the molecular weight standard.
Figure 5B:
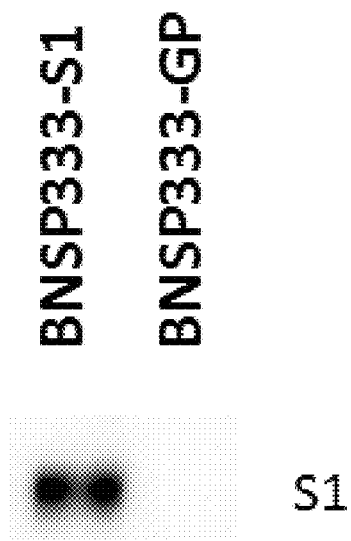
Figure 5C:
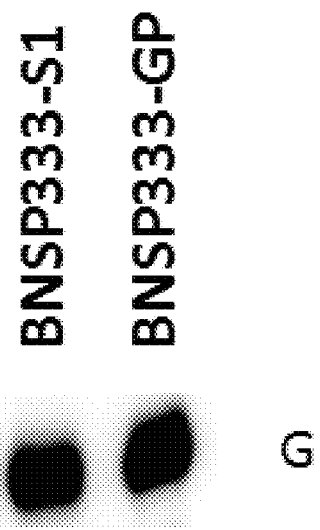

To analyze incorporation of the chimeric glycoprotein into RABV particles, Vero cells were infected with BNSP333, BNSP333-S1, or a control virus expressing Ebola GP (BNSP333-GP) and virus particles purified as described above. SDS-PAGE analysis of the purified virions revealed a strong band of approximately 150 kDa in the supernatant of Vero cells infected with BNSP333-S1 (FIG. 5A), which reacted strongly with antibodies specific for the S1 subunit of MERS-CoV S and was absent in the control virus (FIG. 5B), indicating efficient incorporation of the S1-G fusion protein into BNSP333-S1 particles. All three viruses contained a similar amount of RABV G (FIG. 5C), indicating that the chimeric S1-G protein that lacks the S2 subunit no longer blocks transport and incorporates the RABV glycoprotein and would be a suitable vaccine candidate.

Figure 6A:
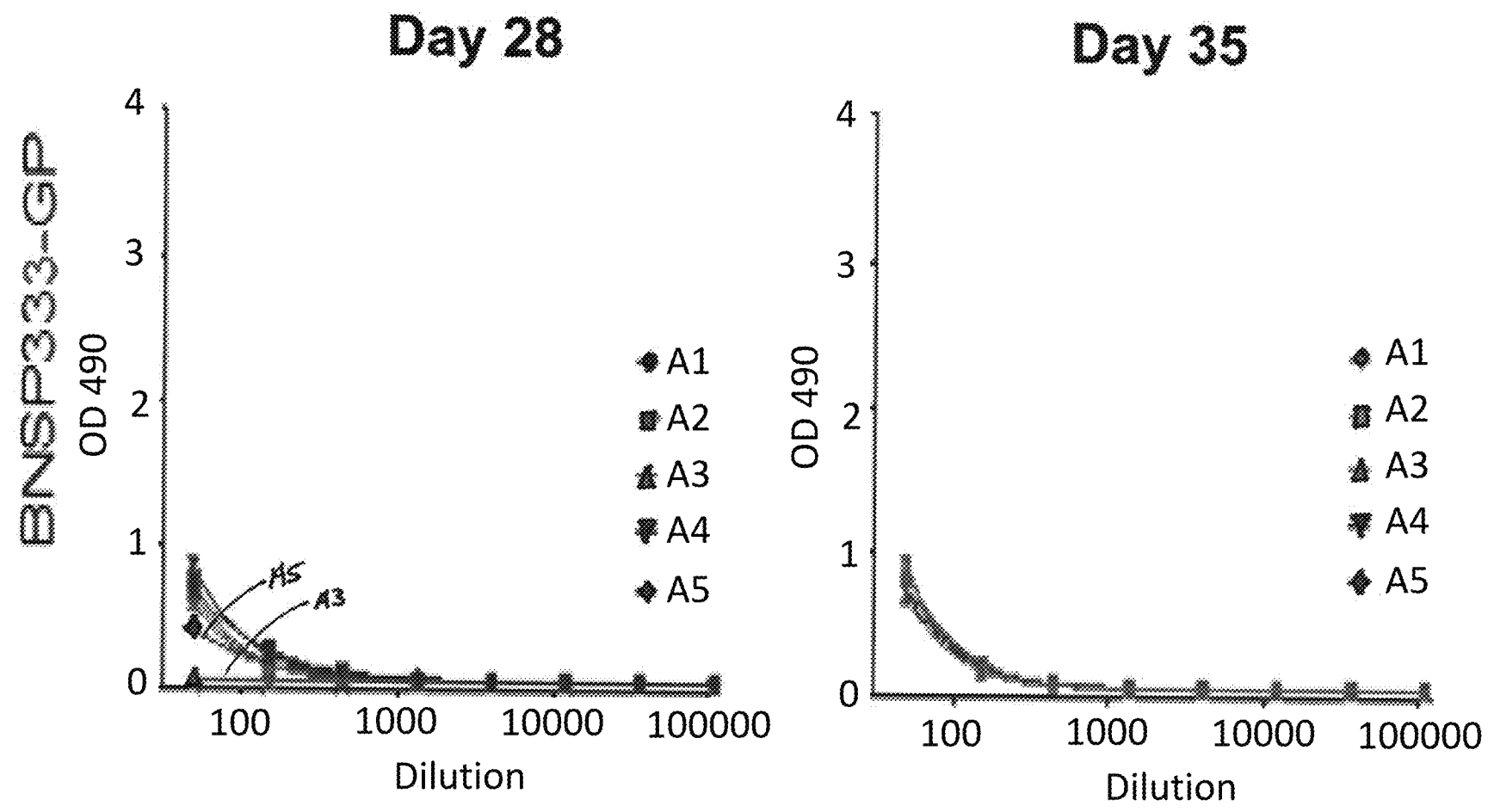
Figure 6B:
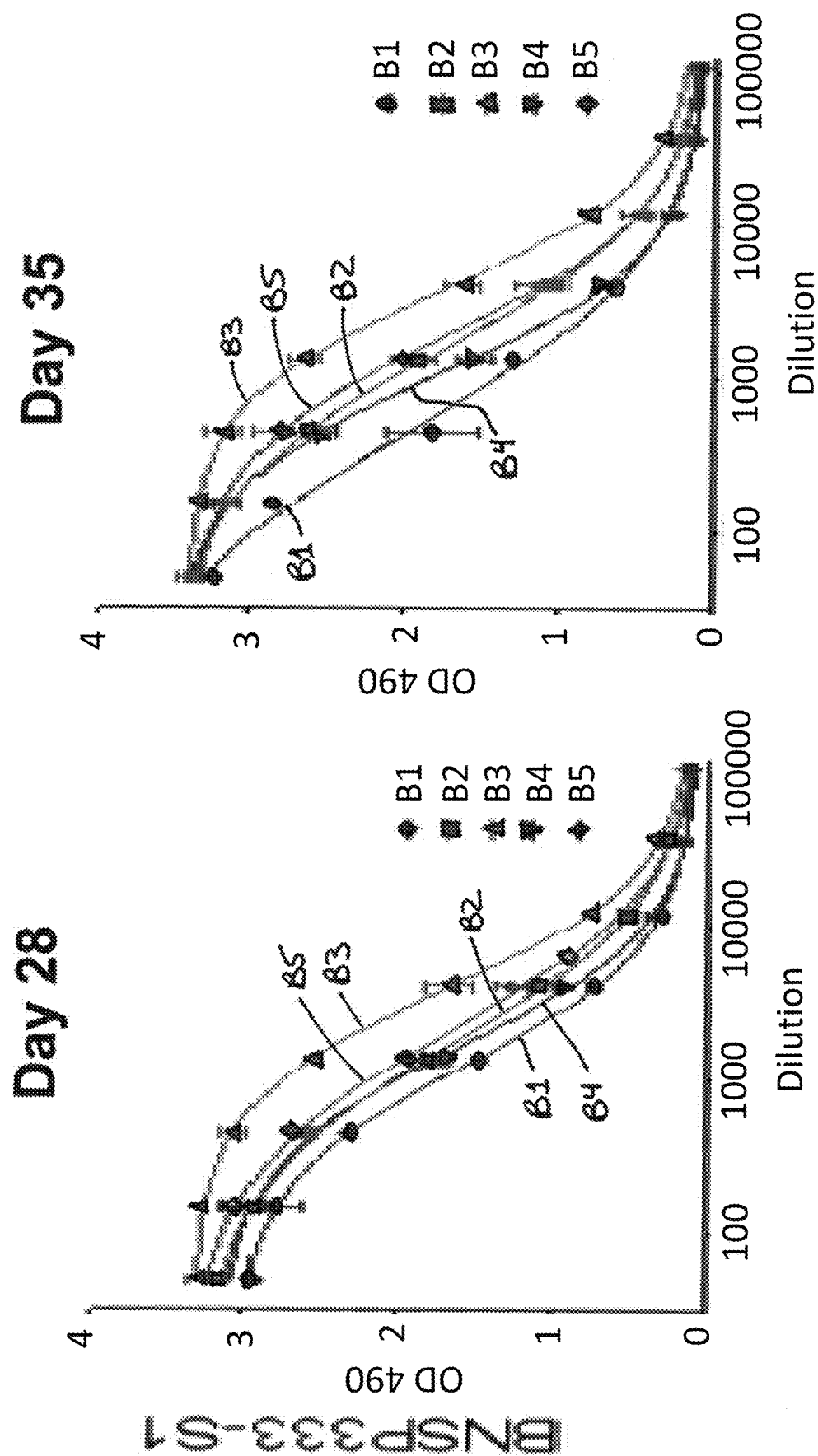
Figure 6C:
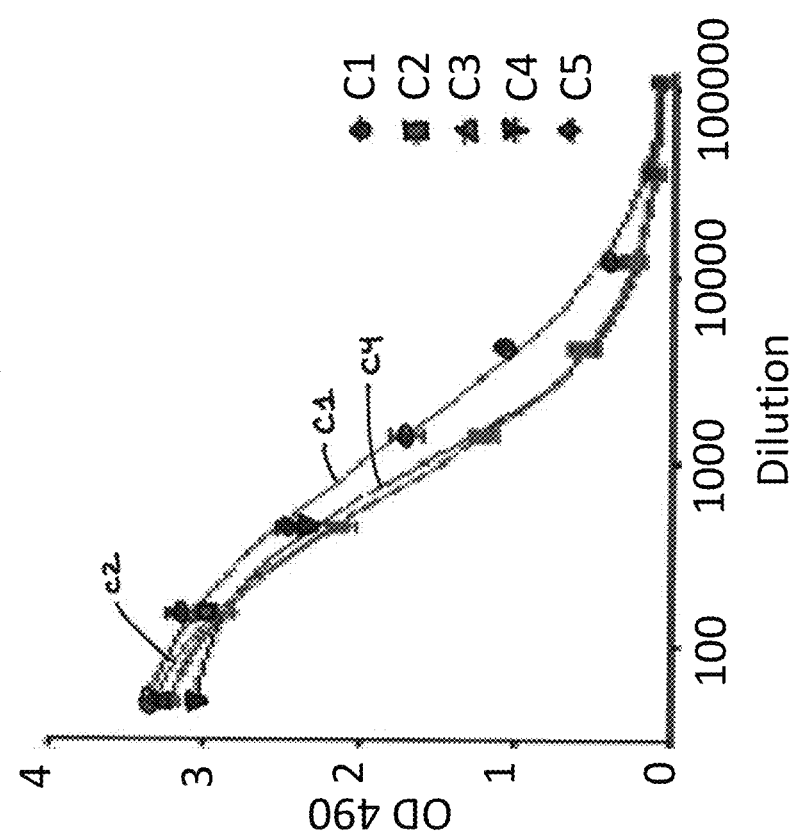
Figure 6C:
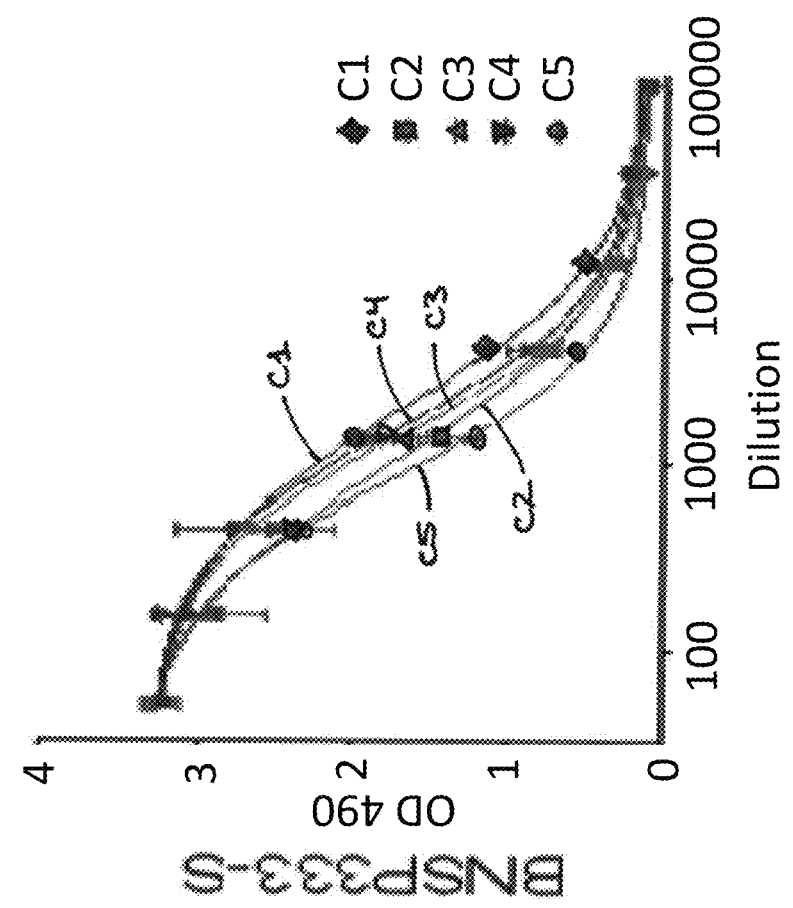
Figure 6D:
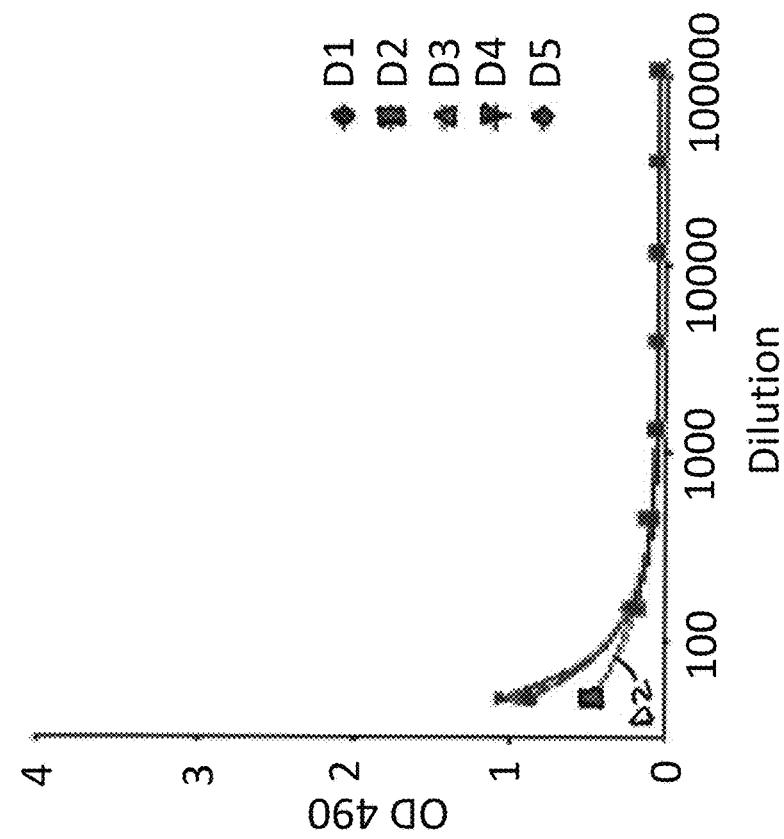
Figure 6D:
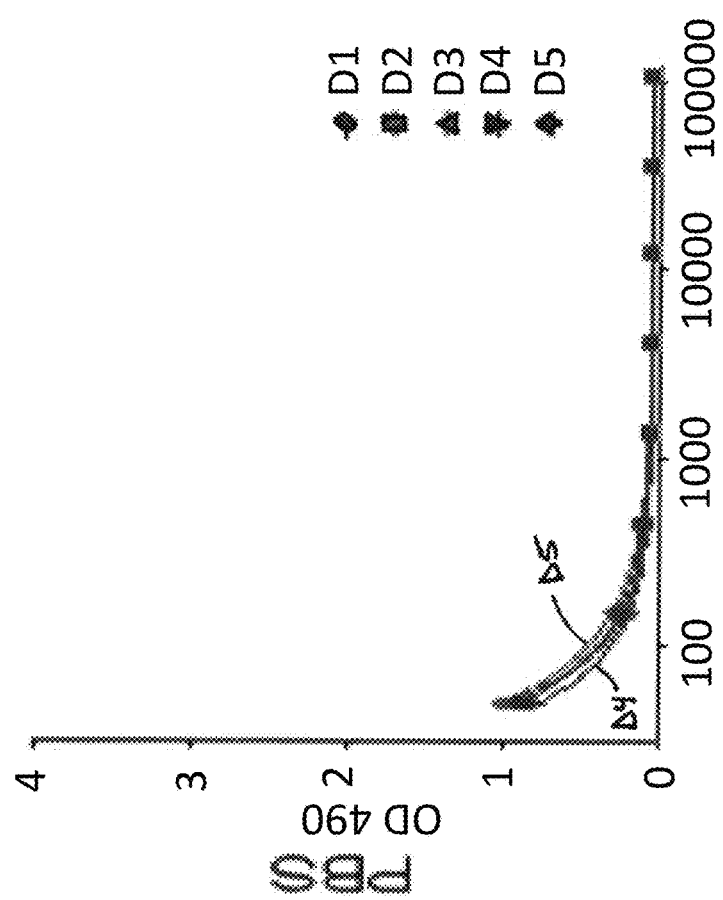

Example 6. BNSP333-S1 is Immunogenic in Mice and Protects Against Challenge with Pathogenic MERS-CoV To analyze the immunogenicity of the BNSP333-S1, the inventors immunized 4 groups of BALB/c mice (5 mice per group) with 10 μg of BNSP333-GP (group1), 10 μg of BNSP333-S1 (groups 2 and 3), or PBS (group 4) at day 0, 7, and 21. The inventors followed the immune response against RABV G and MERS-CoV S by antigen-specific ELISAs. The antigen-specific IgG responses increased over time and after each immunization; high antibody levels were obtained against both RABV G and MERS-CoV S after the third inoculations. MERS-CoV-S specific immune responses were only detected in groups 2 and 3, but RABV G specific IgG was detected in groups 1-3 (data not shown). None of the animals of group 4, which were mock immunized, demonstrated immune responses against RABV G or MERS-CoV S protein, confirming the specificity of the ELISAs. Whereas the RABV G-specific ELISA titers are known to predict protection against RABV challenge, the protective abilities of the MERS-CoV S-directed antibodies are unknown. The inventors therefore performed VNA against MERS-CoV of sera on day 35 of the immunized mice of all four groups. The inventors detected no MERS- CoV neutralizing antibodies in the sera of mice from group 1 (BNSP333-GP; FIG. 6A) or mock (PBS) immunized mice (group 4; FIG. 6B), but the sera of mice immunized with BNSP333-S1 (group 2 and 3; FIGS. 6B and 6C) neutralized MERS-CoV at serum dilutions between 1:160 (7 mice) and 1:320 (3 mice).

Efficacy testing of the RABV-MERS vaccine was performed using the adenovirus-hDPP4 transduced mouse model. All four groups of mice were transduced, and after five days, mice in groups 1, 2, and 4 were challenged intranasally (IN) with MERS-CoV at $1\times10^5$ pfu/mouse (strain Jordan-n3/2012). Four days after the challenge, the mice were euthanized, and their lungs were dissected, homogenized, and assayed for viral load by qRT-PCR and a viral plaque assay. For BNSP333-S1 immunized mice, both genomic and mRNA were reduced to background levels similar to those found in mice not transduced by the Ad5-expressing hDPP4 (Table 2). Moreover, the immunization with BNSP333-S1 reduced the viral load in the lungs to a level below detection of the assay ($2.5\times10^2$, Table 3).

TABLE 2

RT-PCR for genomic RNA and mRNA after challenge with MERS-CoV.

| Group Immunization | MERS-CoV Challenge | UpE | | mRNA | |
|---|---|---|---|---|---|
| | | Mean | Standard Deviation | Mean | Standard Deviation |
| G1/FILORAB1 | YES | 17871.24 | 12935.90 | 506.73 | 353.30 |
| G2/BNSP333-S1 | YES | 46.03 | 41.91 | 3.57 | 2.88 |
| G3/BNSP333-S1 | NO | 23.52 | 25.97 | 1.83 | 2.17 |
| G4/PBS | YES | 12047.57 | 3833.46 | 357.89 | 116.37 |

TABLE 3

Recovered MERS-CoV from lungs of mice immunized as indicated.

| | | Titer of recovered MERS-CoV | |
|---|---|---|---|
| Group Immunization | MERS-CoV Challenge | Mean | Standard deviation |
| G1/FILORAB1 | YES | $7.65 \times 10^6$ | $4.04 \times 10^2$ |
| G2/BNSP333-S1 | YES | ND | — |
| G3/BNSP333-S1 | NO | ND | — |
| G4/PBS | YES | $7.65 \times 10^6$ | $2.09 \times 10^2$ |

ND = not detected (assay detection level is $2.5 \times 10^2$)

Discussion of Examples 1-6

Various live and killed RABV vaccines expressing MERS-CoV S have been constructed and their S expression, safety, immunogenicity, and protective efficacy in mice have been compared. A novel RABV-based vaccine expressing MERS-CoV S1 protein as a potential vaccine against MERS-CoV is described herein. Similar to our previous vaccine approaches, the inventors expressed the target antigen for the vaccine (MERS-CoV S) from the highly attenuated vector RABV backbone BNSP333. However, MERS-CoV S expression dramatically reduced incorporation of RABV G into virions. Furthermore, RABV virions only contained a low amount of MERS-CoV S. Similar findings were observed with a VSV vector, where again the expression of MERS-CoV S from the genome led to low levels of VSV G in the virions (data not shown). These findings indicated that expression of MERS-CoV S interferes with the expression or transport of other viral glycoproteins.

Therefore, based on previous work in which the inventors successfully expressed different viral glycoproteins from RABV-based vectors and noticed only modest effects in viral replication kinetics and final titers, it was hypothesized that the retention of the MERS-CoV S protein prevented processing of RABV G in the ER and/or Golgi apparatus and possibly the transport to the cytoplasmic membrane. The alternative hypothesis that the heavy glycosylation of MERS-CoV S was responsible has been excluded based on the fact that both HIV-1 glycoprotein gp160 and Ebola virus GP are heavily glycosylated, but are well-expressed from RABV, and they are incorporated into virions without inhibiting RABV G incorporation.

Based on the hypothesis that ER retention of MERS-CoV S is responsible for the reduction of the RABV G transport to the surface, the potential ER retention signal of MERS-CoV was removed. It was determined that this slightly restored RABV G and MERS-CoV S expression, as well as the incorporation into RABV virions. These data indicated that MERS-CoV S expression can prevent RABV G transport. An alternative approach to the expression of the full-length MERS-CoV S was taken that focused on the expression of MERS-CoV S1, which contains the RBD; the RBD has been shown to be sufficient to induce VNA antibody against MERS-CoV. Because MERS-CoV S1 protein is secreted due to the lack of a membrane anchor, the proper signal to direct MERS-CoV S1 into budding RABV virions was added. Using the part of the RABV G ED containing the potential trimerization domain, in addition to the RABV G TM and CD, proved useful for the highly efficient incorporation of foreign glycoprotein into rhabdoviruses. In contrast to MERS-CoV S, the MERS-CoV S1 RABV G fusion protein was efficiently incorporated into the RABV virions.

A good small animal model is essential to vaccine research; however, in contrast to SARS-CoV, there is currently no good small animal model for MERS-CoV. MERS-CoV does not replicate in mice due to species-specific differences in the DPP4 receptor. Mouse DPP4 is very similar to the human DPP4, varying at only 62 positions out of 767 amino acids residues total (92% similarity), however, the differences tend to be on surface-exposed residues which might affect binding of MERS-CoV S protein to mouse DPP4. An alternative model system is the rhesus macaque. Rhesus macaques infected with MERS-CoV display some clinical signs like reduced appetite, and inflammatory infiltrates in the lung. The disease course, however, is mild compared to MERS-CoV infection in humans, and the animals do not succumb to infection. Therefore, the adenovirus transduced mouse model was utilized. This model expresses human DPP4 in the lungs after i.n. inoculation with an adenoviral vector followed by infection with MERS-CoV 5 days later. When used to test vaccination with inactivated RABV virions containing MERS-CoV S1, the results demonstrated that the vaccination was highly effective: it induced a strong humoral immune response against RABV-G, as well as MERS-CoV. Vaccination with the recombinant rabies vaccine reduced viral titer of MERS-CoV in the lungs of vaccinated animals below detection levels, whereas high viral loads were detected in control subjects.

The impact of cellular immune response for protection against MERS-CoV is less clear, but prior studies have shown that vaccination with DNA or a recombinant MVA expressing SARS-CoV S induces strong cellular responses. However, only adaptive transfer experiments of specific cellular populations will allow a final conclusion of the effect of cellular immune responses against MERS-CoV infection.

A live RABV-based vaccine will probably not be considered for human use, but it is highly effective and safe for different animal species; it is a valid option for animal vaccines, which are currently being analyzed for a RABV-based EBOV vaccine. Based on our study, the inactivated rabies virus vaccine incorporating MERS-CoV S1 now has demonstrated efficacy in the adenovirus-DPP4 mouse model of MERS and appears to be promising for further MERS-CoV vaccine studies. The RABV vector itself has an excellent safety record, and more than 20 million individuals have been immunized against RABV. A similar inactivated vaccine is currently advancing to a phase 1 study for Ebola virus disease, FILORAB1, so additional safety data will become available in the near future.

BRIEF SUMMARY OF THE SEQUENCE LISTING

Below is a summary of the sequences found in the Sequence Listing:
SEQ ID NO: 1—Middle East Respiratory Syndrome Coronavirus (MERS-CoV) Genome found in NCBI Reference No. NC_019843;
SEQ ID NO: 2—MERS-CoV Spike DNA sequence with NCBI Reference No. NC 019843.3;
SEQ ID NO: 3—MERS-CoV Spike protein sequence with GenBank Accession No. AHX00731.1;
SEQ ID NO: 4—MERS-CoV Spike protein sequence with GenBank Accession No. AHX00721.1;
SEQ ID NO: 5—Severe Acute Respiratory Syndrome Coronavirus (SARS-CoV) Spike protein sequence for strain Shanghai QXC12 with GenBank Accession No. AAR86788.1;
SEQ ID NO: 6—SARS-CoV Spike protein sequence for strain ShanghaiQXC2 with GenBank Reference No. AAR86775.1;
SEQ ID NO: 7—DNA sequence of S1 insert of BNSP333-S1 with Accession No. KU696644 (please note that this sequence is nucleotides 1462-4005 of SEQ ID NO: 21);
SEQ ID NO: 8—protein sequence of S1 insert of BNSP333-S1;
SEQ ID NO: 9—DNA sequence of S of BNSP333-S with GenBank Accession No. KU KU696640 (please note that this sequence is nucleotides 1462-5523 of SEQ ID NO: 22);
SEQ ID NO: 10—protein sequence of S of BNSP333-S;
SEQ ID NO: 11—DNA sequence of SΔ29 of BNSP333-Sde129 with Accession No. KU696643 (please note that this sequence is nucleotides 1562-5436 of SEQ ID NO: 23);
SEQ ID NO: 12—protein sequence of SΔ29 of BNSP333-SΔ29;
SEQ ID NO: 13—DNA sequence of SΔ19 of BNSP333-SΔ19 with GenBank Accession No. KY696642 (please note that this sequence is nucleotides 1462-5466 of SEQ ID NO: 24);
SEQ ID NO: 14—protein sequence of SΔ19 of BNSP333-SΔ19;
SEQ ID NO: 15—Rabies virus G glycoprotein DNA sequence with GenBank Accesion No. E02022.1;
SEQ ID NO: 16—Rabies virus G glycoprotein protein sequence with GenBank Accession No. AAA47213.1;
SEQ ID NO: 17—DNA sequence of TRFC forward primer;
SEQ ID NO: 18—DNA sequence of TRFC reverse primer;
SEQ ID NO: 19—DNA sequence of TRFC probe, which is as follows (fluorochrome) ABY-ATCAGGGA-TATGGGTCTAAGTCTACAGTGG-QSY (quencher);
SEQ ID NO: 20—SAD B19 genome sequence;
SEQ ID NO: 21—BNSP333-S1 genome sequence;
SEQ ID NO: 22—BNSP333-S genome sequence;
SEQ ID NO: 23—BNSP333-SΔ29 genome sequence; and
SEQ ID NO: 24—BNSP333-SΔ19 genome sequence.

Specific Embodiments

According to an aspect, the present disclosure provides a recombinant rabies virus vector comprising a nucleotide sequence encoding at least one immunogenic glycoprotein or fragment thereof of at least one coronavirus.

In any aspect or embodiment described herein, the at least one immunogenic glycoprotein fragment is a truncation of a coronavirus glycoprotein.

In any aspect or embodiment described herein, the at least one immunogenic glycoprotein fragment is a c-terminal truncation of a spike protein.

In any aspect or embodiment described herein, the truncation includes the deletion of from about 15 to about 25 amino acids from the c-terminus.

In any aspect or embodiment described herein, the truncation includes the deletion of about 19 amino acids from the c-terminus.

In any aspect or embodiment described herein, the immunogenic glycoprotein fragment includes the S1 domain of a spike protein.

In any aspect or embodiment described herein, the coronavirus is Middle East Respiratory Coronavirus (MERS-CoV) or Severe Acute Respiratory Syndrome Coronavirus (SARS-CoV).

In any aspect or embodiment described herein, the immunogenic glycoprogein fragment is a chimeric protein including an immunogenic glycoprotein fragment and a membrane anchor from a virus other than a coronavirus.

In any aspect or embodiment described herein, the membrane anchor is from a RABV glycoprotein.

In any aspect or embodiment described herein, the membrane anchor includes at least a portion of at least one of the ectodomain, the transmembrane domain, and the cytoplasmic domain of the RABV glycoprotein.

In any aspect or embodiment described herein, an amino acid sequence of the at least one immunogenic glycoprotein fragment is selected from the group consisting of SEQ ID NO: 8, 12, or 14.

In any aspect or embodiment described herein, the rabies virus genome is attenuated.

In any aspect or embodiment described herein, the rabies virus vector is derived from the live attenuated SAD B19 RABV vaccine.

According to another aspect, the present disclosure provides a host cell comprising the recombinant rabies virus vector of the present disclosure.

According to a further aspect, the present disclosure provides an isolated virion prepared from a host cell infected with the recombinant rabies virus vector of the present disclosure.

According to yet another aspect, the present disclosure provides a multivalent vaccine effective to protect against both rabies and at least one coronavirus, comprising a recombinant rabies virus vector that expresses at least one immunogenic glycoprotein or fragment thereof of at least one coronavirus.

In any aspect or embodiment described herein, the coronavirus is at least one of MERS-CoV, SARS-CoV, or both.

In any aspect or embodiment described herein, the immunogenic glycoprotein or fragment thereof is of a coronavirus spike glycoprotein.

In any aspect or embodiment described herein, the immunogenic glycoprotein or fragment thereof has an amino acid sequence selected from the group consisting of SEQ ID NO: 8, 12, or 14.

In any aspect or embodiment described herein, the rabies virus genome is attenuated.

In any aspect or embodiment described herein, the rabies virus genome is derived from the live attenuated SAD B19 RABV vaccine.

In any aspect or embodiment described herein, the rabies virus genome further expresses one or more additional coronavirus protein or immunogenic fragment thereof.

In any aspect or embodiment described herein, the additional coronavirus protein is selected from the group consisting of a replicase polyprotein, E protein, N protein, M protein, or nonstructural proteins from MERS-CoV or SARS-CoV.

According to yet a further aspect, the present disclosure provides a host cell comprising the multivalent vaccine of the present disclosure.

According to an aspect, the present disclosure provides an isolated virion prepared from host cells infected with the multivalent vaccine of the present disclosure.

According a yet another aspect, the present disclosure provides a vaccine composition comprising one or more multivalent vaccine of the present disclosure and a pharmaceutically acceptable carrier.

In any aspect or embodiment described herein, the vaccine composition further comprising at least one additional therapeutic agent.

In any aspect or embodiment described herein, the therapeutic agent is at least one of an anti-viral drug, anti-viral antibody, an immunostimulatory agent, an adjuvant, or a combination thereof.

In any aspect or embodiment described herein, the therapeutic agent is (i) an anti-viral drug, and (ii) an anti-viral antibody, an immunostimulatory agent, and/or an adjuvant.

According to an aspect, the present disclosure provides a virus vaccine comprising an attenuated recombinant rabies virus vector which expresses a MERS-CoV glycoprotein or a fragment thereof, wherein the virus vaccine is protective against both a rabies virus infection and a MERS-CoV infection.

In any aspect or embodiment described herein, the MERS-CoV glycoprotein or a fragment thereof comprises an amino acid sequence selected from the group consisting of SEQ ID NO: 8, 12 or 14.

In any aspect or embodiment described herein, the recombinant rabies virus vector is derived from SAD B19 RABV vaccine.

According to an additional aspect, the present disclosure provides a method of inducing an immune response protective against a coronavirus and/or a rabies virus in a subject, comprising administering to the subject a therapeutically effective amount of a multivalent vaccine comprising a recombinant rabies virus vector that expresses at least one immunogenic glycoprotein or fragment thereof from at least one coronavirus.

In any aspect or embodiment described herein, the at least one immunogenic glycoprotein or fragment thereof is a MERS-CoV or SARS-CoV glycoprotein or fragment thereof.

In any aspect or embodiment described herein, the at least one coronavirus is MERS-CoV or SARS-CoV.

In any aspect or embodiment described herein, the at least one immunogenic fragment comprises an amino acid sequence selected from the group consisting of SEQ ID NO: 8, 12, or 14.

In any aspect or embodiment described herein, the rabies virus vector is attenuated.

In any aspect or embodiment described herein, the rabies virus vector is inactivated.

In any aspect or embodiment described herein, the rabies virus vector is derived from the live attenuated SAD B19 RABV vaccine.

According to another aspect, the present disclosure provides a method of inducing neutralizing antibodies against coronavirus and/or a rabies virus in a subject infected with or having been exposed to either or both of said viruses, comprising administering to the subject a therapeutically effective amount of a multivalent vaccine comprising a recombinant rabies virus vector that expresses at least one immunogenic glycoprotein or fragment thereof of at least one coronavirus.

In any aspect or embodiment described herein, the at least one immunogenic glycoprotein or fragment thereof is derived from a MERS-CoV or a SARS-CoV.

In any aspect or embodiment described herein, the at least one coronavirus is MERS-CoV or SARS-CoV.

In any aspect or embodiment described herein, the at least one fragment has an amino acid sequence selected from the group consisting of SEQ ID NO: 8, 12, or 14.

In any aspect or embodiment described herein, the rabies virus vector is attenuated.

In any aspect or embodiment described herein, the rabies virus vector is derived from the live attenuated SAD B19 RABV vaccine.

In any aspect or embodiment described herein, the rabies virus vector is inactivated.

According to an aspect, the present disclosure provides a method of treating a subject infected with a coronavirus and/or a rabies virus, comprising administering to the subject a therapeutically effective amount of a multivalent vaccine comprising a recombinant rabies virus vector that expresses at least one coronavirus immunogenic glycoprotein or fragment thereof, wherein said vaccine induces an effective immune response against one or both of said viruses.

In any aspect or embodiment described herein, the at least one immunogenic glycoprotein or fragment is derived from a MERS-CoV glycoprotein or a SARS-CoV glycoprotein.

In any aspect or embodiment described herein, the at least one coronavirus glycoprotein or fragment thereof has an amino acid sequence selected from the group consisting of SEQ ID NO: 8, 12, or 14.

In any aspect or embodiment described herein, the rabies virus vector is attenuated.

In any aspect or embodiment described herein, the rabies virus vector is inactivated.

In any aspect or embodiment described herein, the rabies virus vector is derived from the live attenuated SAD B19 RABV vaccine.

According to another aspect, the present disclosure provides a live, replication-competent, rabies virus based vector expressing at least one glycoprotein or fragment thereof derived from at least one coronavirus.

In any aspect or embodiment described herein, the vector has the nucleotide sequence of SEQ ID NO: 21, 23, or 24.

According to yet another aspect, the present disclosure provides a live, replication-deficient, rabies virus based vector expressing at least one immunogenic glycoprotein or fragment thereof derived from at least one coronavirus glycoprotein.

In any aspect or embodiment described herein, the vector has the nucleotide sequence of SEQ ID NO: 21, 23, or 24.

While the present disclosure has been described in some detail, including preferred embodiments of the present disclosure, for purposes of clarity and understanding, one skilled in the art will appreciate that various changes in form and detail can be made without departing from the true scope of the disclosure. As such, it is to be understood that the disclosure defined by the above paragraphs is not to be limited to particular details set forth in the above description as many apparent variations thereof are possible without departing from the spirit or scope of the present disclosure.

REFERENCES

All documents cited in this list of References, and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

1 Milne-Price S, Miazgowicz K L, Munster V J. 2014. The emergence of the Middle East respiratory syndrome coronavirus. Pathog Dis 71:121-136.
2. Zaki A M, van Boheemen S, Bestebroer T M, Osterhaus A D, Fouchier R A. 2012. Isolation of a novel coronavirus from a man with pneumonia in Saudi Arabia. N Engl J Med 367:1814-1820.
3. Anonymous. 2013. WHO Statement on the third meeting of the IHR Emergency committee concerning Middle East respiratory syndrome coronavirus (MERS-CoV). Wkly Epidemiol Rec 88:435-436.
4. Memish Z A, Zumla A I, Assiri A. 2013. Middle East respiratory syndrome coronavirus infections in health care workers. N Engl J Med 369:884-886.
5. Drosten C, Kellam P, Memish Z A. 2014. Evidence for camel-to-human transmission of MERS coronavirus. N Engl J Med 371:1359-1360.
6. Madani T A, Azhar E I, Hashem A M. 2014. Evidence for camel-to-human transmission of MERS coronavirus. N Engl J Med 371:1360.
7. Azhar E I, El-Kafrawy S A, Farraj S A, Hassan A M, Al-Saeed M S, Hashem A M, Madani T A. 2014. Evidence for camel-to-human transmission of MERS coronavirus. N Engl J Med 370:2499-2505.
8. Khan A, Farooqui A, Guan Y, Kelvin D J. 2015. Lessons to learn from MERS-CoV outbreak in South Korea. J Infect Dev Ctries 9:543-546.
9. Park H Y, Lee E J, Ryu Y W, Kim Y, Kim H, Lee H, Yi S J. 2015. Epidemiological investigation of MERS-CoV spread in a single hospital in South Korea, May to June 2015. Euro Surveill 20:1-6.
10. Petersen E, Pollack M M, Madoff L C. 2014. Health-care associate transmission of Middle East Respiratory Syndrome Corona virus, MERS-CoV, in the Kingdom of Saudi Arabia. Int J Infect Dis 29:299-300.
11. Cauchemez S, Van Kerkhove M D, Riley S, Donnelly C A, Fraser C, Ferguson N M. 2013. Transmission scenarios for Middle East Respiratory Syndrome Coronavirus (MERS-CoV) and how to tell them apart. Euro Surveill 18.
12. Chan P K, Ma S, Ngai S M. 2011. Identification of T-cell epitopes of SARS-coronavirus for development of peptide-based vaccines and cellular immunity assessment methods. Hong Kong Med J 17 Suppl 6:26-30.
13. Roper R L, Rehm K E. 2009. SARS vaccines: where are we? Expert Rev Vaccines 8:887-898.
14. Zhu X, Liu Q, Du L, Lu L, Jiang S. 2013. Receptor-binding domain as a target for developing SARS vaccines. J Thorac Dis 5 Suppl 2:S142-148.
15. Du L, Jiang S. 2015. Middle East respiratory syndrome: current status and future prospects for vaccine development. Expert Opin Biol Ther 15:1647-1651.
16. Volz A, Kupke A, Song F, Jany S, Fux R, Shams-Eldin H, Schmidt J, Becker C, Eickmann M, Becker S, Sutter G. 2015. Protective Efficacy of Recombinant Modified Vaccinia Virus Ankara Delivering Middle East Respiratory Syndrome Coronavirus Spike Glycoprotein. J Virol 89:8651-8656.
17. Ma C, Wang L, Tao X, Zhang N, Yang Y, Tseng C T, Li F, Zhou Y, Jiang S, Du L. 2014. Searching for an ideal vaccine candidate among different MERS coronavirus receptor-binding fragments—the importance of immuno-focusing in subunit vaccine design. Vaccine 32:6170-6176.
18. Ma C, Li Y, Wang L, Zhao G, Tao X, Tseng C T, Zhou Y, Du L, Jiang S. 2014. Intranasal vaccination with recombinant receptor-binding domain of MERS-CoV spike protein induces much stronger local mucosal immune responses than subcutaneous immunization: Implication for designing novel mucosal MERS vaccines. Vaccine 32:2100-2108.
19. Muthumani K, Falzarano D, Reuschel E L, Tingey C, Flingai S, Villarreal D O, Wise M, Patel A, Izmirly A, Aljuaid A, Seliga A M, Soule G, Morrow M, Kraynyak K A, Khan A S, Scott D P, Feldmann F, LaCasse R, Meade-White K, Okumura A, Ugen K E, Sardesai N Y, Kim J J, Kobinger G, Feldmann H, Weiner D B. 2015. A synthetic consensus anti-spike protein DNA vaccine induces protective immunity against Middle East respiratory syndrome coronavirus in nonhuman primates. Sci Transl Med 7:301ra132.
20. Coleman C M, Liu Y V, Mu H, Taylor J K, Massare M, Flyer D C, Glenn G M, Smith G E, Frieman M B. 2014. Purified coronavirus spike protein nanoparticles induce coronavirus neutralizing antibodies in mice. Vaccine 32:3169-3174.
21. Mou H, Raj V S, van Kuppeveld F J, Rottier P J, Haagmans B L, Bosch B J. 2013. The receptor binding domain of the new Middle East respiratory syndrome coronavirus maps to a 231-residue region in the spike protein that efficiently elicits neutralizing antibodies. J Virol 87:9379-9383.
22. Du L, Zhao G, Kou Z, Ma C, Sun S, Poon V K, Lu L, Wang L, Debnath A K, Zheng B J, Zhou Y, Jiang S. 2013. Identification of a receptor-binding domain in the S protein of the novel human coronavirus Middle East respiratory syndrome coronavirus as an essential target for vaccine development. J Virol 87:9939-9942.
23. Zhang N, Channappanavar R, Ma C, Wang L, Tang J, Garron T, Tao X, Tasneem S, Lu L, Tseng C T, Zhou Y, Perlman S, Jiang S, Du L. 2015. Identification of an ideal adjuvant for receptor-binding domain-based subunit vaccines against Middle East respiratory syndrome coronavirus. Cell Mol Immunol doi:10.1038/cmi.2015.03.

24. Yang Y, Deng Y, Wen B, Wang H, Meng X, Lan J, Gao G F, Tan W. 2014. The amino acids 736-761 of the MERS-CoV spike protein induce neutralizing antibodies: implications for the development of vaccines and antiviral agents. Viral Immunol 27:543-550.

25. Kim E, Okada K, Kenniston T, Raj V S, AlHajri M M, Farag E A, AlHajri F, Osterhaus A D, Haagmans B L, Gambotto A. 2014. Immunogenicity of an adenoviral-based Middle East Respiratory Syndrome coronavirus vaccine in BALB/c mice. Vaccine 32:5975-5982.

26. Guo X, Deng Y, Chen H, Lan J, Wang W, Zou X, Hung T, Lu Z, Tan W. 2015. Systemic and mucosal immunity in mice elicited by a single immunization with human adenovirus type 5 or 41 vector-based vaccines carrying the spike protein of Middle East respiratory syndrome coronavirus. Immunology 145:476-484.

27. Pfaller C K, Cattaneo R, Schnell M J. 2015. Reverse genetics of Mononegavirales: How they work, new vaccines, and new cancer therapeutics. Virology (60 year edition), accepted.

28. Willet M, Kurup D, Papaneri A, Wirblich C, Hooper J W, Kwilas S A, Keshwara R, Hudacek A, Beilfuss S, Rudolph G, Pommerening E, Vos A, Neubert A, Jahrling P, Blaney J E, Johnson R F, Schnell M J. 2015. Preclinical Development of Inactivated Rabies Virus-Based Polyvalent Vaccine Against Rabies and Filoviruses. J Infect Dis doi:10.1093/infdis/jiv251.

29. Huttner A, Dayer J A, Yerly S, Combescure C, Auderset F, Desmeules J, Eickmann M, Finckh A, Goncalves A R, Hooper J W, Kaya G, Krahling V, Kwilas S, Lemaitre B, Matthey A, Silvera P, Becker S, Fast P E, Moorthy V, Kieny M P, Kaiser L, Siegrist C A, Consortium VS-E. 2015. The effect of dose on the safety and immunogenicity of the VSV Ebola candidate vaccine: a randomised double-blind, placebo-controlled phase 1/2 trial. Lancet Infect Dis 15:1156-1166.

30. Blaney J E, Marzi A, Willet M, Papaneri A B, Wirblich C, Feldmann F, Holbrook M, Jahrling P, Feldmann H, Schnell M J. 2013. Antibody quality and protection from lethal Ebola virus challenge in nonhuman primates immunized with rabies virus based bivalent vaccine. PLoS Pathog 9:e1003389.

31. Blaney J E, Wirblich C, Papaneri A B, Johnson R F, Myers C J, Juelich T L, Holbrook M R, Freiberg A N, Bernbaum J G, Jahrling P B, Paragas J, Schnell M J. 2011. Inactivated or live-attenuated bivalent vaccines that confer protection against rabies and Ebola viruses. J Virol 85:10605-10616.

32. Papaneri A B, Wirblich C, Cann J A, Cooper K, Jahrling P B, Schnell M J, Blaney J E. 2012. A replication-deficient rabies virus vaccine expressing Ebola virus glycoprotein is highly attenuated for neurovirulence. Virology 434:18-26.

33. Papaneri A B, Wirblich C, Cooper K, Jahrling P B, Schnell M J, Blaney J E. 2012. Further characterization of the immune response in mice to inactivated and live rabies vaccines expressing Ebola virus glycoprotein. Vaccine 30:6136-6141.

34. Cliquet F, Aubert M. 2004. Elimination of terrestrial rabies in Western European countries. Dev Biol (Basel) 119:185-204.

35. WHO. 2015. Rabies, Fact Sheet #99.

36. McGettigan J P, Pomerantz R J, Siler C A, McKenna P M, Foley H D, Dietzschold B, Schnell M J. 2003. Second-generation rabies virus-based vaccine vectors expressing human immunodeficiency virus type 1 gag have greatly reduced pathogenicity but are highly immunogenic. J Virol 77:237-244.

37. Papaneri A B, Wirblich C, Marissen W E, Schnell M J. 2013. Alanine scanning of the rabies virus glycoprotein antigenic site III using recombinant rabies virus: implication for post-exposure treatment. Vaccine 31:5897-5902.

38. Kurup D, Wirblich C, Feldmann H, Marzi A, Schnell M J. 2014. Rhabdoviral-Based Vaccine Platforms against Henipaviruses. J Virol doi:10.1128/JVI.02308-14.

39. Zhao J, Li K, Wohlford-Lenane C, Agnihothram S S, Fett C, Gale M J, Jr., Baric R S, Enjuanes L, Gallagher T, McCray P B, Jr., Perlman S. 2014. Rapid generation of a mouse model for Middle East respiratory syndrome. Proceedings of the National Academy of Sciences of the United States of America 111:4970-4975.

40. Pascal K E, Coleman C M, Mujica A O, Kamat V, Badithe A, Fairhurst J, Hunt C, Strein J, Berrebi A, Sisk J M, Matthews K L, Babb R, Chen G, Lai K M, Huang T T, Olson W, Yancopoulos G D, Stahl N, Frieman M B, Kyratsous C A. 2015. Pre- and postexposure efficacy of fully human antibodies against Spike protein in a novel humanized mouse model of MERS-CoV infection. Proceedings of the National Academy of Sciences of the United States of America 112:8738-8743.

41. Coleman C M, Frieman M B. 2015. Growth and Quantification of MERS-CoV Infection. Current protocols in microbiology 37:15E 12 11-19.

42. Conzelmann K K, Cox J H, Schneider L G, Thiel H J. 1990. Molecular cloning and complete nucleotide sequence of the attenuated rabies virus SAD B19. Virology 175:485-499.

43. Hudacek A W, Al-Saleem F H, Willet M, Eisemann T, Mattis J A, Simpson L L, Schnell M J. 2014. Recombinant rabies virus particles presenting botulinum neurotoxin antigens elicit a protective humoral response in vivo. Molecular Therapy-Methods & Clinical Development 1.

44. McGettigan J P, Naper K, Orenstein J, Koser M, McKenna P M, Schnell M J. 2003. Functional human immunodeficiency virus type 1 (HIV-1) Gag-Pol or HIV-1 Gag-Pol and env expressed from a single rhabdovirus-based vaccine vector genome. J Virol 77:10889-10899.

45. Lontok E, Corse E, Machamer C E. 2004. Intracellular targeting signals contribute to localization of coronavirus spike proteins near the virus assembly site. J Virol 78:5913-5922.

46. Schwegmann-Wessels C, Glende J, Ren X, Qu X, Deng H, Enjuanes L, Herrler G. 2009. Comparison of vesicular stomatitis virus pseudotyped with the S proteins from a porcine and a human coronavirus. J Gen Virol 90:1724-1729.

47. Fukushi S, Mizutani T, Saijo M, Matsuyama S, Miyajima N, Taguchi F, Itamura S, Kurane I, Morikawa S. 2005. Vesicular stomatitis virus pseudotyped with severe acute respiratory syndrome coronavirus spike protein. J Gen Virol 86:2269-2274.

48. Smith M E, Koser M, Xiao S, Siler C, McGettigan J P, Calkins C, Pomerantz R J, Dietzschold B, Schnell M J. 2006. Rabies virus glycoprotein as a carrier for anthrax protective antigen. Virology 353:344-356.

49. McKenna P M, Pomerantz R J, Dietzschold B, McGettigan J P, Schnell M J. 2003. Covalently linked human immunodeficiency virus type 1 gp120/gp41 is stably anchored in rhabdovirus particles and exposes critical neutralizing epitopes. J Virol 77:12782-12794.
50. Siler C A, McGettigan J P, Dietzschold B, Herrine S K, Dubuisson J, Pomerantz R J, Schnell M J. 2002. Live and killed rhabdovirus-based vectors as potential hepatitis C vaccines. Virology 292:24-34.
51. Schnell M J, Foley H D, Siler C A, McGettigan J P, Dietzschold B, Pomerantz R J. 2000. Recombinant rabies virus as potential live-viral vaccines for HIV-1. Proc Natl Acad Sci USA 97:3544-3549.
52. Winter C, Schwegmann-Wessels C, Neumann U, Herrler G. 2008. The spike protein of infectious bronchitis virus is retained intracellularly by a tyrosine motif J Virol 82:2765-2771.
53. Schwegmann-Wessels C, Ren X, Herrler G. 2006. Intracellular transport of the S proteins of coronaviruses. Adv Exp Med Biol 581:271-275.
54. Schwegmann-Wessels C, Al-Falah M, Escors D, Wang Z, Zimmer G, Deng H, Enjuanes L, Naim H Y, Herrler G. 2004. A novel sorting signal for intracellular localization is present in the S protein of a porcine coronavirus but absent from severe acute respiratory syndrome-associated coronavirus. J Biol Chem 279:43661-43666.
55. Coleman C M, Matthews K L, Goicochea L, Frieman M B. 2013. Wild type and innate immune deficient mice are not susceptible to the Middle East Respiratory Syndrome Coronavirus. J Gen Virol doi:10.1099/vir.0.060640-0.
56. May 18, 2013. 16. Pneumonia from Human Coronavirus in a Macaque Model. N Engl J Med, 368.1560-1562. http://www.nejm.org/doi/abs/10.1056/NEJMc1215691.
57. Wang L, Shi W, Joyce M G, Modjarrad K, Zhang Y, Leung K, Lees C R, Zhou T, Yassine H M, Kanekiyo M, Yang Z Y, Chen X, Becker M M, Freeman M, Vogel L, Johnson J C, Olinger G, Todd J P, Bagci U, Solomon J, Mollura D J, Hensley L, Jahrling P, Denison M R, Rao S S, Subbarao K, Kwong P D, Mascola J R, Kong W P, Graham B S. 2015. Evaluation of candidate vaccine approaches for MERS-CoV. Nat Commun 6:7712.

What is claimed is:

1. A recombinant rabies virus vector comprising a nucleotide sequence encoding at least one immunogenic glycoprotein fragment comprising a C-terminal truncation of a spike protein of Middle East Respiratory Coronavirus (MERS-CoV) or Severe Acute Respiratory Syndrome Coronavirus (SARS-COV).

2. The recombinant rabies virus vector of claim 1, wherein the truncation includes at least one selected from the group consisting of (a) the deletion of from about 15 to about 35 amino acids from the c-terminus (b) and the deletion of about 19 amino acids from the C-terminus.

3. The recombinant rabies virus vector of claim 1, wherein the immunogenic glycoprotein fragment includes the S1 domain of a spike protein.

4. The recombinant rabies virus vector of claim 1, wherein the immunogenic glycoprotein fragment is a chimeric protein including the immunogenic glycoprotein fragment and a membrane anchor from a virus other than a coronavirus.

5. The recombinant rabies virus vector of claim 4, wherein the membrane anchor is from a RABV glycoprotein.

6. The recombinant rabies virus vector of claim 5, wherein the membrane anchor includes at least a portion of at least one of the ectodomain, the transmembrane domain, the cytoplasmic domain of the RABV glycoprotein, or a combination thereof.

7. The recombinant rabies virus vector of claim 1, wherein an amino acid sequence of the at least one immunogenic glycoprotein fragment is selected from the group consisting of SEQ ID NO: 8, 12, or 14.

8. The recombinant rabies virus vector of claim 1, wherein the rabies virus genome is attenuated.

9. The recombinant rabies virus vector of claim 1, wherein the rabies virus vector is derived from the live attenuated SAD B19 RABV vaccine.

10. A host cell comprising the recombinant rabies virus vector of claim 1.

11. An isolated virion prepared from a host cell infected with the recombinant rabies virus vector of claim 1.

12. A multivalent vaccine effective to induce an immune response against both rabies and at least one coronavirus, comprising the recombinant rabies virus vector of claim 1.

13. The multivalent vaccine according to claim 12, wherein the rabies virus genome further expresses one or more additional coronavirus protein or immunogenic fragment thereof.

14. The multivalent vaccine according to claim 13, wherein the additional coronavirus protein is selected from the group consisting of a replicase polyprotein, E protein, N protein, M protein, or nonstructural proteins from MERS-COV or SARS-COV.

15. A vaccine composition comprising one or more multivalent vaccine of claim 12 and a pharmaceutically acceptable carrier.

16. The vaccine composition according to claim 15, further comprising at least one additional therapeutic agent.

17. The vaccine composition according to claim 16, wherein the therapeutic agent is at least one of an anti-viral drug, an anti-viral antibody, an immunostimulatory agent, an adjuvant, or a combination thereof.

18. A method of inducing an immune response against a coronavirus or a rabies virus, or both, in a subject, comprising administering to the subject a therapeutically effective amount of a multivalent vaccine comprising a recombinant rabies virus vector of claim 1.

19. A method of inducing neutralizing antibodies against coronavirus or a rabies virus, or both, in a subject infected with or having been exposed to either or both of said viruses, comprising administering to the subject a therapeutically effective amount of a multivalent vaccine of claim 12.

20. A method of treating a subject infected with a coronavirus or a rabies virus, or both, comprising administering to the subject a therapeutically effective amount of a multivalent vaccine of claim 12, wherein said vaccine induces an effective immune response against one or both of said viruses.

21. A live, replication-competent, rabies virus based vector expressing at least one immunogenic glycoprotein fragment comprising a C-terminal truncation of a spike protein of Middle East Respiratory Coronavirus (MERS-COV) or Severe Acute Respiratory Syndrome Coronavirus (SARS-COV).

22. The vector according to claim 21, wherein the vector has the nucleotide sequence of SEQ ID NO: 21, 23, or 24.

23. A live, replication-deficient, rabies virus based vector expressing at least one immunogenic glycoprotein fragment comprising a C-terminal truncation of a spike protein of Middle East Respiratory Coronavirus (MERS-COV) or Severe Acute Respiratory Syndrome Coronavirus (SARS-COV).

24. The vector according to claim 23, wherein the vector has the nucleotide sequence of SEQ ID NO: 21, 23, or 24.

\* \* \* \* \*

SEQUENCE LISTING

<160> NUMBER OF SEQ ID NOS: 24

<210> SEQ ID NO 1
<211> LENGTH: 30119
<212> TYPE: DNA
<213> ORGANISM: Middle East Respiratory Syndrome Coronavirus

<400> SEQUENCE: 1

```
gatttaagtg aatagcttgg ctatctcact tccctcgtt ctcttgcaga actttgattt      60
taacgaactt aaataaaagc cctgttgttt agcgtatcgt tgcacttgtc tggtgggatt     120
gtggcattaa tttgcctgct catctaggca gtggacatat gctcaacact gggtataatt    180
ctaattgaat actattttc agttagagcg tcgtgtctct tgtacgtctc ggtcacaata     240
cacggtttcg tccggtgcgt ggcaattcgg ggcacatcat gtctttcgtg gctggtgtga    300
ccgcgcaagg tgcgcgcggt acgtatcgag cagcgctcaa ctctgaaaaa catcaagacc    360
atgtgtctct aactgtgcca ctctgtggtt caggaaacct ggttgaaaaa ctttcaccat    420
ggttcatgga tggcgaaaat gcctatgaag tggtgaaggc catgttactt aaaaaggagc    480
cacttctcta tgtgcccatc cggctggctg gacacactag acacctccca ggtcctcgtg    540
tgtacctggt tgagaggctc attgcttgtg aaaatccatt catggttaac caattggctt    600
atagctctag tgcaaatggc agcctggttg gcacaacttt gcagggcaag cctattggta    660
tgttcttccc ttatgacatc gaacttgtca caggaaagca aaatattctc ctgcgcaagt    720
atggccgtgg tggttatcac tacaccccat tccactatga gcgagacaac acctcttgcc    780
ctgagtggat ggacgatttt gaggcggatc ctaaaggcaa atatgcccag aatctgctta    840
agaagttgat tggcggtgat gtcactccag ttgaccaata catgtgtggc gttgatggaa    900
aacccattag tgcctacgca tttttaatgg ccaaggatga ataaccaaa ctggctgatg    960 ttgaagcgga cgtcgcagca cgtgctgatg acgaaggctt catcacatta aagaacaatc   1020
tatatagatt ggtttggcat gttgagcgta aagacgttcc atatcctaag caatctattt   1080
ttactattaa tagtgtggtc caaaaggatg gtgttgaaaa cactcctcct cactatttta   1140
ctcttggatg caaaattta acgctcaccc cacgcaacaa gtggagtggc gtttctgact   1200
tgtccctcaa acaaaaactc ctttacacct tctatggtaa ggagtcactt gagaacccaa   1260
cctacattta ccactccgca ttcattgagt gtggaagttg tggtaatgat tcctggctta   1320
```

```
cagggaatgc tatccaaggg tttgcctgtg gatgtggggc atcatataca gctaatgatg   1380
tcgaagtcca atcatctggc atgattaagc caaatgctct tctttgtgct acttgcccct   1440
ttgctaaggg tgatagctgt tcttctaatt gcaaacattc agttgctcag ttggttagtt   1500
acctttctga acgctgtaat gttattgctg attctaagtc cttcacactt atctttggtg   1560
gcgtagctta cgcctacttt ggatgtgagg aaggtactat gtactttgtg cctagagcta   1620
agtctgttgt ctcaaggatt ggagactcca tctttacagg ctgtactggc tcttggaaca   1680
aggtcactca aattgctaac atgttcttgg aacagactca gcattccctt aactttgtgg   1740
gagagttcgt tgtcaacgat gttgtcctcg caattctctc tggaaccaca actaatgttg   1800
acaaaatacg ccagcttctc aaaggtgtca cccttgacaa gttgcgtgat tatttagctg   1860
actatgacgt agcagtcact gccggcccat tcatggataa tgctattaat gttggtggta   1920
caggattaca gtatgccgcc attactgcac cttatgtagt tctcactggc ttaggtgagt   1980
cctttaagaa agttgcaacc ataccgtata aggtttgcaa ctctgttaag gatactctgg   2040
cttattatgc tcacagcgtg ttgtacagag ttttccctta tgacatggat tctggtgtgt   2100
catcctttag tgaactactt tttgattgcg ttgatctttc agtagcttct acctattttt   2160
tagtccgcat cttgcaagat aagactggcg actttatgtc tacaattatt acttcctgcc   2220
aaactgctgt tagtaagctt ctagatacat gttttgaagc tacagaagca acatttaact   2280
tcttgttaga tttggcagga ttgttcagaa tcttctccg caatgcctat gtgtacactt   2340
cacaagggtt tgtggtggtc aatggcaaag tttctacact tgtcaaacaa gtgttagact   2400
tgcttaataa gggtatgcaa cttttgcata caaaggtctc ctgggctggt tctaaaatca   2460
ttgctgttat ctacagcggc agggagtctc taatattccc atcgggaacc tattactgtg   2520
tcaccactaa ggctaagtcc gttcaacaag atcttgacgt tattttgcct ggtgagtttt   2580
ccaagaagca gttaggactg ctccaaccta ctgacaattc tacaactgtt agtgttactg   2640
tatccagtaa catggttgaa actgttgtgg gtcaacttga gcaaactaat atgcatagtc   2700
ctgatgttat agtaggtgac tatgtcatta ttagtgaaaa attgtttgtg cgtagtaagg   2760
aagaagacgg atttgccttc tacccctgctt gcactaatgg tcatgctgta ccgactctct   2820
ttagacttaa gggaggtgca cctgtaaaaa aagtagcctt tggcggtgat caagtacatg   2880
aggttgctgc tgtaagaagt gttactgtcg agtacaacat tcatgctgta ttagacacac   2940
tacttgcttc ttctagtctt agaacctttg ttgtagataa gtctttgtca attgaggagt   3000
ttgctgacgt agtaaaggaa caagtctcag acttgcttgt taaattactg cgtggaatgc   3060
cgattccaga ttttgattta gacgatttta ttgacgcacc atgctattgc tttaacgctg   3120
agggtgatgc atcctggtct tctactatga tcttctctct tcaccccgtc gagtgtgacg   3180
aggagtgttc tgaagtagag gcttcagatt tagaagaagg tgaatcagag tgcatttctg   3240
agacttcaac tgaacaagtt gacgtttctc atgagacttc tgacgacgag tgggctgctg   3300
cagttgatga agcgttccct ctcgatgaag cagaagatgt tactgaatct gtgcaagaag   3360
aagcacaacc agtagaagta cctgttgaag atattgcgca ggttgtcata gctgacacct   3420
tacaggaaac tcctgttgtg cctgatactg ttgaagtccc accgcaagtg gtgaaacttc   3480
cgtctgcacc tcagactatc cagcccgagg taaagaagt tgcacctgtc tatgaggctg   3540
ataccgaaca gacacagaat gttactgtta aacctaagag gttacgcaaa aagcgtaatg   3600 ttgaccccttt gtccaatttt gaacataagg ttattacaga gtgcgttacc atagttttag   3660
gtgacgcaat tcaagtagcc aagtgctatg gggagtctgt gttagttaat gctgctaaca   3720
```

```
cacatcttaa gcatggcggt ggtatcgctg gtgctattaa tgcggcttca aaaggggctg    3780
tccaaaaaga gtcagatgag tatattctgg ctaaagggcc gttacaagta ggagattcag    3840
ttctcttgca aggccattct ctagctaaga atatcctgca tgtcgtaggc ccagatgccc    3900
gcgctaaaca ggatgtttct ctccttagta agtgctataa ggctatgaat gcatatcctc    3960
ttgtagtcac tcctcttgtt tcagcaggca tatttggtgt aaaaccagct gtgtcttttg    4020
attatcttat tagggaggct aagactagag ttttagtcgt cgttaattcc caagatgtct    4080
ataagagtct taccatagtt gacattccac agagtttgac ttttttcatat gatgggttac    4140 gtggcgcaat acgtaaagct aaagattatg gttttactgt ttttgtgtgc acagacaact    4200
ctgctaacac taaagttctt aggaacaagg gtgttgatta tactaagaag tttcttacag    4260
ttgacggtgt gcaatattat tgctacacgt ctaaggacac tttagatgat atcttacaac    4320
aggctaataa gtctgttggt attatatcta tgcctttggg atatgtgtct catggtttag    4380
acttaatgca agcagggagt gtcgtgcgta gagttaacgt gccctacgtg tgtctcctag    4440
ctaataaaga gcaagaagct attttgatgt ctgaagacgt taagttaaac ccttcagaag    4500
attttataaa gcacgtccgc actaatggtg gttacaattc ttggcattta gtcgagggtg    4560
aactattggt gcaagactta cgcttaaata agctcctgca ttggtctgat caaaccatat    4620
gctacaagga tagtgtgttt tatgttgtaa agaatagtac agcttttcca tttgaaacac    4680
tttcagcatg tcgtgcgtat ttggattcac gcacgacaca gcagttaaca atcgaagtct    4740
tagtgactgt cgatggtgta aattttagaa cagtcgttct aaataataag aacacttata    4800
gatcacagct tggatgcgtt ttctttaatg gtgctgatat ttctgacacc attcctgatg    4860
agaaacagaa tggtcacagt ttatatctag cagacaattt gactgctgat gaaacaaagg    4920
cgcttaaaga gttatatggc cccgttgatc ctacttcctt acacagattc tattcactta    4980
aggctgcagt ccatgggtgg aagatggttg tgtgtgataa ggtacgttct ctcaaattga    5040
gtgataataa ttgttatctt aatgcagtta ttatgacact tgatttattg aaggacatta    5100
aatttgttat acctgctcta cagcatgcat ttatgaaaca taagggcggt gattcaactg    5160
acttcatagc cctcattatg gcttatggca attgcacatt tggtgctcca gatgatgcct    5220
ctcggttact tcataccgtg cttgcaaagg ctgagttatg ctgttctgca cgcatggttt    5280
ggagagagtg gtgcaatgtc tgtggcataa agatgttgt tctacaaggc ttaaaagctt    5340
gttgttacgt gggtgtgcaa actgttgaag atctgcgtgc tcgcatgaca tatgtatgcc    5400
agtgtggtgg tgaacgtcat cggcaattag tcgaacacac caccccctgg ttgctgctct    5460
caggcacacc aaatgaaaaa ttggtgacaa cctccacggc gcctgatttt gtagcattta    5520 atgtcttttca gggcattgaa acggctgttg gccattatgt tcatgctcgc ctgaagggtg    5580
gtcttatttt aaagtttgac tctggcaccg ttagcaagac ttcagactgg aagtgcaagg    5640
tgacagatgt acttttcccc ggccaaaaat acagtagcga ttgtaatgtc gtacggtatt    5700
ctttggacgg taatttcaga acagaggttg atcccgacct atctgctttc tatgttaagg    5760
atggtaaata ctttacaagt gaaccacccg taacatattc accagctaca attttagctg    5820
gtagtgtcta cactaatagc tgccttgtat cgtctgatgg acaacctggc ggtgatgcta    5880
ttagtttgag ttttaataac ctttagggt ttgattctag taaaccagtc actaagaaat    5940
acacttactc cttcttgcct aaagaagacg gcgatgtgtt gttggctgag tttgacactt    6000
atgaccctat ttataagaat ggtgccatgt ataaaggcaa accaattctt tgggtcaata    6060
```

```
aagcatctta tgatactaat cttaataagt tcaatagagc tagtttgcgt caaattttg    6120 acgtagcccc cattgaactc gaaaataaat tcacaccttt gagtgtggag tctacaccag   6180
ttgaacctcc aactgtagat gtggtagcac ttcaacagga aatgacaatt gtcaaatgta   6240
agggtttaaa taaacctttc gtgaaggaca atgtcagttt cgttgctgat gattcaggta   6300
ctcccgttgt tgagtatctg tctaaagaag acctacatac attgtatgta gaccctaagt   6360
atcaagtcat tgtcttaaaa gacaatgtac tttcttctat gcttagattg cacaccgttg   6420
agtcaggtga tattaacgtt gttgcagctt ccggatcttt gacacgtaaa gtgaagttac   6480
tatttagggc ttcattttat ttcaaagaat ttgctacccg cactttcact gctaccactg   6540
ctgtaggtag ttgtataaag agtgtagtgc ggcatctagg tgttactaaa ggcatattga   6600
caggctgttt tagttttgcc aagatgttat ttatgcttcc actagcttac tttagtgatt   6660
caaaactcgg caccacagag gttaaagtga gtgctttgaa aacagccggc gttgtgacag   6720
gtaatgttgt aaaacagtgt tgcactgctg ctgttgattt aagtatggat aagttgcgcc   6780
gtgtggattg gaaatcaacc ctacggttgt tacttatgtt atgcacaact atggtattgt   6840
tgtcttctgt gtatcacttg tatgtcttca atcaggtctt atcaagtgat gttatgtttg   6900
aagatgccca aggtttgaaa aagttctaca agaagttag agcttaccta ggaatctctt    6960
ctgcttgtga cggtcttgct tcagcttata gggcgaattc ctttgatgta cctacattct   7020
gcgcaaaccg ttctgcaatg tgtaattggt gcttgattag ccaagattcc ataactcact   7080
acccagctct taagatggtt caaacacatc ttagccacta tgttcttaac atagattggt   7140
tgtggtttgc atttgagact ggtttggcat acatgctcta tacctcggcc ttcaactggt   7200
tgttgttggc aggtacattg cattatttct ttgcacagac ttccatattt gtagactggc   7260
ggtcatacaa ttatgctgtg tctagtgcct tctggttatt cacccacatt ccaatggcgg   7320
gtttggtacg aatgtataat ttgttagcat gcctttggct tttacgcaag ttttatcagc   7380
atgtaatcaa tggttgcaaa gatacggcat gcttgctctg ctataagagg aaccgactta   7440
ctagagttga agcttctacc gttgtctgtg gtggaaaacg tacgtttat atcacagcaa    7500 atggcggtat ttcattctgt cgtaggcata attggaattg tgtggattgt gacactgcag   7560
gtgtggggaa taccttcatc tgtgaagaag tcgcaaatga cctcactacc gccctacgca   7620
ggcctattaa cgctacggat agatcacatt attatgtgga ttccgttaca gttaaagaga   7680
ctgttgttca gtttaattat cgtagagacg gtcaaccatt ctacgagcgg tttcccctct   7740
gcgcttttac aaatctagat aagttgaagt tcaaagaggg ctgtaaaact actactggta   7800
tacctgaata caactttatc atctacgact catcagatcg tggccaggaa agtttagcta   7860
ggtctgcatg tgtttattat tctcaagtct tgtgtaaatc aattcttttg gttgactcaa   7920
gtttggttac ttctgttggt gattctagtg aaatcgccac taaaatgttt gattcctttg   7980
ttaatagttt cgtctcgctg tataatgtca cacgcgataa gttggaaaaa cttatctcta   8040
ctgctcgtga tggcgtaagg cgaggcgata acttccatag tgtcttaaca acattcattg   8100
acgcagcacg aggccccgca ggtgtggagt ctgatgttga gaccaatgaa attgttgact   8160
ctgtgcagta tgctcataaa catgacatac aaattactaa tgagagctac aataattatg   8220
taccctcata tgttaaacct gatagtgtgt ctaccagcga tttaggtagt ctcattgatt   8280
gtaatgcggc ttcagttaac caaattgtct tgcgtaattc taatggtgct tgcatttgga   8340
acgctgctgc atatatgaaa ctctcggatg cacttaaacg acagattcgc attgcatgcc   8400
gtaagtgtaa tttagcttc cggttaacca cctcaaagct acgcgctaat gataatatct    8460
```

```
tatcagttag attcactgct aacaaaattg ttggtggtgc tcctacatgg tttaatgcgt    8520
tgcgtgactt tacgttaaag ggttatgttc ttgctaccat tattgtgttt ctgtgtgctg    8580
tactgatgta tttgtgttta cctacatttt ctatggcacc tgttgaattt tatgaagacc    8640
gcatcttgga ctttaaagtt cttgataatg gtatcattag ggatgtaaat cctgatgata    8700
agtgctttgc taataagcac cggtccttca cacaatggta tcatgagcat gttggtggtg    8760
tctatgacaa ctctatcaca tgcccattga cagttgcagt aattgctgga gttgctggtg    8820
ctcgcattcc agacgtacct actacattgg cttgggtgaa caatcagata attttctttg    8880
tttctcgagt ctttgctaat acaggcagtg tttgctacac tcctatagat gagataccct    8940
ataagagttt ctctgatagt ggttgcattc ttccatctga gtgcactatg tttagggatg    9000
cagagggccg tatgacacca tactgccatg atcctactgt tttgcctggg cttttgcgt    9060 acagtcagat gaggcctcat gttcgttacg acttgtatga tggtaacatg tttattaaat    9120
ttcctgaagt agtatttgaa agtacactta ggattactag aactctgtca actcagtact    9180
gccggttcgg tagttgtgag tatgcacaag agggtgtttg tattaccaca aatggctcgt    9240
gggccatttt taatgaccac catcttaata gacctggtgt ctattgtggc tctgattta    9300 ttgacattgt caggcggtta gcagtatcac tgttccagcc tattacttat ttccaattga    9360
ctacctcatt ggtcttgggt ataggtttgt gtgcgttcct gactttgctc ttctattata    9420
ttaataaagt aaaacgtgct tttgcagatt acacccagtg tgctgtaatt gctgttgttg    9480
ctgctgttct taatagcttg tgcatctgct ttgttacctc tataccattg tgtatagtac    9540
cttacactgc attgtactat tatgctacat tctatttac taatgagcct gcatttatta    9600
tgcatgtttc ttggtacatt atgttcgggc ctatcgttcc catatggatg acctgcgtct    9660
atacagttgc aatgtgcttt agacacttct tctgggtttt agcttatttt agtaagaaac    9720
atgtagaagt ttttactgat ggtaagctta attgtagttt ccaggacgct gcctctaata    9780
tctttgttat taacaaggac acttatgcag ctcttagaaa ctctttaact aatgatgcct    9840
attcacgatt tttggggttg tttaacaagt ataagtactt ctctggtgct atggaaacag    9900
ccgcttatcg tgaagctgca gcatgtcatc ttgctaaagc cttacaaaca tacagcgaga    9960
ctggtagtga tcttctttac caaccaccca actgtagcat aacctctggc gtgttgcaaa   10020
gcggtttggt gaaaatgtca catcccagtg gagatgttga ggcttgtatg gttcaggtta   10080
cctgcggtag catgactctt aatggtcttt ggcttgacaa cacagtctgg tgcccacgac   10140
acgtaatgtg cccggctgac cagttgtctg atcctaatta tgatgccttg ttgatttcta   10200
tgactaatca tagtttcagt gtgcaaaaac acattggcgc tccagcaaac ttgcgtgttg   10260
ttggtcatgc catgcaaggc actctttga agttgactgt cgatgttgct aaccctagca   10320
ctccagccta cactttaca acagtgaaac ctggcgcagc atttagtgtg ttagcatgct   10380
ataatggtcg tccgactggt acattcactg ttgtaatgcg ccctaactac acaattaagg   10440
gttcctttct gtgtggttct tgtggtagtg ttggttacac caaggagggt agtgtgatca   10500
atttctgtta catgcatcaa atggaacttg ctaatggtac atataccggt tcagcatttg   10560
atggtactat gtatggtgcc tttatggata aacaagtgca ccaagttcag ttaacagaca   10620
aatactgcag tgttaatgta gtagcttggc tttacgcagc aatacttaat ggttgcgctt   10680
ggtttgtaaa acctaatcgc actagtgttg tttcttttaa tgaatgggct cttgccaacc   10740
aattcactga atttgttggc actcaatccg ttgacatgtt agctgtcaaa acaggcgttg   10800
```

```
ctattgaaca gctgctttat gcgatccaac aactgtatac tgggttccag ggaaagcaaa    10860
tccttggcag taccatgttg gaagatgaat tcacacctga ggatgttaat atgcagatta    10920
tgggtgtggt tatgcagagt ggtgtgagaa aagttacata tggtactgcg cattggttgt    10980
ttgcgaccct tgtctcaacc tatgtgataa tcttacaagc cactaaattt actttgtgga    11040
actacttgtt tgagactatt cccacacagt tgttcccact cttatttgtg actatggcct    11100
tcgttatgtt gttggttaaa cacaaacaca ccttttttgac acttttcttg ttgcctgtgg    11160
ctatttgttt gacttatgca aacatagtct acgagcccac tactcccatt tcgtcagcgc    11220
tgattgcagt tgcaaattgg cttgccccca ctaatgctta tgcgcacact acacatactg    11280
atattggtgt ctacattagt atgtcacttg tattagtcat tgtagtgaag agattgtaca    11340
acccatcact ttctaacttt gcgttagcat tgtgcagtgg tgtaatgtgg ttgtacactt    11400
atagcattgg agaagcctca agccccattg cctatctggt ttttgtcact acactcacta    11460
gtgattatac gattacagtc tttgttactg tcaaccttgc aaaagtttgc acttatgcca    11520
tctttgctta ctcaccacag cttacacttg tgtttccgga agtgaagatg atacttttat    11580
tatacacatg tttaggtttc atgtgtactt gctattttgg tgtcttctct cttttgaacc    11640
ttaagcttag agcacctatg ggtgtctatg actttaaggt ctcaacacaa gagttcagat    11700
tcatgactgc taacaatcta actgcaccta gaaattcttg ggaggctatg ctctgaact    11760 ttaagttaat aggtattggc ggtacacctt gtataaaggt tgctgctatg cagtctaaac    11820
ttacagatct taaatgcaca tctgtggttc tcctctctgt gctccaacag ttacacttag    11880
aggctaatag tagggcctgg gctttctgtg ttaaatgcca taatgatata ttggcagcaa    11940
cagaccccag tgaggctttc gagaaattcg taagtctctt tgctacttta atgactttt    12000 ctggtaatgt agatcttgat gcgttagcta gtgatatttt tgacactcct agcgtacttc    12060
aagctactct ttctgagttt cacacttag ctacctttgc tgagttggaa gctgcgcaga    12120
aagcctatca ggaagctatg gactctggtg acacctcacc acaagttctt aaggctttgc    12180
agaaggctgt taatatagct aaaaacgcct atgagaagga taggcagtg gccgtaagt    12240 tagaacgtat ggctgatcag gctatgactt ctatgtataa gcaagcacgt gctgaagaca    12300
agaaagcaaa aattgtcagt gctatgcaaa ctatgttgtt tggatgatt aagaagctcg    12360 acaacgatgt tcttaatggt atcatttcta acgctaggaa tggttgtata cctcttagtg    12420
tcatcccact gtgtgcttca ataaaacttc gcgttgtaat tcctgacttc accgtctgga    12480
atcaggtagt cacatatccc tcgcttaact acgctgggc tttgtgggac attacagtta    12540
taaacaatgt ggacaatgaa attgttaagt cttcagatgt tgtagacagc aatgaaaatt    12600
taacatggcc acttgtttta gaatgcacta gggcatccac ttctgccgtt aagttgcaaa    12660
ataatgagat caaaccttca ggtctaaaaa ccatggttgt gtctgcgggt caagagcaaa    12720
ctaactgtaa tactagttcc ttagcttatt acgaacctgt gcagggtcgt aaaatgctga    12780
tggctcttct ttctgataat gcctatctca aatgggcgcg tgttgaaggt aaggacggat    12840
ttgtcagtgt agagctacaa cctccttgca aattcttgat tgcgggacca aaaggacctg    12900
aaatccgata tctctatttt gttaaaaatc ttaacaacct tcatcgcggg caagtgttag    12960
ggcacattgc tgcgactgtt agattgcaag ctggttctaa caccgagttt gcctctaatt    13020
cctcggtgtt gtcacttgtt aacttcaccg ttgatcctca aaaagcttat ctcgatttcg    13080
tcaatgcggg aggtgcccca ttgacaaatt gtgttaagat gcttactcct aaaactggta    13140
caggtatagc tatatctgtt aaaccagaga gtacagctga tcaagagact tatggtggag    13200
```

```
cttcagtgtg tctctattgc cgtgcgcata tagaacatcc tgatgtctct ggtgtttgta   13260
aatataaggg taagtttgtc caaatccctg ctcagtgtgt ccgtgaccct gtgggatttt   13320
gtttgtcaaa taccccctgt aatgtctgtc aatattggat tggatatggg tgcaattgtg   13380
actcgcttag gcaagcagca ctgccccaat ctaaagattc caattttta aacgagtccg    13440 gggttctatt gtaaatgccc gaatagaacc ctgttcaagt ggtttgtcca ctgatgtcgt   13500
ctttagggca tttgacatct gcaactataa ggctaaggtt gctggtattg gaaaatacta   13560
caagactaat acttgtaggt ttgtagaatt agatgaccaa gggcatcatt tagactccta   13620
ttttgtcgtt aagaggcata ctatggagaa ttatgaacta gagaagcact gttacgactt   13680
gttacgtgac tgtgatgctg tagctcccca tgatttcttc atctttgatg tagacaaagt   13740
taaaacacct catattgtac gtcagcgttt aactgagtac actatgatgg atcttgtata   13800
tgccctgagg cactttgatc aaaatagcga agtgcttaag gctatcttag tgaagtatgg   13860
ttgctgtgat gttacctact ttgaaaataa actctggttt gattttgttg aaaatcccag   13920
tgttattggt gtttatcata aacttggaga acgtgtacgc caagctatct taaacactgt   13980
taaattttgt gaccacatgg tcaaggctgg tttagtcggt gtgctcacac tagacaacca   14040
ggaccttaat ggcaagtggt atgattttgg tgacttcgta atcactcaac ctggttcagg   14100
agtagctata gttgatagct actattctta tttgatgcct gtgctctcaa tgaccgattg   14160
tctggccgct gagacacata gggattgtga ttttaataaa ccactcattg agtggccact   14220
tactgagtat gattttactg attataaggt acaactcttt gagaagtact ttaaatattg   14280
ggatcagacg tatcacgcaa attgcgttaa ttgtactgat gaccgttgtg tgttacattg   14340
tgctaatttc aatgtattgt ttgctatgac catgcctaag acttgtttcg gacccatagt   14400
ccgaaagatc tttgttgatg gcgtgccatt tgtagtatct tgtggttatc actacaaaga   14460
attaggttta gtcatgaata tggatgttag tctccataga cataggctct ctcttaagga   14520
gttgatgatg tatgccgctg atccagccat gcacattgcc tcctctaacg cttttcttga   14580
tttgaggaca tcatgtttta gtgtcgctgc acttacaact ggtttgactt tcaaactgt    14640 gcggcctggc aattttaacc aagacttcta tgatttcgtg gtatctaaag gtttctttaa   14700
ggagggctct tcagtgacgc tcaaacattt tttctttgct caagatggta atgctgctat   14760
tacagattat aattactatt cttataatct gcctactatg tgtgacatca acaaatgtt    14820 gttctgcatg gaagttgtaa acaagtactt cgaaatctat gacggtggtt gtcttaatgc   14880
ttctgaagtg gttgttaata atttagacaa gagtgctggc catccttta ataagtttgg    14940 caaagctcgt gtctattatg agagcatgtc ttaccaggag caagatgaac ttttgccat    15000 gacaaagcgt aacgtcattc ctaccatgac tcaaatgaat ctaaaatatg ctattagtgc   15060
taagaataga gctcgcactg ttgcaggcgt gtccatactt agcacaatga ctaatcgcca   15120
gtaccatcag aaaatgctta agtccatggc tgcaactcgt ggagcgactt gcgtcattgg   15180
tactacaaag ttctacggtg gctgggattt catgcttaaa acattgtaca agatgttga    15240 taatccgcat cttatgggtt gggattaccc taagtgtgat agagctatgc ctaatatgtg   15300
tagaatcttc gcttcactca tattagctcg taaacatggc acttgttgta ctacaagga    15360 cagattttat cgcttggcaa atgagtgtgc tcaggtgcta agcgaatatg ttctatgtgg   15420
tggtggttac tacgtcaaac ctggaggtac cagtagcgga gatgccacca ctgcatatgc   15480
caatagtgtc tttaacattt tgcaggcgac aactgctaat gtcagtgcac ttatgggtgc   15540
```

```
taatggcaac aagattgttg acaaagaagt taaagacatg cagtttgatt tgtatgtcaa   15600
tgtttacagg agcactagcc cagacccaa atttgttgat aaatactatg cttttcttaa   15660 taagcactt tctatgatga tactgtctga tgacggtgtc gtttgctata atagtgatta   15720
tgcagctaag ggttacattg ctggaataca gaattttaag gaaacgctgt attatcagaa   15780
caatgtcttt atgtctgaag ctaaatgctg ggtggaaacc gatctgaaga aagggccaca   15840
tgaattctgt tcacagcata cgctttatat taaggatggc gacgatggtt acttccttcc   15900
ttatccagac ccttcaagaa ttttgtctgc cggttgcttt gtagatgata tcgttaagac   15960
tgacggtaca ctcatggtag agcggttttgt gtctttggct atagatgctt accctctcac   16020
aaagcatgaa gatatagaat accagaatgt attctgggtc tacttacagt atatagaaaa   16080
actgtataaa gaccttacag gacacatgct tgacagttat tctgtcatgc tatgtggtga   16140
taattctgct aagttttggg aagaggcatt ctatagagat ctctatagtt cgcctaccac   16200
tttgcaggct gtcggttcat gcgttgtatg ccattcacag acttccctac gctgtgggac   16260
atgcatccgt agaccatttc tctgctgtaa atgctgctat gatcatgtta tagcaactcc   16320
acataagatg gttttgtctg tttctcctta cgtttgtaat gcccctggtt gtggcgtttc   16380
agacgttact aagctatatt taggtggtat gagctacttt tgtgtagatc atagacctgt   16440
gtgtagtttt ccactttgcg ctaatggtct tgtattcggc ttatacaaga atatgtgcac   16500
aggtagtcct tctatagttg aatttaatag gttggctacc tgtgactgga ctgaaagtgg   16560
tgattacacc cttgccaata ctacaacaga accactcaaa ctttttgctg ctgagacttt   16620
acgtgccact gaagaggcgt ctaagcagtc ttatgctatt gccaccatca agaaattgt   16680 tggtgagcgc caactattac ttgtgtggga ggctggcaag tccaaaccac cactcaatcg   16740
taattatgtt tttactggtt atcatataac caaaaatagt aaagtgcagc tcggtgagta   16800
cattttcgag cgcattgatt atagtgatgc tgtatcctac aagtctagta caacgtataa   16860
actgactgta ggtgacatct tcgtacttac ctctcactct gtggctacct tgacggcgcc   16920
cacaattgtg aatcaagaga ggtatgttaa aattactggg ttgtacccaa ccattacggt   16980
acctgaagag ttcgcaagtc atgttgccaa cttccaaaaa tcaggttata gtaaatatgt   17040
cactgttcag ggaccacctg gcactggcaa aagtcatttt gctatagggt tagcgattta   17100 ctacccctaca gcacgtgttg tttatacagc atgttcacac gcagctgttg atgctttgtg   17160
tgaaaaagct tttaaatatt tgaacattgc taaatgttcc cgtatcattc ctgcaaaggc   17220
acgtgttgag tgctatgaca ggtttaaagt taatgagaca aattctcaat attgtttag   17280 tactattaat gctctaccag aaacttctgc cgatattctg gtggttgatg aggttagtat   17340
gtgcactaat tatgatcttt caattattaa tgcacgtatt aaagctaagc acattgtcta   17400
tgtaggagat ccagcacagt tgccagctcc taggactttg ttgactagag gcacattgga   17460
accagaaaat ttcaatagtg tcactagatt gatgtgtaac ttaggtcctg acatattttt   17520
aagtatgtgc tacaggtgtc ctaaggaaat agtaagcact gtgagcgctc ttgtctacaa   17580
taataaattg ttagccaaga aggagctttc aggccagtgc tttaaaatac tctataaggg   17640
caatgtgacg catgatgcta gctctgccat taatagacca caactcacat tgtgaagaa   17700 ttttattact gccaatccgg catggagtaa ggcagtcttt atttcgcctt acaattcaca   17760
gaatgctgtg tctcgttcaa tgctgggtct taccactcag actgttgatt cctcacaggg   17820
ttcagaatac cagtacgtta tcttctgtca aacagcagat acggcacatg ctaacaacat   17880
taacagattt aatgttgcaa tcactcgtgc ccaaaaaggt attctttgtg ttatgacatc   17940
```

```
tcaggcactc tttgagtcct tagagtttac tgaattgtct tttactaatt acaagctcca   18000
gtctcagatt gtaactggcc tttttaaaga ttgctctaga gaaacttctg gcctctcacc   18060
tgcttatgca ccaacatatg ttagtgttga tgacaagtat aagacgagtg atgagctttg   18120
cgtgaatctt aatttacccg caaatgtccc atactctcgt gttatttcca ggatgggctt   18180
taaactcgat gcaacagttc ctggatatcc taagcttttc attactcgtg aagaggctgt   18240
aaggcaagtt cgaagctgga taggcttcga tgttgagggt gctcatgctt cccgtaatgc   18300
atgtggcacc aatgtgcctc tacaattagg attttcaact ggtgtgaact tgttgttcca   18360
gccagttggt gttgtagaca ctgagtgggg taacatgtta acgggcattg ctgcacgtcc   18420
tccaccaggt gaacagttta agcacctcgt gcctcttatg cataagggg ctgcgtggcc    18480 tattgttaga cgacgtatag tgcaaatgtt gtcagacact ttagacaaat tgtctgatta   18540
ctgtacgttt gtttgttggg ctcatggctt tgaattaacg tctgcatcat acttttgcaa   18600
gataggtaag aacagaagt gttgcatgtg caatagacgc gctgcagcgt actcttcacc    18660
tctgcaatct tatgcctgct ggactcattc ctgcggttat gattatgtct acaacccttt   18720
ctttgtcgat gttcaacagt ggggttatgt aggcaatctt gctactaatc acgatcgtta   18780
ttgctctgtc catcaaggag ctcatgtggc ttctaatgat gcaataatga ctcgttgttt   18840
agctattcat tcttgtttta tagaacgtgt ggattgggat atagagtatc cttatatctc   18900
acatgaaaag aaattgaatt cctgttgtag aatcgttgag cgcaacgtcg tacgtgctgc   18960
tcttcttgcc ggttcatttg acaaagtcta tgatattggc aatcctaaag gaattcctat   19020
tgttgatgac cctgtggttg attggcatta ttttgatgca cagcccttga ccaggaaggt   19080
acaacagctt ttctatacag aggacatggc ctcaagattt gctgatgggc tctgcttatt   19140
ttggaactgt aatgtaccaa aatatcctaa taatgcaatt gtatgcaggt ttgacacacg   19200
tgtgcattct gagttcaatt tgccaggttg tgatggcggt agtttgtatg ttaacaagca   19260
cgcttttcat acaccagcat atgatgtgag tgcattccgt gatctgaaac ctttaccatt   19320
cttttattat tctactacac catgtgaagt gcatggtaat ggtagtatga tagaggatat   19380
tgattatgta cccctaaaat ctgcagtctg tattacagct tgtaatttag gggcgctgt    19440 ttgtaggaag catgctacag agtacagaga gtatatggaa gcataatc ttgtctctgc     19500 atcaggttc cgcctttggt gttataagac ctttgatatt tataatctct ggtctacttt    19560
tacaaaagtt caaggttggg aaaacattgc ttttaatgtt gttaaacaag gccattttat   19620
tggtgttgag ggtgaactac ctgtagctgt agtcaatgat aagatcttca ccaagagtgg   19680
cgttaatgac atttgtatgt ttgagaataa aaccactttg cctactaata tagcttttga   19740
actctatgct aagcgtgctg tacgctcgca tcccgatttc aaattgctac acaatttaca   19800
agcagacatt tgctacaagt tcgtcctttg ggattatgaa cgtagcaata tttatggtac   19860
tgctactatt ggtgtatgta agtacactga tattgatgtt aattcagctt gaatatatg    19920 ttttgacata cgcgataatt gttcattgga gaagttcatg tctactccca atgccatctt   19980
tatttctgat agaaaatca agaaatacc ttgtatggta ggtcctgatt atgcttactt      20040
caatggtgct atcatccgtg atagtgatgt tgttaaacaa ccagtgaagt tctacttgta   20100
taagaaagtc aataatgagt ttattgatcc tactgagtgt atttacactc agagtcgctc   20160
ttgtagtgac ttcctacccc tttctgacat ggagaaagac tttctatctt ttgatagtga   20220
tgttttcatt aagaagtatg gcttggaaaa ctatgctttt gagcacgtag tctatggaga   20280
```

```
cttctctcat actacgttag gcggtcttca cttgcttatt ggtttataca agaagcaaca    20340
ggaaggtcat attattatgg aagaaatgct aaaaggtagc tcaactattc ataactattt    20400
tattactgag actaacacag cggcttttaa ggcggtgtgt tctgttatag atttaaagct    20460
tgacgacttt gttatgattt taaagagtca agaccttggc gtagtatcca aggttgtcaa    20520
ggttcctatt gacttaacaa tgattgagtt tatgttatgg tgtaaggatg gacaggttca    20580
aaccttctac cctcgactcc aggcttctgc agattggaaa cctggtcatg caatgccatc    20640
cctctttaaa gttcaaaatg taaaccttga acgttgtgag cttgctaatt acaagcaatc    20700
tattcctatg cctcgcggtg tgcacatgaa catcgctaaa tatatgcaat gtgtgccagta   20760
tttaaatact tgcacattag ccgtgcctgc caatatgcgt gttatacatt ttggcgctgg    20820
ttctgataaa ggtatcgctc ctggtacctc agttttacga cagtggcttc ctacagatgc    20880
cattattata gataatgatt taaatgagtt cgtgtcagat gctgacataa ctttatttgg    20940
agattgtgta actgtacgtg tcggccaaca agtggatctt gttatttccg acatgtatga    21000
tcctactact aagaatgtaa caggtagtaa tgagtcaaag ctttattct  ttacttacct    21060
gtgtaacctc attaataata atcttgctct tggtgggtct gttgctatta aaataacaga    21120
acactcttgg agcgttgaac tttatgaact tatgggaaaa tttgcttggt ggactgtttt    21180
ctgcaccaat gcaaatgcat cctcatctga aggattcctc ttaggtatta attacttggg    21240
tactattaaa gaaaatatag atggtggtgc tatgcacgcc aactatatat tttggagaaa    21300
ttccactcct atgaatctga gtacttactc actttttgat ttatccaagt ttcaattaaa    21360
attaaaagga acaccagttc ttcaattaaa ggagagtcaa attaacgaac tcgtaatatc    21420
tctcctgtcg cagggtaagt tacttatccg tgacaatgat acactcagtg tttctactga    21480
tgttcttgtt aacacctaca gaaagttacg ttgatgtagg gccagattct gttaagtctg    21540
cttgtattga ggttgatata caacagactt tctttgataa aacttggcct aggccaattg    21600
atgtttctaa ggctgacggt attatatacc ctcaaggccg tacatattct aacataacta    21660
tcacttatca aggtctttt ccctatcagg agaccatgg tgatatgtat gtttactctg     21720
caggacatgc tacaggcaca actccacaaa agttgtttgt agctaactat tctcaggacg    21780
tcaaacagtt tgctaatggg tttgtcgtcc gtataggagc agctgccaat tccactggca    21840
ctgttattat tagcccatct accagcgcta ctatacgaaa aatttaccct gcttttatgc    21900
tgggttcttc agttggtaat ttctcagatg gtaaaatggg ccgcttcttc aatcatactc    21960
tagttctttt gcccgatgga tgtggcactt tacttagagc ttttttattgt attctagagc   22020
ctcgctctgg aaatcattgt cctgctggca attcctatac ttcttttgcc acttatcaca    22080
ctcctgcaac agattgttct gatggcaatt acaatcgtaa tgccagtctg aactcttta    22140
aggagtattt taatttacgt aactgcacct ttatgtacac ttataacatt accgaagatg    22200
agatttaga gtggtttggc attacacaaa ctgctcaagg tgttcacctc ttctcatctc    22260
ggtatgttga tttgtacggc ggcaatatgt ttcaatttgc caccttgcct gtttatgata    22320
ctattaagta ttattctatc attcctcaca gtattcgttc tatccaaagt gatagaaaag    22380
cttgggctgc cttctacgta tataaacttc aaccgttaac tttcctgttg gattttttctg    22440
ttgatggtta tacgcagaga ctatagact gtggttttaa tgatttgtca caactccact    22500
gctcatatga atccttcgat gttgaatctg gagtttattc agtttcgtct ttcgaagcaa    22560
aaccttctgg ctcagttgtg gaacaggctg aaggtgttga atgtgatttt tcacctcttc    22620
tgtctggcac acctcctcag gtttataatt tcaagcgttt ggttttttacc aattgcaatt   22680
```

```
ataatcttac caaattgctt tcactttttt ctgtgaatga ttttacttgt agtcaaatat   22740
ctccagcagc aattgctagc aactgttatt cttcactgat tttggattac ttttcatacc   22800
cacttagtat gaaatccgat ctcagtgtta gttctgctgg tccaatatcc cagtttaatt   22860
ataaacagtc cttttctaat cccacatgtt tgattttagc gactgttcct cataacctta   22920
ctactattac taagcctctt aagtacagct atattaacaa gtgctctcgt cttctttctg   22980
atgatcgtac tgaagtacct cagttagtga acgctaatca atactcaccc tgtgtatcca   23040
ttgtcccatc cactgtgtgg gaagacggtg attattatag gaaacaacta tctccacttg   23100
aaggtggtgg ctggcttgtt gctagtggct caactgttgc catgactgag caattacaga   23160
tgggctttgg tattacagtt caatatggta cagacaccaa tagtgtttgc cccaagcttg   23220
aatttgctaa tgcacacaaa attgcctctc aattaggcaa ttgcgtggaa tattccctct   23280
atggtgtttc gggccgtggt gttttcaga attgcacagc tgtaggtgtt cgacagcagc   23340
gctttgttta tgatgcgtac cagaatttag ttggctatta ttctgatgat ggcaactact   23400
actgtttgcg tgcttgtgtt agtgttcctg tttctgtcat ctatgataaa gaaactaaaa   23460
cccacgctac tctatttggt agtgttgcat gtgaacacat ttcttctacc atgtctcaat   23520
actcccgttc tacgcgatca atgcttaaac ggcgagattc tacatatggc ccccttcaga   23580
cacctgttgg ttgtgtccta ggacttgtta attcctcttt gttcgtagag gactgcaagt   23640
tgcctcttgg tcaatctctc tgtgctcttc ctgacacacc tagtactctc acacctcgca   23700
gtgtgcgctc tgttccaggt gaaatgcgct tggcatccat tgcttttaat catcctattc   23760
aggttgatca acttaatagt agttatttta aattaagtat acccactaat ttttcctttg   23820
gtgtgactca ggagtacatt cagacaacca ttcagaaagt tactgttgat tgtaaacagt   23880
acgtttgcaa tggtttccag aagtgtgagc aattactgcg cgagtatggc cagttttgtt   23940
ccaaaataaa ccaggctctc catggtgcca atttacgcca ggatgattct gtacgtaatt   24000
tgtttgcgag cgtgaaaagc tctcaatcat ctcctatcat accaggtttt ggaggtgact   24060
ttaatttgac acttctagaa cctgtttcta tatctactgg cagtcgtagt gcacgtagtg   24120
ctattgagga tttgctattt gacaaagtca ctatagctga tcctggttat atgcaaggtt   24180
acgatgattg catgcagcaa ggtccagcat cagctcgtga tcttatttgt gctcaatatg   24240
tggctggtta caaagtatta cctcctctta tggatgttaa tatggaagcc gcgtatactt   24300
catctttgct tggcagcata gcaggtgttg gctggactgc tggcttatcc tcctttgctg   24360
ctattccatt tgcacagagt atctttata ggttaaacgg tgttggcatt actcaacagg   24420
ttctttcaga gaaccaaaag cttattgcca ataagtttaa tcaggctctg ggagctatgc   24480
aaacaggctt cactacaact aatgaagctt ttcagaaggt tcaggatgct gtgaacaaca   24540
atgcacaggc tctatccaaa ttagctagcg agctatctaa tacttttggt gctatttccg   24600
cctctattgg agacatcata caacgtcttg atgttctcga acaggacgcc caaatagaca   24660
gacttattaa tggccgtttg acaacactaa atgcttttgt tgcacagcag cttgttcgtt   24720
ccgaatcagc tgctctcttc cgctcaattgg ctaaagataa agtcaatgag tgtgtcaagg   24780
cacaatccag gcgttctgga ttttgcggtc aaggcacaca tatagtgtcc tttgttgtaa   24840
atgcccctaa tggcctttac ttcatgcatg ttggttatta ccctagcaac cacattgagg   24900
ttgtttctgc ttatggtctt tgcgatgcag ctaaccctac taattgtata gcccctgtta   24960
atggctactt tattaaaact aataacacta ggattgttga tgagtggtca tatactggct   25020
```

```
cgtccttcta tgcacctgag cccattacct cccttaatac taagtatgtt gcaccacagg    25080
tgacatacca aaacatttct actaacctcc ctcctcctct tctcggcaat tccaccggga    25140
ttgacttcca agatgagttg gatgagtttt tcaaaaatgt tagcaccagt atacctaatt    25200
ttggttccct aacacagatt aatactacat tactcgatct tacctacgag atgttgtctc    25260
ttcaacaagt tgttaaagcc cttaatgagt cttacataga ccttaaagag cttggcaatt    25320
atacttatta caacaaatgg ccgtggtaca tttggcttgg tttcattgct gggcttgttg    25380
ccttagctct atgcgtcttc ttcatactgt gctgcactgg ttgtggcaca aactgtatgg    25440
gaaaacttaa gtgtaatcgt tgttgtgata gatacgagga atacgacctc gagccgcata    25500
aggttcatgt tcactaatta acgaactatt aatgagagtt caaagaccac ccactctctt    25560
gttagtgttt tcactctctc ttttggtcac tgcatcctca aaacctctct atgtacctga    25620
gcattgtcag aattattctg gttgcatgct tagggcttgt attaaaactg cccaagctga    25680
tacagctggt ctttatacaa attttcgaat tgacgtccca tctgcagaat caactggtac    25740
tcaatcagtt tctgtcgatc ttgagtcaac ttcaactcat gatggtccta ccgaacatgt    25800
tactagtgtg aatctttttg acgttggtta ctcagttaat taacgaactc tatggattac    25860
gtgtctctgc ttaatcaaat ttggcagaag taccttaact caccgtatac tacttgtttg    25920
tacatcccta aacccacagc taagtataca cctttagttg gcacttcatt gcaccctgtg    25980
ctgtggaact gtcagctatc ctttgctggt tatactgaat ctgctgttaa ttctacaaaa    26040
gctttggcca acaggacgc agctcagcga atcgcttggt tgctacataa ggatggagga    26100
atccctgatg atgttccct ctacctccgg cactcaagtt tattcgcgca aagcgaggaa    26160
gaggagccat tctccaacta agaaactgcg ctacgttaag cgtagatttt ctcttctgcg    26220
ccatgaagac cttagtgtta ttgtccaacc aacacactat gtcagggtta cattttcaga    26280
ccccaacatg tggtatctac gttcgggtca tcatttacac tcagttcaca attggcttaa    26340
accttatggc ggccaacctg tttctgagta ccatatact ctagctttgc taaatctcac    26400
tgatgaagat ttagctagag attttcacc cattgcgctc tttttgcgca atgtcagatt    26460
tgagctacat gagttcgcct tgctgcgcaa aactcttgtt cttaatgcat cagagatcta    26520
ctgtgctaac atacatagat ttaagcctgt gtatagagtt aacacggcaa tccctactat    26580
taaggattgg cttctcgttc agggattttc cctttaccat agtggcctcc ctttacatat    26640
gtcaatctct aaattgcatg cactggatga tgttactcgc aattacatca ttacaatgcc    26700
atgctttaga acttaccctc aacaaatgtt tgttactcct ttggccgtag atgttgtctc    26760
catacggtct tccaatcagg gtaataaaca aattgttcat tcttatccca ttttacatca    26820
tccaggattt taacgaacta tggctttctc ggcgtcttta tttaaacccg tccagctagt    26880
cccagtttct cctgcatttc atcgcattga gtctactgac tctattgttt tcacatacat    26940
tcctgctagc ggctatgtag ctgctttagc tgtcaatgtg tgtctcattc ccctattatt    27000
actgctacgt caagatactt gtcgtcgcag cattatcaga actatggttc tctatttcct    27060
tgttctgtat aacttttat tagccattgt actagtcaat ggtgtacatt atccaactgg    27120
aagttgcctg atagccttct tagttatcct cataatactt tggtttgtag atagaattcg    27180
tttctgtctc atgctgaatt cctacattcc actgtttgac atgcgttccc actttattcg    27240
tgttagtaca gtttcttctc atggtatggt ccctgtaata cacaccaaac cattatttat    27300
tagaaacttc gatcagcgtt gcagctgttc tcgttgtttt tatttgcact cttccactta    27360
tatagagtgc acttatatta gccgttttag taagattagc ctagtttctg taactgactt    27420
```

```
ctccttaaac ggcaatgttt ccactgtttt cgtgcctgca acgcgcgatt cagttcctct   27480
tcacataatc gcccccgagct cgcttatcgt ttaagcagct ctgcgctact atgggtcccg   27540
tgtagaggct aatccattag tctctctttg gacatatgga aaacgaacta tgttacccct   27600
tgtccaagaa cgaatagggt tgttcatagt aaactttttc attttaccg tagtatgtgc   27660 tataacactc ttggtgtgta tggctttcct tacggctact agattatgtg tgcaatgtat   27720
gacaggcttc aataccctgt tagttcagcc cgcattatac ttgtataata ctggacgttc   27780
agtctatgta aaattccagg atagtaaacc ccctctacca cctgacgagt gggtttaacg   27840
aactccttca taatgtctaa tatgacgcaa ctcactgagg cgcagattat tgccattatt   27900
aaagactgga actttgcatg gtccctgatc tttctcttaa ttactatcgt actacagtat   27960
ggatacccat cccgtagtat gactgtctat gtctttaaaa tgtttgtttt atggctccta   28020
tggccatctt ccatggcgct atcaatattt agcgccgttt atccaattga tctagcttcc   28080
cagataatct ctggcattgt agcagctgtt tcagctatga tgtggatttc ctactttgtg   28140
cagagtatcc ggctgtttat gagaactgga tcatggtggt cattcaatcc tgagactaat   28200
tgccttttga acgttccatt tggtggtaca actgtcgtac gtccactcgt agaggactct   28260
accagtgtaa ctgctgttgt aaccaatggc cacctcaaaa tggctggcat gcatttcggt   28320
gcttgtgact acgacagact tcctaatgaa gtcaccgtgg ccaaacccaa tgtgctgatt   28380
gctttaaaaa tggtgaagcg gcaaagctac ggaactaatt ccggcgttgc catttaccat   28440
agatataagg caggtaatta caggagtccg cctattacgg cggatattga acttgcattg   28500
cttcgagctt aggctcttta gtaagagtat cttaattgat tttaacgaat ctcaatttca   28560
ttgttatggc atccctgct gcacctcgtg ctgtttcctt tgccgataac aatgatataa   28620
caaatacaaa cctatctcga ggtagaggac gtaatccaaa accacgagct gcaccaaata   28680
acactgtctc ttggtacact gggcttaccc aacacgggaa agtccctctt acctttccac   28740
ctgggcaggg tgtacctctt aatgccaatt ctaccctgc gcaaaatgct gggtattggc   28800
ggagacagga cagaaaaatt aataccggga atggaattaa gcaactggct cccaggtggt   28860
acttctacta cactggaact ggacccgaag cagcactccc attccgggct gttaaggatg   28920
gcatcgtttg ggtccatgaa gatggcgcca ctgatgctcc ttcaactttt gggacgcgga   28980
accctaacaa tgattcagct attgttacac aattcgcgcc cggtactaag cttcctaaaa   29040
acttccacat tgaggggact ggaggcaata gtcaatcatc ttcaagagcc tctagcttaa   29100
gcagaaactc ttccagatct agttcacaag gttcaagatc aggaaactct acccgcggca   29160
cttctccagg tccatctgga atcggagcag taggaggtga tctactttac cttgatcttc   29220
tgaacagact acaagccctt gagtctggca aagtaaagca atcgcagcca aaagtaatca   29280
ctaagaaaga tgctgctgct gctaaaaata gatgcgcca caagcgcact tccaccaaaa   29340
gtttcaacat ggtgcaagct tttggtcttc gcgaccagg agacctccag ggaaactttg   29400
gtgatcttca attgaataaa ctcggcactg aggacccacg ttggccccaa attgctgagc   29460
ttgctcctac agccagtgct tttatgggta tgtcgcaatt taaacttacc catcagaaca   29520
atgatgatca tggcaaccct gtgtacttcc ttcggtacag tggagccatt aaacttgacc   29580
caaagaatcc caactacaat aagtggttgg agcttcttga gcaaaatatt gatgcctaca   29640
aaaccttccc taagaaggaa aagaaacaaa aggcaccaaa agaagaatca acagaccaaa   29700
tgtctgaacc tccaaaggag cagcgtgtgc aaggtagcat cactcagcgc actcgcaccc   29760
```

| | | | | |
|---|---|---|---|---|
| gtccaagtgt | tcagcctggt | ccaatgattg | atgttaacac | tgattagtgt | cactcaaagt | 29820 |
| aacaagatcg | cggcaatcgt | ttgtgtttgg | caacccccatc | tcaccatcgc | ttgtccactc | 29880 |
| ttgcacagaa | tggaatcatg | ttgtaattac | agtgcaataa | ggtaattata | acccatttaa | 29940 |
| ttgatagcta | tgctttatta | aagtgtgtag | ctgtagagag | aatgttaaag | actgtcacct | 30000 |
| ctgcttgatt | gcaagtgaac | agtgcccccc | gggaagagct | ctacagtgtg | aaatgtaaat | 30060 |
| aaaaaatagc | tattattcaa | ttagattagg | ctaattagat | gatttgcaaa | aaaaaaaaa | 30119 |

<210> SEQ ID NO 2
<211> LENGTH: 4062
<212> TYPE: DNA
<213> ORGANISM: Middle East Respiratory Syndrome Coronavirus

<400> SEQUENCE: 2

| | | | | | | |
|---|---|---|---|---|---|---|
| atgatacact | cagtgtttct | actgatgttc | ttgttaacac | ctacagaaag | ttacgttgat | 60 |
| gtagggccag | attctgttaa | gtctgcttgt | attgaggttg | atatacaaca | gactttcttt | 120 |
| gataaaactt | ggcctaggcc | aattgatgtt | tctaaggctg | acggtattat | ataccctcaa | 180 |
| ggccgtacat | attctaacat | aactatcact | tatcaaggtc | ttttcccta | tcagggagac | 240 |
| catggtgata | tgtatgttta | ctctgcagga | catgctacag | gcacaactcc | acaaaagttg | 300 |
| tttgtagcta | actattctca | ggacgtcaaa | cagtttgcta | tgggtttgt | cgtccgtata | 360 |
| ggagcagctg | ccaattccac | tggcactgtt | attattagcc | catctaccag | cgctactata | 420 |
| cgaaaaattt | accctgcttt | tatgctgggt | tcttcagttg | gtaatttctc | agatggtaaa | 480 |
| atgggccgct | tcttcaatca | tactctagtt | cttttgcccg | atggatgtgg | cactttactt | 540 |
| agagcttttt | attgtattct | agagcctcgc | tctggaaatc | attgtcctgc | tggcaattcc | 600 |
| tatacttctt | ttgccactta | tcacactcct | gcaacagatt | gttctgatgg | caattacaat | 660 |
| cgtaatgcca | gtctgaactc | ttttaaggag | tattttaatt | tacgtaactg | caccttatg | 720 |
| tacacttata | acattaccga | agatgagatt | ttagagtggg | ttggcattac | acaaactgct | 780 |
| caaggtgttc | acctcttctc | atctcggtat | gttgatttgt | acggcggcaa | tatgtttcaa | 840 |
| tttgccacct | tgcctgttta | tgatactatt | aagtattatt | ctatcattcc | tcacagtatt | 900 |
| cgttctatcc | aaagtgatag | aaaagcttgg | gctgccttct | acgtatataa | acttcaaccg | 960 |
| ttaactttcc | tgttggattt | ttctgttgat | ggttatatac | gcagagctat | agactgtggt | 1020 |
| tttaatgatt | tgtcacaact | ccactgctca | tatgaatcct | tcgatgttga | atctggagtt | 1080 |
| tattcagttt | cgtcttttcga | agcaaaacct | tctggctcag | ttgtggaaca | ggctgaaggt | 1140 |
| gttgaatgtg | atttttcacc | tcttctgtct | ggcacacctc | ctcaggttta | aatttcaag | 1200 |
| cgtttggttt | ttaccaattg | caattataat | cttaccaaat | tgctttcact | tttttctgtg | 1260 |
| aatgatttta | cttgtagtca | aatatctcca | gcagcaattg | ctagcaactg | ttattcttca | 1320 |
| ctgattttgg | attactttc | atacccactt | agtatgaaat | ccgatctcag | tgttagttct | 1380 |
| gctggtccaa | tatcccagtt | taattataaa | cagtcctttt | ctaatccac | atgtttgatt | 1440 |
| ttagcgactg | ttcctcataa | ccttactact | attactaagc | ctcttaagta | cagctatatt | 1500 |
| aacaagtgct | ctcgtcttct | ttctgatgat | cgtactgaag | tacctcagtt | agtgaacgct | 1560 |
| aatcaatact | caccctgtgt | atccattgtc | ccatccactg | tgtgggaaga | cggtgattat | 1620 |
| tataggaaac | aactatctcc | acttgaaggt | ggtggctggc | ttgttgctag | tggctcaact | 1680 |
| gttgccatga | ctgagcaatt | acagatgggc | tttggtatta | cagttcaata | tggtacagac | 1740 |
| accaatagtg | tttgccccaa | gcttgaattt | gctaatgaca | caaaaattgc | ctctcaatta | 1800 |

-continued

```
ggcaattgcg tggaatattc cctctatggt gtttcgggcc gtggtgtttt tcagaattgc    1860
acagctgtag gtgttcgaca gcagcgcttt gtttatgatg cgtaccagaa tttagttggc    1920
tattattctg atgatggcaa ctactactgt ttgcgtgctt gtgttagtgt tcctgtttct    1980
gtcatctatg ataaagaaac taaaacccac gctactctat tggtagtgt tgcatgtgaa     2040 cacatttctt ctaccatgtc tcaatactcc cgttctacgc gatcaatgct taaacggcga    2100
gattctacat atggccccct tcagacacct gttggttgtg tcctaggact tgttaattcc    2160
tctttgttcg tagaggactg caagttgcct cttggtcaat ctctctgtgc tcttcctgac    2220
acacctagta ctctcacacc tcgcagtgtg cgctctgttc caggtgaaat gcgcttggca    2280
tccattgctt ttaatcatcc tattcaggtt gatcaactta atagtagtta ttttaaatta    2340
agtataccca ctaattttc ctttggtgtg actcaggagt acattcagac aaccattcag     2400
aaagttactg ttgattgtaa acagtacgtt tgcaatggtt ccagaagtg tgagcaatta    2460 ctgcgcgagt atggccagtt tgttccaaa ataaaccagg ctctccatgg tgccaattta     2520
cgccaggatg attctgtacg taatttgttt gcgagcgtga aaagctctca atcatctcct    2580
atcataccag gttttggagg tgactttaat ttgacacttc tagaacctgt ttctatatct    2640
actggcagtc gtagtgcacg tagtgctatt gaggatttgc tatttgacaa agtcactata    2700
gctgatcctg ttatatgca aggttacgat gattgcatgc agcaaggtcc agcatcagct     2760
cgtgatctta tttgtgctca atatgtggct ggttacaaag tattacctcc tcttatggat    2820
gttaatatgg aagccgcgta tacttcatct ttgcttggca gcatagcagg tgttggctgg    2880
actgctggct tatcctcctt tgctgctatt ccatttgcac agagtatctt ttataggtta    2940
aacggtgttg gcattactca acaggttctt tcagagaacc aaaagcttat tgccaataag    3000
tttaatcagg ctctgggagc tatgcaaaca ggcttcacta caactaatga gcttttcag     3060 aaggttcagg atgctgtgaa caacaatgca caggctctat ccaaattagc tagcgagcta    3120
tctaatactt ttggtgctat ttccgcctct attggagaca tcatacaacg tcttgatgtt    3180
ctcgaacagg acgcccaaat agacagactt attaatggcc gtttgacaac actaaatgct    3240
tttgttgcac agcagcttgt tcgttccgaa tcagctgctc tttccgctca attggctaaa    3300
gataaagtca atgagtgtgt caaggcacaa tccaagcgtt ctggattttg cggtcaaggc    3360
acacatatag tgtcctttgt tgtaaatgcc cctaatggcc tttacttcat gcatgttggt    3420
tattacccta gcaaccacat tgaggttgtt tctgcttatg gtctttgcga tgcagctaac    3480
cctactaatt gtatagcccc tgttaatggc tactttatta aaactaataa cactaggatt    3540
gttgatgagt ggtcatatac tggctcgtcc ttctatgcac ctgagcccat tacctcctt     3600 aatactaagt atgttgcacc acaggtgaca taccaaaaca tttctactaa cctccctcct    3660
cctcttctcg gcaattccac cgggattgac ttccaagatg agttggatga gttttcaaa     3720 aatgttagca ccagtatacc taattttggt tccctaacac agattaatac tacattactc    3780
gatcttacct acgagatgtt gtctcttcaa caagttgtta agcccttaa tgagtcttac    3840 atagacctta aagagcttgg caattatact tattacaaca aatggccgtg gtacatttgg    3900
cttggtttca ttgctgggct tgttgcctta gctctatgcg tcttcttcat actgtgctgc    3960
actggttgtg gcacaaactg tatgggaaaa cttaagtgta atcgttgttg tgatagatac    4020
gaggaatacg acctcgagcc gcataaggtt catgttcact aa                       4062
```

<210> SEQ ID NO 3

-continued

```
<211> LENGTH: 1353
<212> TYPE: PRT
<213> ORGANISM: Middle East Respiratory Syndrome Coronavirus

<400> SEQUENCE: 3

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
```

```
              385                 390                 395                 400
        Arg Leu Val Phe Thr Asn Cys Asn Tyr Asn Leu Thr Lys Leu Leu Ser
                        405                 410                 415

Leu Phe Ser Val Asn Asp Phe Thr Cys Ser Gln Ile Ser Pro Ala Ala
                    420                 425                 430

Ile Ala Ser Asn Cys Tyr Ser Leu Ile Leu Asp Tyr Phe Ser Tyr
                    435                 440                 445

Pro Leu Ser Met Lys Ser Asp Leu Gly Val Ser Ser Ala Gly Pro Ile
                450                 455                 460

Ser Gln Phe Asn Tyr Lys Gln Ser Phe Ser Asn Pro Thr Cys Leu Ile
        465                 470                 475                 480

Leu Ala Thr Val Pro His Asn Leu Thr Thr Ile Thr Lys Pro Leu Lys
                        485                 490                 495

Tyr Ser Tyr Ile Asn Lys Cys Ser Arg Leu Leu Ser Asp Asp Arg Thr
                        500                 505                 510

Glu Val Pro Gln Leu Val Asn Ala Asn Gln Tyr Ser Pro Cys Val Ser
                    515                 520                 525

Ile Val Pro Ser Thr Val Trp Glu Asp Gly Asp Tyr Tyr Arg Lys Gln
                    530                 535                 540

Leu Ser Pro Leu Glu Gly Gly Gly Trp Leu Val Ala Ser Gly Ser Thr
        545                 550                 555                 560

Val Ala Met Thr Glu Gln Leu Gln Met Gly Phe Gly Ile Thr Val Gln
                        565                 570                 575

Tyr Gly Thr Asp Thr Asn Ser Val Cys Pro Lys Leu Glu Phe Ala Asn
                    580                 585                 590

Asp Thr Lys Ile Ala Ser Gln Leu Gly Asn Cys Val Glu Tyr Ser Leu
                    595                 600                 605

Tyr Gly Val Ser Gly Arg Gly Val Phe Gln Asn Cys Thr Ala Val Gly
                    610                 615                 620

Val Arg Gln Gln Arg Phe Val Tyr Asp Ala Tyr Gln Asn Leu Val Gly
        625                 630                 635                 640

Tyr Tyr Ser Asp Asp Gly Asn Tyr Tyr Cys Leu Arg Ala Cys Val Ser
                        645                 650                 655

Val Pro Val Ser Val Ile Tyr Asp Lys Glu Thr Lys Thr His Ala Thr
                        660                 665                 670

Leu Phe Gly Ser Val Ala Cys Glu His Ile Ser Ser Thr Met Ser Gln
                    675                 680                 685

Tyr Ser Arg Ser Thr Arg Ser Met Leu Lys Arg Arg Asp Ser Thr Tyr
                    690                 695                 700

Gly Pro Leu Gln Thr Pro Val Gly Cys Val Leu Gly Leu Val Asn Ser
        705                 710                 715                 720

Ser Leu Phe Val Glu Asp Cys Lys Leu Pro Leu Gly Gln Ser Leu Cys
                        725                 730                 735

Ala Leu Pro Asp Thr Pro Ser Thr Leu Thr Pro Arg Ser Val Arg Ser
                        740                 745                 750

Val Pro Gly Glu Met Arg Leu Ala Ser Ile Ala Phe Asn His Pro Ile
                    755                 760                 765

Gln Val Asp Gln Phe Asn Ser Ser Tyr Phe Lys Leu Ser Ile Pro Thr
                    770                 775                 780

Asn Phe Ser Phe Gly Val Thr Gln Glu Tyr Ile Gln Thr Thr Ile Gln
        785                 790                 795                 800

Lys Val Thr Val Asp Cys Lys Gln Tyr Ile Cys Asn Gly Phe Gln Lys
                        805                 810                 815
```

```
Cys Glu Gln Leu Leu Arg Glu Tyr Gly Gln Phe Cys Ser Lys Ile Asn
                820                 825                 830

Gln Ala Leu His Gly Ala Asn Leu Arg Gln Asp Asp Ser Val Arg Asn
                835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
                900                 905                 910

Met Gln Gln Gly Pro Ala Ser Ala Arg Asp Leu Ile Cys Ala Gln Tyr
                915                 920                 925

Val Ala Gly Tyr Lys Val Leu Pro Pro Leu Met Asp Val Asn Met Glu
                930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
                980                 985                 990

Asn Gln Lys Leu Ile Ala Asn Lys Phe Asn Gln Ala Leu Gly Ala Met
                995                 1000                1005

Gln Thr Gly Phe Thr Thr Thr Asn Glu Ala Phe Arg Lys Val Gln
        1010                1015                1020

Asp Ala Val Asn Asn Asn Ala Gln Ala Leu Ser Lys Leu Ala Ser
        1025                1030                1035

Glu Leu Ser Asn Thr Phe Gly Ala Ile Ser Ala Ser Ile Gly Asp
        1040                1045                1050

Ile Ile Gln Arg Leu Asp Val Leu Glu Gln Asp Ala Gln Ile Asp
        1055                1060                1065

Arg Leu Ile Asn Gly Arg Leu Thr Thr Leu Asn Ala Phe Val Ala
        1070                1075                1080

Gln Gln Leu Val Arg Ser Glu Ser Ala Ala Leu Ser Ala Gln Leu
        1085                1090                1095

Ala Lys Asp Lys Val Asn Glu Cys Val Lys Ala Gln Ser Lys Arg
        1100                1105                1110

Ser Gly Phe Cys Gly Gln Gly Thr His Ile Val Ser Phe Val Val
        1115                1120                1125

Asn Ala Pro Asn Gly Leu Tyr Phe Met His Val Gly Tyr Tyr Pro
        1130                1135                1140

Ser Asn His Ile Glu Val Val Ser Ala Tyr Gly Leu Cys Asp Ala
        1145                1150                1155

Ala Asn Pro Thr Asn Cys Ile Ala Pro Val Asn Gly Tyr Phe Ile
        1160                1165                1170

Lys Thr Asn Asn Thr Arg Ile Val Asp Glu Trp Ser Tyr Thr Gly
        1175                1180                1185

Ser Ser Phe Tyr Ser Pro Glu Pro Ile Thr Ser Leu Asn Thr Lys
        1190                1195                1200

Tyr Val Ala Pro Gln Val Thr Tyr Gln Asn Ile Ser Thr Asn Leu
        1205                1210                1215
```

-continued

Pro Pro Pro Leu Leu Gly Asn Ser Thr Gly Ile Asp Phe Gln Asp
    1220            1225            1230

Glu Leu Asp Glu Phe Phe Lys Asn Val Ser Thr Ser Ile Pro Asn
    1235            1240            1245

Phe Gly Ser Leu Thr Gln Ile Asn Thr Thr Leu Leu Asp Leu Thr
    1250            1255            1260

Tyr Glu Met Leu Ser Leu Gln Gln Val Val Lys Ala Leu Asn Glu
    1265            1270            1275

Ser Tyr Ile Asp Leu Lys Glu Leu Gly Asn Tyr Thr Tyr Tyr Asn
    1280            1285            1290

Lys Trp Pro Trp Tyr Ile Trp Leu Gly Phe Ile Ala Gly Leu Val
    1295            1300            1305

Ala Leu Ala Leu Cys Val Phe Phe Ile Leu Cys Cys Thr Gly Cys
    1310            1315            1320

Gly Thr Asn Cys Met Gly Lys Leu Lys Cys Asn Arg Cys Cys Asp
    1325            1330            1335

Arg Tyr Glu Glu Tyr Asp Leu Glu Pro His Lys Val His Val His
    1340            1345            1350

<210> SEQ ID NO 4
<211> LENGTH: 1353
<212> TYPE: PRT
<213> ORGANISM: Middle East Respiratory Syndrome Coronavirus

<400> SEQUENCE: 4

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
                20                  25                  30

Val Asp Ile Gln Gln Thr Phe Phe Asp Lys Thr Trp Pro Arg Pro Ile
            35                  40                  45

Asp Val Ser Lys Ala Asp Gly Ile Ile Tyr Pro Gln Gly Arg Thr Tyr
        50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                    85                  90                  95

Pro Gln Lys Leu Phe Val Ala Asn Tyr Ser Gln Asp Val Lys Gln Phe
                100                 105                 110

Ala Asn Gly Phe Val Val Arg Ile Gly Ala Ala Ala Asn Ser Thr Gly
            115                 120                 125

Thr Val Ile Ile Ser Pro Ser Thr Ser Ala Thr Ile Arg Lys Ile Tyr
        130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                    165                 170                 175

Gly Thr Leu Leu Arg Ala Phe Tyr Cys Ile Leu Glu Pro Arg Ser Gly
                180                 185                 190

Asn His Cys Pro Ala Gly Asn Ser Tyr Thr Ser Phe Ala Thr Tyr His
            195                 200                 205

Thr Pro Ala Thr Asp Cys Ser Asp Gly Asn Tyr Asn Arg Asn Ala Ser
        210                 215                 220

Leu Asn Ser Phe Lys Glu Tyr Phe Asn Leu Arg Asn Cys Thr Phe Met
225                 230                 235                 240

```
Tyr Thr Tyr Asn Ile Thr Glu Asp Glu Ile Leu Glu Trp Phe Gly Ile
            245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
            275                 280                 285

Thr Ile Lys Tyr Tyr Ser Ile Ile Pro His Ser Ile Arg Ser Ile Gln
            290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
            325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
            355                 360                 365

Lys Pro Ser Gly Ser Val Val Glu Gln Ala Glu Gly Val Glu Cys Asp
            370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
            405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
            435                 440                 445

Pro Leu Ser Met Lys Ser Asp Leu Gly Val Ser Ser Ala Gly Pro Ile
            450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
            485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
            515                 520                 525

Ile Val Pro Ser Thr Val Trp Glu Asp Gly Asp Tyr Tyr Arg Lys Gln
            530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
            565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
            610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
            645                 650                 655
```

```
Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
            675                 680                 685

Tyr Ser Arg Ser Thr Arg Ser Met Leu Lys Arg Arg Asp Ser Thr Tyr
            690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
            755                 760                 765

Gln Val Asp Gln Phe Asn Ser Ser Tyr Phe Lys Leu Ser Ile Pro Thr
            770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Ile Cys Asn Gly Phe Gln Lys
                    805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
            835                 840                 845

Leu Phe Ala Ser Val Lys Ser Ser Gln Ser Ser Pro Ile Ile Pro Gly
            850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                    885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
            915                 920                 925

Val Ala Gly Tyr Lys Val Leu Pro Pro Leu Met Asp Val Asn Met Glu
            930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                    965                 970                 975

Phe Tyr Arg Leu Asn Gly Val Gly Ile Thr Gln Gln Val Leu Ser Glu
            980                 985                 990

Asn Gln Lys Leu Ile Ala Asn Lys  Phe Asn Gln Ala Leu Gly Ala Met
            995                 1000                1005

Gln Thr Gly Phe Thr Thr Thr  Asn Glu Ala Phe Arg  Lys Val Gln
       1010                1015                1020

Asp Ala Val Asn Asn Asn Ala  Gln Ala Leu Ser Lys  Leu Ala Ser
       1025                1030                1035

Glu Leu Ser Asn Thr Phe Gly  Ala Ile Ser Ala Ser  Ile Gly Asp
       1040                1045                1050

Ile Ile Gln Arg Leu Asp Val  Leu Glu Gln Asp Ala  Gln Ile Asp
       1055                1060                1065

Arg Leu Ile Asn Gly Arg Leu  Thr Thr Leu Asn Ala  Phe Val Ala
```

```
               1070                1075                1080
 Gln Gln Leu Val Arg Ser Glu Ser Ala Ala Leu Ser Ala Gln Leu
         1085                1090                1095

Ala Lys Asp Lys Val Asn Glu Cys Val Lys Ala Gln Ser Lys Arg
         1100                1105                1110

Ser Gly Phe Cys Gly Gln Gly Thr His Ile Val Ser Phe Val Val
         1115                1120                1125

Asn Ala Pro Asn Gly Leu Tyr Phe Met His Val Gly Tyr Tyr Pro
         1130                1135                1140

Ser Asn His Ile Glu Val Val Ser Ala Tyr Gly Leu Cys Asp Ala
         1145                1150                1155

Ala Asn Pro Thr Asn Cys Ile Ala Pro Val Asn Gly Tyr Phe Ile
         1160                1165                1170

Lys Thr Asn Asn Thr Arg Ile Val Asp Glu Trp Ser Tyr Thr Gly
         1175                1180                1185

Ser Ser Phe Tyr Ser Pro Glu Pro Ile Thr Ser Leu Asn Thr Lys
         1190                1195                1200

Tyr Val Ala Pro Gln Val Thr Tyr Gln Asn Ile Ser Thr Asn Leu
         1205                1210                1215

Pro Pro Pro Leu Leu Gly Asn Ser Thr Gly Ile Asp Phe Gln Asp
         1220                1225                1230

Glu Leu Asp Glu Phe Phe Lys Asn Val Ser Thr Ser Ile Pro Asn
         1235                1240                1245

Phe Gly Ser Leu Thr Gln Ile Asn Thr Thr Leu Leu Asp Leu Thr
         1250                1255                1260

Tyr Glu Met Leu Ser Leu Gln Gln Val Val Lys Ala Leu Asn Glu
         1265                1270                1275

Ser Tyr Ile Asp Leu Lys Glu Leu Gly Asn Tyr Thr Tyr Tyr Asn
         1280                1285                1290

Lys Trp Pro Trp Tyr Ile Trp Leu Gly Phe Ile Ala Gly Leu Val
         1295                1300                1305

Ala Leu Ala Leu Cys Val Phe Phe Ile Leu Cys Cys Thr Gly Cys
         1310                1315                1320

Gly Thr Asn Cys Met Gly Lys Leu Lys Cys Asn Arg Cys Cys Asp
         1325                1330                1335

Arg Tyr Glu Glu Tyr Asp Leu Glu Pro His Lys Val His Val His
         1340                1345                1350

<210> SEQ ID NO 5
<211> LENGTH: 1255
<212> TYPE: PRT
<213> ORGANISM: Severe Acute Respiratory Syndrome Coronavirus

<400> SEQUENCE: 5

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80
```

```
Ile Pro Phe Lys Asp Gly Ile Tyr Phe Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
```

```
                500             505             510
Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
            530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                    565                 570                 575

Ala Phe Gly Gly Val Ser Val Ile Thr Pro Gly Thr Asn Ala Ser Ser
                580                 585                 590

Glu Val Ala Val Leu Tyr Gln Asp Val Asn Cys Thr Asn Val Ser Ala
            595                 600                 605

Ala Ile His Ala Asp Gln Leu Thr Pro Ala Trp Arg Ile Tyr Ser Thr
            610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
                675                 680                 685

Tyr Ser Asn Asn Thr Ile Ala Ile Pro Thr Asn Phe Ser Ile Ser Ile
                690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
            770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
                900                 905                 910

Ile Ser Gln Ile Gln Glu Ser Leu Thr Thr Thr Ser Thr Ala Leu Gly
            915                 920                 925
```

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Gly Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 6
<211> LENGTH: 1255
<212> TYPE: PRT
<213> ORGANISM: Severe Acute Respiratory Syndrome Coronavirus

<400> SEQUENCE: 6

Met Phe Ile Phe Leu Leu Phe Leu Thr Le

-continued

```
                20                  25                  30
His Thr Ser Ser Met Arg Gly Val Tyr Tyr Pro Asp Glu Ile Phe Arg
            35                  40                  45
Ser Asp Thr Leu Tyr Leu Thr Gln Asp Leu Phe Leu Pro Phe Tyr Ser
 50                  55                  60
Asn Val Thr Gly Phe His Thr Ile Asn His Thr Phe Gly Asn Pro Val
 65                  70                  75                  80
Ile Pro Phe Lys Asp Gly Ile Tyr Phe Ala Ala Thr Glu Lys Ser Asn
                85                  90                  95
Val Val Arg Gly Trp Val Phe Gly Ser Thr Met Asn Asn Lys Ser Gln
                100                 105                 110
Ser Val Ile Ile Ile Asn Asn Ser Thr Asn Val Val Ile Arg Ala Cys
                115                 120                 125
Asn Phe Glu Leu Cys Asp Asn Pro Phe Phe Ala Val Ser Lys Pro Met
                130                 135                 140
Gly Thr Gln Thr His Thr Met Ile Phe Asp Asn Ala Phe Asn Cys Thr
145                 150                 155                 160
Phe Glu Tyr Ile Ser Asp Ala Phe Ser Leu Asp Val Ser Glu Lys Ser
                165                 170                 175
Gly Asn Phe Lys His Leu Arg Glu Phe Val Phe Lys Asn Lys Asp Gly
                180                 185                 190
Phe Leu Tyr Val Tyr Lys Gly Tyr Gln Pro Ile Asp Val Val Arg Asp
                195                 200                 205
Leu Pro Ser Gly Phe Asn Thr Leu Lys Pro Ile Phe Lys Leu Pro Leu
                210                 215                 220
Gly Ile Asn Ile Thr Asn Phe Arg Ala Ile Leu Thr Ala Phe Ser Pro
225                 230                 235                 240
Ala Gln Asp Ile Trp Gly Thr Ser Ala Ala Ala Tyr Phe Val Gly Tyr
                245                 250                 255
Leu Lys Pro Thr Thr Phe Met Leu Lys Tyr Asp Glu Asn Gly Thr Ile
                260                 265                 270
Thr Asp Ala Val Asp Cys Ser Gln Asn Pro Leu Ala Glu Leu Lys Cys
                275                 280                 285
Ser Val Lys Ser Phe Glu Ile Asp Lys Gly Ile Tyr Gln Thr Ser Asn
                290                 295                 300
Phe Arg Val Val Pro Ser Gly Asp Val Val Arg Phe Pro Asn Ile Thr
305                 310                 315                 320
Asn Leu Cys Pro Phe Gly Glu Val Phe Asn Ala Thr Lys Phe Pro Ser
                325                 330                 335
Val Tyr Ala Trp Glu Arg Lys Lys Ile Ser Asn Cys Val Ala Asp Tyr
                340                 345                 350
Ser Val Leu Tyr Asn Ser Thr Phe Phe Ser Thr Phe Lys Cys Tyr Gly
                355                 360                 365
Val Ser Ala Thr Lys Leu Asn Asp Leu Cys Phe Ser Asn Val Tyr Ala
                370                 375                 380
Asp Ser Phe Val Lys Gly Asp Asp Val Arg Gln Ile Ala Pro Gly
385                 390                 395                 400
Gln Thr Gly Val Ile Ala Asp Tyr Asn Tyr Lys Leu Pro Asp Asp Phe
                405                 410                 415
Met Gly Cys Val Leu Ala Trp Asn Thr Arg Asn Ile Asp Ala Thr Ser
                420                 425                 430
Thr Gly Asn Tyr Asn Tyr Lys Tyr Arg Tyr Leu Arg His Gly Lys Leu
                435                 440                 445
```

```
Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                    485                 490                 495

Val Val Leu Ser Phe Glu Leu Leu Asn Ala Pro Ala Thr Val Cys Gly
                500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
                580                 585                 590

Glu Val Ala Val Leu Tyr Gln Asp Val Asn Cys Thr Asn Val Ser Ala
            595                 600                 605

Ala Ile His Ala Asp Gln Leu Thr Pro Ala Trp Arg Ile Tyr Ser Thr
        610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
        690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
850                 855                 860
```

```
Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
            885                 890                 895

Val Leu Tyr Glu Asn Gln Lys Gln Ile Ala Asn Gln Phe Asn Lys Ala
        900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
        930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
            965                 970                 975

Arg Leu Ile Thr Gly Arg Leu Gln Ser Leu Gln Thr Tyr Val Thr Gln
        980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Gly Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255
```

<210> SEQ ID NO 7
<211> LENGTH: 2544
<212> TYPE: DNA
<213> ORGANISM: Artificial Sequence
<220> FEATURE:
<223> OTHER INFORMATION: Chimeric protein that includes the S1 subunit
of Middle East Respiratory Syndrome Coronavirus rused to a
C-terminal part of Rabies virus G glycoprotein (amino acids
428-524)

<400> SEQUENCE: 7

```
atgattcact ctgtgttcct gctgatgttc ctgctgacac aacagagtc ctatgtggat      60
gtgggacctg actctgtgaa gtctgcctgt attgaggtgg acatccaaca gaccttcttt    120
gacaagacct ggccaagacc aattgatgtg agcaaggctg atggcatcat ctacccacag    180
ggcaggacct acagcaacat caccatcacc taccagggac tgtttccata ccagggagat    240
catggagata tgtatgtcta ctctgctggt catgccacag gcaccacacc acagaaactg    300
tttgtggcta actacagcca ggatgtgaag cagtttgcca atggctttgt ggtgaggatt    360
ggagcagcag ccaacagcac aggcacagtg attatcagcc caagcacctc tgccaccatc    420
aggaagattt accctgcctt tatgctgggc tcctctgtgg gcaacttctc tgatggcaag    480
atgggcaggt tcttcaacca cacctggtg ctgctgcctg atggctgtgg cacccctgctg    540
agggctttct actgtatctt ggaaccaagg tctggcaacc actgtcctgc tggcaactcc    600
tacacctcct tgccaccta ccacacacct gccacagact gttctgatgg caactacaac    660
aggaatgcct ccctgaactc cttcaaggaa tacttcaacc tgaggaactg tacctttatg    720
tacacctaca acatcacaga ggatgagatt ttggagtggt ttggcatcac ccagacagcc    780
cagggagtgc atctgttctc gagcagatat gtggacctct atgagaggcaa tatgttccag    840
tttgccaccc tgcctgtcta tgacaccatc aaatactaca gcatcatccc acacagcatc    900
aggagcatcc agtctgacag gaaggcttgg gctgccttct atgtctacaa actccaacca    960
ctgaccttcc tgctggactt ctctgtggat ggctacatca ggagggctat tgactgtggc   1020
ttcaatgacc tgagccaact tcactgttcc tatgagtcct ttgatgtgga gtctggagtc   1080
tactctgtgt cctcctttga ggctaagcca tctggctctg tggtggaaca ggctgaggga   1140
gtggagtgtg acttcagccc actgctgtct ggcacacctc cacaggtcta caacttcaag   1200
agactggtgt tcaccaactg taactacaac ctgaccaaac tgctgtccct gttctctgtg   1260
aatgacttca cttgtagcca gattagccct gctgccattg ccagcaactg ttactcctcc   1320
ctgattctgg actactctc ctacccactg agtatgaagt ctgacctgtc tgtgtcctct   1380
gctggaccaa tcagccagtt caactacaag cagtccttca gcaacccaac ttgtctgatt   1440
ctggctacag tgccacacaa cctgaccacc atcaccaagc cactgaaata ctcctacatc   1500
aacaagtgta gcagactgct gtctgatgac aggacagagg tgccacaact agtgaatgcc   1560
aaccaataca gccatgtgt gagcattgtg ccaagcacag tgggagga tggagactac   1620
tacaggaagc aacttagccc attggaggga ggaggctggc tggtgcatc tggcagcaca   1680
gtggctatga cagaacaact ccaaatgggc tttggcatca cagtccaata tggcacagac   1740
accaactctg tgtgtccaaa attggagttt gccaatgaca ccaagattgc cagccaactt   1800
ggcaactgtg tggaatactc cctctatgga gtgtctggca ggggagtgtt ccagaactgt   1860
actgctgtgg gagtgagaca acagagggtt gtctatgatg cctaccagaa cctggtgggc   1920
tactactctg atgatggcaa ctactactgt ctgagggctt gtgtgtctgt gcctgtgtct   1980
gtgatttatg acaaggagac caagacccat gccaccctgt ttggctctgt ggcttgtgaa   2040
```

-continued

```
cacatctcca gcacaatgag tcaatacagc aggagcacca ggagtatgct gaaaaggagg    2100
gacagcacat atggaccact ccaaacacct gtgggctgtg tgctgggact ggtgaactcc    2160
tccctgtttg tggaggactg taaactgcca ctgggacaat ccctgtgtgc cctgcctgac    2220
acaccaagca ccctgacacc aaggtctgtg ggagatgagg ccgaagactt tgtggaagtc    2280
cacctgcctg atgtgcataa ccaggtgtct ggcgtcgacc tgggactgcc aaattggggc    2340
aagtacgtgc tgctgagtgc tggagcactg actgccctga tgctgatcat tttcctgatg    2400
acctgctgtc ggcgcgtgaa cagaagtgag cccactcagc acaatctgcg aggaaccggg    2460
agagaagtgt cagtcacacc tcagagcggg aaaatcatta gtagttggga atcacataaa    2520
agcgggggcg agaccaggct gtga                                           2544
```

<210> SEQ ID NO 8
<211> LENGTH: 847
<212> TYPE: PRT
<213> ORGANISM: Artificial Sequence
<220> FEATURE:
<223> OTHER INFORMATION: Chimeric protein that includes the S1 subunit
of Middle East Respiratory Syndrome Coronavirus rused to a
C-terminal part of Rabies virus G glycoprotein (amino acids
428-524)

<400> SEQUENCE: 8

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255
```

```
Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
            275                 280                 285

Thr Ile Lys Tyr Tyr Ser Ile Ile Pro His Ser Ile Arg Ser Ile Gln
290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
            355                 360                 365

Lys Pro Ser Gly Ser Val Val Glu Gln Ala Glu Gly Val Glu Cys Asp
            370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
                420                 425                 430

Ile Ala Ser Asn Cys Tyr Ser Ser Leu Ile Leu Asp Tyr Phe Ser Tyr
            435                 440                 445

Pro Leu Ser Met Lys Ser Asp Leu Ser Val Ser Ser Ala Gly Pro Ile
            450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
            515                 520                 525

Ile Val Pro Ser Thr Val Trp Glu Asp Gly Asp Tyr Tyr Arg Lys Gln
            530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
            610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670
```

| | | | | | | | | | | | |
|---|---|---|---|---|---|---|---|---|---|---|---|
|Leu|Phe|Gly|Ser|Val|Ala|Cys|Glu|His|Ile|Ser|Ser|Thr|Met|Ser|Gln|
| | | |675| | | | |680| | | | | |685| |
|Tyr|Ser|Arg|Ser|Thr|Arg|Ser|Met|Leu|Lys|Arg|Arg|Asp|Ser|Thr|Tyr|
| |690| | | | |695| | | | | |700| | | |
|Gly|Pro|Leu|Gln|Thr|Pro|Val|Gly|Cys|Val|Leu|Gly|Leu|Val|Asn|Ser|
|705| | | | |710| | | | |715| | | | |720|
|Ser|Leu|Phe|Val|Glu|Asp|Cys|Lys|Leu|Pro|Leu|Gly|Gln|Ser|Leu|Cys|
| | | | |725| | | | |730| | | | |735| |
|Ala|Leu|Pro|Asp|Thr|Pro|Ser|Thr|Leu|Thr|Pro|Arg|Ser|Val|Gly|Asp|
| | | |740| | | | |745| | | | |750| | |
|Glu|Ala|Glu|Asp|Phe|Val|Glu|Val|His|Leu|Pro|Asp|Val|His|Asn|Gln|
| | | |755| | | | |760| | | | |765| | |
|Val|Ser|Gly|Val|Asp|Leu|Gly|Leu|Pro|Asn|Trp|Gly|Lys|Tyr|Val|Leu|
| |770| | | | |775| | | | |780| | | | |
|Leu|Ser|Ala|Gly|Ala|Leu|Thr|Ala|Leu|Met|Leu|Ile|Ile|Phe|Leu|Met|
|785| | | | |790| | | | |795| | | | |800|
|Thr|Cys|Cys|Arg|Arg|Val|Asn|Arg|Ser|Glu|Pro|Thr|Gln|His|Asn|Leu|
| | | | |805| | | | |810| | | | |815| |
|Arg|Gly|Thr|Gly|Arg|Glu|Val|Ser|Val|Thr|Pro|Gln|Ser|Gly|Lys|Ile|
| | | |820| | | | |825| | | | |830| | |
|Ile|Ser|Ser|Trp|Glu|Ser|His|Lys|Ser|Gly|Gly|Glu|Thr|Arg|Leu| |
| | |835| | | | |840| | | | |845| | | |

<210> SEQ ID NO 9
<211> LENGTH: 4062
<212> TYPE: DNA
<213> ORGANISM: Middle East Respiratory Syndrome Coronavirus

<400> SEQUENCE: 9

```
atgatacact cagtgtttct actgatgttc ttgttaacac ctacagaaag ttacgttgat      60
gtagggccag attctgttaa gtctgcttgt attgaggttg atatacaaca gactttcttt     120
gataaaactt ggcctaggcc aattgatgtt tctaaggctg acggtattat atacccctcaa    180
ggccgtacat attctaacat aactatcact tatcaaggtc ttttcccta tcagggagac      240
catggtgata tgtatgttta ctctgcagga catgctacag gcacaactcc acaaaagttg    300
tttgtagcta actattctca ggacgtcaaa cagtttgcta tgggtttgt cgtccgtata      360
ggagcagctg ccaattccac tggcactgtt attattagcc atctaccag cgctactata     420
cgaaaaattt accctgcttt tatgctgggt tcttcagttg gtaatttctc agatggtaaa   480
atgggccgct tcttcaatca tactctagtt cttttgcccg atggatgtgg cactttactt   540
agagcttttt attgtattct agagcctcgc tctggaaatc attgtcctgc tggcaattcc   600
tatacttctt tgccacctta tcacactcct gcaacagatt gttctgatgg caattacaat   660
cgtaatgcca gtctgaactc ttttaaggag tattttaatt tacgtaactg cacctttatg   720
tacacttata acattaccga agatgagatt ttagagtggt ttggcattac acaaactgct   780
caaggtgttc acctcttctc atctcggtat gttgatttgt acggcggcaa tatgtttcaa   840
tttgccacct tgcctgttta tgatactatt aagtattatt ctatcattcc tcacagtatt   900
cgttctatcc aaagtgatag aaaagcttgg gctgccttct acgtatataa acttcaaccg   960
ttaacttttc tgttggattt ttctgttgat ggttatatac gcagagctat agactgtggt  1020
tttaatgatt tgtcacaact ccactgctca tatgaatcct tcgatgttga atctggagtt  1080
tattcagttt cgtctttcga agcaaaacct tctggctcag ttgtggaaca ggctgaaggt  1140
```

```
gttgaatgtg attttttcacc tcttctgtct ggcacacctc ctcaggttta aatttcaag      1200
cgtttggttt ttaccaattg caattataat cttaccaaat tgctttcact tttttctgtg     1260
aatgatttta cttgtagtca aatatctcca gcagcaattg ctagcaactg ttattcttca     1320
ctgattttgg attacttttc atacccactt agtatgaaat ccgatctcag tgttagttct     1380
gctggtccaa tatcccagtt taattataaa cagtccttt ctaatcccac atgtttgatt      1440
ttagcgactg ttcctcataa ccttactact attactaagc ctcttaagta cagctatatt     1500
aacaagtgct ctcgtcttct ttctgatgat cgtactgaag tacctcagtt agtgaacgct     1560
aatcaatact caccctgtgt atccattgtc ccatccactg tgtgggaaga cggtgattat     1620
tataggaaac aactatctcc acttgaaggt ggtggctggc ttgttgctag tggctcaact     1680
gttgccatga ctgagcaatt acagatgggc tttggtatta cagttcaata tggtacagac     1740
accaatagtg tttgccccaa gcttgaattt gctaatgaca caaaaattgc ctctcaatta     1800
ggcaattgcg tggaatattc cctctatggt gtttcgggcc gtggtgtttt tcagaattgc     1860
acagctgtag gtgttcgaca gcagcgcttt gtttatgatg cgtaccagaa tttagttggc     1920
tattattctg atgatggcaa ctactactgt ttgcgtgctt gtgttagtgt tcctgtttct     1980
gtcatctatg ataaagaaac taaacccac gctactctat ttggtagtgt tgcatgtgaa      2040
cacatttctt ctaccatgtc tcaatactcc cgttctacgc gatcaatgct taaacggcga     2100
gattctacat atggccccct tcagacacct gttggttgtg tcctaggact tgttaattcc     2160
tctttgttcg tagaggactg caagttgcct cttggtcaat ctctctgtgc tcttcctgac     2220
acacctagta ctctcacacc tcgcagtgtg cgctctgttc caggtgaaat gcgcttggca     2280
tccattgctt ttaatcatcc tattcaggtt gatcaactta atagtagtta ttttaaatta     2340
agtatacccca ctaattttc ctttggtgtg actcaggagt acattcagac aaccattcag     2400
aaagttactg ttgattgtaa acagtacgtt tgcaatggtt tccagaagtg tgagcaatta     2460
ctgcgcgagt atggccagtt tgttccaaa ataaaccagg ctctccatgg tgccaattta     2520
cgccaggatg attctgtacg taatttgttt gcgagcgtga aaagctctca atcatctcct     2580
atcataccag gttttggagg tgactttaat ttgacacttc tagaacctgt ttctatatct     2640
actggcagtc gtagtgcacg tagtgctatt gaggatttgc tatttgacaa agtcactata     2700
gctgatcctg ttatatgca aggttacgat gattgcatgc agcaaggtcc agcatcagct     2760
cgtgatctta tttgtgctca atatgtggct ggttacaaag tattacctcc tcttatggat     2820
gttaatatgg aagccgcgta tacttcatct ttgcttggca gcatagcagg tgttggctgg     2880
actgctggct tatcctcctt tgctgctatt ccatttgcac agagtatctt ttataggtta     2940
aacggtgttg gcattactca acaggttctt tcagagaacc aaaagcttat tgccaataag     3000
tttaatcagg ctctgggagc tatgcaaaca ggcttcacta caactaatga agcttttcag     3060
aaggttcagg atgctgtgaa caacaatgca caggctctat ccaaattagc tagcgagcta     3120
tctaatactt ttggtgctat ttccgcctct attggagaca tcatacaacg tcttgatgtt     3180
ctcgaacagg acgcccaaat agacagactt attaatggcc gtttgacaac actaaatgct     3240
tttgttgcac agcagcttgt tcgttccgaa tcagctgctc tttccgctca attggctaaa     3300
gataaagtca atgagtgtgt caaggcacaa tccaagcgtt ctggattttg cggtcaaggc     3360
acacatatag tgtcctttgt tgtaaatgcc cctaatggcc tttacttcat gcatgttggt     3420
tattacccta gcaaccacat tgaggttgtt tctgcttatg gtctttgcga tgcagctaac     3480
cctactaatt gtatagcccc tgttaatggc tactttatta aaactaataa cactaggatt     3540
```

```
gttgatgagt ggtcatatac tggctcgtcc ttctatgcac ctgagcccat acctcccctt    3600
aatactaagt atgttgcacc acaggtgaca taccaaaaca tttctactaa cctccctcct    3660
cctcttctcg gcaattccac cgggattgac ttccaagatg agttggatga gtttttcaaa    3720
aatgttagca ccagtatacc taattttggt tccctaacac agattaatac tacattactc    3780
gatcttacct acgagatgtt gtctcttcaa caagttgtta agcccttaa tgagtcttac      3840 atagacctta aagagcttgg caattatact tattacaaca aatggccgtg gtacatttgg    3900
cttggtttca ttgctgggct tgttgcctta gctctatgcg tcttcttcat actgtgctgc    3960
actggttgtg gcacaaactg tatgggaaaa cttaagtgta atcgttgttg tgatagatac    4020
gaggaatacg acctcgagcc gcataaggtt catgttcact aa                       4062
```

```
<210> SEQ ID NO 10
<211> LENGTH: 1353
<212> TYPE: PRT
<213> ORGANISM: Middle East Respiratory Syndrome Coronavirus

<400> SEQUENCE: 10

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
```

```
              275                 280                 285
Thr Ile Lys Tyr Tyr Ser Ile Ile Pro His Ser Ile Arg Ser Ile Gln
290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
                340                 345                 350

Ser Phe Asp Val Glu Ser Gly Val Tyr Ser Val Ser Ser Phe Glu Ala
                355                 360                 365

Lys Pro Ser Gly Ser Val Val Glu Gln Ala Glu Gly Val Glu Cys Asp
370                 375                 380

Phe Ser Pro Leu Leu Ser Gly Thr Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
                420                 425                 430

Ile Ala Ser Asn Cys Tyr Ser Ser Leu Ile Leu Asp Tyr Phe Ser Tyr
                435                 440                 445

Pro Leu Ser Met Lys Ser Asp Leu Ser Val Ser Ser Ala Gly Pro Ile
                450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
                500                 505                 510

Glu Val Pro Gln Leu Val Asn Ala Asn Gln Tyr Ser Pro Cys Val Ser
                515                 520                 525

Ile Val Pro Ser Thr Val Trp Glu Asp Gly Asp Tyr Tyr Arg Lys Gln
                530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
                595                 600                 605

Tyr Gly Val Ser Gly Arg Gly Val Phe Gln Asn Cys Thr Ala Val Gly
                610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
                675                 680                 685

Tyr Ser Arg Ser Thr Arg Ser Met Leu Lys Arg Arg Asp Ser Thr Tyr
                690                 695                 700
```

-continued

```
Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Arg Ser Val Arg Ser
        740                 745                 750

Val Pro Gly Glu Met Arg Leu Ala Ser Ile Ala Phe Asn His Pro Ile
    755                 760                 765

Gln Val Asp Gln Leu Asn Ser Ser Tyr Phe Lys Leu Ser Ile Pro Thr
770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys  Phe Asn Gln Ala Leu  Gly Ala Met
            995                 1000                1005

Gln Thr  Gly Phe Thr Thr Thr  Asn Glu Ala Phe Gln  Lys Val Gln
    1010                 1015                 1020

Asp Ala  Val Asn Asn Asn Ala  Gln Ala Leu Ser Lys  Leu Ala Ser
    1025                 1030                 1035

Glu Leu  Ser Asn Thr Phe Gly  Ala Ile Ser Ala Ser  Ile Gly Asp
    1040                 1045                 1050

Ile Ile  Gln Arg Leu Asp Val  Leu Glu Gln Asp Ala  Gln Ile Asp
    1055                 1060                 1065

Arg Leu  Ile Asn Gly Arg Leu  Thr Thr Leu Asn Ala  Phe Val Ala
    1070                 1075                 1080

Gln Gln  Leu Val Arg Ser Glu  Ser Ala Ala Leu Ser  Ala Gln Leu
    1085                 1090                 1095

Ala Lys  Asp Lys Val Asn Glu  Cys Val Lys Ala Gln  Ser Lys Arg
    1100                 1105                 1110
```

```
Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr Tyr Asn
    1280                1285                1290

Lys Trp Pro Trp Tyr Ile Trp Leu Gly Phe Ile Ala Gly Leu Val
    1295                1300                1305

Ala Leu Ala Leu Cys Val Phe Phe Ile Leu Cys Cys Thr Gly Cys
    1310                1315                1320

Gly Thr Asn Cys Met Gly Lys Leu Lys Cys Asn Arg Cys Cys Asp
    1325                1330                1335

Arg Tyr Glu Glu Tyr Asp Leu Glu Pro His Lys Val His Val His
    1340                1345                1350

<210> SEQ ID NO 11
<211> LENGTH: 3975
<212> TYPE: DNA
<213> ORGANISM: Artificial Sequence
<220> FEATURE:
<223> OTHER INFORMATION: Middle Easter Respiratory Syndrom Coronavirus
      spike glycoprotein tuncation - 29 amino acid deleted from the
      C-terminus

<400> SEQUENCE: 11
atgatacact cagtgtttct actgatgttc ttgttaacac ctacagaaag ttacgttgat      60
gtagggccag attctgttaa gtctgcttgt attgaggttg atatacaaca gactttcttt     120
gataaaactt ggcctaggcc aattgatgtt tctaaggctg acggtattat atacctcaa      180 ggccgtacat attctaacat aactatcact tatcaaggtc ttttcccta tcagggagac      240 catggtgata tgtatgttta ctctgcagga catgctacag gcacaactcc acaaaagttg     300
tttgtagcta actattctca ggacgtcaaa cagtttgcta tgggtttgt cgtccgtata      360 ggagcagctg ccaattccac tggcactgtt attattagcc catctaccag cgctactata     420
cgaaaaattt accctgcttt tatgctgggt tcttcagttg gtaatttctc agatggtaaa     480
atgggccgct tcttcaatca tactctagtt cttttgcccg atggatgtgg cactttactt     540
agagcttttt attgtattct agagcctcgc tctggaaatc attgtcctgc tggcaattcc     600
```

```
tatacttctt ttgccactta tcacactcct gcaacagatt gttctgatgg caattacaat    660
cgtaatgcca gtctgaactc ttttaaggag tattttaatt tacgtaactg cacctttatg    720
tacacttata acattaccga agatgagatt ttagagtggt ttggcattac acaaactgct    780
caaggtgttc acctcttctc atctcggtat gttgatttgt acggcggcaa tatgtttcaa    840
tttgccacct tgcctgttta tgatactatt aagtattatt ctatcattcc tcacagtatt    900
cgttctatcc aaagtgatag aaaagcttgg gctgccttct acgtatataa acttcaaccg    960
ttaactttcc tgttggattt ttctgttgat ggttatatac gcagagctat agactgtggt   1020
tttaatgatt tgtcacaact ccactgctca tatgaatcct tcgatgttga atctggagtt   1080
tattcagttt cgtctttcga agcaaaacct tctggctcag ttgtggaaca ggctgaaggt   1140
gttgaatgtg attttcacc tcttctgtct ggcacacctc ctcaggttta taatttcaag   1200
cgtttggttt ttaccaattg caattataat cttaccaaat tgctttcact ttttctgtg   1260 aatgatttta cttgtagtca aatatctcca gcagcaattg ctagcaactg ttattcttca   1320
ctgattttgg attactttc ataccacttt agtatgaaat ccgatctcag tgttagttct   1380
gctggtccaa tatcccagtt taattataaa cagtcctttt ctaatcccac atgtttgatt   1440
ttagcgactg ttcctcataa ccttactact attactaagc ctcttaagta cagctatatt   1500
aacaagtgct ctcgtcttct ttctgatgat cgtactgaag tacctcagtt agtgaacgct   1560
aatcaatact caccctgtgt atccattgtc ccatccactg tgtgggaaga cggtgattat   1620
tataggaaac aactatctcc acttgaaggt ggtggctggc ttgttgctag tggctcaact   1680
gttgccatga ctgagcaatt acagatgggc tttggtatta cagttcaata tggtacagac   1740
accaatagtg tttgccccaa gcttgaattt gctaatgaca caaaaattgc ctctcaatta   1800
ggcaattgcg tggaatattc cctctatggt gtttcgggcc gtggtgtttt tcagaattgc   1860
acagctgtag gtgttcgaca gcagcgcttt gtttatgatg cgtaccagaa tttagttggc   1920
tattattctg atgatggcaa ctactactgt ttgcgtgctt gtgttagtgt tcctgtttct   1980
gtcatctatg ataaagaaac taaaacccac gctactctat ttggtagtgt tgcatgtgaa   2040
cacatttctt ctaccatgtc tcaatactcc cgttctacgc gatcaatgct taaacggcga   2100
gattctacat atggccccct tcagacacct gttggttgtg tcctaggact tgttaattcc   2160
tctttgttcg tagaggactg caagttgcct cttggtcaat ctctctgtgc tcttcctgac   2220
acacctagta ctctcacacc tcgcagtgtg cgctctgttc caggtgaaat gcgcttggca   2280
tccattgctt ttaatcatcc tattcaggtt gatcaactta atagtagtta ttttaaatta   2340
agtataccca ctaattttc ctttggtgtg actcaggagt acattcagac aaccattcag   2400
aaagttactg ttgattgtaa acagtacgtt tgcaatggtt tccagaagtg tgagcaatta   2460
ctgcgcgagt atggccagtt tgttccaaa ataaaccagg ctctccatgg tgccaattta   2520
cgccaggatg attctgtacg taatttgttt gcgagcgtga aaagctctca atcatctcct   2580
atcataccag gttttggagg tgactttaat ttgacacttc tagaacctgt ttctatatct   2640
actggcagtc gtagtgcacg tagtgctatt gaggatttgc tatttgacaa agtcactata   2700
gctgatcctg gttatatgca aggttacgat gattgcatgc agcaaggtcc agcatcagct   2760
cgtgatctta tttgtgctca atatgtggct ggttacaaag tattacctcc tcttatggat   2820
gttaatatgg aagccgcgta tacttcatct ttgcttggca gcatagcagg tgttggctgg   2880
actgctggct tatcctcctt tgctgctatt ccatttgcac agagtatctt ttataggtta   2940
```

```
aacggtgttg gcattactca acaggttctt tcagagaacc aaaagcttat tgccaataag    3000
tttaatcagg ctctgggagc tatgcaaaca ggcttcacta caactaatga agcttttcag    3060
aaggttcagg atgctgtgaa caacaatgca caggctctat ccaaattagc tagcgagcta    3120
tctaatactt ttggtgctat ttccgcctct attggagaca tcatacaacg tcttgatgtt    3180
ctcgaacagg acgcccaaat agacagactt attaatggcc gtttgacaac actaaatgct    3240
tttgttgcac agcagcttgt tcgttccgaa tcagctgctc tttccgctca attggctaaa    3300
gataaagtca atgagtgtgt caaggcacaa tccaagcgtt ctggattttg cggtcaaggc    3360
acacatatag tgtcctttgt tgtaaatgcc cctaatggcc tttacttcat gcatgttggt    3420
tattacccta gcaaccacat tgaggttgtt tctgcttatg gtctttgcga tgcagctaac    3480
cctactaatt gtatagcccc tgttaatggc tactttatta aaactaataa cactaggatt    3540
gttgatgagt ggtcatatac tggctcgtcc ttctatgcac ctgagcccat tacctccctt    3600
aatactaagt atgttgcacc acaggtgaca taccaaaaca tttctactaa cctccctcct    3660
cctcttctcg gcaattccac cgggattgac ttccaagatg agttggatga gttttcaaa     3720 aatgttagca ccagtatacc taattttggt tccctaacac agattaatac tacattactc    3780
gatcttacct acgagatgtt gtctcttcaa caagttgtta agcccttaa tgagtcttac      3840 atagacctta aagagcttgg caattatact tattacaaca atggccgtg gtacatttgg      3900 cttggtttca ttgctgggct tgttgcctta gctctatgcg tcttcttcat actgtgctgc    3960
actggttgtg gctaa                                                     3975
```

<210> SEQ ID NO 12
<211> LENGTH: 1324
<212> TYPE: PRT
<213> ORGANISM: Artificial Sequence
<220> FEATURE:
<223> OTHER INFORMATION: Middle Easter Respiratory Syndrom Coronavirus
      spike glycoprotein tuncation - 29 amino acid deleted from the
      C-terminus

<400> SEQUENCE: 12

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
```

-continued

```
                165                 170                 175
Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590
```

```
Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
            675                 680                 685

Tyr Ser Arg Ser Thr Arg Ser Met Leu Lys Arg Arg Asp Ser Thr Tyr
        690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
                740                 745                 750

Val Pro Gly Glu Met Arg Leu Ala Ser Ile Ala Phe Asn His Pro Ile
            755                 760                 765

Gln Val Asp Gln Leu Asn Ser Ser Tyr Phe Lys Leu Ser Ile Pro Thr
        770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
                820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
                900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
                980                 985                 990

Asn Gln Lys Leu Ile Ala Asn Lys  Phe Asn Gln Ala Leu  Gly Ala Met
        995                 1000                1005
```

| | | | | | | | | | |
|---|---|---|---|---|---|---|---|---|---|
| Gln | Thr | Gly | Phe | Thr | Thr | Thr | Asn | Glu | Ala | Phe | Gln | Lys | Val | Gln |

```
Gln Thr Gly Phe Thr Thr Thr Asn Glu Ala Phe Gln Lys Val Gln
    1010            1015            1020

Asp Ala Val Asn Asn Asn Ala Gln Ala Leu Ser Lys Leu Ala Ser
    1025            1030            1035

Glu Leu Ser Asn Thr Phe Gly Ala Ile Ser Ala Ser Ile Gly Asp
    1040            1045            1050

Ile Ile Gln Arg Leu Asp Val Leu Glu Gln Asp Ala Gln Ile Asp
    1055            1060            1065

Arg Leu Ile Asn Gly Arg Leu Thr Thr Leu Asn Ala Phe Val Ala
    1070            1075            1080

Gln Gln Leu Val Arg Ser Glu Ser Ala Ala Leu Ser Ala Gln Leu
    1085            1090            1095

Ala Lys Asp Lys Val Asn Glu Cys Val Lys Ala Gln Ser Lys Arg
    1100            1105            1110

Ser Gly Phe Cys Gly Gln Gly Thr His Ile Val Ser Phe Val Val
    1115            1120            1125

Asn Ala Pro Asn Gly Leu Tyr Phe Met His Val Gly Tyr Tyr Pro
    1130            1135            1140

Ser Asn His Ile Glu Val Val Ser Ala Tyr Gly Leu Cys Asp Ala
    1145            1150            1155

Ala Asn Pro Thr Asn Cys Ile Ala Pro Val Asn Gly Tyr Phe Ile
    1160            1165            1170

Lys Thr Asn Asn Thr Arg Ile Val Asp Glu Trp Ser Tyr Thr Gly
    1175            1180            1185

Ser Ser Phe Tyr Ala Pro Glu Pro Ile Thr Ser Leu Asn Thr Lys
    1190            1195            1200

Tyr Val Ala Pro Gln Val Thr Tyr Gln Asn Ile Ser Thr Asn Leu
    1205            1210            1215

Pro Pro Pro Leu Leu Gly Asn Ser Thr Gly Ile Asp Phe Gln Asp
    1220            1225            1230

Glu Leu Asp Glu Phe Phe Lys Asn Val Ser Thr Ser Ile Pro Asn
    1235            1240            1245

Phe Gly Ser Leu Thr Gln Ile Asn Thr Thr Leu Leu Asp Leu Thr
    1250            1255            1260

Tyr Glu Met Leu Ser Leu Gln Gln Val Val Lys Ala Leu Asn Glu
    1265            1270            1275

Ser Tyr Ile Asp Leu Lys Glu Leu Gly Asn Tyr Thr Tyr Tyr Asn
    1280            1285            1290

Lys Trp Pro Trp Tyr Ile Trp Leu Gly Phe Ile Ala Gly Leu Val
    1295            1300            1305

Ala Leu Ala Leu Cys Val Phe Phe Ile Leu Cys Cys Thr Gly Cys
    1310            1315            1320

Gly
```

<210> SEQ ID NO 13
<211> LENGTH: 4005
<212> TYPE: DNA
<213> ORGANISM: Artificial Sequence
<220> FEATURE:
<223> OTHER INFORMATION: Middle Easter Respiratory Syndrom Coronavirus
      spike glycoprotein tuncation - 19 amino acid deleted from the
      C-terminus

<400> SEQUENCE: 13
atgatacact cagtgtttct actgatgttc ttgttaacac ctacagaaag ttacgttgat    60

```
gtagggccag attctgttaa gtctgcttgt attgaggttg atatacaaca gactttcttt    120
gataaaactt ggcctaggcc aattgatgtt tctaaggctg acggtattat atacccctcaa   180
ggccgtacat attctaacat aactatcact tatcaaggtc ttttttccta tcagggagac   240
catggtgata tgtatgttta ctctgcagga catgctacag gcacaactcc acaaaagttg   300
tttgtagcta actattctca ggacgtcaaa cagtttgcta atgggtttgt cgtccgtata   360
ggagcagctg ccaattccac tggcactgtt attattagcc catctaccag cgctactata   420
cgaaaatttt accctgcttt tatgctgggt tcttcagttg gtaatttctc agatggtaaa   480
atgggccgct tcttcaatca tactctagtt cttttgcccg atggatgtgg cactttactt   540
agagcttttt attgtattct agagcctcgc tctggaaatc attgtcctgc tggcaattcc   600
tatacttctt ttgccactta tcacactcct gcaacagatt gttctgatgg caattacaat   660
cgtaatgcca gtctgaactc ttttaaggag tattttaatt tacgtaactg cacctttatg   720
tacacttata acattaccga agatgagatt ttagagtggt ttggcattac acaaactgct   780
caaggtgttc acctcttctc atctcggtat gttgatttgt acggcggcaa tatgtttcaa   840
tttgccacct tgcctgttta tgatactatt aagtattatt ctatcattcc tcacagtatt   900
cgttctatcc aaagtgatag aaaagcttgg gctgccttct acgtatataa acttcaaccg   960
ttaactttcc tgttggattt ttctgttgat ggttatatac gcagagctat agactgtggt  1020
tttaatgatt tgtcacaact ccactgctca tatgaatcct tcgatgttga atctggagtt  1080
tattcagttt cgtctttcga agcaaaacct tctggctcag ttgtggaaca ggctgaaggt  1140
gttgaatgtg attttcacc tcttctgtct ggcacacctc ctcaggttta taatttcaag  1200
cgtttggttt ttaccaattg caattataat cttaccaaat tgctttcact ttttttctgtg  1260
aatgatttta cttgtagtca aatatctcca gcagcaattg ctagcaactg ttattcttca  1320
ctgattttgg attacttttc atacccactt agtatgaaat ccgatctcag tgttagttct  1380
gctggtccaa tatcccagtt taattataaa cagtccttt ctaatcccac atgtttgatt  1440
ttagcgactg ttcctcataa ccttactact attactaagc ctcttaagta cagctatatt  1500
aacaagtgct ctcgtcttct ttctgatgat cgtactgaag tacctcagtt agtgaacgct  1560
aatcaatact caccctgtgt atccattgtc ccatccactg tgtgggaaga cggtgattat  1620
tataggaaac aactatctcc acttgaaggt ggtggctggc ttgttgctag tggctcaact  1680
gttgccatga ctgagcaatt acagatgggc tttggtatta cagttcaata tggtacagac  1740
accaatagtg tttgccccaa gcttgaattt gctaatgaca caaaaattgc ctctcaatta  1800
ggcaattgcg tggaatattc cctctatggt gtttcgggcc gtggtgtttt tcagaattgc  1860
acagctgtag gtgttcgaca gcagcgcttt gtttatgatg cgtaccagaa tttagttggc  1920
tattattctg atgatggcaa ctactactgt ttgcgtgctt gtgttagtgt tcctgtttct  1980
gtcatctatg ataaagaaac taaaacccac gctactctat ttggtagtgt tgcatgtgaa  2040
cacatttctt ctaccatgtc tcaatactcc cgttctacgc gatcaatgct taaacggcga  2100
gattctacat atggcccct tcagacacct gttggttgtg tcctaggact tgttaattcc  2160
tctttgttcg tagaggactg caagttgcct cttggtcaat ctctctgtgc tcttcctgac  2220
acacctagta ctctcacacc tcgcagtgtg cgctctgttc caggtgaaat gcgcttggca  2280
tccattgctt ttaatcatcc tattcaggtt gatcaactta atagtagttta ttttaaatta  2340
agtatacca ctaattttc ctttggtgtg actcaggagt acattcagac aaccattcag  2400
aaagttactg ttgattgtaa acagtacgtt tgcaatggtt tccagaagtg tgagcaatta  2460
```

```
ctgcgcgagt atggccagtt ttgttccaaa ataaaccagg ctctccatgg tgccaattta    2520
cgccaggatg attctgtacg taatttgttt gcgagcgtga aaagctctca atcatctcct    2580
atcataccag gttttggagg tgactttaat ttgacacttc tagaacctgt ttctatatct    2640
actggcagtc gtagtgcacg tagtgctatt gaggatttgc tatttgacaa agtcactata    2700
gctgatcctg gttatatgca aggttacgat gattgcatgc agcaaggtcc agcatcagct    2760
cgtgatctta tttgtgctca atatgtggct ggttacaaag tattacctcc tcttatggat    2820
gttaatatgg aagccgcgta tacttcatct ttgcttggca gcatagcagg tgttggctgg    2880
actgctggct tatcctcctt tgctgctatt ccatttgcac agagtatctt ttataggtta    2940
aacggtgttg gcattactca acaggttctt tcagagaacc aaaagcttat tgccaataag    3000
tttaatcagg ctctgggagc tatgcaaaca ggcttcacta caactaatga agcttttcag    3060
aaggttcagg atgctgtgaa caacaatgca caggctctat ccaaattagc tagcgagcta    3120
tctaatactt ttggtgctat ttccgcctct attggagaca tcatacaacg tcttgatgtt    3180
ctcgaacagg acgcccaaat agacagactt attaatggcc gtttgacaac actaaatgct    3240
tttgttgcac agcagcttgt tcgttccgaa tcagctgctc tttccgctca attggctaaa    3300
gataaagtca atgagtgtgt caaggcacaa tccaagcgtt ctggattttg cggtcaaggc    3360
acacatatag tgtcctttgt tgtaaatgcc cctaatggcc tttacttcat gcatgttggt    3420 tattcccta gcaaccacat tgaggttgtt tctgcttatg gtctttgcga tgcagctaac    3480
cctactaatt gtatagcccc tgttaatggc tactttatta aaactaataa cactaggatt    3540
gttgatgagt ggtcatatac tggctcgtcc ttctatgcac ctgagcccat tacctccctt    3600
aatactaagt atgttgcacc acaggtgaca taccaaaaca tttctactaa cctcccctcct    3660 cctcttctcg gcaattccac cgggattgac ttccaagatg agttggatga ttttttcaaa    3720
aatgttagca ccagtatacc taattttggt tccctaacac agattaatac tacattactc    3780
gatcttacct acgagatgtt gtctcttcaa caagttgtta agcccttaa tgagtcttac    3840 atagacctta aagagcttgg caattatact tattacaaca atggccgtg gtacatttgg    3900 cttggtttca ttgctgggct tgttgcctta gctctatgcg tcttcttcat actgtgctgc    3960
actggttgtg gcacaaactg tatgggaaaa cttaagtgta attaa               4005
```

<210> SEQ ID NO 14
<211> LENGTH: 1334
<212> TYPE: PRT
<213> ORGANISM: Artificial Sequence
<220> FEATURE:
<223> OTHER INFORMATION: Middle Easter Respiratory Syndrom Coronavirus
       spike glycoprotein tuncation - 19 amino acid deleted from the
       C-terminus

<400> SEQUENCE: 14

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80
```

```
His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495
```

-continued

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
            515                 520                 525

Ile Val Pro Ser Thr Val Trp Glu Asp Gly Asp Tyr Tyr Arg Lys Gln
            530                 535                 540

Leu Ser Pro Leu Glu Gly Gly Trp Leu Val Ala Ser Gly Ser Thr
545                 550                 555                 560

Val Ala Met Thr Glu Gln Leu Gln Met Gly Phe Gly Ile Thr Val Gln
            565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
            610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
            645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
            675                 680                 685

Tyr Ser Arg Ser Thr Arg Ser Met Leu Lys Arg Arg Asp Ser Thr Tyr
            690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
            755                 760                 765

Gln Val Asp Gln Leu Asn Ser Ser Tyr Phe Lys Leu Ser Ile Pro Thr
            770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
            805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
            835                 840                 845

Leu Phe Ala Ser Val Lys Ser Ser Gln Ser Ser Pro Ile Ile Pro Gly
            850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
            885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr

-continued

```
            915                 920                 925
Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
            995                 1000                1005

Gln Thr Gly Phe Thr Thr Thr Asn Glu Ala Phe Gln Lys Val Gln
    1010                1015                1020

Asp Ala Val Asn Asn Asn Ala Gln Ala Leu Ser Lys Leu Ala Ser
    1025                1030                1035

Glu Leu Ser Asn Thr Phe Gly Ala Ile Ser Ala Ser Ile Gly Asp
    1040                1045                1050

Ile Ile Gln Arg Leu Asp Val Leu Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110

Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr Tyr Asn
    1280                1285                1290

Lys Trp Pro Trp Tyr Ile Trp Leu Gly Phe Ile Ala Gly Leu Val
    1295                1300                1305

Ala Leu Ala Leu Cys Val Phe Phe Ile Leu Cys Cys Thr Gly Cys
    1310                1315                1320
```

Gly Thr Asn Cys Met Gly Lys Leu Lys Cys Asn
    1325            1330

<210> SEQ ID NO 15
<211> LENGTH: 2123
<212> TYPE: DNA
<213> ORGANISM: Rabies virus

<400> SEQUENCE: 15

| | | | | | |
|---|---|---|---|---|---|
| aaaaaaaaaa | aaaaaaaaa | aaaaaaaaa | aaactattaa | catccctcaa | aagacttagg | 60 |
| gaaagatggt | tccgcaagct | cttctgcttg | tacccattct | gggttttcc | tcgtgtttcg | 120 |
| ggaaattccc | tatttacacg | ataccagaca | cacttggtcc | ctggagcccg | atcgatatac | 180 |
| atcatctcag | ttgcccaaac | aatttggttg | tagaggacga | aggatgcacc | aacctgtcag | 240 |
| ggttctccta | catggaactt | aaagttggac | acatctcagc | cataaaggtg | aacgggttca | 300 |
| cttgcacagg | cgttgtaaca | gaggcagaaa | cctacactaa | ctttgttggt | tatgtcacca | 360 |
| ccactttcaa | aagaaagcat | ttccgcccaa | caccagatgc | ttgtagagct | gcgtacaact | 420 |
| ggaagatggc | cggtgacccc | agatatgaag | agtctctaca | cagtccgtac | cctgactacc | 480 |
| attggcttcg | aactgtaaaa | accacaaagg | agtccctcgt | tatcatatct | ccaagtgtgg | 540 |
| tagatttgga | cccatatgac | aactcccttc | actcgagggt | cttccctagc | ggaaagtgct | 600 |
| caggaataac | agtatcttct | gtctactgct | caactaacca | cgattacacc | gtttggatgc | 660 |
| ctgaaagtct | gagactaggg | acatcttgtg | acatttttac | caatagtaga | gggaagagag | 720 |
| tatccaaggg | gagcaagacc | tgtggctttg | tagatgaaag | aggcctatat | aagtctctaa | 780 |
| aaggcgcatg | caaactcaag | ttgtgtggag | ttcgtggact | tagacttatg | gacggaacat | 840 |
| gggtcgcgat | gcagacatca | aatgagacca | aatggtgtcc | tcccgatcag | ttggttaatc | 900 |
| tgcacgacct | tcgctcagat | gaaatcgagc | atcttgttat | agaggagttg | gtcaagaaaa | 960 |
| gagaggagtg | tctggatgca | ttagagtcca | tcataaccac | caagtcagtg | agtttcagac | 1020 |
| gtctcagtta | tttaagaaaa | cttgtccccg | ggttcggaaa | agcatatacc | atattcaaca | 1080 |
| agaccttgat | ggaggctgaa | gctcactaca | agtcagtcag | gacttggaat | gagatcatcc | 1140 |
| cctcaaaagg | atgtttgaga | gttggaggga | ggtgtcatcc | tcatgtaaac | ggggtgtttt | 1200 |
| tcaatggtat | aatattaggg | cctgacggtc | atgttttaat | cccagagatg | caatcatccc | 1260 |
| tcctccagca | acatatagag | ttattggaat | cctcagttat | tcccctgatg | cacccccttg | 1320 |
| cagacccgtt | cacagttttc | aaggacggcg | atgagactga | ggattttata | gaagttcacc | 1380 |
| ttcccgatgt | gcacgaacaa | gtctcagggg | ttgacctggg | tctcccgaac | tggggggagt | 1440 |
| atgtattact | aagtgcaggg | accttgattg | ccttgatgtt | gataatttc | ctaatgacat | 1500 |
| gttgtagaaa | agtcgatcgg | ccagaatcta | cacaacgcag | tctcagaggg | acaggaagga | 1560 |
| atgtgtcagt | cacctcccaa | agcgggaaat | tcataccttc | atgggagtcg | tataaaagtg | 1620 |
| ggggtgagac | tggactgtga | agatttgtca | tcttttcgac | gcttcaagtt | ctgaagataa | 1680 |
| ccttccctct | aagctggggg | gaatctctga | gttcaatagt | cctccttgaa | ctccattcaa | 1740 |
| cagggtggat | tcaaaagtca | tgagactttc | attaatcatc | tcagttgatc | aaacaaggtc | 1800 |
| atgtagattc | tcataattcg | ggaaatcttc | tagtagtttc | agtgaccgac | agtgctttca | 1860 |
| ttccccagga | actgatgtca | aaggttgttg | acgggtcaag | aggtattct | gatgactccg | 1920 |
| tgcgtgggcc | cggacagagg | tcatagtacg | tcccatgata | gcggactcag | catgagtcga | 1980 |
| ttgagaaaag | taatctgcct | cccatgaagg | acaccggcaa | taactcacaa | tcatcttgca | 2040 |

```
tctcagcgaa gtgtgcataa ttataaaggg gctagatcat ctaagctttt cagttgagaa    2100
aaaaaaaaaa aaaaaaaaaa aaa                                            2123
```

<210> SEQ ID NO 16
<211> LENGTH: 524
<212> TYPE: PRT
<213> ORGANISM: Rabies virus

<400> SEQUENCE: 16

```
Met Val Pro Gln Val Leu Leu Phe Ala Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Leu His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Asn Cys Ser Gly Ile Thr Val Ser Ser Thr Tyr Cys Ser Thr Asn His
            180                 185                 190

Asp Tyr Thr Ile Trp Met Pro Glu Asn Leu Arg Leu Gly Thr Ser Cys
        195                 200                 205

Asp Ile Phe Thr His Ser Arg Gly Lys Arg Ala Ser Lys Gly Asp Lys
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Pro Gly Gln Leu Val Asn Leu His Asp Phe Arg Ser Asp Glu Ile Glu
        275                 280                 285

His Leu Val Glu Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Gln
            340                 345                 350
```

Thr Trp Asn Glu Ile Ile Pro Ser Lys Gly Cys Leu Arg Val Gly Glu
            355                 360                 365

Arg Cys His Pro His Val Asn Gly Val Phe Phe Asn Gly Ile Ile Leu
        370                 375                 380

Gly Ser Asp Gly His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415

Pro Leu Ala Asp Pro Ser Thr Val Phe Lys Asp Gly Asp Glu Val Glu
            420                 425                 430

Asp Phe Val Glu Val His Leu Pro Asp Val His Lys Gln Val Ser Gly
        435                 440                 445

Val Asp Leu Gly Leu Pro Lys Trp Gly Lys Tyr Val Leu Met Ile Ala
    450                 455                 460

Gly Ala Leu Ile Ala Leu Met Leu Ile Ile Phe Leu Met Thr Cys Cys
465                 470                 475                 480

Arg Arg Val Asn Arg Pro Glu Ser Thr Gln Ser Asn Leu Gly Gly Thr
                485                 490                 495

Gly Arg Asn Val Ser Val Pro Ser Gln Ser Gly Lys Val Ile Ser Ser
            500                 505                 510

Trp Glu Ser Tyr Lys Ser Gly Gly Glu Thr Arg Leu
        515                 520

<210> SEQ ID NO 17
<211> LENGTH: 25
<212> TYPE: DNA
<213> ORGANISM: Artificial Sequence
<220> FEATURE:
<223> OTHER INFORMATION: TRFC forward primer

<400> SEQUENCE: 17
atgacgttga attgaacctg gacta                                         25

<210> SEQ ID NO 18
<211> LENGTH: 21
<212> TYPE: DNA
<213> ORGANISM: Artificial Sequence
<220> FEATURE:
<223> OTHER INFORMATION: TRFC reverse primer

<400> SEQUENCE: 18
gtctccacga gcggaataca g                                             21

<210> SEQ ID NO 19
<211> LENGTH: 30
<212> TYPE: DNA
<213> ORGANISM: Artificial Sequence
<220> FEATURE:
<223> OTHER INFORMATION: TRC probe

<400> SEQUENCE: 19
atcagggata tgggtctaag tctacagtgg                                    30

<210> SEQ ID NO 20
<211> LENGTH: 11928
<212> TYPE: DNA
<213> ORGANISM: Artificial Sequence
<220> FEATURE:
<223> OTHER INFORMATION: Rabies virus vector SAD B19 genome

<400> SEQUENCE: 20

-continued

```
acgcttaaca accagatcaa agaaaaaaca gacattgtca attgcaaagc aaaaatgtaa      60
caccccctaca atggatgccg acaagattgt attcaaagtc aataatcagg tggtctcttt    120
gaagcctgag attatcgtgg atcaatatga gtacaagtac cctgccatca aagatttgaa    180
aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatggaa ttgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgccgtcctta gtcggtcttc tcttgagtct gtataggttg agcaaaatat ccgggcaaaa    540
cactggtaac tataagacaa acattgcaga caggatagag cagattttg agacagcccc    600
ttttgttaaa atcgtggaac accatactct aatgacaact cacaaaatgt gtgctaattg    660
gagtactata ccaaacttca gattttggc cggaacctat gacatgtttt tctcccggat      720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga gagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctaggggct atctgggaga ggaattcttc gggaaaggga catttgaaag    1140
aagattcttc agagatgaga aagaacttca agaatacgag gcggctgaac tgacaaagac   1200
tgacgtagca ctggcagatg atggaactgt caactctgac gacgaggact acttttcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacgattg tgtatatcca tcatgaaaaa aactaacacc cctcctttcg    1500
aaccatccca acatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaggt ggacaatctc cctgaggata tggggcgact   1680
tcacctggat gatggaaaat cgcccaacca tggtgagata gccaaggtgg agaaggcaa    1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggctacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
```

-continued

```
ttgctaaccg aacctctccc ctcagtccct ctagacaata aaatccgaga tgtcccaaag    2460
tcaacatgaa aaaacaggc aacaccactg ataaaatgaa cctcctacgt aagatagtga    2520
aaaaccgcag ggacgaggac actcaaaaat cctctcccgc gtcagcccct ctggatgacg    2580
atgacttgtg gcttccaccc cctgaatacg tcccgctgaa agaacttaca ggcaagaaga    2640
acatgaggaa cttttgtatc aacggaaggg ttaaagtgtg tagcccgaat ggttactcgt    2700
tcaggatcct gcggcacatt ctgaaatcat tcgacgagat atattctggg aatcatagga    2760
tgatcgggtt agtcaaagtg gttattggac tggctttgtc aggatctcca gtccctgagg    2820
gcctgaactg ggtatacaaa ttgaggagaa cctttatctt ccagtgggct gattccaggg    2880
gccctcttga aggggaggag ttggaatact ctcaggagat cacttgggat gatgatactg    2940
agttcgtcgg attgcaaata agagtgattg caaaacagtg tcatatccag ggcagagtct    3000
ggtgtatcaa catgaacccg agagcatgtc aactatggtc tgacatgtct cttcagacac    3060
aaaggtccga agaggacaaa gattcctctc tgcttctaga ataatcagat tatatcccgc    3120
aaatttatca cttgtttacc tctggaggag agaacatatg ggctcaactc caacccttgg    3180
gagcaatata acaaaaaaca tgttatggtg ccattaaacc gctgcatttc atcaaagtca    3240
agttgattac ctttacattt tgatcctctt ggatgtgaaa aaaactatta acatccctca    3300
aaagactcaa ggaaagatgg ttcctcaggc tctcctgttt gtaccccttc tggtttttcc    3360
attgtgtttt gggaaattcc ctatttacac gataccagac aagcttggtc cctggagtcc    3420
gattgacata catcacctca gctgcccaaa caatttggta gtggaggacg aaggatgcac    3480
caacctgtca gggttctcct acatggaact taaagttgga tacatcttag ccataaaagt    3540
gaacgggttc acttgcacag gcgttgtgac ggaggctgaa acctacacta acttcgttgg    3600
ttatgtcaca accacgttca aaagaaagca tttccgccca acaccagatg catgtagagc    3660
cgcgtacaac tggaagatgg ccggtgaccc cagatatgaa gagtctctac acaatccgta    3720
ccctgactac cgctggcttc gaactgtaaa aaccaccaag gagtctctcg ttatcatatc    3780
tccaagtgtg gcagatttgg acccatatga cagatccctt cactcgaggg tcttccctag    3840
cgggaagtgc tcaggagtag cggtgtcttc tacctactgc tccactaacc acgattacac    3900
catttggatg cccgagaatc cgagactagg gatgtcttgt gacatttttta ccaatagtag    3960 agggaagaga gcatccaaag ggagtgagac ttgcggcttt gtagatgaaa gaggcctata    4020 taagtctttta aaaggagcat gcaaactcaa gttatgtgga gttctaggac ttagacttat    4080
ggatggaaca tgggtctcga tgcaaacatc aaatgaaacc aaatggtgcc ctcccgataa    4140
gttggtgaac ctgcacgact ttcgctcaga cgaaattgag caccttgttg tagaggagtt    4200
ggtcaggaag agagaggagt gtctggatgc actagagtcc atcatgacaa ccaagtcagt    4260
gagtttcaga cgtctcagtc atttaagaaa acttgtccct gggtttggaa aagcatatac    4320
catattcaac aagaccttga tggaagccga tgctcactac aagtcagtca gaacttggaa    4380
tgagatcctc ccttcaaaag ggtgtttaag agttgggggg aggtgtcatc ctcatgtgaa    4440
cggggtgttt ttcaatggta taatattagg acctgacggc aatgtcttaa tcccagagat    4500
gcaatcatcc ctcctccagc aacatatgga gttgttggaa tcctcggtta tccccttgt    4560 gcacccctg gcagacccgt ctaccgttttt caaggacggt gacgaggctg aggattttgt    4620
tgaagttcac cttcccgatg tgcacaatca ggtctcagga gttgacttgg gtctcccgaa    4680
ctgggggaag tatgtattac tgagtgcagg ggccctgact gccttgatgt tgataatttt    4740
```

```
cctgatgaca tgttgtagaa gagtcaatcg atcagaacct acgcaacaca atctcagagg    4800
gacagggagg gaggtgtcag tcactcccca aagcgggaag atcatatctt catgggaatc    4860
acacaagagt gggggtgaga ccagactgta aggactggcc gtcctttcaa cgatccaagt    4920
cctgaagatc acctcccctt gggggggttct ttttgaaaaa cctgggttca atagtcctcc    4980
ttgaactcca tgcaactggg tagattcaag agtcatgaga ttttcattaa tcctctcagt    5040
tgatcaagca agatcatgtc gattctcata taggggaga tcttctagca gtttcagtga    5100
ctaacggtac tttcattctc caggaactga caccaacagt tgtagacaaa ccacggggtg    5160
tctcgggtga ctctgtgctt gggcacagac aaaggtcatg gtgtgttcca tgatagcgga    5220
ctcaggatga gttaattgag agaggcagtc ttcctcccgt gaaggacata agcagtagct    5280
cacaatcatc tcgcgtctca gcaaagtgtg cataattata aagtgctggg tcatctaagc    5340
ttttcagtcg agaaaaaaac attagatcag aagaacaact ggcaacactt ctcaacctga    5400
gacttacttc aagatgctcg atcctggaga ggtctatgat gaccctattg acccaatcga    5460
gttagaggct gaacccagag gaaccccat tgtccccaac atcttgagga actctgacta    5520
caatctcaac tctcctttga tagaagatcc tgctagacta atgttagaat ggttaaaaac    5580
agggaataga ccttatcgga tgactctaac agacaattgc tccaggtctt tcagagtttt    5640
gaaagattat ttcaagaagg tagatttggg ttctctcaag gtgggcggaa tggctgcaca    5700
gtcaatgatt tctctctggt tatatggtgc ccactctgaa tccaacagga gccggagatg    5760
tataacagac ttggcccatt tctattccaa gtcgtccccc atagagaagc tgttgaatct    5820
cacgctagga aatagagggc tgagaatccc cccagaggga gtgttaagtt gccttgagag    5880
ggttgattat gataatgcat ttggaaggta tcttgccaac acgtattcct cttacttgtt    5940
cttccatgta atcaccttat acatgaacgc cctagactgg gatgaagaaa agaccatcct    6000
agcattatgg aaagatttaa cctcagtgga catcgggaag gacttggtaa agttcaaaga    6060
ccaaatatgg ggactgctga tcgtgacaaa ggactttgtt tactcccaaa gttccaattg    6120 tcttttgac agaaactaca cacttatgct aaaagatctt ttcttgtctc gcttcaactc    6180
cttaatggtc ttgctctctc ccccagagcc ccgatactca gatgacttga tatctcaact    6240
atgccagctg tacattgctg gggatcaagt cttgtctatg tgtggaaact ccggctatga    6300
agtcatcaaa atattggagc catatgtcgt gaatagttta gtccagagag cagaaaagtt    6360
taggcctctc attcattcct tgggagactt tcctgtattt ataaaagaca aggtaagtca    6420
acttgaagag acgttcggtc cctgtgcaag aaggttcttt agggctctgg atcaattcga    6480
caacatacat gacttggttt tgtgtttgg ctgttacagg cattgggggc acccatatat    6540
agattatcga aagggtctgt caaaactata tgatcaggtt caccttaaaa aaatgataga    6600
taagtcctac caggagtgct tagcaagcga cctagccagg aggatccta gatggggttt    6660 tgataagtac tccaagtggt atctggattc aagattccta gcccgagacc accccttgac    6720
tccttatatc aaaacccaaa catggccacc caaacatatt gtagacttgg tgggggatac    6780
atggcacaag ctcccgatca cgcagatctt tgagattcct gaatcaatgg atccgtcaga    6840
aatattggat gacaaatcac attctttcac cagaacgaga ctagcttctt ggctgtcaga    6900
aaaccgaggg gggcctgttc ctagcgaaaa agttattatc acggccctgt ctaagccgcc    6960
tgtcaatccc cgagagtttc tgaggtctat agacctcgga ggattgccag atgaagactt    7020
gataattggc ctcaagccaa aggaacggga attgaagatt gaaggtcgat tctttgctct    7080
aatgtcatgg aatctaagat tgtattttgt catcactgaa aaactcttgg ccaactacat    7140
```

```
cttgccactt tttgacgcgc tgactatgac agacaacctg aacaaggtgt ttaaaaagct   7200
gatcgacagg gtcaccgggc aagggctttt ggactattca agggtcacat atgcatttca   7260
cctggactat gaaaagtgga acaaccatca aagattagag tcaacagagg atgtattttc   7320
tgtcctagat caagtgtttg gattgaagag agtgttttct agaacacacg agttttttca   7380
aaaggcctgg atctattatt cagacagatc agacctcatc gggttacggg aggatcaaat   7440
atactgctta gatgcgtcca acggcccaac ctgttggaat ggccaggatg gcgggctaga   7500
aggcttacgg cagaagggct ggagtctagt cagcttattg atgatagata gagaatctca   7560
aatcaggaac acaagaacca aaatactagc tcaaggagac aaccaggttt tatgtccgac   7620
atacatgttg tcgccagggc tatctcaaga ggggctcctc tatgaattgg agagaatatc   7680
aaggaatgca ctttcgatat acagagccgt cgaggaaggg gcatctaagc tagggctgat   7740
catcaagaaa gaagagacca tgtgtagtta tgacttcctc atctatggaa aaaccccttt   7800
gtttagaggt aacatattgg tgcctgagtc caaaagatgg gccagagtct cttgcgtctc   7860
taatgaccaa atagtcaacc tcgccaatat aatgtcgaca gtgtccacca atgcgctaac   7920
agtggcacaa cactctcaat cttttgatcaa accgatgagg gattttctgc tcatgtcagt   7980
acaggcagtc tttcactacc tgctatttag cccaatctta aagggaagag tttacaagat   8040
tctgagcgct gaaggggaga gcttttctcct agccatgtca aggataatct atctagatcc   8100
ttctttggga gggatatctg gaatgtccct cggaagattc catatacgac agttctcaga   8160
ccctgtctct gaagggttat ccttctggag agagatctgg ttaagctccc aagagtcctg   8220
gattcacgcg ttgtgtcaag aggctggaaa cccagatctt ggagagagaa cactcgagag   8280
cttcactcgc cttctagaag atccgaccac cttaaatatc agaggagggg ccagtcctac   8340
cattctactc aaggatgcaa tcagaaaggc tttatatgac gaggtggaca aggtggaaaa   8400
ttcagagttt cgagaggcaa tcctgttgtc caagacccat agagataatt ttatactctt   8460
cttaatatct gttgagcctc tgtttcctcg atttctcagt gagctattca gttcgtcttt   8520
tttgggaatc cccgagtcaa tcattggatt gatacaaaac tcccgaacga taagaaggca   8580
gtttagaaag agtctctcaa aaactttaga agaatccttc tacaactcag agatccacgg   8640
gattagtcgg atgacccaga cacctcagag ggttgggggg gtgtggcctt gctcttcaga   8700
gagggcagat ctactaggg agatctcttg gggaagaaaa gtggtaggca cgacagttcc   8760
tcacccttct gagatgttgg gattacttcc caagtcctct atttcttgca cttgtggagc   8820
aacaggagga ggcaatccta gagtttctgt atcagtactc ccgtcctttg atcagtcatt   8880
tttttcacga ggcccccctaa agggatactt gggctcgtcc acctctatgt cgacccagct   8940
attccatgca tgggaaaaag tcactaatgt tcatgtggtg aagagagctc tatcgttaaa   9000
agaatctata aactggttca ttactagaga ttccaacttg gctcaagctc taattaggaa   9060
cattatgtct ctgacaggcc ctgatttccc tctagaggag gcccctgtct tcaaaaggac   9120
ggggtcagcc ttgcataggt tcaagtctgc cagatacagc gaaggagggt attcttctgt   9180
ctgcccgaac ctcctctctc atatttctgt tagtacagac accatgtctg atttgaccca   9240
agacgggaag aactacgatt tcatgttcca gccattgatg ctttatgcac agacatggac   9300
atcagagctg gtacagagag acacaaggct aagagactct acgtttcatt ggcacctccg   9360
atgcaacagg tgtgtgagac ccattgacga cgtgaccctg gagacctctc agatcttcga   9420
gtttccggat gtgtcgaaaa gaatatccag aatggtttct ggggctgtgc ctcacttcca   9480
```

```
gaggcttccc gatatccgtc tgagaccagg agattttgaa tctctaagcg gtagagaaaa    9540
gtctcaccat atcggatcag ctcaggggct cttatactca atcttagtgg caattcacga    9600
ctcaggatac aatgatggaa ccatcttccc tgtcaacata tacggcaagg tttcccctag    9660
agactatttg agagggctcg caaggggagt attgatagga tcctcgattt gcttcttgac    9720
aagaatgaca aatatcaata ttaatagacc tcttgaattg gtctcagggg taatctcata    9780
tattctcctg aggctagata accatccctc cttgtacata atgctcagag aaccgtctct    9840
tagaggagag atattttcta tccctcagaa aatccccgcc gcttatccaa ccactatgaa    9900
agaaggcaac agatcaatct tgtgttatct ccaacatgtg ctacgctatg agcgagagat    9960
aatcacggcg tctccagaga atgactggct atggatcttt tcagacttta gaagtgccaa   10020
aatgacgtac ctatccctca ttacttacca gtctcatctt ctactccaga gggttgagag   10080
aaacctatct aagagtatga gagataacct gcgacaattg agttctttga tgaggcaggt   10140
gctgggcggg cacggagaag ataccttaga gtcagacgac aacattcaac gactgctaaa   10200
agactcttta cgaaggacaa gatgggtgga tcaagaggtg cgccatgcag ctagaaccat   10260
gactggagat tacagcccca acaagaaggt gtcccgtaag gtaggatgtt cagaatgggt   10320
ctgctctgct caacaggttg cagtctctac ctcagcaaac ccggcccctg tctcggagct   10380
tgacataagg gccctctcta agaggttcca gaaccctttg atctcgggct gagagtggt   10440
tcagtgggca accggtgctc attataagct taagcctatt ctagatgatc tcaatgtttt   10500
cccatctctc tgccttgtag ttggggacgg gtcagggggg atatcaaggg cagtcctcaa   10560
catgtttcca gatgccaagc ttgtgttcaa cagtctttta gaggtgaatg acctgatggc   10620
ttccggaaca catccactgc ctccttcagc aatcatgagg ggaggaaatg atatcgtctc   10680
cagagtgata gatcttgact caatctggga aaaaccgtcc gacttgagaa acttggcaac   10740
ctggaaatac ttccagtcag tccaaaagca ggtcaacatg tcctatgacc tcattatttg   10800
cgatgcagaa gttactgaca ttgcatctat caaccggatc accctgttaa tgtccgattt   10860
tgcattgtct atagatggac cactctattt ggtcttcaaa acttatggga ctatgctagt   10920
aaatccaaac tacaaggcta ttcaacacct gtcaagagcg ttcccctcgg tcacagggtt   10980
tatcacccaa gtaacttcgt cttttcatc tgagctctac ctccgattct ccaaacgagg   11040
gaagttttc agagatgctg agtacttgac ctcttccacc cttcgagaaa tgagccttgt   11100
gttattcaat tgtagcagcc ccaagagtga gatgcagaga gctcgttcct tgaactatca   11160
ggatcttgtg agaggatttc ctgaagaaat catatcaaat ccttacaatg agatgatcat   11220
aactctgatt gacagtgatg tagaatcttt tctagtccac aagatggttg atgatcttga   11280
gttacagagg ggaactctgt ctaaagtggc tatcattata gccatcatga tagttttctc   11340
caacagagtc ttcaacgttt ccaaacccct aactgacccc tcgttctatc caccgtctga   11400
tcccaaaatc ctgaggcact tcaacatatg ttgcagtact atgatgtatc tatctactgc   11460
tttaggtgac gtccctagct tcgcaagact tcacgacctg tataacagac ctataactta   11520
ttacttcaga aagcaagtca ttcgagggaa cgtttatcta tcttggagtt ggtccaacga   11580
cacctcagtt ttcaaaaggg tagcctgtaa ttctagcctg agtctgtcat ctcactggat   11640
caggttgatt tacaagatag tgaagactac cagactcgtt ggcagcatca aggatctatc   11700
cagagaagtg gaaagacacc ttcataggta caacaggtgg atcaccctag aggatatcag   11760
atctagatca tccctactag actacagttg cctgtgaacc ggatactcct ggaagcctgc   11820
ccatgctaag actcttgtgt gatgtatctt gaaaaaaaca agatcctaaa tctgaacctt   11880
```

```
tggttgtttg attgttttc tcattttgt tgtttatttg ttaagcgt        11928
```

<210> SEQ ID NO 21
<211> LENGTH: 14108
<212> TYPE: DNA
<213> ORGANISM: Artificial Sequence
<220> FEATURE:
<223> OTHER INFORMATION: Recombinant Rabies virus vector BNSP333
      expressing a chimeric protein comprising the S1 domain of Middle
      East Respiratory Syndrome Coronavirus fused to the C-terminal part
      of the Rabies virus G glycoprotein (amino acids 428-524)

<400> SEQUENCE: 21

```
acgcttaaca accagatcaa agaaaaaaca gacattgtca attgcaaagc aaaaatgtaa       60
caccccctaca atggatgccg acaagattgt attcaaagtc aataatcagg tggtctcttt     120
gaagcctgag attatcgtgg atcaatatga gtacaagtac cctgccatca agatttgaa       180
aaagcccctgt ataaccctag aaaggctcc cgatttaaat aaagcataca agtcagtttt     240
gtcaggcatg agcgccgcca acttaatcc tgacgatgta tgttcctatt tggcagcggc      300
aatgcagttt tttgagggga catgtccgga agactggacc agctatggaa ttgtgattgc     360
acgaaaagga gataagatca ccccaggttc tctggtggga ataaaacgta ctgatgtaga    420
agggaattgg gctctgacag gaggcatgga actgacaaga gaccccactg tccctgagca   480
tgcgtcctta gtcggtcttc tcttgagtct gtataggttg agcaaaatat ccgggcaaaa   540
cactggtaac tataagacaa acattgcaga caggatagag cagattttg agacagcccc    600
ttttgttaaa atcgtggaac accatactct aatgacaact cacaaaatgt gtgctaattg     660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcattactg ggttcataaa acaaatcaat ctcaccgcta gagaggcaat     840
actatattc ttccacaaga actttgagga agagataaga gaatgtttg agccagggca     900
ggagacagct gttcctcact cttattttcat ccacttccgt tcactaggct gagtgggaa    960
atctccttat tcatcaaatg ctgttggtca cgtgttcaat ctcattcact tgtaggatg    1020
ctatatgggt caagtcagat ccctaaatgc aacggttatt gctgcatgtg ctcctcatga   1080
aatgtctgtt ctaggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttttcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taacatgaaa aaaactaaca   1440
ccccctcccgt acgccgccac catgattcac tctgtgttcc tgctgatgtt cctgctgaca   1500
ccaacagagt cctatgtgga tgtgggacct gactctgtga gtctgcctg tattgaggtg    1560
gacatccaac agaccttctt tgacaagacc tggccaagac caattgatgt gagcaaggct   1620
gatggcatca tctacccaca gggcaggacc tacagcaaca tcaccatcac ctaccaggga   1680
ctgtttccat accagggaga tcatggagat atgtatgtct actctgctgg tcatgccaca   1740
ggcaccacac acagaaaact gtttgtggct aactacagcc aggatgtgaa gcagtttgcc   1800
aatggctttg tggtgaggat tggagcagca gccaacagca caggcacagt gattatcagc   1860
ccaagcacct ctgccaccat caggaagatt taccctgcct ttatgctggg ctcctctgtg   1920
```

```
ggcaacttct ctgatggcaa gatgggcagg ttcttcaacc acaccctggt gctgctgcct   1980
gatggctgtg gcaccctgct gagggctttc tactgtatct tggaaccaag gtctggcaac   2040
cactgtcctg ctggcaactc ctacacctcc tttgccacct accacacacc tgccacagac   2100
tgttctgatg gcaactacaa caggaatgcc tccctgaact ccttcaagga atacttcaac   2160
ctgaggaact gtacctttat gtacacctac aacatcacag aggatgagat tttggagtgg   2220
tttggcatca cccagacagc ccaggggagtg catctgttct cgagcagata tgtggacctc   2280
tatggaggca atatgttcca gtttgccacc ctgcctgtct atgacaccat caaatactac   2340
agcatcatcc cacacagcat caggagcatc cagtctgaca ggaaggcttg ggctgccttc   2400
tatgtctaca aactccaacc actgaccttc ctgctggact tctctgtgga tggctacatc   2460
aggagggcta ttgactgtgg cttcaatgac ctgagccaac ttcactgttc ctatgagtcc   2520
tttgatgtgg agtctggagt ctactctgtg tcctcctttg aggctaagcc atctggctct   2580
gtggtggaac aggctgaggg agtggagtgt gacttcagcc cactgctgtc tggcacacct   2640
ccacaggtct acaacttcaa gagactggtg ttcaccaact gtaactacaa cctgaccaaa   2700
ctgctgtccc tgttctctgt gaatgacttc acttgtagcc agattagccc tgctgccatt   2760
gccagcaact gttactcctc cctgattctg gactacttct cctacccact gagtatgaag   2820
tctgacctgt ctgtgtcctc tgctggacca atcagccagt tcaactacaa gcagtccttc   2880
agcaacccaa cttgtctgat tctggctaca gtgccacaca acctgaccac catcaccaag   2940
ccactgaaat actcctacat caacaagtgt agcagactgc tgtctgatga caggacagag   3000
gtgccacaac tagtgaatgc caaccaatac agcccatgtg tgagcattgt gccaagcaca   3060
gtgtgggagg atgagactac tacaggaag caacttagcc cattggaggg aggaggctgg   3120
ctggtggcat ctggcagcac agtggctatg acagaacaac tccaaatggg ctttggcatc   3180
acagtccaat atggcacaga caccaactct gtgtgtccaa aattggagtt tgccaatgac   3240
accaagattg ccagccaact tggcaactgt gtggaatact ccctctatgg agtgtctggc   3300
aggggagtgt tccagaactg tactgctgtg ggagtgagac aacagaggtt tgtctatgat   3360
gcctaccaga acctggtggg ctactactct gatgatggca actactactg tctgagggct   3420
tgtgtgtctg tgcctgtgtc tgtgatttat acaaggaga ccaagaccca tgccaccctg   3480
tttggctctg tggcttgtga acacatctcc agcacaatga gtcaatacag caggagcacc   3540
aggagtatgc tgaaaaggag ggacagcaca tatggaccac tccaaacacc tgtgggctgt   3600
gtgctgggac tggtgaactc ctccctgttt gtggaggact gtaaactgcc actgggacaa   3660
tccctgtgtg ccctgcctga cacaccaagc accctgacac caaggtctgt gggagatgag   3720
gccgaagact ttgtggaagt ccacctgcct gatgtgcata accaggtgtc tggcgtcgac   3780
ctgggactgc caaattgggg caagtacgtg ctgctgagtg ctggagcact gactgccctg   3840
atgctgatca ttttcctgat gacctgctgt cggcgcgtga acagaagtga gcccactcag   3900
cacaatctgc gaggaaccgg gagagaagtg tcagtcacac ctcagagcgg gaaaatcatt   3960
agtagttggg aatcacataa agcgggggc gagaccaggc tgtgagctag ccatgaaaaa   4020
aactaacacc cctccttcg aaccatccca aacatgagca agatctttgt caatcctagt   4080
gctattagag ccggtctggc cgatcttgag atggctgaag aaactgttga tctgatcaat   4140
agaaatatcg aagacaatca ggctcatctc caagggaac ccatagaggt ggacaatctc   4200
cctgaggata tggggcgact tcacctggat gatggaaaat cgcccaacca tggtgagata   4260
```

```
gccaaggtgg gagaaggcaa gtatcgagag gactttcaga tggatgaagg agaggatcct    4320
agcttcctgt tccagtcata cctggaaaat gttggagtcc aaatagtcag acaaatgagg    4380
tcaggagaga gatttctcaa gatatggtca cagaccgtag aagagattat atcctatgtc    4440
gcggtcaact ttcccaaccc tccaggaaag tcttcagagg ataaatcaac ccagactact    4500
ggccgagagc tcaagaagga gacaacaccc actccttctc agagagaaag ccaatcatcg    4560
aaagccagga tggcggctca aattgcttct ggccctccag cccttgaatg gtcggctacc    4620
aatgaagagg atgatctatc agtggaggct gagatcgctc accagattgc agaaagtttc    4680
tccaaaaaat ataagtttcc ctctcgatcc tcagggatac tcttgtataa ttttgagcaa    4740
ttgaaaatga accttgatga tatagttaaa gaggcaaaaa atgtaccagg tgtgacccgt    4800
ttagcccatg acgggtccaa actcccccta agatgtgtac tgggatgggt cgctttggcc    4860
aactctaaga aattccagtt gttagtcgaa tccgacaagc tgagtaaaat catgcaagat    4920
gacttgaatc gctatacatc ttgctaaccg aacctctccc ctcagtccct ctagacaata    4980
aaatccgaga tgtcccaaag tcaacatgaa aaaacaggaa acaccactga ataaaatgaa    5040
cctcctacgt aagatagtga aaaaccgcag ggacgaggac actcaaaaat cctctcccgc    5100
gtcagcccct ctggatgacg atgacttgtg gcttccaccc cctgaatacg tcccgctgaa    5160
agaacttaca ggcaagaaga acatgaggaa cttttgtatc aacggaaggg ttaaagtgtg    5220
tagcccgaat ggttactcgt tcaggatcct gcggcacatt ctgaaatcat tcgacgagat    5280
atattctggg aatcatagga tgatcgggtt agtcaaagtg ttattggac tggctttgtc     5340 aggatctcca gtccctgagg gcctgaactg ggtatacaaa ttgaggagaa cctttatctt    5400
ccagtgggct gattccaggg gccctcttga aggggaggag ttggaatact ctcaggagat    5460
cacttgggat gatgatactg agttcgtcgg attgcaaata agagtgattg caaaacagtg    5520
tcatatccag ggcagagtct ggtgtatcaa catgaacccg agagcatgtc aactatggtc    5580
tgacatgtct cttcagacac aaaggtccga agaggacaaa gattcctctc tgcttctaga    5640
ataatcagat tatatcccgc aaatttatca cttgtttacc tctggaggag agaacatatg    5700
ggctcaactc caacccttgg gagcaatata acaaaaaaca tgttatggtg ccattaaacc    5760
gctgcatttc atcaaagtca agttgattac ctttacattt tgatcctctt ggatgtgaaa    5820
aaaactatta acatccctca aaagaccccg ggaaagatgg ttcctcaggc tctcctgttt    5880
gtaccccttc tggttttttcc attgtgtttt gggaaattcc ctatttacac gataccagac    5940
aagcttggtc cctggagtcc gattgacata catcacctca gctgcccaaa caatttggta    6000
gtggaggacg aaggatgcac caacctgtca gggttctcct acatggaact taaagttgga    6060
tacatcttag cctataaagt gaacgggttc acttgcacag gcgttgtgac ggaggctgaa    6120
acctacacta acttcgttgg ttatgtcaca accacgttca aaagaaagca tttccgccca    6180
acaccagatg catgtagagc cgcgtacaac tggaagatgg ccggtgaccc cagatatgaa    6240
gagtctctac acaatccgta ccctgactac cgctggcttc gaactgtaaa aaccaccaag    6300
gagtctctcg ttatcatatc tccaagtgtg gcagatttgg acccatatga cagatcccttt   6360 cactcgaggg tcttccctag cgggaagtgc tcaggagtag cggtgtcttc tacctactgc    6420
tccactaacc acgattacac catttggatg cccgagaatc cgagactagg gatgtcttgt    6480
gacattttta ccaatagtag agggaagaga gcatccaaag ggagtgagac ttgcggcttt    6540
gtagatgaaa gaggcctata taagtcttta aaggagcat gcaaactcaa gttatgtgga    6600
gttctaggac ttagacttat ggatggaaca tgggtctcga tgcaaacatc aaatgaaacc    6660
```

```
aaatggtgcc ctcccgataa gttggtgaac ctgcacgact ttcgctcaga cgaaattgag   6720
caccttgttg tagaggagtt ggtcaggaag agagaggagt gtctggatgc actagagtcc   6780
atcatgacaa ccaagtcagt gagtttcaga cgtctcagtc atttaagaaa acttgtccct   6840
gggtttggaa aagcatatac catattcaac aagaccttga tggaagccga tgctcactac   6900
aagtcagtcg agacttggaa tgagatcctc ccttcaaaag ggtgtttaag agttgggggg   6960
aggtgtcatc ctcatgtgaa cggggtgttt ttcaatggta taatattagg acctgacggc   7020
aatgtcttaa tcccagagat gcaatcatcc ctcctccagc aacatatgga gttgttggaa   7080
tcctcggtta tcccccttgt gcacccctg gcagacccgt ctaccgtttt caaggacggt    7140
gacgaggctg aggattttgt tgaagttcac cttcccgatg tgcacaatca ggtctcagga   7200
gttgacttgg gtctcccgaa ctgggggaag tatgtattac tgagtgcagg ggccctgact   7260
gccttgatgt tgataatttt cctgatgaca tgttgtagaa gagtcaatcg atcagaacct   7320
acgcaacaca atctcagagg gacagggagg gaggtgtcag tcactcccca aagcgggaag   7380
atcatatctt catgggaatc acacaagagt gggggtgaga ccagactgta attaattaac   7440
gtcctttcaa cgatccaagt ccatgaaaaa aactaacacc cctcccgtac ctagcttata   7500
aagtgctggg tcatctaagc ttttcagtcg agaaaaaaac attagatcag aagaacaact   7560
ggcaacactt ctcaacctga gacttacttc aagatgctcg atcctggaga ggtctatgat   7620
gaccctattg acccaatcga gttagaggct gaacccagag gaaccccat tgtccccaac    7680 atcttgagga actctgacta caatctcaac tctcctttga tagaagatcc tgctagacta   7740
atgttagaat ggttaaaaac agggaataga ccttatcgga tgactctaac agacaattgc   7800
tccaggtctt tcagagtttt gaaagattat ttcaagaagg tagatttggg ttctctcaag   7860
gtgggcggaa tggctgcaca gtcaatgatt tctctctggt tatatggtgc ccactctgaa   7920
tccaacagga gccggagatg tataacagac ttggcccatt tctattccaa gtcgtccccc   7980
atagagaagc tgttgaatct cacgctagga aatagagggc tgagaatccc cccagaggga   8040
gtgttaagtt gccttgagag ggttgattat gataatgcat ttggaaggta tcttgccaac   8100
acgtattcct cttacttgtt cttccatgta atcacccttat acatgaacgc cctagactgg   8160
gatgaagaaa agaccatcct agcattatgg aaagatttaa cctcagtgga catcgggaag   8220
gacttggtaa agttcaaaga ccaaatatgg ggactgctga tcgtgacaaa ggactttgtt   8280
tactcccaaa gttccaattg tcttttttgac agaaactaca cacttatgct aaaagatctt   8340
ttcttgtctc gcttcaactc cttaatggtc ttgctctctc ccccagagcc ccgatactca   8400
gatgacttga tatctcaact atgccagctg tacattgctg gggatcaagt cttgtctatg   8460
tgtgaaaact ccggctatga agtcatcaaa atattggagc catatgtcgt gaatagttta   8520
gtccagagag cagaaaagtt taggcctctc attcattcct tgggagactt tcctgtattt   8580
ataaaagaca aggtaagtca acttgaagag acgttcggtc cctgtgcaag aaggttcttt   8640
agggctctgg atcaattcga caacatacat gacttggttt ttgtgtttgg ctgttacagg   8700 cattggggc acccatatat agattatcga aagggtctgt caaaactata tgatcaggtt   8760
caccttaaaa aaatgataga taagtcctac caggagtgct tagcaagcga cctagccagg   8820
aggatcctta gatgggtttt tgataagtac tccaagtggt atctggattc aagattccta   8880
gcccgagacc accccttgac tccttatatc aaaaacccaaa catggccacc caaacatatt   8940
gtagacttgg tgggggatac atggcacaag ctcccgatca cgcagatctt tgagattcct   9000
```

```
gaatcaatgg atccgtcaga aatattggat gacaaatcac attctttcac cagaacgaga    9060
ctagcttctt ggctgtcaga aaaccgaggg gggcctgttc ctagcgaaaa agttattatc    9120
acggccctgt ctaagccgcc tgtcaatccc cgagagtttc tgaggtctat agacctcgga    9180
ggattgccag atgaagactt gataattggc ctcaagccaa aggaacggga attgaagatt    9240
gaaggtcgat tctttgctct aatgtcatgg aatctaagat tgtattttgt catcactgaa    9300
aaactcttgg ccaactacat cttgccactt tttgacgcgc tgactatgac agacaacctg    9360
aacaaggtgt ttaaaaagct gatcgacagg gtcaccgggc aagggctttt ggactattca    9420
agggtcacat atgcatttca cctggactat gaaaagtgga acaaccatca agattagag    9480
tcaacagagg atgtattttc tgtcctagat caagtgtttg gattgaagag agtgttttct    9540
agaacacacg agttttttca aaaggcctgg atctattatt cagacagatc agacctcatc    9600
gggttacggg aggatcaaat atactgctta gatgcgtcca acggcccaac ctgttggaat    9660
ggccaggatg gcgggctaga aggcttacgg cagaagggct ggagtctagt cagcttattg    9720
atgatagata gagaatctca aatcaggaac acaagaacca aaatactagc tcaaggagac    9780
aaccaggttt tatgtccgac atacatgttg tcgccagggc tatctcaaga ggggctcctc    9840
tatgaattgg agagaatatc aaggaatgca ctttcgatat acagagccgt cgaggaaggg    9900
gcatctaagc tagggctgat catcaagaaa gaagagacca tgtgtagtta tgacttcctc    9960
atctatggaa aaccccttt gtttagaggt aacatattgg tgcctgagtc caaaagatgg   10020
gccagagtct cttgcgtctc taatgaccaa atagtcaacc tcgccaatat aatgtcgaca   10080
gtgtccacca atgcgctaac agtggcacaa cactctcaat ctttgatcaa accgatgagg   10140
gattttctgc tcatgtcagt acaggcagtc tttcactacc tgctatttag cccaatctta   10200
aagggaagag tttacaagat tctgagcgct gaaggggaga gctttctcct agccatgtca   10260
aggataatct atctagatcc ttctttggga gggatatctg gaatgtccct cggaagattc   10320
catatacgac agttctcaga ccctgtctct gaagggttat ccttctggag agagatctgg   10380
ttaagctccc aagagtcctg gattcacgcg ttgtgtcaag aggctggaaa cccagatctt   10440
ggagagagaa cactcgagag cttcactcgc cttctagaag atccgaccac cttaaatatc   10500
agaggagggg ccagtcctac cattctactc aaggatgcaa tcagaaaggc tttatatgac   10560
gaggtggaca aggtggaaaa ttcagagttt cgagaggcaa tcctgttgtc caagacccat   10620
agagataatt ttatactctt cttaatatct gttgagcctc tgtttcctcg atttctcagt   10680
gagctattca gttcgtcttt tttgggaatc cccgagtcaa tcattggatt gatacaaaac   10740
tcccgaacga taagaaggca gtttagaaag agtctctcaa aaactttaga agaatccttc   10800
tacaactcag agatccacgg gattagtcgg atgaccaga cacctcagag ggttgggggg   10860
gtgtggcctt gctcttcaga gagggcagat ctacttaggg agatctcttg gggaagaaaa   10920
gtggtaggca cgacagttcc tcaccttct gagatgttgg gattacttcc caagtcctct   10980
atttcttgca cttgtggagc aacaggagga ggcaatccta gagtttctgt atcagtactc   11040
ccgtcctttg atcagtcatt ttttttcacga ggcccctaa agggatactt gggctcgtcc   11100
acctctatgt cgacccagct attccatgca tgggaaaaag tcactaatgt tcatgtggtg   11160
aagagagctc tatcgttaaa agaatctata aactggttca ttactagaga ttccaacttg   11220
gctcaagctc taattaggaa cattatgtct ctgacaggcc ctgatttccc tctagaggag   11280
gcccctgtct tcaaaaggac ggggtcagcc ttgcataggt tcaagtctgc cagatacagc   11340
gaaggagggt attcttctgt ctgcccgaac ctcctctctc atatttctgt tagtacagac   11400
```

```
accatgtctg atttgaccca agacgggaag aactacgatt tcatgttcca gccattgatg   11460
ctttatgcac agacatggac atcagagctg gtacagagag acacaaggct aagagactct   11520
acgtttcatt ggcacctccg atgcaacagg tgtgtgagac ccattgacga cgtgaccctg   11580
gagacctctc agatcttcga gtttccggat gtgtcgaaaa gaatatccag aatggtttct   11640
ggggctgtgc ctcacttcca gaggcttccc gatatccgtc tgagaccagg agattttgaa   11700
tctctaagcg gtagagaaaa gtctcaccat atcggatcag ctcaggggct cttatactca   11760
atcttagtgg caattcacga ctcaggatac aatgatggaa ccatcttccc tgtcaacata   11820
tacggcaagg tttcccctag agactatttg agagggctcg caaggggagt attgatagga   11880
tcctcgattt gcttcttgac aagaatgaca aatatcaata ttaatagacc tcttgaattg   11940
gtctcagggg taatctcata tattctcctg aggctagata accatccctc cttgtacata   12000
atgctcagag aaccgtctct tagaggagag atattttcta tccctcagaa aatccccgcc   12060
gcttatccaa ccactatgaa agaaggcaac agatcaatct tgtgttatct ccaacatgtg   12120
ctacgctatg agcgagagat aatcacggcg tctccagaga atgactggct atggatcttt   12180
tcagacttta gaagtgccaa aatgacgtac ctatccctca ttacttacca gtctcatctt   12240
ctactccaga gggttgagag aaacctatct aagagtatga gagataacct gcgacaattg   12300
agttctttga tgaggcaggt gctgggcggg cacggagaag atacccttaga gtcagacgac   12360 aacattcaac gactgctaaa agactctttta cgaaggacaa gatgggtgga tcaagaggtg   12420
cgccatgcag ctagaaccat gactggagat tacagcccca acaagaaggt gtcccgtaag   12480
gtaggatgtt cagaatgggt ctgctctgct caacaggttg cagtctctac ctcagcaaac   12540
ccggcccctg tctcggagct tgacataagg gccctctcta agaggttcca gaaccctttg   12600
atctcgggct tgagagtggt tcagtgggca accggtgctc attataagct taagcctatt   12660
ctagatgatc tcaatgtttt cccatctctc tgccttgtag ttggggacgg gtcaggggg   12720 atatcaaggg cagtcctcaa catgtttcca gatgccaagc ttgtgttcaa cagtctttta   12780
gaggtgaatg acctgatggc ttccggaaca catccactgc ctccttcagc aatcatgagg   12840
ggaggaaatg atatcgtctc cagagtgata gatcttgact caatctggga aaaaccgtcc   12900
gacttgagaa acttggcaac ctggaaatac ttccagtcag tccaaaagca ggtcaacatg   12960
tcctatgacc tcattatttg cgatgcagaa gttactgaca ttgcatctat caaccggatc   13020
accctgttaa tgtccgattt tgcattgtct atagatggac cactctattt ggtcttcaaa   13080
acttatggga ctatgctagt aaatccaaac tacaaggcta ttcaacacct gtcaagagcg   13140
ttcccctcgg tcacagggtt tatcacccaa gtaacttcgt cttttttcatc tgagctctac   13200 ctccgattct ccaaacgagg gaagttttttc agagatgctg agtacttgac ctcttccacc   13260
cttcgagaaa tgagccttgt gttattcaat tgtagcagcc ccaagagtga gatgcagaga   13320
gctcgttcct tgaactatca ggatcttgtg agaggatttc ctgaagaaat catatcaaat   13380
ccttacaatg agatgatcat aactctgatt gacagtgatg tagaatcttt tctagtccac   13440
aagatggttg atgatcttga gttacagagg ggaactctgt ctaaagtggc tatcattata   13500
gccatcatga tagtttttctc caacagagtc ttcaacgttt ccaaaccccct aactgacccc   13560 tcgttctatc caccgtctga tcccaaaatc ctgaggcact tcaacatatg ttgcagtact   13620
atgatgtatc tatctactgc tttaggtgac gtccctagct tcgcaagact tcacgacctg   13680
tataacagac ctataactta ttacttcaga aagcaagtca ttcgagggaa cgtttatcta   13740
```

```
tcttggagtt ggtccaacga cacctcagtg ttcaaaaggg tagcctgtaa ttctagcctg    13800
agtctgtcat ctcactggat caggttgatt tacaagatag tgaagactac cagactcgtt    13860
ggcagcatca aggatctatc cagagaagtg gaaagacacc ttcataggta caacaggtgg    13920
atcaccctag aggatatcag atctagatca tccctactag actacagttg cctgtgaacc    13980
ggatactcct ggaagcctgc ccatgctaag actcttgtgt gatgtatctt gaaaaaaaca    14040
agatcctaaa tctgaacctt tggttgtttg attgtttttc tcattttgt tgtttatttg     14100 ttaagcgt                                                             14108
```

<210> SEQ ID NO 22
<211> LENGTH: 15629
<212> TYPE: DNA
<213> ORGANISM: Artificial Sequence
<220> FEATURE:
<223> OTHER INFORMATION: Recombinant Rabies virus vector BNSP333
      expressing a wild type Middle East Respiratory Syndrome spike
      glycoprotein.

<400> SEQUENCE: 22

```
acgcttaaca accagatcaa agaaaaaaca gacattgtca attgcaaagc aaaaatgtaa      60 caccccctaca atggatgccg acaagattgt attcaaagtc aataatcagg tggtctcttt     120
gaagcctgag attatcgtgg atcaatatga gtacaagtac cctgccatca agatttgaa      180 aaagccctgt ataaccctag aaaggctcc cgatttaaat aaagcataca agtcagtttt     240
gtcaggcatg agcgccgcca aacttaatcc tgacgatgta tgttcctatt tggcagcggc     300
aatgcagttt tttgagggga catgtccgga agactggacc agctatggaa ttgtgattgc     360
acgaaaagga gataagatca ccccaggttc tctggtggag ataaaacgta ctgatgtaga     420
agggaattgg gctctgacag gaggcatgga actgacaaga ccccactg tccctgagca      480 tgcgtcctta gtcggtcttc tcttgagtct gtataggttg agcaaaatat ccgggcaaaa     540
cactggtaac tataagacaa acattgcaga caggatagag cagattttg agacagcccc     600 ttttgttaaa atcgtggaac accatactct aatgacaact cacaaaatgt gtgctaattg     660
gagtactata ccaaacttca gatttttggc cggaacctat gacatgtttt ctcccggat      720 tgagcatcta tattcagcaa tcagagtggg cacagttgtc actgcttatg aagactgttc     780
aggactggta tcatttactg ggttcataaa acaaatcaat ctcaccgcta gagaggcaat    840
actatatttc ttccacaaga actttgagga agagataaga gaatgttg agccagggca     900 ggagacagct gttcctcact cttattcat ccacttccgt tcactaggct tgagtggaa     960 atctccttat tcatcaaatg ctgttggtca cgtgttcaat ctcattcact ttgtaggatg    1020
ctatatgggt caagtcagat ccctaaatgc aacggttatt gctgcatgtg ctcctcatga    1080
aatgtctgtt ctagggggct atctgggaga ggaattcttc ggaagggaa catttgaaag    1140 aagattcttc agagatgaga agaacttca gaatacgag gcggctgaac tgacaaagac     1200
tgacgtagca ctggcagatg atggaactgt caactctgac gacgaggact acttttcagg    1260
tgaaaccaga agtccggagg ctgtttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acgccgccac catgatacac tcagtgtttc tactgatgtt cttgttaaca    1500
cctacagaaa gttacgttga tgtagggcca gattctgtta agtctgcttg tattgaggtt    1560
gatatacaac agactttctt tgataaaact tggcctaggc caattgatgt ttctaaggct    1620
```

```
gacggtatta tatacccTca aggccgtaca tattctaaca taactatcac ttatcaaggt    1680
cttttTccct atcagggaga ccatggTgat atgtatgttt actctgcagg acatgctaca    1740
ggcacaactc cacaaaagtt gtttgtagct aactattctc aggacgtcaa acagtttgct    1800
aatgggtttg tcgtccgtat aggagcagct gccaattcca ctggcactgt tattattagc    1860
ccatctacca gcgctactat acgaaaaatt taccctgctt ttatgctggg ttcttcagtt    1920
ggtaatttct cagatggtaa aatgggccgc ttcttcaatc atactctagt tcttttgccc    1980
gatggatgtg gcactttact tagagctttt tattgtattc tagagcctcg ctctggaaat    2040
cattgtcctg ctggcaattc ctatacttct tttgccactt atcacactcc tgcaacagat    2100
tgttctgatg gcaattacaa tcgtaatgcc agtctgaact cttttaagga gtattttaat    2160
ttacgtaact gcacctttat gtacacttat aacattaccg aagatgagat ttagagtgg     2220 tttggcatta cacaaactgc tcaaggtgtt cacctcttct catctcggta tgttgatttg    2280
tacggcggca atatgtttca atttgccacc ttgcctgttt atgatactat taagtattat    2340
tctatcattc ctcacagtat tcgttctatc caaagtgata gaaaagcttg gctgccttc     2400 tacgtatata aacttcaacc gttaactttc ctgttggatt tttctgttga tggttatata    2460
cgcagagcta tagactgtgg ttttaatgat ttgtcacaac tccactgctc atatgaatcc    2520
ttcgatgttg aatctggagt ttattcagtt tcgtctttcg aagcaaaacc ttctggctca    2580
gttgtggaac aggctgaagg tgttgaatgt gatttttcac ctcttctgtc tggcacacct    2640
cctcaggttt ataatttcaa gcgtttggtt tttaccaatt gcaattataa tcttaccaaa    2700
ttgctttcac ttttttctgt gaatgatttt acttgtagtc aaatatctcc agcagcaatt    2760
gctagcaact gttattcttc actgattttg gattactttt catacccact tagtatgaaa    2820
tccgatctca gtgttagttc tgctggtcca atatcccagt ttaattataa acagtccttt    2880
tctaatccca catgtttgat tttagcgact gttcctcata accttactac tattactaag    2940
cctcttaagt acagctatat taacaagtgc tctcgtcttc tttctgatga tcgtactgaa    3000
gtacctcagt tagtgaacgc taatcaatac tcaccctgtg tatccattgt cccatccact    3060
gtgtgggaag acggtgatta ttataggaaa caactatctc cacttgaagg tggtggctgg    3120
cttgttgcta gtggctcaac tgttgccatg actgagcaat tacagatggg ctttggtatt    3180
acagttcaat atggtacaga caccaatagt gtttgcccca gcttgaatt tgctaatgac     3240 acaaaaattg cctctcaatt aggcaattgc gtggaatatt ccctctatgg tgtttcgggc    3300
cgtggtgttt tcagaattg cacagctgta ggtgttcgac agcagcgctt tgtttatgat     3360
gcgtaccaga atttagttgg ctattattct gatgatggca actactactg tttgcgtgct    3420
tgtgttagtg ttcctgtttc tgtcatctat gataaagaaa ctaaaaccca cgctactcta    3480
tttggtagtg ttgcatgtga acacatttct tctaccatgt ctcaatactc ccgttctacg    3540
cgatcaatgc ttaaacggcg agattctaca tatggccccc ttcagacacc tgttggttgt    3600
gtcctaggac ttgttaattc ctctttgttc gtagaggact gcaagttgcc tcttggtcaa    3660
tctctctgtg ctcttcctga cacacctagt actctcacac ctcgcagtgt gcgctctgtt    3720
ccaggtgaaa tgcgcttggc atccattgct tttaatcatc ctattcaggt tgatcaactt    3780
aatagtagtt atttaaatt aagtatacc actaatttt cctttggtgt gactcaggag     3840
tacattcaga caaccattca gaaagttact gttgattgta acagtacgt ttgcaatggt     3900 ttccagaagt gtgagcaatt actgcgcgag tatggccagt tttgttccaa aataaaccag    3960
```

```
gctctccatg gtgccaatttt acgccaggat gattctgtac gtaatttgtt tgcgagcgtg    4020
aaaagctctc aatcatctcc tatcatacca ggttttggag gtgactttaa tttgacactt    4080
ctagaacctg tttctatatc tactggcagt cgtagtgcac gtagtgctat tgaggatttg    4140
ctatttgaca aagtcactat agctgatcct ggttatatgc aaggttacga tgattgcatg    4200
cagcaaggtc cagcatcagc tcgtgatctt atttgtgctc aatatgtggc tggttacaaa    4260
gtattacctc ctcttatgga tgttaatatg gaagccgcgt atacttcatc tttgcttggc    4320
agcatagcag gtgttggctg gactgctggc ttatcctcct tgctgctat tccatttgca     4380 cagagtatct tttataggtt aaacggtgtt ggcattactc aacaggttct ttcagagaac    4440
caaaagctta ttgccaataa gtttaatcag gctctgggag ctatgcaaac aggcttcact    4500
acaactaatg aagcttttca gaaggttcag gatgctgtga acaacaatgc acaggctcta    4560
tccaaattag ctagcgagct atctaatact tttggtgcta tttccgcctc tattggagac    4620
atcatacaac gtcttgatgt tctcgaacag gacgcccaaa tagacagact tattaatggc    4680
cgtttgacaa cactaaatgc ttttgttgca cagcagcttg ttcgttccga atcagctgct    4740
ctttccgctc aattggctaa agataaagtc aatgagtgtg tcaaggcaca atccaagcgt    4800
tctggatttt gcggtcaagg cacacatata gtgtcctttg ttgtaaatgc ccctaatggc    4860
ctttacttca tgcatgttgg ttattaccct agcaaccaca ttgaggttgt ttctgcttat    4920
ggtctttgcg atgcagctaa ccctactaat tgtatagccc ctgttaatgg ctactttatt    4980
aaaactaata acactaggat tgttgatgag tggtcatata ctggctcgtc cttctatgca    5040
cctgagccca ttacctccct taatactaag tatgttgcac cacaggtgac ataccaaaac    5100
atttctacta acctccctcc tcctcttctc ggcaattcca ccgggattga cttccaagat    5160
gagttggatg agttttttcaa aaatgttagc accagtatac taatttttgg ttccctaaca    5220
cagattaata ctacattact cgatcttacc tacgagatgt tgtctcttca acaagttgtt    5280
aaagccctta atgagtctta catagacctt aaagagcttg gcaattatac ttattacaac    5340
aaatggccgt ggtacatttg gcttggtttc attgctgggc ttgttgcctt agctctatgc    5400
gtcttcttca tactgtgctg cactggttgt ggcacaaact gtatgggaaa acttaagtgt    5460
aatcgttgtt gtgatagata cgaggaatac gacctcgagc cgcataaggt tcatgttcac    5520
taattagcta gccatgaaaa aaactaacac ccctcctttc gaaccatccc aaacatgagc    5580
aagatctttg tcaatcctag tgctattaga gccggtctgg ccgatcttga gatggctgaa    5640
gaaactgttg atctgatcaa tagaaatatc gaagacaatc aggctcatct ccaaggggaa    5700
cccatagagg tggacaatct ccctgaggat atggggcgac ttcacctgga tgatggaaaa    5760
tcgcccaacc atggtgagat agccaaggtg ggagaaggca agtatcgaga ggactttcag    5820
atggatgaag gagaggatcc tagcttcctg ttccagtcat acctggaaaa tgttggagtc    5880
caaatagtca gacaaatgag gtcaggagag agatttctca agatatggtc acagaccgta    5940
gaagagatta tatcctatgt cgcggtcaac tttcccaacc ctccaggaaa gtcttcagag    6000
gataaatcaa cccagactac tggccgagag ctcaagaagg agacaacacc cactccttct    6060
cagagagaaa gccaatcatc gaaagccagg atggcggctc aaattgcttc tggccctcca    6120
gcccttgaat ggtcggctac caatgaagag gatgatctat cagtggaggc tgagatcgct    6180
caccagattg cagaaagttt ctccaaaaaa tataagtttc cctctcgatc ctcagggata    6240
ctcttgtata ttttgagca attgaaaatg aaccttgatg atatagttaa agaggcaaaa    6300
aatgtaccag gtgtgacccg tttagcccat gacgggtcca aactcccct aagatgtgta    6360
```

```
ctgggatggg tcgctttggc caactctaag aaattccagt tgttagtcga atccgacaag   6420
ctgagtaaaa tcatgcaaga tgacttgaat cgctatacat cttgctaacc gaacctctcc   6480
cctcagtccc tctagacaat aaaatccgag atgtcccaaa gtcaacatga aaaaacagg    6540 caacaccact gataaaatga acctcctacg taagatagtg aaaaaccgca gggacgagga   6600
cactcaaaaa tcctctcccg cgtcagcccc tctggatgac gatgacttgt ggcttccacc   6660
ccctgaatac gtcccgctga agaacttac aggcaagaag aacatgagga acttttgtat    6720
caacggaagg gttaaagtgt gtagcccgaa tggttactcg ttcaggatcc tgcggcacat   6780
tctgaaatca ttcgacgaga tatattctgg aatcatagg atgatcgggt tagtcaaagt    6840
ggttattgga ctggctttgt caggatctcc agtccctgag ggcctgaact gggtatacaa   6900
attgaggaga acctttatct tccagtgggc tgattccagg ggccctcttg aaggggagga   6960
gttggaatac tctcaggaga tcacttggga tgatgatact gagttcgtcg gattgcaaat   7020
aagagtgatt gcaaaacagt gtcatatcca gggcagagtc tggtgtatca acatgaaccc   7080
gagagcatgt caactatggt ctgacatgtc tcttcagaca caaaggtccg aagaggacaa   7140
agattcctct ctgcttctag aataatcaga ttatatcccg caaatttatc acttgtttac   7200
ctctggagga gagaacatat gggctcaact ccaacccttg ggagcaatat aacaaaaaac   7260
atgttatggt gccattaaac cgctgcattt catcaaagtc aagttgatta cctttacatt   7320
ttgatcctct tggatgtgaa aaaactatt aacatccctc aaaagacccc gggaaagatg    7380
gttcctcagg ctctcctgtt tgtacccctt ctggtttttc cattgtgttt tgggaaattc   7440
cctatttaca cgataccaga caagcttggt ccctggagtc cgattgacat acatcacctc   7500
agctgcccaa acaatttggt agtggaggac gaaggatgca ccaacctgtc agggttctcc   7560
tacatggaac ttaaagttgg atacatctta gccataaaag tgaacgggtt cacttgcaca   7620
ggcgttgtga cggaggctga aacctacact aacttcgttg gttatgtcac aaccacgttc   7680
aaaagaaagc atttccgccc aacaccagat gcatgtagag ccgcgtacaa ctggaagatg   7740
gccggtgacc ccagatatga agagtctcta cacaatccgt accctgacta ccgctggctt   7800
cgaactgtaa aaaccaccaa ggagtctctc gttatcatat ctccaagtgt ggcagatttg   7860
gacccatatg acagatccct tcactcgagg gtcttcccta gcgggaagtg ctcaggagta   7920
gcggtgtctt ctacctactg ctccactaac cacgattaca ccatttggat gcccgagaat   7980
ccgagactag ggatgtcttg tgacattttt accaatagta gagggaagag agcatccaaa   8040
gggagtgaga cttgcggctt tgtagatgaa agaggcctat ataagtcttt aaaaggagca   8100
tgcaaactca gttatgtgg agttctagga cttagactta tggatggaac atgggtctcg    8160
atgcaaacat caaatgaaac caaatggtgc cctcccgata gttggtgaa cctgcacgac    8220 tttcgctcag acgaaattga gcaccttgtt gtagaggagt tggtcaggaa gagagaggag   8280
tgtctggatg cactagagtc catcatgaca accaagtcag tgagtttcag acgtctcagt   8340
catttaagaa aacttgtccc tgggtttgga aaagcatata ccatattcaa caagaccttg   8400
atggaagccg atgctcacta caagtcagtc gagacttgga atgagatcct cccttcaaaa   8460
gggtgtttaa gagttggggg gaggtgtcat cctcatgtga acggggtgtt tttcaatggt   8520
ataatattag gacctgacgg caatgtctta atcccagaga tgcaatcatc cctcctccag   8580
caacatatgg agttgttgga atcctcggtt atcccccttg tgcacccct ggcagacccg    8640 tctaccgttt tcaaggacgg tgacgaggct gaggattttg ttgaagttca ccttcccgat   8700
```

```
gtgcacaatc aggtctcagg agttgacttg ggtctcccga actgggggaa gtatgtatta    8760
ctgagtgcag gggccctgac tgccttgatg ttgataattt tcctgatgac atgttgtaga    8820
agagtcaatc gatcagaacc tacgcaacac aatctcagag ggacagggag ggaggtgtca    8880
gtcactcccc aaagcgggaa gatcatatct tcatgggaat cacacaagag tgggggtgag    8940
accagactgt aattaattaa cgtcctttca acgatccaag tccatgaaaa aaactaacac    9000
ccctcccgta cctagcttat aaagtgctgg gtcatctaag cttttcagtc gagaaaaaaa    9060
cattagatca gaagaacaac tggcaacact tctcaacctg agacttactt caagatgctc    9120
gatcctggag aggtctatga tgaccctatt gacccaatcg agttagaggc tgaacccaga    9180
ggaaccccca ttgtccccaa catcttgagg aactctgact acaatctcaa ctctcctttg    9240
atagaagatc ctgctagact aatgttagaa tggttaaaaa cagggaatag accttatcgg    9300
atgactctaa cagacaattg ctccaggtct ttcagagttt tgaaagatta tttcaagaag    9360
gtagatttgg gttctctcaa ggtgggcgga atggctgcac agtcaatgat ttctctctgg    9420
ttatatggtg cccactctga atccaacagg agccggagat gtataacaga cttggcccat    9480
ttctattcca agtcgtcccc catagagaag ctgttgaatc tcacgctagg aaatagaggg    9540
ctgagaatcc ccccagaggg agtgttaagt tgccttgaga gggttgatta tgataatgca    9600
tttggaaggt atcttgccaa cacgtattcc tcttacttgt tcttccatgt aatcaccta    9660
tacatgaacg ccctagactg ggatgaagaa aagaccatcc tagcattatg gaaagattta    9720
acctcagtgg acatcgggaa ggacttggta aagttcaaag accaaatatg gggactgctg    9780
atcgtgacaa aggactttgt ttactcccaa agttccaatt gtcttttga cagaaactac    9840
acacttatgc taaaagatct tttcttgtct cgcttcaact ccttaatggt cttgctctct    9900
cccccagagc cccgatactc agatgacttg atatctcaac tatgccagct gtacattgct    9960
ggggatcaag tcttgtctat gtgtggaaac tccggctatg aagtcatcaa atattggag    10020
ccatatgtcg tgaatagttt agtccagaga gcagaaaagt ttaggcctct cattcattcc    10080
ttgggagact ttcctgtatt tataaaagac aaggtaagtc aacttgaaga gacgttcggt    10140
ccctgtgcaa gaaggttctt tagggctctg gatcaattcg acaacataca tgacttggtt    10200
tttgtgtttg gctgttacag gcattggggg cacccatata tagattatcg aaagggtctg    10260
tcaaaactat atgatcaggt tcaccttaaa aaaatgatag ataagtccta ccaggagtgc    10320
ttagcaagcg acctagccag gaggatcctt agatgggggtt ttgataagta ctccaagtgg    10380
tatctggatt caagattcct agcccgagac cacccccttga ctccttatat caaaaccccaa    10440
acatggccac ccaaacatat tgtagacttg gtgggggata catggcacaa gctcccgatc    10500
acgcagatct ttgagattcc tgaatcaatg gatccgtcag aaatattgga tgacaaatca    10560
cattctttca ccagaacgag actagcttct tggctgtcag aaaaccgagg ggggcctgtt    10620
cctagcgaaa aagttattat cacggccctg tctaagccgc ctgtcaatcc ccgagagttt    10680
ctgaggtcta tagacctcgg aggattgcca gatgaagact tgataattgg cctcaagcca    10740
aaggaacggg aattgaagat tgaaggtcga ttctttgctc taatgtcatg gaatctaaga    10800
ttgtattttg tcatcactga aaaactcttg gccaactaca tcttgccact ttttgacgcg    10860
ctgactatga cagacaacct gaacaaggtg tttaaaaagc tgatcgacag ggtcaccggg    10920
caagggcttt tggactattc aagggtcaca tatgcatttc acctggacta tgaaaagtgg    10980
aacaaccatc aaagattaga gtcaacgagg gatgtatttt ctgtcctaga tcaagtgttt    11040
ggattgaaga gagtgttttc tagaacacac gagttttttc aaaaggcctg gatctattat    11100
```

```
tcagacagat cagacctcat cgggttacgg gaggatcaaa tatactgctt agatgcgtcc   11160
aacggcccaa cctgttggaa tggccaggat ggcgggctag aaggcttacg gcagaagggc   11220
tggagtctag tcagcttatt gatgatagat agagaatctc aaatcaggaa cacaagaacc   11280
aaaatactag ctcaaggaga caaccaggtt ttatgtccga catacatgtt gtcgccaggg   11340
ctatctcaag aggggctcct ctatgaattg gagagaatat caaggaatgc actttcgata   11400
tacagagccg tcgaggaagg ggcatctaag ctagggctga tcatcaagaa agaagagacc   11460
atgtgtagtt atgacttcct catctatgga aaaccccctt tgtttagagg taacatattg   11520
gtgcctgagt ccaaaagatg ggccagagtc tcttgcgtct ctaatgacca aatagtcaac   11580
ctcgccaata taatgtcgac agtgtccacc aatgcgctaa cagtggcaca acactctcaa   11640
tctttgatca aaccgatgag ggattttctg ctcatgtcag tacaggcagt ctttcactac   11700
ctgctattta gcccaatctt aaagggaaga gtttacaaga ttctgagcgc tgaaggggag   11760
agctttctcc tagccatgtc aaggataatc tatctagatc cttctttggg agggatatct   11820
ggaatgtccc tcggaagatt ccatatacga cagttctcag accctgtctc tgaagggtta   11880
tccttctgga gagagatctg gttaagctcc aagagtcctg gattcacgc gttgtgtcaa   11940 gaggctggaa acccagatct tggagagaga acactcgaga gcttcactcg ccttctagaa   12000
gatccgacca ccttaaatat cagaggaggg gccagtccta ccattctact caaggatgca   12060
atcagaaagg ctttatatga cgaggtggac aaggtggaaa attcagagtt tcgagaggca   12120
atcctgttgt ccaagaccca tagagataat tttatactct tcttaatatc tgttgagcct   12180
ctgtttcctc gatttctcag tgagctattc agttcgtctt ttttgggaat ccccgagtca   12240
atcattggat tgatacaaaa ctcccgaacg ataagaaggc agtttagaaa gagtctctca   12300
aaaactttag aagaatcctt ctacaactca gagatccacg ggattagtcg gatgacccag   12360
acacctcaga gggttggggg ggtgtggcct tgctcttcag agagggcaga tctacttagg   12420
gagatctctt ggggaagaaa agtggtaggc acgacagttc ctcacccttc tgagatgttg   12480
ggattacttc ccaagtcctc tatttcttgc acttgtggag caacaggagg aggcaatcct   12540
agagtttctg tatcagtact cccgtccttt gatcagtcat ttttttcacg aggcccccta   12600
aagggatact tgggctcgtc cacctctatg tcgacccagc tattccatgc atgggaaaaa   12660
gtcactaatg ttcatgtggt gaagagagct ctatcgttaa aagaatctat aaactggttc   12720
attactagag attccaactt ggctcaagct ctaattagga acattatgtc tctgacaggc   12780
cctgatttcc ctctagagga ggcccctgtc ttcaaaagga cggggtcagc cttgcatagg   12840
ttcaagtctg ccagatacag cgaaggaggg tattcttctg tctgcccgaa cctcctctct   12900
catatttctg ttagtacaga caccatgtct gatttgaccc aagacgggaa gaactacgat   12960
ttcatgttcc agccattgat gctttatgca cagacatgga catcagagct ggtacagaga   13020
gacacaaggc taagagactc tacgtttcat tggcacctcc gatgcaacag gtgtgtgaga   13080
cccattgacg acgtgaccct ggagacctct cagatcttcg agtttccgga tgtgtcgaaa   13140
agaatatcca gaatggtttc tggggctgtg cctcacttcc agaggcttcc cgatatccgt   13200
ctgagaccag gagattttga atctctaagc ggtagagaaa agtctcacca tatcggatca   13260
gctcaggggc tcttatactc aatcttagtg gcaattcacg actcaggata caatgatgga   13320
accatcttcc ctgtcaacat atacggcaag gtttccccta gagactattt gagagggctc   13380
gcaaggggag tattgatagg atcctcgatt tgcttcttga caagaatgac aaatatcaat   13440
```

```
attaatagac ctcttgaatt ggtctcaggg gtaatctcat atattctcct gaggctagat    13500
aaccatccct ccttgtacat aatgctcaga gaaccgtctc ttagaggaga gatattttct    13560
atccctcaga aaatccccgc cgcttatcca accactatga aagaaggcaa cagatcaatc    13620
ttgtgttatc tccaacatgt gctacgctat gagcgagaga taatcacggc gtctccagag    13680
aatgactggc tatggatctt ttcagacttt agaagtgcca aaatgacgta cctatccctc    13740
attacttacc agtctcatct tctactccag agggttgaga gaaacctatc taagagtatg    13800
agagataacc tgcgacaatt gagttctttg atgaggcagg tgctgggcgg gcacggagaa    13860
gataccttag agtcagacga caacattcaa cgactgctaa aagactcttt acgaaggaca    13920
agatgggtgg atcaagaggt gcgccatgca gctagaacca tgactggaga ttacagcccc    13980
aacaagaagg tgtcccgtaa ggtaggatgt tcagaatggg tctgctctgc tcaacaggtt    14040
gcagtctcta cctcagcaaa cccggcccct gtctcggagc ttgacataag ggccctctct    14100
aagaggttcc agaaccettt gatctcgggc ttgagagtgg ttcagtgggc aaccggtgct    14160
cattataagc ttaagcctat tctagatgat ctcaatgttt tcccatctct ctgccttgta    14220 gttgggacg ggtcagggg gatatcaagg gcagtcctca acatgtttcc agatgccaag    14280
cttgtgttca acagtctttt agaggtgaat gacctgatgg cttccggaac acatccactg    14340
cctccttcag caatcatgag gggaggaaat gatatcgtct ccagagtgat agatcttgac    14400
tcaatctggg aaaaaccgtc cgacttgaga aacttggcaa cctggaaata cttccagtca    14460
gtccaaaagc aggtcaacat gtcctatgac ctcattattt gcgatgcaga agttactgac    14520
attgcatcta tcaaccggat caccctgtta atgtccgatt ttgcattgtc tatagatgga    14580
ccactctatt tggtcttcaa aacttatggg actatgctag taaatccaaa ctacaaggct    14640
attcaacacc tgtcaagagc gttcccctcg gtcacagggt ttatcaccca agtaacttcg    14700 tcttttttcat ctgagctcta cctccgattc tccaaacgag ggaagttttt cagagatgct    14760
gagtacttga cctcttccac ccttcgagaa atgagccttg tgttattcaa ttgtagcagc    14820
cccaagagtg agatgcagag agctcgttcc ttgaactatc aggatcttgt gagaggattt    14880
cctgaagaaa tcatatcaaa tccttacaat gagatgatca taactctgat tgacagtgat    14940
gtagaatctt ttctagtcca caagatggtt gatgatcttg agttacagag gggaactctg    15000
tctaaagtgg ctatcattat agccatcatg atagttttct ccaacagagt cttcaacgtt    15060
tccaaacccc taactgaccc ctcgttctat ccaccgtctg atcccaaaat cctgaggcac    15120
ttcaacatat gttgcagtac tatgatgtat ctatctactg ctttaggtga cgtccctagc    15180
ttcgcaagac ttcacgacct gtataacaga cctataactt attacttcag aaagcaagtc    15240
attcgaggga acgtttatct atcttggagt tggtccaacg acacctcagt gttcaaaagg    15300
gtagcctgta attctagcct gagtctgtca tctcactgga tcaggttgat ttacaagata    15360
gtgaagacta ccagactcgt tggcagcatc aaggatctat ccagagaagt ggaaagacac    15420
cttcataggt acaacaggtg gatcacccta gaggatatca gatctagatc atccctacta    15480
gactacagtt gcctgtgaac cggatactcc tggaagcctg cccatgctaa gactcttgtg    15540
tgatgtatct tgaaaaaaac aagatcctaa atctgaacct ttggttgttt gattgttttt    15600
ctcatttttg ttgtttattt gttaagcgt                                      15629
```

<210> SEQ ID NO 23
<211> LENGTH: 15539
<212> TYPE: DNA
<213> ORGANISM: Artificial Sequence
<220> FEATURE:
<223> OTHER INFORMATION: Recombinant Rabies virus vector BNSP333
      expressing a Middle East Respiratory Syndrome Coronavirus spike
      glycoprotein with a 29 amino acid C-terminal truncation

<400> SEQUENCE: 23

| | | | | | |
|---|---|---|---|---|---|
| acgcttaaca | accagatcaa | agaaaaaaca | gacattgtca | attgcaaagc | aaaaatgtaa | 60 |
| caccccctaca | atggatgccg | acaagattgt | attcaaagtc | aataatcagg | tggtctcttt | 120 |
| gaagcctgag | attatcgtgg | atcaatatga | gtacaagtac | cctgccatca | agatttgaa | 180 |
| aaagccctgt | ataaccctag | gaaaggctcc | cgatttaaat | aaagcataca | agtcagtttt | 240 |
| gtcaggcatg | agcgccgcca | aacttaatcc | tgacgatgta | tgttcctatt | tggcagcggc | 300 |
| aatgcagttt | tttgagggga | catgtccgga | agactggacc | agctatggaa | ttgtgattgc | 360 |
| acgaaaagga | gataagatca | ccccaggttc | tctggtggag | ataaaacgta | ctgatgtaga | 420 |
| agggaattgg | gctctgacag | gaggcatgga | actgacaaga | gacccccactg | tccctgagca | 480 |
| tgcgtcctta | gtcggtcttc | tcttgagtct | gtataggttg | agcaaaatat | ccgggcaaaa | 540 |
| cactggtaac | tataagacaa | acattgcaga | caggatagag | cagattttg | agacagcccc | 600 |
| ttttgttaaa | atcgtggaac | accatactct | aatgacaact | cacaaaatgt | gtgctaattg | 660 |
| gagtactata | ccaaacttca | gatttttggc | cggaacctat | gacatgtttt | tctcccggat | 720 |
| tgagcatcta | tattcagcaa | tcagagtggg | cacagttgtc | actgcttatg | aagactgttc | 780 |
| aggactggta | tcatttactg | ggttcataaa | acaaatcaat | ctcaccgcta | gagaggcaat | 840 |
| actatatttc | ttccacaaga | acttggagga | agagataaga | agaatgtttg | agccagggca | 900 |
| ggagacagct | gttcctcact | cttatttcat | ccacttccgt | tcactaggct | gagtgggaa | 960 |
| atctccttat | tcatcaaatg | ctgttggtca | cgtgttcaat | ctcattcact | tgtaggatg | 1020 |
| ctatatgggt | caagtcagat | ccctaaatgc | aacggttatt | gctgcatgtg | ctcctcatga | 1080 |
| aatgtctgtt | ctagggggct | atctgggaga | ggaattcttc | gggaaaggga | catttgaaag | 1140 |
| aagattcttc | agagatgaga | aagaacttca | agaatacgag | gcggctgaac | tgacaaagac | 1200 |
| tgacgtagca | ctggcagatg | atggaactgt | caactctgac | gacgaggact | acttttcagg | 1260 |
| tgaaaccaga | agtccggagg | ctgtttatac | tcgaatcatg | atgaatggag | tcgactaaa | 1320 |
| gagatctcac | atacggagat | atgtctcagt | cagttccaat | catcaagccc | gtccaaactc | 1380 |
| attcgccgag | tttctaaaca | agacatattc | gagtgactca | taacatgaaa | aaactaaca | 1440 |
| ccccctcccgt | acgccgccac | catgatacac | tcagtgtttc | tactgatgtt | cttgttaaca | 1500 |
| cctacagaaa | gttacgttga | tgtagggcca | gattctgtta | agtctgcttg | tattgaggtt | 1560 |
| gatatacaac | agactttctt | tgataaaact | tggcctaggc | caattgatgt | ttctaaggct | 1620 |
| gacggtatta | tacccctca | aggccgtaca | tattctaaca | taactatcac | ttatcaaggt | 1680 |
| cttttttccct | atcagggaga | ccatggtgat | atgtatgttt | actctgcagg | acatgctaca | 1740 |
| ggcacaactc | cacaaaagtt | gtttgtagct | aactattctc | aggacgtcaa | acagtttgct | 1800 |
| aatgggtttg | tcgtccgtat | aggagcagct | gccaattcca | ctggcactgt | tattattagc | 1860 |
| ccatctacca | gcgctactat | acgaaaaatt | taccctgctt | ttatgctggg | ttcttcagtt | 1920 |
| ggtaatttct | cagatggtaa | aatgggccgc | ttcttcaatc | atactctagt | tcttttgccc | 1980 |
| gatggatgtg | gcactttact | tagagctttt | tattgtattc | tagagcctcg | ctctggaaat | 2040 |
| cattgtcctg | ctggcaattc | ctatacttct | tttgccactt | atcacactcc | tgcaacagat | 2100 |
| tgttctgatg | gcaattacaa | tcgtaatgcc | agtctgaact | cttttaagga | gtattttaat | 2160 |

```
ttacgtaact gcacctttat gtacacttat aacattaccg aagatgagat tttagagtgg    2220
tttggcatta cacaaactgc tcaaggtgtt cacctcttct catctcggta tgttgatttg    2280
tacggcggca atatgtttca atttgccacc ttgcctgttt atgatactat taagtattat    2340
tctatcattc ctcacagtat tcgttctatc caaagtgata gaaaagcttg gctgccttc     2400 tacgtatata aacttcaacc gttaactttc ctgttggatt tttctgttga tggttatata    2460
cgcagagcta tagactgtgg ttttaatgat ttgtcacaac tccactgctc atatgaatcc    2520
ttcgatgttg aatctggagt ttattcagtt tcgtctttcg aagcaaaacc ttctggctca    2580
gttgtggaac aggctgaagg tgttgaatgt gatttttcac ctcttctgtc tggcacacct    2640
cctcaggttt ataatttcaa gcgtttggtt tttaccaatt gcaattataa tcttaccaaa    2700 ttgcttttcac tttttctgt gaatgatttt acttgtagtc aaatatctcc agcagcaatt    2760
gctagcaact gttattcttc actgattttg gattactttt catacccact tagtatgaaa    2820
tccgatctca gtgttagttc tgctggtcca atatcccagt ttaattataa acagtccttt    2880
tctaatccca catgtttgat tttagcgact gttcctcata accttactac tattactaag    2940
cctcttaagt acagctatat taacaagtgc tctcgtcttc tttctgatga tcgtactgaa    3000
gtacctcagt tagtgaacgc taatcaatac tcaccctgtg tatccattgt cccatccact    3060
gtgtgggaag acggtgatta ttataggaaa caactatctc cacttgaagg tggtggctgg    3120
cttgttgcta gtggctcaac tgttgccatg actgagcaat tacagatggg ctttggtatt    3180
acagttcaat atggtacaga caccaatagt gtttgcccca agcttgaatt tgctaatgac    3240
acaaaaattg cctctcaatt aggcaattgc gtggaatatt ccctctatgg tgtttcgggc    3300
cgtggtgttt ttcagaattg cacagctgta ggtgttcgac agcagcgctt tgtttatgat    3360
gcgtaccaga atttagttgg ctattattct gatgatggca actactactg tttgcgtgct    3420
tgtgttagtg ttcctgtttc tgtcatctat gataaagaaa ctaaaaccca cgctactcta    3480
tttggtagtg ttgcatgtga acacatttct tctaccatgt ctcaatactc ccgttctacg    3540
cgatcaatgc ttaaacggcg agattctaca tatggccccc ttcagacacc tgttggttgt    3600
gtcctaggac ttgttaattc ctcttttgttc gtagaggact gcaagttgcc tcttggtcaa    3660
tctctctgtg ctcttcctga cacacctagt actctcacac ctcgcagtgt gcgctctgtt    3720
ccaggtgaaa tgcgcttggc atccattgct tttaatcatc ctattcaggt tgatcaactt    3780
aatagtagtt attttaaatt aagtataccc actaattttt cctttggtgt gactcaggag    3840
tacattcaga caaccattca gaaagttact gttgattgta acagtacgt ttgcaatggt    3900 ttccagaagt gtgagcaatt actgcgcgag tatggccagt tttgttccaa aataaaccag    3960
gctctccatg gtgccaattt acgccaggat gattctgtac gtaatttgtt tgcgagcgtg    4020
aaaagctctc aatcatctcc tatcatacca ggttttggag gtgactttaa tttgacactt    4080
ctagaacctg tttctatatc tactggcagt cgtagtgcac gtagtgctat tgaggatttg    4140
ctatttgaca aagtcactat agctgatcct ggttatatgc aaggttacga tgattgcatg    4200
cagcaaggtc cagcatcagc tcgtgatctt atttgtgctc aatatgtggc tggttacaaa    4260
gtattacctc tcttatggga tgttaatatg gaagccgcgt atacttcatc tttgcttggc    4320
agcatagcag gtgttggctg gactgctggc ttatcctcct tgctgctat tccatttgca    4380 cagagtatct tttataggtt aaacggtgtt ggcattactc aacaggttct ttcagagaac    4440
caaaagctta ttgccaataa gtttaatcag gctctgggag ctatgcaaac aggcttcact    4500
acaactaatg aagcttttca gaaggttcag gatgctgtga acaacaatgc acaggctcta    4560
```

```
tccaaattag ctagcgagct atctaatact tttggtgcta tttccgcctc tattggagac    4620
atcatacaac gtcttgatgt tctcgaacag gacgcccaaa tagacagact tattaatggc    4680
cgtttgacaa cactaaatgc ttttgttgca cagcagcttg ttcgttccga atcagctgct    4740
ctttccgctc aattggctaa agataaagtc aatgagtgtg tcaaggcaca atccaagcgt    4800
tctggatttt gcggtcaagg cacacatata gtgtcctttg ttgtaaatgc ccctaatggc    4860
ctttacttca tgcatgttgg ttattaccct agcaaccaca ttgaggttgt ttctgcttat    4920
ggtctttgcg atgcagctaa ccctactaat tgtatagccc ctgttaatgg ctactttatt    4980
aaaactaata acactaggat tgttgatgag tggtcatata ctggctcgtc cttctatgca    5040
cctgagccca ttacctccct taatactaag tatgttgcac cacaggtgac ataccaaaac    5100
atttctacta acctccctcc tcctcttctc ggcaattcca cgggattga cttccaagat    5160 gagttggatg agttttttcaa aaatgttagc accagtatac ctaattttgg ttccctaaca    5220
cagattaata ctacattact cgatcttacc tacgagatgt tgtctcttca acaagttgtt    5280
aaagccctta atgagtctta catagacctt aaagagcttg gcaattatac ttattacaac    5340
aaatggccgt ggtacatttg gcttggtttc attgctgggc ttgttgcctt agctctatgc    5400
gtcttcttca tactgtgctg cactggttgt ggctaagcta gtcatgaaaa aaactaacac    5460
ccctcctttc gaaccatccc aaacatgagc aagatctttg tcaatcctag tgctattaga    5520
gccggtctgg ccgatcttga gatggctgaa gaaactgttg atctgatcaa tagaaatatc    5580
gaagacaatc aggctcatct ccaaggggaa cccatagagg tggacaatct ccctgaggat    5640
atggggcgac ttcacctgga tgatggaaaa tcgcccaacc atggtgagat agccaaggtg    5700
ggagaaggca gtatcgaga ggactttcag atggatgaag gagaggatcc tagcttcctg    5760
ttccagtcat acctggaaaa tgttggagtc caaatagtca gacaaatgag gtcaggagag    5820
agatttctca agatatggtc acagaccgta gaagagatta tatcctatgt cgcggtcaac    5880
tttcccaacc ctccaggaaa gtcttcagag gataaatcaa cccagactac tggccgagag    5940
ctcaagaagg agacaacacc cactccttct cagagagaaa gccaatcatc gaaagccagg    6000
atggcggctc aaattgcttc tggccctcca gcccttgaat ggtcggctac caatgaagag    6060
gatgatctat cagtggaggc tgagatcgcc caccagattg cagaaagttt ctccaaaaaa    6120
tataagtttc cctctcgatc ctcagggata ctcttgtata attttgagca attgaaaatg    6180
aaccttgatg atatagttaa agaggcaaaa aatgtaccag gtgtgacccg tttagcccat    6240
gacgggtcca aactccccct aagatgtgta ctgggatggg tcgctttggc caactctaag    6300
aaattccagt tgttagtcga atccgacaag ctgagtaaaa tcatgcaaga tgacttgaat    6360
cgctatacat cttgctaacc gaacctctcc cctcagtccc tctagacaat aaaatccgag    6420
atgtcccaaa gtcaacatga aaaaacagg caacaccact gataaaatga acctcctacg    6480
taagatagta aaaaaccgca gggacgagga cactcaaaaa tcctctcccg cgtcagcccc    6540
tctggatgac gatgacttgt ggcttccacc ccctgaatac gtcccgctga agaacttac    6600 aggcaagaag aacatgagga acttttgtat caacggaagg gttaaagtgt gtagcccgaa    6660
tggttactcg ttcaggatcc tgcggcacat tctgaaatca ttcgacgaga tatattctgg    6720
gaatcatagg atgatcgggt tagtcaaagt ggttattgga ctggctttgt caggatctcc    6780
agtccctgag ggcctgaact gggtatacaa attgaggaga acctttatct tccagtgggc    6840
tgattccagg ggccctcttg aagggagga gttggaatac tctcaggaga tcacttggga    6900
```

```
tgatgatact gagttcgtcg gattgcaaat aagagtgatt gcaaaacagt gtcatatcca    6960
gggcagagtc tggtgtatca acatgaaccc gagagcatgt caactatggt ctgacatgtc    7020
tcttcagaca caaaggtccg aagaggacaa agattcctct ctgcttctag aataatcaga    7080
ttatatcccg caaatttatc acttgtttac ctctggagga gagaacatat gggctcaact    7140 ccaaccettg ggagcaatat aacaaaaaac atgttatggt gccattaaac cgctgcattt    7200
catcaaagtc aagttgatta cctttacatt ttgatcctct tggatgtgaa aaaaactatt    7260
aacatccctc aaaagacccc gggaaagatg gttcctcagg ctctcctgtt tgtaccccett   7320 ctggtttttc cattgtgttt tgggaaattc cctatttaca cgataccaga caagcttggt    7380
ccctggagtc cgattgacat acatcacctc agctgcccaa acaatttggt agtggaggac    7440
gaaggatgca ccaacctgtc agggttctcc tacatggaac ttaaagttgg atacatctta    7500
gccataaaag tgaacgggtt cacttgcaca ggcgttgtga cggaggctga aacctacact    7560
aacttcgttg gttatgtcac aaccacgttc aaaagaaagc atttccgccc aacaccagat    7620
gcatgtagag ccgcgtacaa ctggaagatg gccggtgacc ccagatatga agagtctcta    7680
cacaatccgt accctgacta ccgctggctt cgaactgtaa aaaccaccaa ggagtctctc    7740
gttatcatat ctccaagtgt ggcagatttg gacccatatg acagatccct tcactcgagg    7800
gtcttcccta gcgggaagtg ctcaggagta gcggtgtctt ctacctactg ctccactaac    7860
cacgattaca ccatttggat gcccgagaat ccgagactag gatgtcttg tgacatttt     7920 accaatagta gagggaagag agcatccaaa gggagtgaga cttgcggctt tgtagatgaa    7980
agaggcctat ataagtcttt aaaaggagca tgcaaactca agttatgtgg agttctagga    8040
cttagactta tggatggaac atgggtctcg atgcaaacat caaatgaaac caaatggtgc    8100
cctcccgata agttggtgaa cctgcacgac tttcgctcag acgaaattga gcaccttgtt    8160
gtagaggagt tggtcaggaa gagagaggag tgtctggatg cactagagtc catcatgaca    8220
accaagtcag tgagtttcag acgtctcagt catttaagaa aacttgtccc tgggtttgga    8280
aaagcatata ccatattcaa caagaccttg atggaagccg atgctcacta caagtcagtc    8340
gagacttgga tgagatcct cccttcaaaa gggtgtttaa gagttggggg gaggtgtcat    8400
cctcatgtga acggggtgtt tttcaatggt ataatattag acctgacgg caatgtctta    8460 atcccagaga tgcaatcatc cctcctccag caacatatgg agttgttgga atcctcggtt    8520
atcccccttg tgcaccccct ggcagacccg tctaccgttt tcaaggacgg tgacgaggct    8580
gaggattttg ttgaagttca ccttcccgat gtgcacaatc aggtctcagg agttgacttg    8640
ggtctcccga actgggggaa gtatgtatta ctgagtgcag gggccctgac tgccttgatg    8700
ttgataattt tcctgatgac atgttgtaga agagtcaatc gatcagaacc tacgcaacac    8760
aatctcagag ggacagggag ggaggtgtca gtcactcccc aaagcgggaa gatcatatct    8820
tcatgggaat cacacaagag tggggtgag accagactgt aattaattaa cgtcctttca    8880
acgatccaag tccatgaaaa aaactaacac ccctcccgta cctagcttat aaagtgctgg    8940
gtcatctaag cttttcagtc gagaaaaaaa cattagatca gaagaacaac tggcaacact    9000
tctcaacctg agacttactt caagatgctc gatcctggag aggtctatga tgaccctatt    9060
gacccaatcg agttagaggc tgaacccaga ggaaccccca ttgtccccaa catcttgagg    9120
aactctgact acaatctcaa ctctcctttg atagaagatc ctgctagact aatgttagaa    9180
tggttaaaaa cagggaatag accttatcgg atgactctaa cagacaattg ctccaggtct    9240
ttcagagttt tgaaagatta tttcaagaag gtagatttgg gttctctcaa ggtgggcgga    9300
```

```
atggctgcac agtcaatgat ttctctctgg ttatatggtg cccactctga atccaacagg    9360
agccggagat gtataacaga cttggcccat ttctattcca agtcgtcccc catagagaag    9420
ctgttgaatc tcacgctagg aaatagaggg ctgagaatcc ccccagaggg agtgttaagt    9480
tgccttgaga gggttgatta tgataatgca tttggaaggt atcttgccaa cacgtattcc    9540
tcttacttgt tcttccatgt aatcacctta tacatgaacg ccctagactg ggatgaagaa    9600
aagaccatcc tagcattatg gaaagattta acctcagtgg acatcgggaa ggacttggta    9660
aagttcaaag accaaatatg gggactgctg atcgtgacaa aggactttgt ttactcccaa    9720
agttccaatt gtcttttttga cagaaactac acacttatgc taaaagatct tttcttgtct    9780
cgcttcaact ccttaatggt cttgctctct cccccagagc ccgatactc agatgacttg    9840 atatctcaac tatgccagct gtacattgct ggggatcaag tcttgtctat gtgtggaaac    9900
tccggctatg aagtcatcaa atattggag ccatatgtcg tgaatagttt agtccagaga    9960
gcagaaaagt ttaggcctct cattcattcc ttgggagact ttcctgtatt tataaaagac    10020
aaggtaagtc aacttgaaga gacgttcggt ccctgtgcaa gaaggttctt tagggctctg    10080
gatcaattcg acaacataca tgacttggtt tttgtgtttg gctgttacag gcattggggg    10140
cacccatata tagattatcg aaagggtctg tcaaaactat atgatcaggt tcaccttaaa    10200
aaaatgatag ataagtccta ccaggagtgc ttagcaagcg acctagccag gaggatcctt    10260
agatggggtt ttgataagta ctccaagtgg tatctggatt caagattcct agcccgagac    10320
caccccttga ctccttatat caaaacccaa acatggccac ccaaacatat tgtagacttg    10380
gtgggggata catggcacaa gctcccgatc acgcagatct ttgagattcc tgaatcaatg    10440
gatccgtcag aaatattgga tgacaaatca cattctttca ccagaacgag actagcttct    10500
tggctgtcag aaaaccgagg ggggcctgtt cctagcgaaa aagttattat cacggccctg    10560
tctaagccgc ctgtcaatcc ccgagagttt ctgaggtcta tagacctcgg aggattgcca    10620
gatgaagact tgataattgg cctcaagcca aaggaacggg aattgaagat tgaaggtcga    10680
ttctttgctc taatgtcatg gaatctaaga ttgtatttg tcatcactga aaaactcttg    10740
gccaactaca tcttgccact ttttgacgcg ctgactatga cagacaaccct gaacaaggtg    10800 tttaaaaagc tgatcgacag ggtcaccggg caagggcttt tggactattc aagggtcaca    10860
tatgcatttc acctggacta tgaaaagtgg acaaccatc aaagattaga gtcaacagag    10920
gatgtatttt ctgtcctaga tcaagtgttt ggattgaaga gagtgttttc tagaacacac    10980 gagtttttc aaaaggcctg gatctattat tcagacagat cagacctcat cgggttacgg    11040
gaggatcaaa tatactgctt agatgcgtcc aacggcccaa cctgttggaa tggccaggat    11100 gcgggctag aaggcttacg gcagaagggc tggagtctag tcagcttatt gatgatagat    11160
agagaatctc aaatcaggaa cacaagaacc aaaatactag ctcaaggaga caaccaggtt    11220
ttatgtccga catacatgtt gtcgccaggg ctatctcaag agggggctcct ctatgaattg    11280 gagagaatat caaggaatgc actttcgata tacagagccg tcgaggaagg ggcatctaag    11340
ctagggctga tcatcaagaa agaagagacc atgtgtagtt atgacttcct catctatgga    11400 aaacccctt tgtttagagg taacatattg gtgcctgagt ccaaaagatg ggccagagtc    11460
tcttgcgtct ctaatgacca aatagtcaac ctcgccaata taatgtcgac agtgtccacc    11520
aatgcgctaa cagtggcaca acactctcaa tctttgatca aaccgatgag ggattttctg    11580
ctcatgtcag tacaggcagt cttccactac ctgctattta gcccaatctt aaagggaaga    11640
```

```
gtttacaaga ttctgagcgc tgaaggggag agctttctcc tagccatgtc aaggataatc    11700
tatctagatc cttctttggg agggatatct ggaatgtccc tcggaagatt ccatatacga    11760
cagttctcag accctgtctc tgaagggtta tccttctgga gagagatctg gttaagctcc    11820
caagagtcct ggattcacgc gttgtgtcaa gaggctggaa acccagatct tggagagaga    11880
acactcgaga gcttcactcg ccttctagaa gatccgacca ccttaaatat cagaggaggg    11940
gccagtccta ccattctact caaggatgca atcagaaagg ctttatatga cgaggtggac    12000
aaggtggaaa attcagagtt tcgagaggca atcctgttgt ccaagaccca tagagataat    12060
tttatactct tcttaatatc tgttgagcct ctgtttcctc gatttctcag tgagctattc    12120
agttcgtctt ttttgggaat ccccgagtca atcattggat tgatacaaaa ctcccgaacg    12180
ataagaaggc agtttagaaa gagtctctca aaaactttag aagaatcctt ctacaactca    12240
gagatccacg ggattagtcg gatgacccag acacctcaga gggttggggg ggtgtggcct    12300
tgctcttcag agagggcaga tctacttagg gagatctctt ggggaagaaa agtggtaggc    12360
acgacagttc ctcacccttc tgagatgttg ggattacttc ccaagtcctc tatttcttgc    12420
acttgtggag caacaggagg aggcaatcct agagtttctg tatcagtact cccgtccttt    12480
gatcagtcat ttttttcacg aggcccccta aagggatact tgggctcgtc cacctctatg    12540
tcgacccagc tattccatgc atgggaaaaa gtcactaatg ttcatgtggt gaagagagct    12600
ctatcgttaa aagaatctat aaactggttc attactagag attccaactt ggctcaagct    12660
ctaattagga acattatgtc tctgacaggc cctgatttcc ctctagagga ggcccctgtc    12720
ttcaaaagga cggggtcagc cttgcatagg ttcaagtctg ccagatacag cgaaggaggg    12780
tattcttctg tctgcccgaa cctcctctct catatttctg ttagtacaga caccatgtct    12840
gatttgaccc aagacgggaa gaactacgat ttcatgttcc agccattgat gctttatgca    12900
cagacatgga catcagagct ggtacagaga gacacaaggc taagagactc tacgtttcat    12960
tggcacctcc gatgcaacag gtgtgtgaga cccattgacg acgtgaccct ggagacctct    13020
cagatcttcg agtttccgga tgtgtcgaaa agaatatcca gaatggtttc tggggctgtg    13080
cctcacttcc agaggcttcc cgatatccgt ctgagaccag gagattttga atctctaagc    13140
ggtagagaaa agtctcacca tatcggatca gctcaggggc tcttatactc aatcttagtg    13200
gcaattcacg actcaggata caatgatgga accatcttcc ctgtcaacat atacggcaag    13260
gtttccccta gagactattt gagagggctc gcaaggggag tattgatagg atcctcgatt    13320
tgcttcttga caagaatgac aaatatcaat attaatagac ctcttgaatt ggtctcaggg    13380
gtaatctcat atattctcct gaggctagat aaccatccct ccttgtacat aatgctcaga    13440
gaaccgtctc ttagaggaga gatattttct atccctcaga aaatcccgc cgcttatcca    13500 accactatga agaaggcaa cagatcaatc ttgtgttatc tccaacatgt gctacgctat    13560
gagcgagaga taatcacggc gtctccagag aatgactggc tatggatctt ttcagacttt    13620
agaagtgcca aaatgacgta cctatccctc attacttacc agtctcatct tctactccag    13680
agggttgaga gaaacctatc taagagtatg agagataacc tgcgacaatt gagttctttg    13740
atgaggcagg tgctgggcgg gcacggagaa gataccttag agtcagacga caacattcaa    13800
cgactgctaa aagactcttt acgaaggaca agatgggtgg atcaagaggt gcgccatgca    13860
gctagaacca tgactggaga ttacagcccc aacaagaagg tgtcccgtaa ggtaggatgt    13920
tcagaatggg tctgctctgc tcaacaggtt gcagtctcta cctcagcaaa cccggccct    13980 gtctcggagc ttgacataag ggccctctct aagaggttcc agaaccctt gatctcgggc    14040
```

```
ttgagagtgg ttcagtgggc aaccggtgct cattataagc ttaagcctat tctagatgat   14100
ctcaatgttt tcccatctct ctgccttgta gttggggacg ggtcagggg gatatcaagg   14160 gcagtcctca acatgtttcc agatgccaag cttgtgttca acagtctttt agaggtgaat   14220
gacctgatgg cttccggaac acatccactg cctccttcag caatcatgag gggaggaaat   14280
gatatcgtct ccagagtgat agatcttgac tcaatctggg aaaaaccgtc cgacttgaga   14340
aacttggcaa cctggaaata cttccagtca gtccaaaagc aggtcaacat gtcctatgac   14400
ctcattattt gcgatgcaga agttactgac attgcatcta tcaaccggat caccctgtta   14460
atgtccgatt ttgcattgtc tatagatgga ccactctatt tggtcttcaa aacttatggg   14520
actatgctag taaatccaaa ctacaaggct attcaacacc tgtcaagagc gttcccctcg   14580
gtcacagggt ttatcaccca agtaacttcg tcttttcat ctgagctcta cctccgattc   14640
tccaaacgag ggaagttttt cagagatgct gagtacttga cctcttccac ccttcgagaa   14700
atgagccttg tgttattcaa ttgtagcagc cccaagagtg agatgcagag agctcgttcc   14760
ttgaactatc aggatcttgt gagaggattt cctgaagaaa tcatatcaaa tccttacaat   14820
gagatgatca taactctgat tgacagtgat gtagaatctt ttctagtcca caagatggtt   14880
gatgatcttg agttacagag gggaactctg tctaaagtgg ctatcattat agccatcatg   14940
atagttttct ccaacagagt cttcaacgtt tccaaacccc taactgaccc ctcgttctat   15000
ccaccgtctg atcccaaaat cctgaggcac ttcaacatat gttgcagtac tatgatgtat   15060
ctatctactg ctttaggtga cgtccctagc ttcgcaagac ttcacgacct gtataacaga   15120
cctataactt attacttcag aaagcaagtc attcgaggga acgtttatct atcttggagt   15180
tggtccaacg acacctcagt gttcaaaagg gtagcctgta attctagcct gagtctgtca   15240
tctcactgga tcaggttgat ttacaagata gtgaagacta ccagactcgt tggcagcatc   15300
aaggatctat ccagagaagt ggaaagacac cttcataggt acaacaggtg atcaccccta   15360
gaggatatca gatctagatc atccctacta gactacagtt gcctgtgaac cggatactcc   15420
tggaagcctg cccatgctaa gactcttgtg tgatgtatct tgaaaaaaac aagatcctaa   15480
atctgaacct ttggttgttt gattgttttt ctcattttg ttgtttattt gttaagcgt   15539
```

<210> SEQ ID NO 24
<211> LENGTH: 15569
<212> TYPE: DNA
<213> ORGANISM: Artificial Sequence
<220> FEATURE:
<223> OTHER INFORMATION: Recombinant Rabies virus vector BNSP333
      expressing a Middle East Respiratory Syndrome Coronavirus spike
      glycoprotein with a 19 amino acid C-terminal truncation

<400> SEQUENCE: 24

```
acgcttaaca accagatcaa agaaaaaaca gacattgtca attgcaaagc aaaaatgtaa    60
cacccctaca atggatgccg acaagattgt attcaaagtc aataatcagg tggtctcttt   120
gaagcctgag attatcgtgg atcaatatga gtacaagtac cctgccatca agatttgaa    180 aaagccctgt ataaccctag gaaaggctcc cgatttaaat aaagcataca agtcagtttt   240
gtcaggcatg agcgccgcca aacttaatcc tgacgatgta tgttcctatt ggcagcggc   300 aatgcagttt tttgagggga catgtccgga agactggacc agctatggaa ttgtgattgc   360
acgaaaagga gataagatca cccaggttc tctggtggag ataaaacgta ctgatgtaga   420
agggaattgg gctctgacag gaggcatgga actgacaaga gaccccactg tccctgagca   480
```

```
tgcgtccttg gtcggtcttc tcttgagtct gtataggttg agcaaaatat ccgggcaaaa    540
cactggtaac tataagacaa acattgcaga caggatagag cagattttg agacagcccc    600 ttttgttaaa atcgtggaac accatactct aatgacaact cacaaaatgt gtgctaattg    660
gagtactata ccaaacttca gattttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctaggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttttcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taacatgaaa aaaactaaca   1440
cccctcccgt acgccgccac catgatacac tcagtgtttc tactgatgtt cttgttaaca   1500
cctacagaaa gttacgttga tgtagggcca gattctgtta agtctgcttg tattgaggtt   1560
gatatacaac agactttctt tgataaaact tggcctaggc caattgatgt ttctaaggct   1620
gacggtatta tacccctca aggccgtaca tattctaaca taactatcac ttatcaaggt   1680
ctttttccct atcagggaga ccatggtgat atgtatgttt actctgcagg acatgctaca   1740
ggcacaactc cacaaaagtt gtttgtagct aactattctc aggacgtcaa acagtttgct   1800
aatgggtttg tcgtccgtat aggagcagct gccaattcca ctggcactgt tattattagc   1860
ccatctacca gcgctactat acgaaaaatt taccctgctt ttatgctggg ttcttcagtt   1920
ggtaatttct cagatggtaa aatgggccgc ttcttcaatc atactctagt tcttttgccc   1980
gatggatgtg gcactttact tagagctttt tattgtattc tagagcctcg ctctggaaat   2040
cattgtcctg ctggcaattc ctatacttct tttgccactt atcacactcc tgcaacagat   2100
tgttctgatg gcaattacaa tcgtaatgcc agtctgaact ctttaagga gtattttaat   2160 ttacgtaact gcacctttat gtacacttat aacattaccg aagatgagat tttagagtgg   2220
tttggcatta cacaaactgc tcaaggtgtt cacctcttct catctcggta tgttgatttg   2280 tacgcggca atatgtttca atttgccacc ttgcctgttt atgatactat taagtattat   2340
tctatcattc ctcacagtat tcgttctatc caaagtgata gaaaagcttg gctgccttc   2400 tacgtatata aacttcaacc gttaactttc ctgttggatt tttctgttga tggttatata   2460
cgcagagcta tagactgtgg ttttaatgat ttgtcacaac tccactgctc atatgaatcc   2520
ttcgatgttg aatctggagt ttattcagtt tcgtctttcg aagcaaaacc ttctggctca   2580
gttgtggaac aggctgaagg tgttaatgt gatttttcac ctcttctgtc tggcacacct   2640
cctcaggttt ataatttcaa gcgtttggtt tttaccaatt gcaattataa tcttaccaaa   2700 ttgcttttcac tttttttctgt gaatgatttt acttgtagtc aaatatctcc agcagcaatt   2760
gctagcaact gttattcttc actgattttg gattacttt catacccact tagtatgaaa   2820
tccgatctca gtgttagttc tgctggtcca atatcccagt ttaattataa acagtccttt   2880
```

```
tctaatccca catgtttgat tttagcgact gttcctcata acctactac tattactaag    2940 cctcttaagt acagctatat taacaagtgc tctcgtcttc tttctgatga tcgtactgaa    3000
gtacctcagt tagtgaacgc taatcaatac tcaccctgtg tatccattgt cccatccact    3060
gtgtgggaag acggtgatta ttataggaaa caactatctc cacttgaagg tggtggctgg    3120
cttgttgcta gtggctcaac tgttgccatg actgagcaat tacagatggg ctttggtatt    3180
acagttcaat atggtacaga caccaatagt gtttgcccca agcttgaatt tgctaatgac    3240
acaaaaattg cctctcaatt aggcaattgc gtggaatatt ccctctatgg tgtttcgggc    3300
cgtggtgttt ttcagaattg cacagctgta ggtgttcgac agcagcgctt tgtttatgat    3360
gcgtaccaga atttagttgg ctattattct gatgatggca actactactg tttgcgtgct    3420
tgtgttagtt ttcctgtttc tgtcatctat gataaagaaa ctaaaaccca cgctactcta    3480
tttggtagtg ttgcatgtga acacatttct tctaccatgt ctcaatactc ccgttctacg    3540
cgatcaatgc ttaaacggcg agattctaca tatggccccc ttcagacacc tgttggttgt    3600
gtcctaggac ttgttaattc ctctttgttc gtagaggact gcaagttgcc tcttggtcaa    3660
tctctctgtg ctcttcctga cacacctagt actctcacac ctcgcagtgt gcgctctgtt    3720
ccaggtgaaa tgcgcttggc atccattgct tttaatcatc ctattcaggt tgatcaactt    3780
aatagtagtt attttaaatt aagtataccc actaattttt cctttggtgt gactcaggag    3840
tacattcaga caaccattca gaaagttact gttgattgta aacagtacgt ttgcaatggt    3900
ttccagaagt gtgagcaatt actgcgcgag tatggccagt tttgttccaa aataaaccag    3960
gctctccatg gtgccaattt acgccaggat gattctgtac gtaatttgtt tgcgagcgtg    4020
aaaagctctc aatcatctcc tatcatacca ggttttggag gtgactttaa tttgacactt    4080
ctagaacctg tttctatatc tactggcagt cgtagtgcac gtagtgctat tgaggatttg    4140
ctatttgaca aagtcactat agctgatcct ggttatatgc aaggttacga tgattgcatg    4200
cagcaaggtc cagcatcagc tcgtgatctt atttgtgctc aatatgtggc tggttacaaa    4260
gtattacctc ctcttatgga tgttaatatg gaagccgcgt atacttcatc tttgcttggc    4320
agcatagcag gtgttggctg gactgctggc ttatcctcct ttgctgctat tccatttgca    4380
cagagtatct tttataggtt aaacggtgtt ggcattactc aacaggttct tcagagaaac    4440
caaaagctta ttgccaataa gtttaatcag gctctgggag ctatgcaaac aggcttcact    4500
acaactaatg aagcttttca gaaggttcag gatgctgtga acaacaatgc acaggctcta    4560
tccaaattag ctagcgagct atctaatact tttggtgcta tttccgcctc tattggagac    4620
atcatacaac gtcttgatgt tctcgaacag gacgcccaaa tagacagact tattaatggc    4680
cgtttgacaa cactaaatgc ttttgttgca cagcagcttg ttcgttccga atcagctgct    4740
ctttccgctc aattggctaa agataaagtc aatgagtgtg tcaaggcaca atccaagcgt    4800
tctggatttt gcggtcaagg cacacatata gtgtcctttg ttgtaaatgc ccctaatggc    4860
ctttacttca tgcatgttgg ttattaccct agcaaccaca ttgaggttgt ttctgcttat    4920
ggtctttgcg atgcagctaa ccctactaat tgtatagccc ctgttaatgg ctactttatt    4980
aaaactaata acactaggat tgttgatgag tggtcatata ctggctcgtc cttctatgca    5040
cctgagccca ttacctcccct taatactaag tatgttgcac cacaggtgac ataccaaaac    5100
atttctacta acctccctcc tcctcttctc ggcaattcca ccgggattga cttccaagat    5160
gagttggatg agttttcaa aaatgttagc accagtatac ctaattttgg ttccctaaca    5220
```

```
cagattaata ctacattact cgatcttacc tacgagatgt tgtctcttca acaagttgtt    5280
aaagccctta atgagtctta catagacctt aaagagcttg gcaattatac ttattacaac    5340
aaatggccgt ggtacatttg gcttggtttc attgctgggc ttgttgcctt agctctatgc    5400
gtcttcttca tactgtgctg cactggttgt ggcacaaact gtatgggaaa acttaagtgt    5460
aattaagcta gtcatgaaaa aaactaacac ccctcctttc gaaccatccc aaacatgagc    5520
aagatctttg tcaatcctag tgctattaga gccggtctgg ccgatcttga gatggctgaa    5580
gaaactgttg atctgatcaa tagaaatatc gaagacaatc aggctcatct ccaaggggaa    5640
cccatagagg tggacaatct ccctgaggat atggggcgac ttcacctgga tgatggaaaa    5700
tcgcccaacc atggtgagat agccaaggtg ggagaaggca agtatcgaga ggactttcag    5760
atggatgaag gagaggatcc tagcttcctg ttccagtcat acctggaaaa tgttggagtc    5820
caaatagtca gacaaatgag gtcaggagag agatttctca agatatggtc acagaccgta    5880
gaagagatta tatcctatgt cgcggtcaac tttcccaacc ctccaggaaa gtcttcagag    5940
gataaatcaa cccagactac tggccgagag ctcaagaagg agacaacacc cactccttct    6000
cagagagaaa gccaatcatc gaaagccagg atggcggctc aaattgcttc tggccctcca    6060
gcccttgaat ggtcggctac caatgaagag gatgatctat cagtggaggc tgagatcgct    6120
caccagattg cagaaagttt ctccaaaaaa tataagtttc cctctcgatc ctcagggata    6180
ctcttgtata attttgagca attgaaaatg aaccttgatg atatagttaa agaggcaaaa    6240
aatgtaccag gtgtgacccg tttagcccat gacgggtcca aactccccct aagatgtgta    6300
ctgggatggg tcgctttggc caactctaag aaattccagt tgttagtcga atccgacaag    6360
ctgagtaaaa tcatgcaaga tgacttgaat cgctatacat cttgctaacc gaacctctcc    6420
cctcagtccc tctagacaat aaaatccgag atgtcccaaa gtcaacatga aaaaacagg     6480 caacaccact gataaaatga acctcctacg taagatagtg aaaaaccgca gggacgagga    6540
cactcaaaaa tcctctcccg cgtcagcccc tctggatgac gatgacttgt ggcttccacc    6600
ccctgaatac gtcccgctga agaacttac aggcaagaag aacatgagga acttttgtat    6660
caacggaagg gttaaagtgt gtagcccgaa tggttactcg ttcaggatcc tgcggcacat    6720
tctgaaatca ttcgacgaga tatattctgg gaatcatagg atgatcgggt tagtcaaagt    6780
ggttattgga ctggctttgt caggatctcc agtccctgag ggcctgaact gggtatacaa    6840
attgaggaga acctttatct tccagtgggc tgattccagg ggccctcttg aagggggagga    6900 gttggaatac tctcaggaga tcacttggga tgatgatact gagttcgtcg gattgcaaat    6960
aagagtgatt gcaaaacagt gtcatatcca gggcagagtc tggtgtatca acatgaaccc    7020
gagagcatgt caactatggt ctgacatgtc tcttcagaca caaaggtccg aagaggacaa    7080
agattcctct ctgcttctag aataatcaga ttatatcccg caaatttatc acttgtttac    7140
ctctggagga gagaacatat gggctcaact ccaacccttg ggagcaatat aacaaaaaac    7200
atgttatggt gccattaaac cgctgcattt catcaaagtc aagttgatta cctttacatt    7260
ttgatcctct tggatgtgaa aaaaactatt aacatccctc aaaagacccc gggaaagatg    7320
gttcctcagg ctctccctgtt tgtacccctt ctggttttc cattgtgttt tgggaaattc    7380
cctatttaca cgataccaga caagcttggt ccctggagtc cgattgacat acatcacctc    7440
agctgcccaa acaatttggt agtggaggac gaaggatgca ccaacctgtc agggttctcc    7500
tacatggaac ttaaagttgg atacatctta gccataaaag tgaacgggtt cacttgcaca    7560
ggcgttgtga cggaggctga aacctacact aacttcgttg gttatgtcac aaccacgttc    7620
```

```
aaaagaaagc atttccgccc aacaccagat gcatgtagag ccgcgtacaa ctggaagatg    7680
gccggtgacc ccagatatga agagtctcta cacaatccgt accctgacta ccgctggctt    7740
cgaactgtaa aaaccaccaa ggagtctctc gttatcatat ctccaagtgt ggcagatttg    7800
gacccatatg acagatccct tcactcgagg gtcttcccta gcgggaagtg ctcaggagta    7860
gcggtgtctt ctacctactg ctccactaac cacgattaca ccatttggat gcccgagaat    7920
ccgagactag ggatgtcttg tgacattttt accaatagta gagggaagag agcatccaaa    7980
gggagtgaga cttgcggctt tgtagatgaa agaggcctat ataagtcttt aaaaggagca    8040
tgcaaactca agttatgtgg agttctagga cttagactta tggatggaac atgggtctcg    8100
atgcaaacat caaatgaaac caaatggtgc cctcccgata agttggtgaa cctgcacgac    8160
tttcgctcag acgaaattga gcaccttgtt gtagaggagt tggtcaggaa gagagaggag    8220
tgtctggatg cactagagtc catcatgaca accaagtcag tgagtttcag acgtctcagt    8280
catttaagaa aacttgtccc tgggtttgga aaagcatata ccatattcaa caagaccttg    8340
atggaagccg atgctcacta caagtcagtc gagacttgga atgagatcct cccttcaaaa    8400
gggtgtttaa gagttggggg gaggtgtcat cctcatgtga acgggtgtt tttcaatggt    8460 ataatattag gacctgacgg caatgtctta atcccagaga tgcaatcatc cctcctccag    8520
caacatatgg agttgttgga atcctcggtt atccccttg tgcaccccct ggcagacccg    8580
tctaccgttt tcaaggacgg tgacgaggct gaggattttg ttgaagttca ccttcccgat    8640
gtgcacaatc aggtctcagg agttgacttg ggtctcccga actgggggaa gtatgtatta    8700
ctgagtgcag gggccctgac tgccttgatg ttgataattt tcctgatgac atgttgtaga    8760
agagtcaatc gatcagaacc tacgcaacac aatctcagag ggacagggag ggaggtgtca    8820
gtcactcccc aaagcgggaa gatcatatct tcatgggaat cacacaagag tggggtgag    8880 accagactgt aattaattaa cgtcctttca acgatccaag tccatgaaaa aaactaacac    8940
ccctcccgta cctagcttat aaagtgctgg gtcatctaag cttttcagtc gagaaaaaaa    9000
cattagatca gaagaacaac tggcaacact tctcaacctg agacttactt caagatgctc    9060
gatcctggag aggtctatga tgaccctatt gacccaatcg agttagaggc tgaacccaga    9120
ggaaccccca ttgtccccaa catcttgagg aactctgact acaatctcaa ctctcctttg    9180
atagaagatc ctgctagact aatgttagaa tggttaaaaa cagggaatag accttatcgg    9240
atgactctaa cagacaattg ctccaggtct ttcagagttt tgaaagatta tttcaagaag    9300
gtagatttgg gttctctcaa ggtgggcgga atggctgcac agtcaatgat ttctctctgg    9360
ttatatggtg cccactctga atccaacagg agccggagat gtataacaga cttggcccat    9420
ttctattcca gtcgtcccc catagagaag ctgttgaatc tcacgctagg aaatagaggg    9480
ctgagaatcc ccccagaggg agtgttaagt tgccttgaga gggttgatta tgataatgca    9540 tttgaaggt atcttgccaa cacgtattcc tcttacttgt tcttccatgt aatcaccta    9600 tacatgaacg ccctagactg ggatgaagaa aagaccatcc tagcattatg gaaagattta    9660
acctcagtgg acatcgggaa ggacttggta aagttcaaag accaaatatg gggactgctg    9720
atcgtgacaa aggactttgt ttactcccaa agttccaatt gtcttttga cagaaactac    9780 acacttatgc taaaagatct tttcttgtct cgcttcaact ccttaatggt cttgctctct    9840
cccccagagc cccgatactc agatgacttg atatctcaac tatgccagct gtacattgct    9900
ggggatcaag tcttgtctat gtgtggaaac tccggctatg aagtcatcaa atatattggag    9960
```

```
ccatatgtcg tgaatagttt agtccagaga gcagaaaagt ttaggcctct cattcattcc    10020
ttgggagact ttcctgtatt tataaaagac aaggtaagtc aacttgaaga gacgttcggt    10080
ccctgtgcaa gaaggttctt tagggctctg gatcaattcg acaacataca tgacttggtt    10140
tttgtgtttg gctgttacag gcattggggg cacccatata tagattatcg aaagggtctg    10200
tcaaaactat atgatcaggt tcaccttaaa aaaatgatag ataagtccta ccaggagtgc    10260
ttagcaagcg acctagccag gaggatcctt agatgggtt ttgataagta ctccaagtgg     10320
tatctggatt caagattcct agcccgagac cacccttga ctccttatat caaaacccaa     10380
acatggccac ccaaacatat tgtagacttg gtgggggata catggcacaa gctcccgatc    10440
acgcagatct ttgagattcc tgaatcaatg gatccgtcag aaatattgga tgacaaatca    10500
cattctttca ccagaacgag actagcttct tggctgtcag aaaaccgagg ggggcctgtt    10560
cctagcgaaa aagttattat cacggccctg tctaagccgc ctgtcaatcc ccgagagttt    10620
ctgaggtcta tagacctcgg aggattgcca gatgaagact tgataattgg cctcaagcca    10680
aaggaacggg aattgaagat tgaaggtcga ttctttgctc taatgtcatg gaatctaaga    10740
ttgtattttg tcatcactga aaaactcttg gccaactaca tcttgccact ttttgacgcg    10800
ctgactatga cagacaacct gaacaaggtg tttaaaaagc tgatcgacag ggtcaccggg    10860
caagggcttt tggactattc aagggtcaca tatgcatttc acctggacta tgaaaagtgg    10920
aacaaccatc aaagattaga gtcaacagag gatgtatttt ctgtcctaga tcaagtgttt    10980
ggattgaaga gagtgttttc tagaacacac gagtttttc aaaaggcctg gatctattat      11040
tcagacagat cagacctcat cgggttacgg gaggatcaaa tatactgctt agatgcgtcc    11100
aacggcccaa cctgttggaa tggccaggat ggcgggctag aaggcttacg gcagaagggc    11160
tggagtctag tcagcttatt gatgatagat agagaatctc aaatcaggaa cacaagaacc    11220
aaaatactag ctcaaggaga caaccaggtt ttatgtccga catacatgtt gtcgccaggg    11280
ctatctcaag aggggctcct ctatgaattg gagagaatat caaggaatgc actttcgata    11340
tacagagccg tcgaggaagg ggcatctaag ctagggctga tcatcaagaa agaagagacc    11400
atgtgtagtt atgacttcct catctatgga aaaaccccctt tgtttagagg taacatattg    11460
gtgcctgagt ccaaaagatg ggccagagtc tcttgcgtct ctaatgacca aatagtcaac    11520
ctcgccaata taatgtcgac agtgtccacc aatgcgctaa cagtggcaca acactctcaa    11580
tctttgatca aaccgatgag ggattttctg ctcatgtcag tacaggcagt ctttcactac    11640
ctgctattta gcccaatctt aaagggaaga gtttacaaga ttctgagcgc tgaaggggag    11700
agctttctcc tagccatgtc aaggataatc tatctagatc cttctttggg agggatatct    11760
ggaatgtccc tcggaagatt ccatatacga cagttctcag accctgtctc tgaagggtta    11820
tccttctgga gagagatctg gttaagctcc caagagtcct ggattcacgc gttgtgtcaa    11880
gaggctggaa acccagatct ggagagaga acactcgaga gcttcactcg ccttctagaa    11940
gatccgacca cccttaaatat cagaggaggg gccagtccta ccattctact caaggatgca   12000
atcagaaagg ctttatatga cgaggtggac aaggtggaaa attcagagtt tcgagaggca    12060
atcctgttgt ccaagaccca tagagataat tttatactct tcttaatatc tgttgagcct    12120
ctgtttcctc gatttctcag tgagctattc agttcgtctt ttttgggaat ccccgagtca    12180
atcattggat tgatacaaaa ctcccgaacg ataagaaggc agtttagaaa gagtctctca    12240
aaaactttag aagaatcctt ctacaactca gagatccacg ggattagtcg gatgacccag    12300
acacctcaga gggttggggg ggtgtggcct tgctcttcag agagggcaga tctacttagg    12360
```

```
gagatctctt ggggaagaaa agtggtaggc acgacagttc ctcacccttc tgagatgttg    12420
ggattacttc ccaagtcctc tatttcttgc acttgtggag caacaggagg aggcaatcct    12480
agagtttctg tatcagtact cccgtccttt gatcagtcat ttttttcacg aggcccccta    12540
aagggatact tgggctcgtc cacctctatg tcgacccagc tattccatgc atgggaaaaa    12600
gtcactaatg ttcatgtggt gaagagagct ctatcgttaa aagaatctat aaactggttc    12660
attactagag attccaactt ggctcaagct ctaattagga acattatgtc tctgacaggc    12720
cctgatttcc ctctagagga ggccctgtc ttcaaaagga cggggtcagc cttgcatagg    12780
ttcaagtctg ccagatacag cgaaggaggg tattcttctg tctgcccgaa cctcctctct    12840
catatttctg ttagtacaga caccatgtct gatttgaccc aagacgggaa gaactacgat    12900
ttcatgttcc agccattgat gctttatgca cagacatgga catcagagct ggtacagaga    12960
gacacaaggc taagagactc tacgtttcat tggcacctcc gatgcaacag gtgtgtgaga    13020
cccattgacg acgtgaccct ggagacctct cagatcttcg agtttccgga tgtgtcgaaa    13080
agaatatcca gaatggtttc tggggctgtg cctcacttcc agaggcttcc cgatatccgt    13140
ctgagaccag gagattttga atctctaagc ggtagagaaa agtctcacca tatcggatca    13200
gctcaggggc tcttatactc aatcttagtg gcaattcacg actcaggata caatgatgga    13260
accatcttcc ctgtcaacat atacggcaag gtttccccta gagactattt gagagggctc    13320
gcaaggggag tattgatagg atcctcgatt tgcttcttga caagaatgac aaatatcaat    13380
attaatagac ctcttgaatt ggtctcaggg gtaatctcat atattctcct gaggctagat    13440
aaccatccct ccttgtacat aatgctcaga gaaccgtctc ttagaggaga gatattttct    13500
atccctcaga aaatccccgc cgcttatcca accactatga agaaggcaa cagatcaatc    13560 ttgtgttatc tccaacatgt gctacgctat gagcgagaga taatcacggc gtctccagag    13620
aatgactggc tatggatctt ttcagacttt agaagtgcca aaatgacgta cctatccctc    13680
attacttacc agtctcatct tctactccag agggttgaga gaaacctatc taagagtatg    13740
agagataacc tgcgacaatt gagttctttg atgaggcagg tgctgggcgg gcacggagaa    13800
gataccttag agtcagacga caacattcaa cgactgctaa aagactcttt acgaaggaca    13860
agatgggtgg atcaagaggt gcgccatgca gctagaacca tgactggaga ttacagcccc    13920
aacaagaagg tgtcccgtaa ggtaggatgt tcagaatggg tctgctctgc tcaacaggtt    13980
gcagtctcta cctcagcaaa cccggcccct gtctcggagc ttgacataag ggccctctct    14040
aagaggttcc agaaccctt gatctcgggc ttgagagtgg ttcagtgggc aaccggtgct    14100
cattataagc ttaagcctat tctagatgat ctcaatgttt tcccatctct ctgccttgta    14160 gttgggacg ggtcaggggg gatatcaagg gcagtcctca acatgttccc agatgccaag    14220
cttgtgttca acagtctttt agaggtgaat gacctgatgg cttccggaac acatccactg    14280
cctccttcag caatcatgag gggaggaaat gatatcgtct ccagagtgat agatcttgac    14340
tcaatctggg aaaaaccgtc cgacttgaga aacttggcaa cctggaaata cttccagtca    14400
gtccaaaagc aggtcaacat gtcctatgac ctcattattt gcgatgcaga agttactgac    14460
attgcatcta tcaaccggat caccctgtta atgtccgatt ttgcattgtc tatagatgga    14520
ccactctatt tggtcttcaa aacttatggg actatgctag taaatccaaa ctacaaggct    14580
attcaacacc tgtcaagagc gttccccctcg gtcacagggt ttatcaccca agtaacttcg    14640 tcttttttcat ctgagctcta cctccgattc tccaaacgag ggaagttttt cagagatgct    14700
```

```
gagtacttga cctcttccac ccttcgagaa atgagccttg tgttattcaa ttgtagcagc    14760
cccaagagtg agatgcagag agctcgttcc ttgaactatc aggatcttgt gagaggattt    14820
cctgaagaaa tcatatcaaa tccttacaat gagatgatca taactctgat tgacagtgat    14880
gtagaatctt ttctagtcca caagatggtt gatgatcttg agttacagag gggaactctg    14940
tctaaagtgg ctatcattat agccatcatg atagttttct ccaacagagt cttcaacgtt    15000
tccaaacccc taactgaccc ctcgttctat ccaccgtctg atcccaaaat cctgaggcac    15060
ttcaacatat gttgcagtac tatgatgtat ctatctactg ctttaggtga cgtccctagc    15120
ttcgcaagac ttcacgacct gtataacaga cctataactt attacttcag aaagcaagtc    15180
attcgaggga acgtttatct atcttggagt tggtccaacg acacctcagt gttcaaaagg    15240
gtagcctgta attctagcct gagtctgtca tctcactgga tcaggttgat ttacaagata    15300
gtgaagacta ccagactcgt tggcagcatc aaggatctat ccagagaagt ggaaagacac    15360
cttcataggt acaacaggtg gatcacccta gaggatatca gatctagatc atccctacta    15420
gactacagtt gcctgtgaac cggatactcc tggaagcctg cccatgctaa gactcttgtg    15480
tgatgtatct tgaaaaaaac aagatcctaa atctgaacct ttggttgttt gattgttttt    15540
ctcatttttg ttgtttattt gttaagcgt                                      15569
```